United States Patent
Lee et al.

(10) Patent No.: US 12,201,771 B2
(45) Date of Patent: Jan. 21, 2025

(54) PATIENT INTERFACE FORMED FROM A TEXTILE CONSTRUCTION AND INCLUDING A STIFFENED PORTION TO PROVIDE FOR CUSTOMIZATION

(71) Applicant: RESMED ASIA PTE. LTD., Singapore (SG)

(72) Inventors: Deng Siong Lee, Singapore (SG); Mohankumar Krishnan Valiyambath, Singapore (SG); Robin Yew, Singapore (SG); Amit Arunchandra Jadhav, Singapore (SG); Wai Hoong Leng, Singapore (SG); Beng Hai Tan, Singapore (SG); Muhammad Adil Bin Abdul Halim, Singapore (SG); Nathalie Aurelie Champier Charpentier, Singapore (SG); Bangzheng Tan, Singapore (SG); Han Seong Chew, Singapore (SG); Barry Eng Keong Tay, Singapore (SG)

(73) Assignee: ResMed Asia Pte. Ltd., Singapore (SG)

( * ) Notice: Subject to any disclaimer, the term of this patent is extended or adjusted under 35 U.S.C. 154(b) by 148 days.

(21) Appl. No.: 17/789,711

(22) PCT Filed: Dec. 30, 2020

(86) PCT No.: PCT/SG2020/050792
§ 371 (c)(1),
(2) Date: Jun. 28, 2022

(87) PCT Pub. No.: WO2021/137765
PCT Pub. Date: Jul. 8, 2021

(65) Prior Publication Data
US 2023/0050356 A1 Feb. 16, 2023

(30) Foreign Application Priority Data

Dec. 31, 2019 (SG) .......................... 10201914125V
Dec. 31, 2019 (SG) .......................... 10201914128Q
(Continued)

(51) Int. Cl.
*A61M 16/06* (2006.01)

(52) U.S. Cl.
CPC .... *A61M 16/0616* (2014.02); *A61M 16/0683* (2013.01); *A61M 2016/0661* (2013.01);
(Continued)

(58) Field of Classification Search
CPC ................................................. A61M 16/0683
See application file for complete search history.

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| JP | 2014-142654 A | 8/2014 |
| JP | 2019-129484 A | 8/2019 |

(Continued)

OTHER PUBLICATIONS

"*Respiratory Physiology*", by John B. West, Lippincott Williams & Wilkins, 9th edition published 2012 (8 pages).
(Continued)

*Primary Examiner* — LaToya M Louis
(74) *Attorney, Agent, or Firm* — Nixon & Vanderhye P.C.

(57) ABSTRACT

The invention relates to a patient interface comprising a plenum chamber, a seal-forming structure, and a positioning and stabilizing structure, as well as the method of operating
(Continued)

the patient interface. The patient's interface is configured to leave a patient's mouth uncovered or if the seal-forming structure is configured to seal around a patient's nose and mouth, the patient interface is configured to allow the patient to breath from the ambient in an absence of the flow of pressurized. The positioning and stabilizing structure includes headgear, and the seal-forming structure and at least a portion of the headgear is formed from a one piece construction of textile material. In another embodiment, the seal-forming structure and/or the positioning and stabilizing structure includes an adaptive portion that adjusts based on usage conditions. In another embodiment, the positioning and stabilizing structure, the seal-forming structure and/or the plenum chamber includes and/or is formed of a textile material, and the textile material includes at least one magnetic thread constructed of magnetic material to provide a magnetic interaction between a first part of the patient interface and a second part of the patient interface. In another embodiment, a stiffener is coupled to the plenum chamber, the seal-forming structure, and/or the positioning and stabilizing structure. In another embodiment, at least one of the plenum chamber and the seal-forming structure includes a textile material; and wherein the textile material includes a surface structure that limits adhesion of debris. A UV cleaning receptacle of the patient interface is also disclosed.

24 Claims, 76 Drawing Sheets

(30) Foreign Application Priority Data

| Dec. 31, 2019 | (SG) | ........................ 10201914129W |
|---|---|---|
| Dec. 31, 2019 | (SG) | ........................ 10201914131Q |
| Mar. 23, 2020 | (SG) | ........................ 10201914123U |

(52) U.S. Cl.
CPC . *A61M 2207/00* (2013.01); *A61M 2210/0618* (2013.01); *A61M 2210/0625* (2013.01)

(56) References Cited

U.S. PATENT DOCUMENTS

| 5,538,000 | A | 7/1996 | Rudolph |
| 5,687,715 | A | 11/1997 | Landis |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,537,200 | B2 | 9/2013 | Zhang et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 8,950,404 | B2 * | 2/2015 | Formica ................. B32B 27/302 2/209.3 |
| 9,731,090 | B2 | 8/2017 | Ovizinsky et al. |
| 9,981,104 | B1 | 5/2018 | Groll |
| 10,675,428 | B2 * | 6/2020 | Guney .............. A61M 16/0816 |
| 11,395,895 | B2 * | 7/2022 | Gibson ............. A61M 16/0683 |
| 11,517,700 | B2 * | 12/2022 | Dunn ....................... D04B 9/44 |
| 11,547,827 | B2 * | 1/2023 | Barlow ............. A61M 16/0605 |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2011/0247628 | A1 | 10/2011 | Ho |
| 2012/0227744 | A1 | 9/2012 | Radney |
| 2014/0053844 | A1 * | 2/2014 | Rummery ......... A61M 16/0622 128/206.21 |
| 2014/0109911 | A1 | 4/2014 | Asvadi et al. |
| 2014/0209098 | A1 | 7/2014 | Dunn et al. |
| 2015/0128953 | A1 * | 5/2015 | Formica .................... B32B 5/18 128/206.21 |
| 2015/0352308 | A1 * | 12/2015 | Cullen .............. A61M 16/0875 128/205.25 |
| 2016/0045701 | A1 | 2/2016 | Arcilla et al. |
| 2016/0082217 | A1 * | 3/2016 | McLaren .......... A61M 16/0816 128/207.11 |
| 2016/0106945 | A1 * | 4/2016 | Swift ................. A61M 16/0622 128/205.25 |
| 2016/0235875 | A1 | 8/2016 | Schmidt et al. |
| 2017/0021121 | A1 * | 1/2017 | Guney .............. A61M 16/0683 |
| 2017/0185140 | A1 | 1/2017 | Yen |
| 2017/0049983 | A1 | 2/2017 | Ellis |
| 2017/0189636 | A1 * | 7/2017 | Gibson ............. A61M 16/0666 |
| 2017/0281893 | A1 | 10/2017 | Kwok et al. |
| 2017/0319806 | A1 | 11/2017 | Teller et al. |
| 2017/0326320 | A1 * | 11/2017 | Baigent ............. A61M 16/0683 |
| 2018/0056023 | A1 | 3/2018 | Han |
| 2018/0126108 | A1 | 5/2018 | Formica et al. |
| 2018/0256845 | A1 | 9/2018 | Gibson et al. |
| 2018/0296786 | A1 * | 10/2018 | Barlow ............. A61M 16/0666 |
| 2019/0009045 | A1 | 1/2019 | Bernard |
| 2019/0070379 | A1 | 3/2019 | Lockhart et al. |
| 2019/0091431 | A1 | 3/2019 | Formica et al. |
| 2019/0290878 | A1 | 9/2019 | Romagnoli et al. |
| 2019/0351172 | A1 * | 11/2019 | Formica .................. B32B 15/14 |
| 2021/0069442 | A1 * | 3/2021 | Baigent .............. A61M 16/0616 |
| 2021/0085908 | A1 * | 3/2021 | Dunn ...................... D04B 1/225 |
| 2021/0205563 | A1 * | 7/2021 | Mah .................. A61M 16/0816 |
| 2022/0218934 | A1 * | 7/2022 | Ozolins ................. A61M 16/16 |
| 2023/0049355 | A1 | 2/2023 | Lee et al. |

FOREIGN PATENT DOCUMENTS

| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/073142 A1 | 7/2010 |
| WO | WO 2010/135785 A1 | 12/2010 |
| WO | WO 2012/027792 A1 | 3/2012 |
| WO | WO 2012/171072 A1 | 12/2012 |
| WO | WO 2013/020167 A1 | 2/2013 |
| WO | WO 2014/125066 A1 | 8/2014 |
| WO | WO 2017/185140 A1 | 11/2017 |
| WO | WO 2018/064712 A2 | 4/2018 |
| WO | WO 2018/179094 A1 | 10/2018 |

OTHER PUBLICATIONS

SoClean® 2 "Fast and Easy Sleep Equipment Maintenance" User Manual, Copyright 2011-2019 (28 pages).
International Search Report and Written Opinion dated Jun. 3, 2021 issued in International Application No. PCT/SG2020/050792 (24 pages).
Written Opinion of the International Preliminary Examining Authority dated Jan. 1, 2022 issued in International Application No. PCT/SG2020/050792 (13 pages).
Notice of Allowance dated Jan. 19, 2023 issued in U.S. Appl. No. 17/498,808 (9 pages) citing US 2009/0180194 A1, US 2009/0173343 A1, and WO 2022/221907 A1.
Office Action and Search Report dated Jan. 31, 2023 issued in Malaysian Application No. PI2022005337 (3 pages).
Extended European Search Report mailed Feb. 6, 2024 in European Application No. 20908622.2, 11 pages.

* cited by examiner

Copyright 2012 ResMed Limited

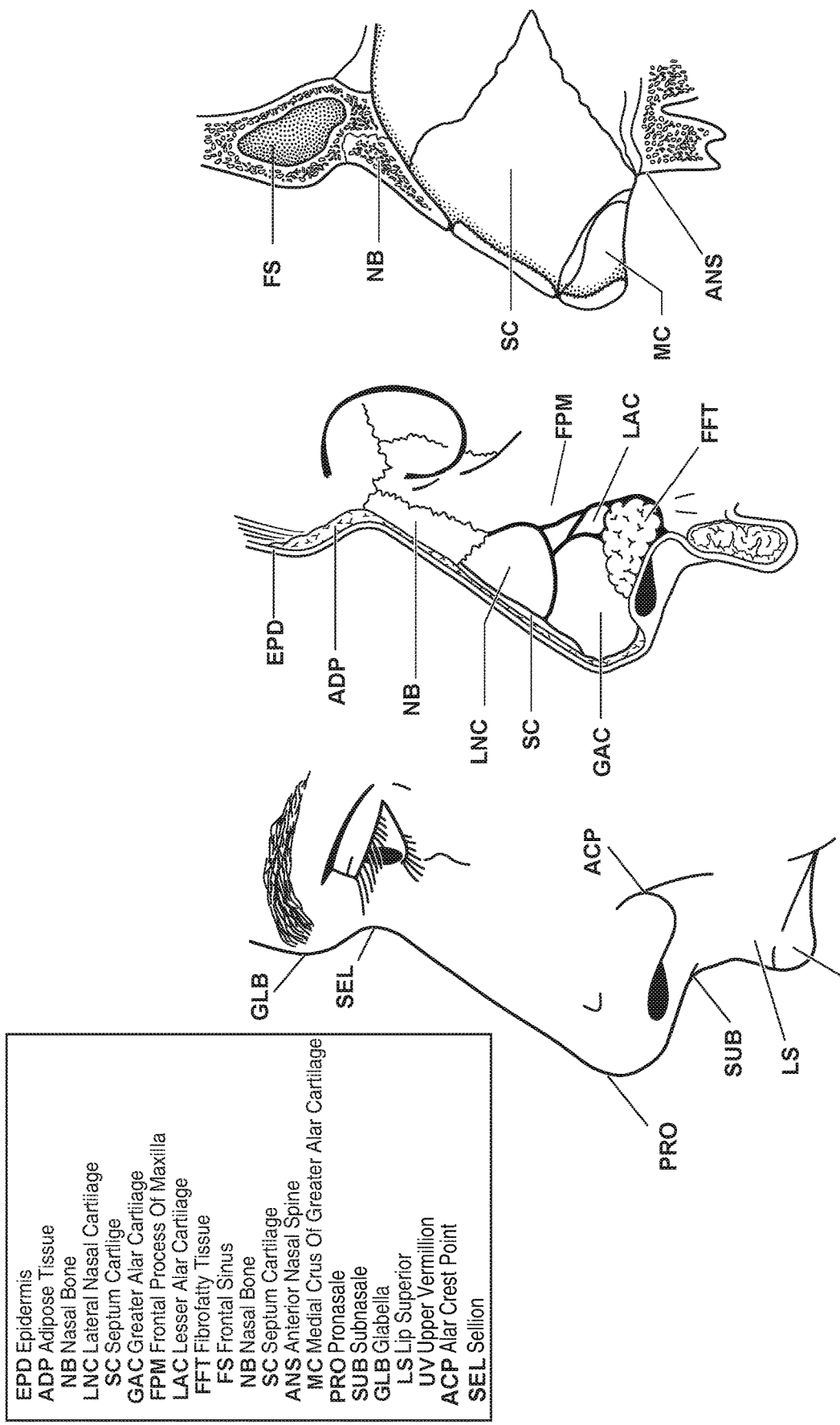

| | |
|---|---|
| FB | Frontal Bone |
| SOF | Supraorbital Foramen |
| NB | Nasal Bones |
| SC | Septal Cartilage |
| LNC | Lateral Nasal Cartilage |
| SES | Sesamoid Cartilage |
| GAC | Greater Alar Cartilage |
| MC | Medial Crus Of Greater Alar Cartilage |
| ANS | Anterior Nasal Spine |
| IOF | Infraorbital Foramen |
| LSC | Lesser Nasal Cartilage |
| AFT | Alar Fibrofatty Tissue |

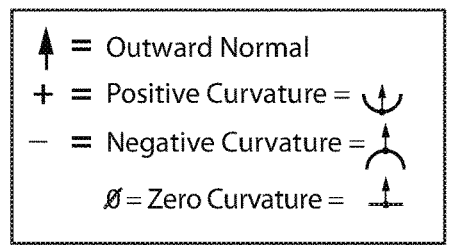

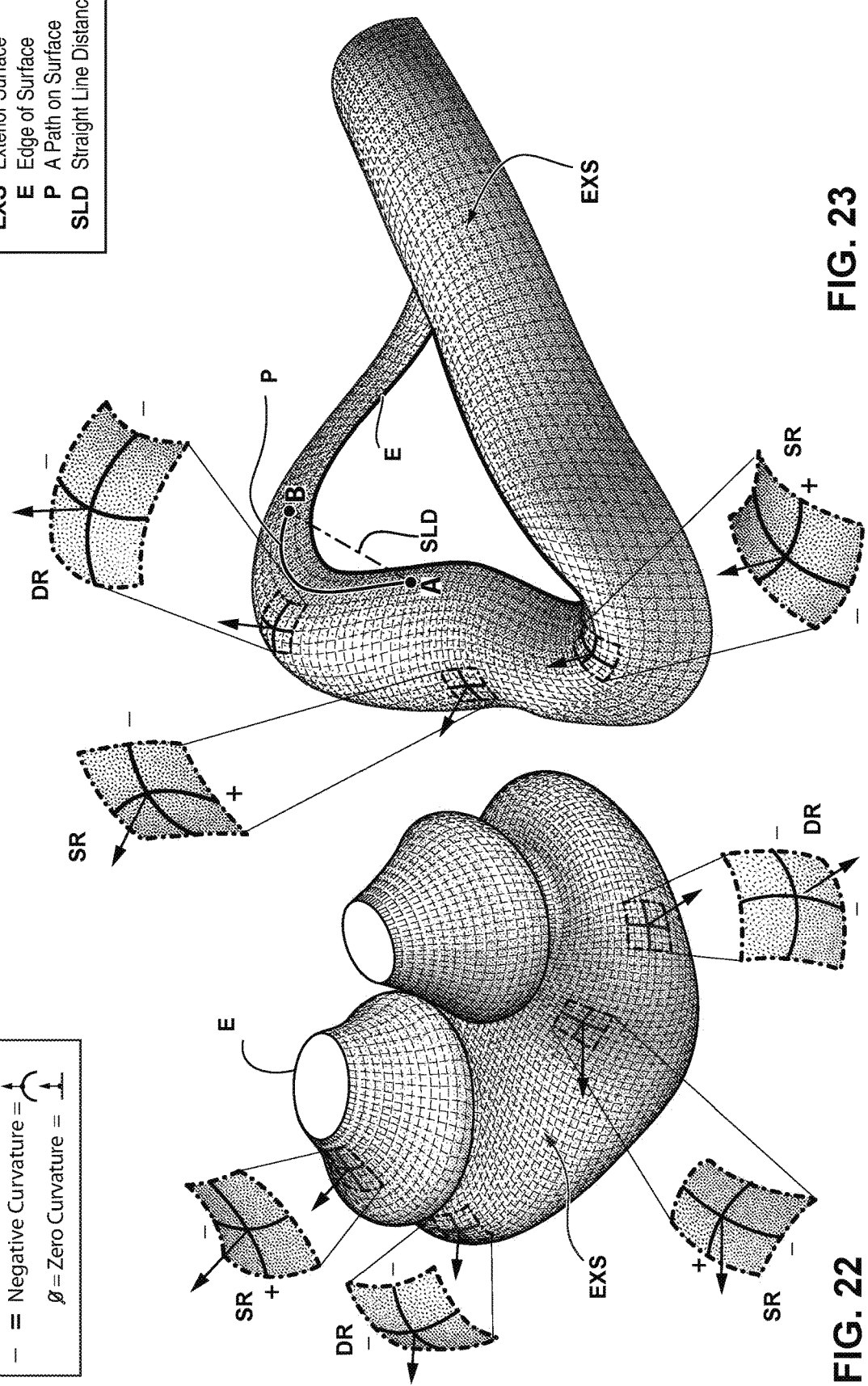

| CUR | Curve |
| --- | --- |
| SRF | Surface |
| INS | Interior Surface |
| OD | Outside Diameter |
| ID | Inside Diameter |

| | |
|---|---|
| LHR | Left-hand Rule |
| RHR | Right-hand Rule |
| B | Binormal |
| OSC | Osculating Plane |
| T | Tangent |
| N | Normal |
| LEH | Left Ear Helix |
| REH | Right Ear Helix |
| RHH | Right-hand Helix |
| RHP | Right-hand Positive |
| RHN | Right-hand Negative |
| RHN-LHP | Right-hand Negative (=left-hand Positive) |

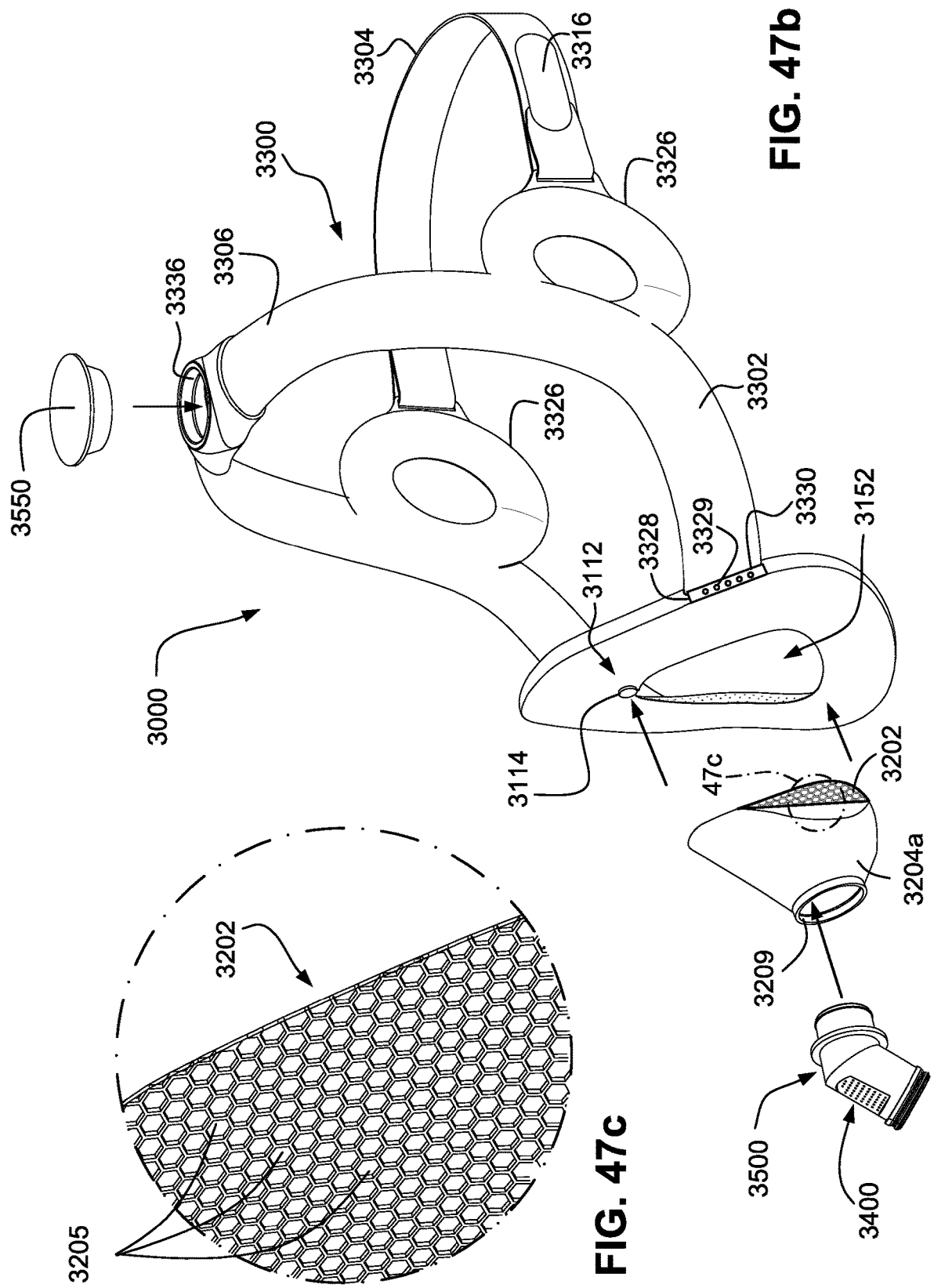

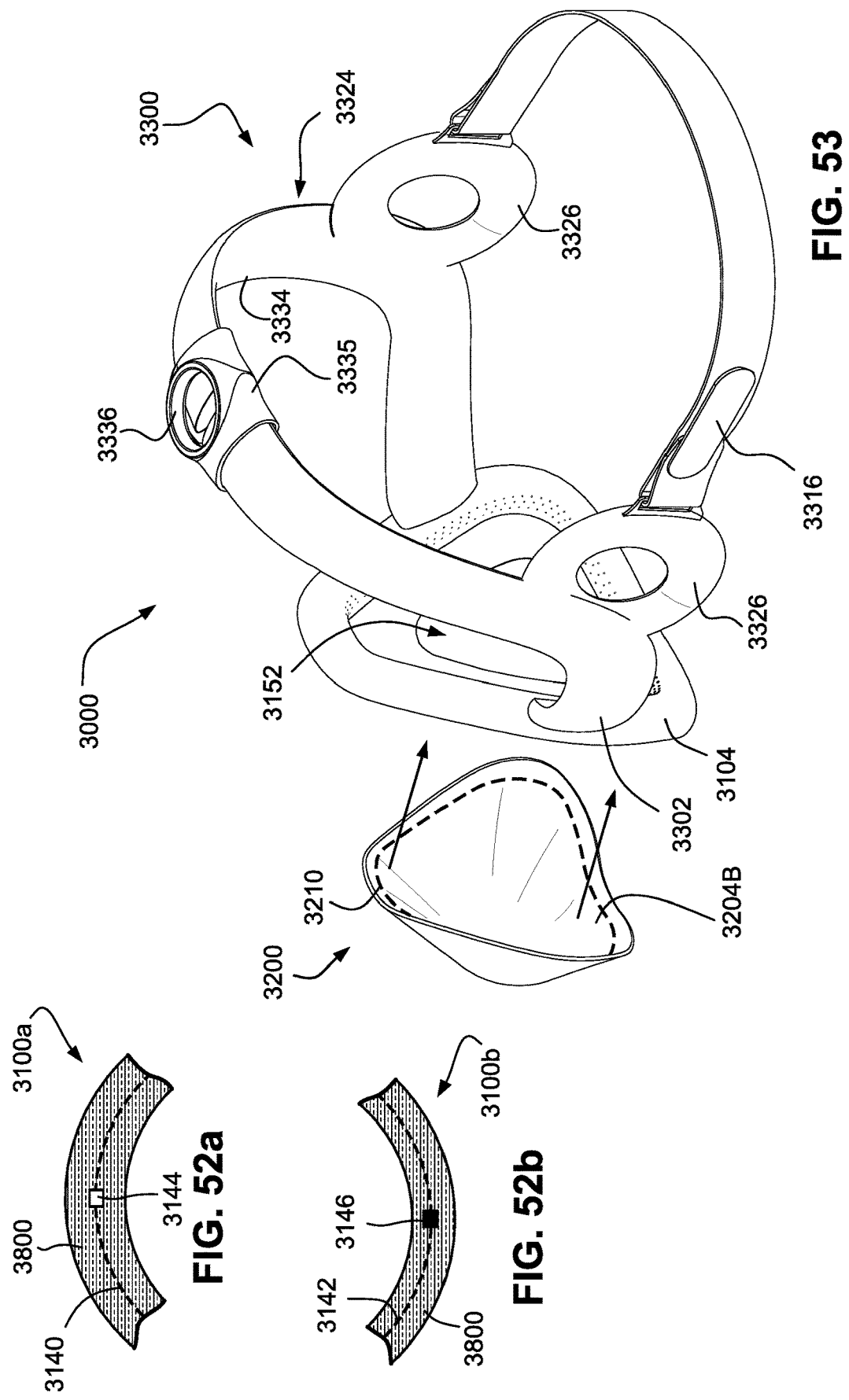

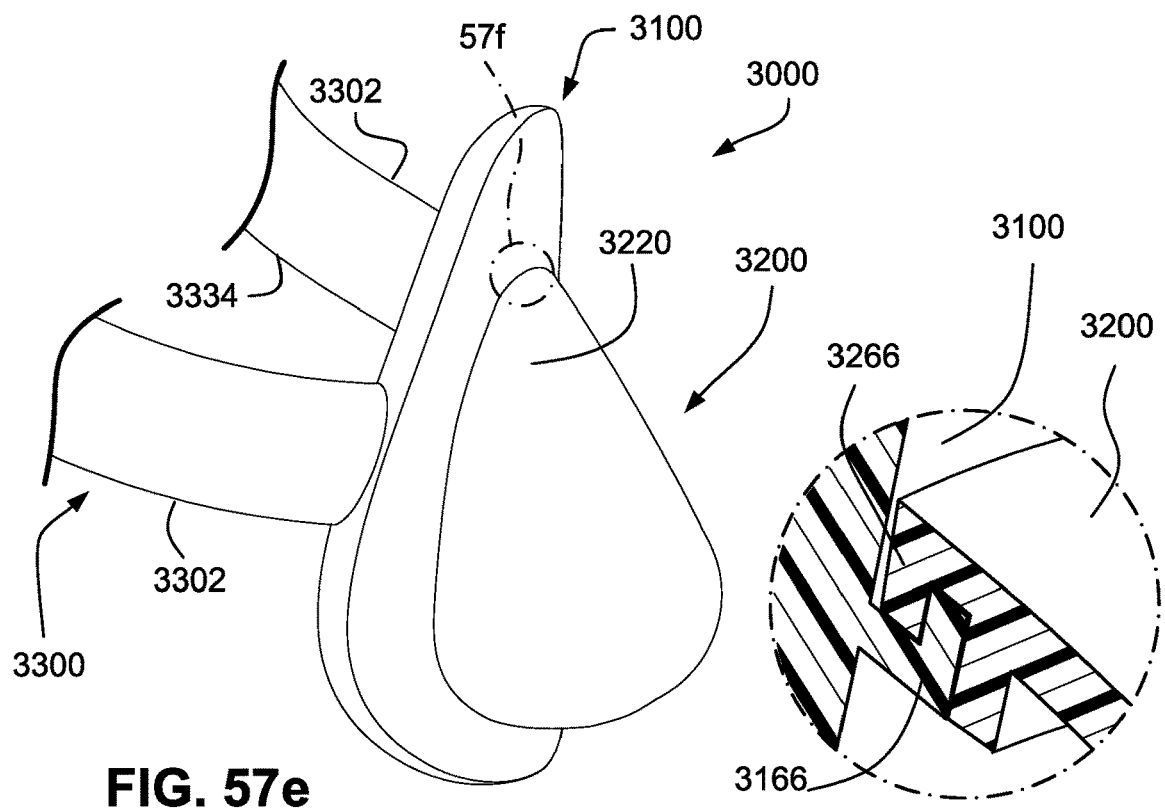
FIG. 57e
FIG. 57f
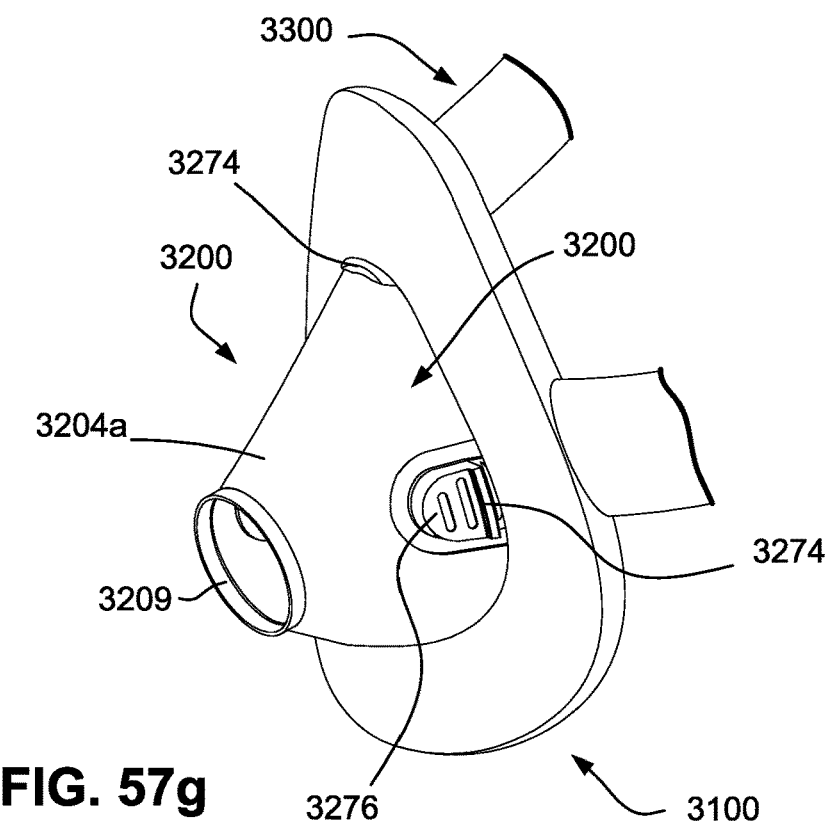
FIG. 57g

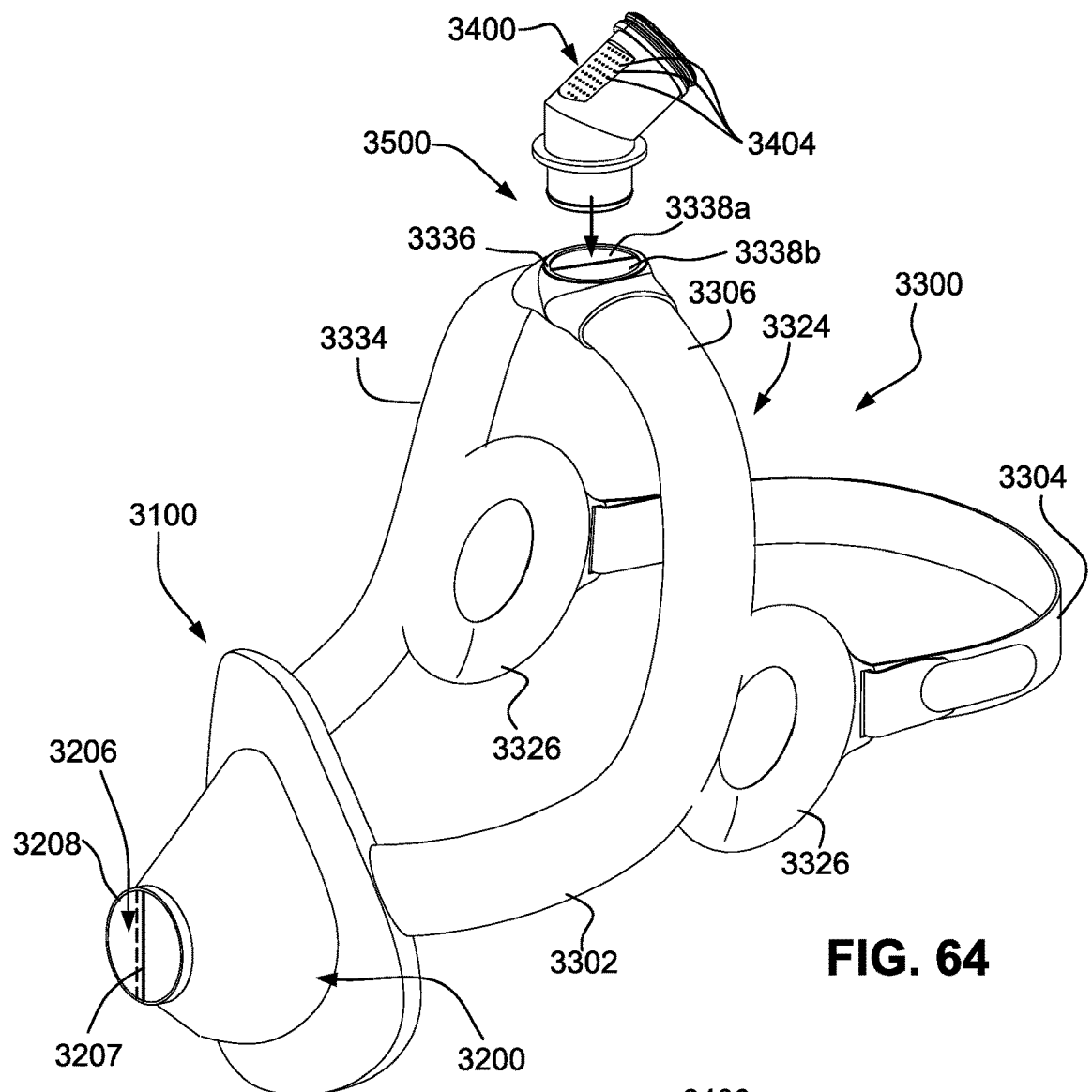
FIG. 64
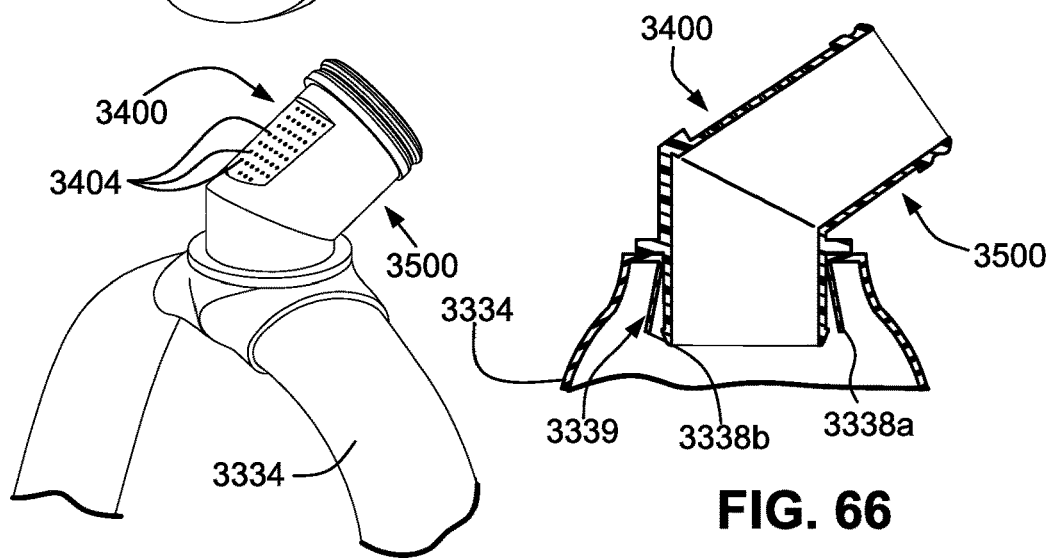
FIG. 65
FIG. 66

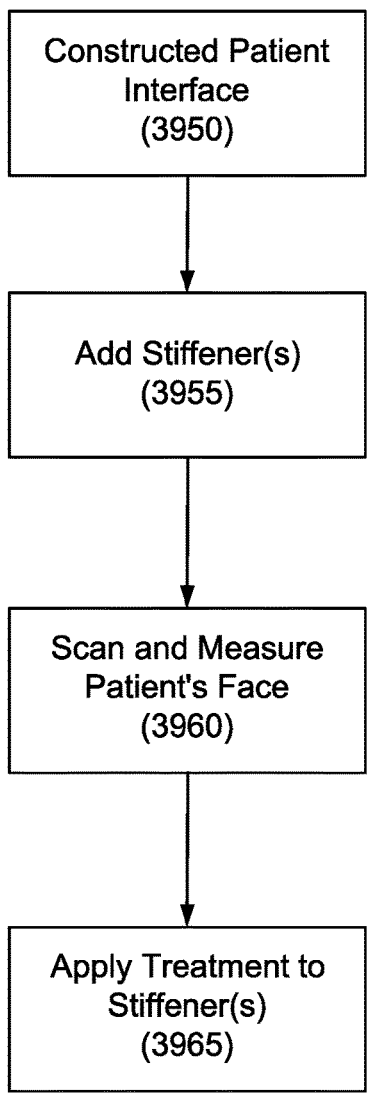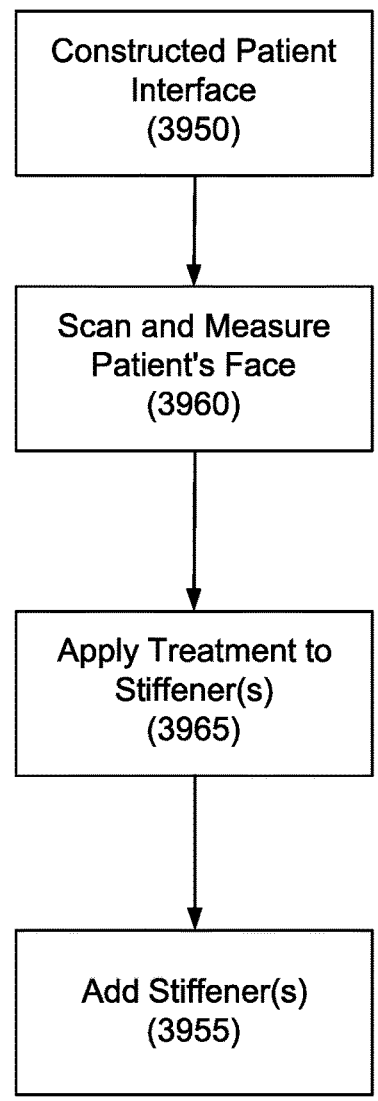
FIG. 101a     FIG. 101b
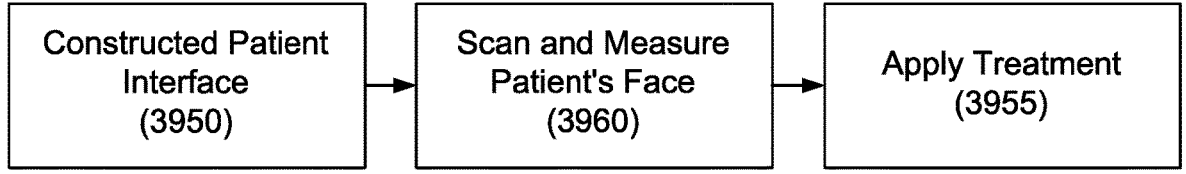
FIG. 101c

PATIENT INTERFACE FORMED FROM A TEXTILE CONSTRUCTION AND INCLUDING A STIFFENED PORTION TO PROVIDE FOR CUSTOMIZATION

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application is the U.S. national phase of International Application No. PCT/SG2020/050792 filed Dec. 30, 2020 which designated the U.S. and claims priority to Singapore Provisional application Ser. No. 10/201,914123U filed Mar. 23, 2020, Singapore Provisional application Ser. No. 10/201,914125V filed Dec. 31, 2019, Singapore Provisional Application Ser. No. 10/201,914128Q filed Dec. 31, 2019, Singapore Provisional Application No. 10201914129 W filed Dec. 31, 2019, and Singapore Provisional Application No. 10201914131Q filed Dec. 31, 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nares and the mouth are the entrances to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterized by particular events, e.g., apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See Sullivan, U.S. Pat. No. 4,944,310.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise at least one of: a Respiratory Pressure Therapy (RPT) device, an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may seal, e.g., with a region of the patient's face, to facilitate the delivery of gas at a pressure at sufficient variance with ambient pressure to effect therapy, e.g., at a positive pressure of about 10 cm $H_2O$ relative to ambient pressure.

For other forms of therapy, such as the delivery of oxygen, the patient interface may not include a seal sufficient to facilitate delivery to the airways of a supply of gas at a positive pressure of about 10 cm $H_2O$. For flow therapies such as nasal HFT, the patient interface is configured to insufflate the nares but specifically to avoid complete sealing. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology, e.g., if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g., for sleeping while lying on one's side in bed with the head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable, especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g., filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable or difficult to use, a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g., aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterized according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to, for example, overlay an upper lip region and a nasal bridge region of a face. In one form of patient interface, a seal-forming structure may comprise an element that surrounds a mouth region in use, e.g., by forming a seal on a lower lip region of the face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g., because of the different shape, structure, variability and sensitivity of different regions of the patient's face. For example, a structure of swimming goggles that overlays a patient's forehead to seal therewith may not be appropriate to use on a patient's nose.

Certain seal-forming structures may be designed for mass manufacture such that one design can fit and be comfortable and effective for a wide range of different face shapes and sizes. To the extent to which there is a mismatch between the shape of the patient's face, and the seal-forming structure of the mass-manufactured patient interface, one or both must adapt in order for the seal-forming structure seal with the patient's face.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force may be required to position the patient interface against the face in order to seal therewith or leak may occur. Additional force may cause discomfort for the patient during use.

Another type of seal-forming structure incorporates a flap of relatively thin material positioned about the periphery of the mask so as to provide a self-sealing action against the face of the patient when positive pressure is applied within the mask. Like the type of seal-forming structure described in the preceding paragraph, if the size and shape of the seal-forming structure does not accurately correspond to the size and shape of the patient's face, additional force may be required to seal against the patient's face, or the mask may leak. Additional force may cause discomfort for the patient during use. Furthermore, if the size and shape of the seal-forming structure does not accurately correspond to that of the patient, then the seal-forming structure may crease or buckle in use due its relative thinness, which may result in leaking.

Another type of seal-forming structure may comprise a friction-fit element, e.g., for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited, Kwok et al., International Publication No. WO 1998/004310 A1; Davidson et al., International Publication No. WO 2006/074513 A1; Dravitzki et al., International Publication No. WO 2010/135785 A1.

One form of nasal pillow is found in the ADAM Circuit manufactured by Puritan-Bennett Corporation. Another nasal pillow, or nasal puff is the subject of Trimble et al., U.S. Pat. No. 4,782,832, assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: Gunaratnam et al., International Publication No. WO 2004/073778 A1 (describing amongst other things aspects of the ResMed Limited SWIFT™ nasal pillows); Guney et al., U.S. Publication No. 2009/0044808 A1 (describing amongst other things aspects of the ResMed Limited SWIFT™ LT nasal pillows); Davidson et al., International Publication No. WO 2005/063328 A1 and Lubke et al., International Publication No. WO 2006/130903 A1 (describing amongst other things aspects of the ResMed Limited MIRAGE LIBERTY™ full-face mask); Rummery et al., International Publication No. WO 2009/052560 A1 (describing amongst other things aspects of the ResMed Limited SWIFT™ FX nasal pillows).

2.2.3.1.2 Positioning and Stabilizing

A seal-forming structure of a patient interface used for positive air pressure therapy is subject to the corresponding force of the air pressure to disrupt a seal. Thus, a variety of techniques have been used to position the seal-forming structure, and to maintain it in sealing relation with the appropriate portion of the face.

One technique is the use of adhesives. See, for example, Kooij et al., U.S. Publication No. 2010/0000534 A1. However, the use of adhesives may be uncomfortable for some.

Another technique is the use of one or more straps and/or stabilizing harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus, RPT devices may also act as flow therapy devices. Examples of RPT devices include a CPAP device and a ventilator.

Air pressure generators are known in a range of applications, e.g., industrial-scale ventilation systems. However, air pressure generators for medical applications have particular requirements not fulfilled by more generalized air pressure generators, such as the reliability, size, and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is minimization of acoustic noise because the patient may be sleeping during operation.

Table of noise output levels of prior RPT devices (one specimen only, measured using test method specified in ISO 3744 in CPAP mode at 10 cm $H_2O$).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9™ Sleep Therapy System, manufactured by ResMed Limited. Another example of an RPT device is a ventilator. Ventilators such as the ResMed STELLAR™ Series of Adult and Paediatric Ventilators may provide support for invasive and non-invasive non-dependent ventilation for a range of patients for treating a number of conditions such as but not limited to NMD, OHS and COPD.

The ELISÉE™ 150 ventilator and VS III™ ventilator, manufactured by ResMed Limited, may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient.

In some cases, the flow of air may be supplied to the airway of the patient at positive pressure. The outlet of the RPT device is connected via an air circuit to a patient interface such as those described above.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, warm air applied generally to the face area in and about the patient interface in cooler climates is more comfortable than cold air. Humidifiers therefore often have the capacity to heat the flow of air was well as humidifying it. Moreover, warmer air has a greater capacity for water vapor.

A range of artificial humidification devices and systems are known, however, they may not fulfill the specialized requirements of a medical humidifier.

Medical humidifiers are used to increase humidity and/or temperature of the flow of air in relation to ambient air when required, typically where the patient may be asleep or resting (e.g., at a hospital). A medical humidifier for bedside placement may be small A medical humidifier may be configured to only humidify and/or heat the flow of air delivered to the patient without humidifying and/or heating the patient's surroundings. Room-based systems (e.g., a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, and some are difficult or inconvenient to use by patients.

2.2.3.5 Data Management

There may be clinical reasons to obtain data to determine whether the patient prescribed with respiratory therapy has been "compliant", e.g., that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Vent Technologies

Some forms of treatment systems may include a vent to allow the washout of exhaled carbon dioxide. The vent may allow a flow of gas from an interior space of a patient interface, e.g., from within the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g., through noise or focused airflow.

ResMed Limited has developed a number of improved mask vent technologies. See Kwok, International Publication No. WO 1998/034665 A1; Gunaratnam et al., International Publication No. WO 2000/078381 A1; Drew et al., U.S. Pat. No. 6,581,594 B1; Ng et al., U.S. Publication No. 2009/0050156 A1; Guney et al., U.S. Publication No. 2009/0044808 A1.

Table of noise of prior masks (ISO 17510-2:2007, 10 cm $H_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

-continued

| Mask name | Mask type | A-weighted sound power level dB(A) (uncertainty) | A-weighted sound pressure dB(A) (uncertainty) | Year (approx.) |
|---|---|---|---|---|

(*one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.7 Heat and Moisture Exchanger (HMX) Technology

A patient may be susceptible to drying of the internal airways passages while undergoing various forms of respiratory therapy as described above. For example, CPAP therapy entails providing the patient with a flow of air pressurized at a pressure greater than ambient continuously, and this continuous flow of air, particularly at an elevated level in conjunction with the positive air pressure, may causing drying of the patient's airways. That drying may cause discomfort, which in turn may negatively impact the patient's compliance with therapy.

To minimize the drying effect of these forms of respiratory therapy, the flow of air provided to the patient may be humidified before it reaches the patient. Certain forms of humidification technology, such as those described above, actively provide humidified air to the patient to reduce the drying effect by heating a reservoir of water and passing air over its surface to increase the absolute humidity of the air, i.e., the air absorbs water vapour from the reservoir. The humidified air is then passed to the patient via the air circuit. The air circuit may also be heated to prevent condensation, also known as rainout, of the water vapour within the air circuit during transport to the patient. These forms of technology typically involve filling the reservoir with water before therapy, and then the reservoir is provided to the RPT system so that the water can be heated to humidify the air for therapy. The reservoir typically requires regular cleaning, there is a risk of spillage, which may be particularly problematic in the context of electrical components, and the reservoir requires refilling by the patient before use.

Eliminating the need for a pre-supplied water source, such as a water-filled reservoir, and input electrical power to heat the water may provide several benefits. For example, the RPT device could be made smaller because it would not require space for the water reservoir and heating plate. Since no electrical energy is consumed in heating of the water, electricity costs may be reduced. Also, fewer electrical components may be needed in the RPT device, which reduces its cost and complexity. Also, the RPT device may be easier to use because there is no water reservoir to fill, empty, and clean. Risk of spillage may be reduced as well.

Also, operation of the RPT device may be simplified because there are no humidification settings to operate.

In operation, the patient breathes out (exhalation) air that has been heated within the patient's body and that has absorbed water vapour from the patient's airways. The heat and moisture in the exhaled air is captured by the HMX material(s), i.e., the HMX material(s) are heated by the relatively warm exhaled air and the HMX material(s) adsorb water vapour from the relatively humid exhaled air, as the exhaled air passes through HMX material(s) prior to being vented to atmosphere. During inhalation, the flow of pressurized air passes through the HMX material(s) in the opposite direction to exhalation to reach the patient's airways, and the source of the incoming air is typically ambient air. Thus, the flow of pressurized air, as it passes through the HMX material(s) prior to reaching the patient's airways, absorbs moisture in the form of water vapour as it is desorbed from the HMX material(s) and the flow of pressurized air is heated by heat released from the HMX material(s).

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of the present technology is directed to a patient interface that may comprise: a plenum chamber; a seal-forming structure; and a positioning and stabilizing structure. The patient interface may further comprise a vent structure. The patient interface may further be configured to leave the patient's mouth uncovered, or if the seal-forming structure is configured to seal around the patient's nose and mouth, the patient interface may be further configured to allow the patient to breathe from ambient in the absence of a flow of pressurized air through the plenum chamber inlet port.

Another aspect of the present technology is directed to a face-mounted interface that may comprises: a facial interface, and a positioning and stabilizing structure. The facial interface may be configured to contact the user's face. The positioning and stabilizing structure structured to hold the facial interface in an effective position against the user's face.

In some aspects, the face-mounted interface is a patient interface used in screening, diagnosis, monitoring, amelioration, treatment or prevention of a respiratory disorder. However, the face-mounted interface may be any device worn on a user's face.

Another aspect of the present technology is directed to a positioning and stabilizing structure for supporting a facial interface on a user's face. The positioning and stabilizing structure includes headgear constructed from at least one strap. The straps may contract the user's head and apply a force to the facial interface where the force is configured to maintain the position of the facial interface in a desired position. The straps may be at least partially constructed from a flexible material.

Another aspect of the present technology is directed to a patient interface comprising: a plenum chamber pressurisable to a therapeutic pressure of at least 4 cm H$_2$O above ambient air pressure, said plenum chamber including a plenum chamber inlet port sized and structured to receive a flow of air at the therapeutic pressure for breathing by a patient; a seal-forming structure constructed and arranged to seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilizing structure configured to hold the seal-forming structure in a therapeutically effective position on the patient's head, the positioning and stabilizing structure comprising a tie, the tie being constructed and arranged so that at least a portion overlies a region of the patient's head superior to an otobasion superior of the patient's head in use; and a vent structure configured to allow a continuous flow of gases exhaled by the patient from an interior of the plenum chamber to ambient, said vent structure being sized and shaped to maintain the therapeutic pressure in the plenum chamber in use; wherein the patient interface is configured to leave the patient's mouth uncovered, or if the seal-forming structure is configured to seal around the patient's nose and mouth, the patient interface is configured to allow the patient to breathe from ambient in the absence of a flow of pressurized air through the plenum chamber inlet port.

Another aspect of the present technology is directed to a patient interface comprising: a plenum chamber pressurisable to a therapeutic pressure of at least 4 cm H$_2$O above ambient air pressure; a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use; and a positioning and stabilizing structure configured to hold the seal-forming structure in a therapeutically effective position on a patient's head, wherein the patient interface is configured to leave a patient's mouth uncovered, or if the seal-forming structure is configured to seal around a patient's nose and mouth, the patient interface is configured to allow the patient to breathe from ambient in the absence of a flow of pressurized air, wherein the positioning and stabilizing structure includes headgear, and wherein the seal-forming structure and at least a portion of the headgear is formed from a one piece construction of textile material.

In examples, the one piece construction can be one piece of continuous textile (e.g., of a homogeneous base material). The one piece of continuous textile may include discrete portions that are treated or otherwise include certain attributes that are specific for a given engagement area with the patient's head. An alternative to the one piece construction would include a number of separate textile components (which may have the same or different properties) that are joined together.

In some aspects, the seal-forming structure comprises an oro-nasal mask, a nasal mask, an under the nose mask, or nasal pillows.

In some aspects, the plenum chamber comprises a skeletal support and/or a textile cover.

In some aspects, the textile cover includes a thermoformed and/or laminate structure in order to define a generally rigid outer perimeter of the plenum chamber.

In some aspects, the plenum chamber includes a concave shape.

In some aspects, the headgear includes side straps configured to extend from the seal-forming structure to a position between a patient's eye and ear.

In some aspects, the side straps and the seal-forming structure are formed in the one piece construction of said textile material.

In some aspects, a joint is disposed between each side strap and the seal-forming structure, the joint being rigidized and/or reinforced.

In some aspects, each joint is rigidized with a rigidized thread and/or a rigidized portion of the textile material.

In some aspects, a part of the one piece construction of textile material is heat treated and/or lased in order to rigidize the joint.

In some aspects, side straps span across a transition from the headgear to the seal-forming structure.

In some aspects, one of the side straps includes a magnetic section.

In some aspects, the magnetic section is a first magnetic section, the one of the side straps further including a second magnetic section having an opposite polarity as the first magnetic section.

In some aspects, the seal-forming structure includes a sleeve, the one of the side straps being receivable through the sleeve, and the one of the side straps removable coupled to itself.

In some aspects, the side straps extend from lateral sides of the seal-forming structure and are adapted to extend along a patient's cheeks and inferior to the patient's eye in use.

In some aspects, the side straps have an inner surface that is substantially flat and the seal-forming structure has an inner surface that is curved as seen in cross section and structure to protrude towards the patient's face in use.

In some aspects, the inner surface of the seal-forming structure includes a layered structure with a foam layer positioned underneath the one piece construction of textile material, the foam layer imparting curvature to the one piece construction textile material of the seal-forming structure.

In some aspects, the seal-forming structure is an oro-nasal mask and the inner surface of the seal-forming structure is adapted to surround the patient's nose and mouth.

In some aspects, each said side strap comprises a hollow tube structured to convey the flow of air to the seal-forming structure.

In some aspects, each said hollow tube extends to an interior surface of the seal-forming structure.

In some aspects, the side strap includes an inlet configured to be positioned proximate a superior of the patient's head, the inlet includes a plug biased toward a closed position, and is adapted to receive an elbow joint.

In some aspects, the elbow is coupled to the side strap with a latch and/or a magnet.

In some aspects, the seal-forming structure includes a hollow sealing tube with the interior surface and adapted to receive the flow of air, the hollow sealing tube including at least one hole.

In some aspects, the seal-forming structure includes a non-permeable layer that directs air toward the at least one hole.

In some aspects, the seal-forming structure includes a hollow sealing tube with the interior surface and adapted to receive the flow of air, the hollow sealing tube including a permeable material proximate the patient's face in other to allow air to pass through, and a non-permeable material opposite the permeable material.

In some aspects, each said hollow tube comprises a dual lumen tube.

In some aspects, said headgear includes a pair of ear pieces each configured to partly or fully surround the ear of the patient.

In some aspects, the pair of ear pieces and the seal-forming structure are formed in the one piece construction of said textile material.

In some aspects, the headgear includes a rear strap to engage an occiput of the patient's head.

In some aspects, the rear strap and the seal-forming structure are formed in the one piece construction of said textile material.

In some aspects, the headgear includes a top strap extending over the top of the patient's head.

In some aspects, the top strap and the seal-forming structure are formed in the one piece construction of said textile material.

In some aspects, the top strap extends between and connects the side straps and/or the pair of ear pieces.

In some aspects, the plenum chamber is structured for detachment from the seal-forming structure while the seal and the headgear remain in place on the patient's head, such that the patient's mouth and nose are freely exposed to ambient air when the plenum chamber is detached.

In some aspects, a finger activated detachment mechanism detaches the plenum chamber from the seal-forming structure.

In some aspects, the finger activated detachment mechanism includes a push button.

In some aspects, a clipping structure secures the plenum chamber to the seal-forming structure.

In some aspects, the clipping structure includes a first clip portion integrated into and/or formed as part of the one piece construction of textile material of the seal-forming structure and a second clip portion on the plenum chamber.

In some aspects, the seal-forming structure is an oro-nasal mask, and the first clip portion is at least part ring shaped and attached to the seal-forming structure, and the second clip portion has a complementary shape and is attached to the plenum chamber.

In some aspects, the first clip portion is formed by a rigidized portion of the one piece construction of textile material.

In some aspects, the rigidized portion includes at least one thread that is more rigid than at least one other thread of the one piece construction of textile material.

In some aspects, the second clip portion is integrated into, and/or formed as part of the textile cover and/or a skeletal support of the plenum chamber.

In some aspects, the first clip portion is removably secured to the second clip portion with a snap fit that substantially prevents a flow of fluid through an interface between the seal-forming structure and the plenum chamber.

In some aspects, the first clip portion is a male clip portion and the second clip portion is a female clip portion.

In some aspects, the clipping structure causes the plenum chamber and the seal-forming structure to be engaged via a press-fit, a snap-fit, and/or a friction fit.

In some aspects, the plenum chamber is coupled to the seal-forming structure using a press-fit, a snap-fit, and/or a friction fit.

In some aspects, an undercut is included on one of the plenum chamber and the seal-forming structure and an overhang is included on the other of the plenum chamber and the seal-forming structure, the undercut engaging the overhang in order to create a sealing engagement.

In some aspects, a magnetic coupling guides the plenum chamber and the seal-forming structure towards a connected position, and/or releasably connects the plenum chamber and the seal-forming structure.

In some aspects, the magnetic coupling includes at least a first magnetic portion on the seal-forming structure and at least a second magnetic portion on the plenum chamber of opposite polarity to the first magnetic portion, the first and second magnetic portions being arranged so that the plenum chamber and the seal-forming structure are attracted to one another when they are oriented in a proper assembly position, and they are repelled from one another when the plenum chamber and the seal-forming structure are not oriented in the proper assembly position.

In some aspects, the first magnetic portion includes a first magnet and/or a first magnetic thread incorporated into the one piece construction of textile material, and the second magnetic portion includes a second magnet and or a second magnetic thread incorporated as part of the textile cover of the plenum chamber.

In some aspects, the first magnetic thread fully defines an inner perimeter of the seal-forming structure and the second magnetic thread fully defines an outer perimeter of the plenum chamber.

In some aspects, the skeletal support includes a framework includes a polygonal latticework attached to the textile cover.

In some aspects, the polygonal latticework includes hexagons.

In some aspects, the first magnetic portion includes a first material incorporated as part of the textile cover of the plenum chamber, and the second magnetic portion includes a second magnet and/or a second magnetic thread incorporated into the one piece construction of textile material of the plenum chamber, the first material configured to attract the second magnetic portion.

In some aspects, the plenum chamber further includes a third magnetic portion with a third magnet and/or a third magnetic thread incorporated into the one piece construction of textile material of the plenum chamber, the second magnetic portion includes the second magnet and/or the second magnetic thread having a first polarity on a right hand side of the plenum chamber, and the third magnetic portion includes the third magnet and/or the third magnetic thread having a second polarity on a left hand side of the plenum chamber, wherein the first material is configured to repel the third magnetic portion.

In some aspects, the plenum chamber further includes a secondary port configured to allow the patient to breathe from the ambient in the absence of a flow of pressurized air while the plenum chamber is selectively coupled to the seal-forming structure.

In some aspects, the plenum chamber and the seal-forming structure are formed in the one piece construction of said textile material.

In some aspects, the plenum chamber is permanently or removably attached to the seal-forming structure.

In some aspects, one of the plenum chamber, the headgear, and the seal-forming structure includes an inlet port adapted to receive an elbow.

In some aspects, the plenum chamber and the seal-forming structure include or form a seal when attached.

In some aspects, the seal-forming structure and the headgear are connected together with a seamless joint.

In some aspects, the seal-forming structure includes at least one fold of the one piece construction of textile material forming a bellows.

In some aspects, the bellows is rigidized to fold or expand in a predetermined manner and/or at a predetermined pressure.

In some aspects, a vent is configured to allow a continuous flow of gases exhaled by the patient from an interior of the plenum chamber to the ambient, said vent being sized and shaped to maintain the therapeutic pressure in the plenum chamber in use.

In some aspects, the vent is formed in the plenum chamber, the textile cover of the plenum chamber, the one piece construction of textile material of the seal-forming structure, and/or headgear.

In some aspects, the seal-forming structure is an oro-nasal mask including an anti-asphyxia valve (AAV).

In some aspects, the AAV comprises a flap of textile material formed on the plenum chamber, the one piece construction of textile material of the seal-forming structure, and/or the headgear.

In some aspects, the AAV selectively covers the inlet port.

In some aspects, the AAV is biased toward an open position to allow the patient to breathe from the ambient in the absence of the flow of pressurized air.

In some aspects, the headgear includes a stretchable portion and a relatively non-stretchable portion.

In some aspects, the seal-forming structure is a gasket type seal or a lip type seal.

In some aspects, the plenum chamber includes a hole to receive pressurized gas.

In some aspects, the seal-forming structure is the under the nose mask, that is adapted to engage a patient's upper lip and seal against a patient's nares while leaving a patient's nasal tip free, and further comprising a mouth seal.

In some aspects, the mouth seal is removably coupled to the under the nose mask with at least one of a clip and a magnet.

In some aspects, the under the nose mask includes a flap biased toward a closed position without the presence of the mouth seal, and movable to an open position when the mouth seal is coupled to the under the nose mask.

In some aspects, the seal-forming structure includes an air bladder configured to be selectively inflated and contact the patient's face.

In some aspects, the seal-forming structure may be a single size and the air bladder may be inflated a varying amount depending on the particular patient's face size.

In some aspects, a method for operating the patient interface comprising, donning the seal-forming structure and the headgear onto the patient's head; and subsequently, removably attaching the plenum chamber to the seal-forming structure.

Some aspects of the method include compressing a finger activated detachment mechanism to detach the plenum chamber from the seal forming structure.

Some aspects of the method include aligning a first magnetic coupling guide of the plenum chamber with a second magnetic coupling guide of the seal-forming structure, the first magnetic coupling guide having an opposite polarity than the first magnetic coupling guide.

Some aspects of the method include selectively engaging a clip on one of the seal-forming structure and the plenum chamber with a complementary shape on the other of the seal-forming structure and the plenum chamber.

In some aspects, the headgear includes a first port and the plenum chamber includes a second port, the method further comprising removably attaching an elbow to one of the first port and the second port.

In some aspects, attaching a plug to the other of the first port and the second port.

Some aspects of the method include an ear piece configured to partly or fully surround the ear of a patient, the donning step further including positioning the ear piece about the ear of the patient.

Some aspects of the method include magnetically decoupling the seal-forming structure from the headgear subsequent to the donning step.

Some aspects of the method include stretching a portion of the headgear to fit the patient's head.

Some aspects of the method include adjusting a side strap spanning across a transition from the headgear to the seal-forming structure to produce a desired fit.

Some aspects of the method include positioning a first magnetic section of the side strap relative to a second magnetic section of the seal-forming structure.

Another aspect of the present technology is directed to a face-mounted interface comprising: a facial interface; a cushion connected to the facial interface and configured to contact at least a portion of a user's face in use; and a positioning and stabilizing structure configured to hold the cushion and/or the facial interface in an effective position on the user's head, wherein the cushion and at least a portion of the positioning and stabilizing structure is formed from a one piece construction of textile material.

Another aspect of the present technology is directed to a patient interface comprising: a plenum chamber pressurisable to a therapeutic pressure of at least 4 cm $H_2O$ above ambient air pressure; a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use; and a positioning and stabilizing structure configured to hold the seal-forming structure in a therapeutically effective position on a patient's head, wherein the patient interface is configured to leave a patient's mouth uncovered, or if the seal-forming structure is configured to seal around a patient's nose and mouth, the patient interface is configured to allow the patient to breathe from ambient in the absence of a flow of pressurized air, wherein the seal-forming structure and/or the positioning and stabilizing structure includes an adaptive portion that adjusts based on usage conditions.

In some aspects, the seal-forming structure includes the adaptive portion configured as an adaptive seal, and the usage conditions include tension, heat, and moisture.

In some aspects, a rigid or stiffened portion (e.g., a metal wire or a stiffened thread) may be positioned within the adaptive portion.

In some aspects, the rigid or stiffened portion may limit the amount of compression and/or expansion of the adaptive portion.

In some aspects, the adaptive portion includes a swellable material that increases in size upon absorption of moisture.

In some aspects, the swellable material includes swellable foam.

In some aspects, the swellable material is polyurethane.

In some aspects, the swellable material is disposed on an outer edge of the seal-forming structure configured to sit adjacent to one of a nasolabial sulcus, a philtrum, a sellion, or a supramenton of a patients face.

In some aspects, one of the seal-forming structure and the plenum chamber including a rigid support that is configured to bias expansion of the swellable material toward the patient's face.

In some aspects, the swellable material returns to approximately its original size with evaporation of moisture.

In some aspects, the seal-forming structure includes the swellable material and a non-swellable material, the non-swellable material extending around a portion of the swellable material in order to direct the expansion of the swellable material.

In some aspects, the non-swellable material is a non-swellable thread sewn around a portion of the swellable material.

In some aspects, the seal-forming structure includes a hollow sealing tube with an interior surface and is adapted to receive the flow of air, the interior surface of the hollow sealing tube including the non-swellable material, and the swellable material positioned radially outside of the non-swellable material.

In some aspects, the adaptive portion includes a heat activated material that increases in size upon application of heat.

In some aspects, the heat activated material is activated between 85° F. and 110° F.

In some aspects, the heat activated material is activated between 90° F. and 100° F.

In some aspects, the heat activated material returns to approximately its original size with removal of heat.

In some aspects, the heat activated material is disposed on an outer edge of the seal-forming structure configured to sit adjacent to one of a nasolabial sulcus, a philtrum, a sellion, or a supramenton of a patients face.

In some aspects, the seal-forming structure includes the heat activated material and a non-heat activated material, the non-heat activated material extending around a portion of the heat activated material in order to direct the expansion of the heat activated material.

In some aspects, the non-heat activated material is a non-heat activated thread sewn around a portion of the heat activated material.

In some aspects, the seal-forming structure includes a hollow sealing tube with an interior surface and is adapted to receive the flow of air, the interior surface of the hollow sealing tube including the non-heat activated material, and the heat activated material positioned radially outside of the non-heat activated material.

In some aspects, the heat activated material has a closed cell foam structure.

In some aspects, the adaptive portion includes an auxetic material that increases in size upon application of tension.

In some forms, the auxetic material increases in size in a direction substantially perpendicular to a direction of tension.

In some aspects, the auxetic material includes a thread having auxetic properties.

In some aspects, the auxetic material on the seal-forming portion is substantially aligned with tension of at least one strap of the positioning and stabilizing structure.

In some aspects, the seal-forming structure includes a rigidizer or a rigidized portion that is positioned to abut the auxetic material, such that the seal forming portion is biased in a direction toward the patient upon the application of tension to the auxetic material, whilst restraining the auxetic material from expanding in at least one other direction.

In some aspects, the seal-forming structure includes a hollow sealing tube with an interior surface and is adapted to receive the flow of air, the interior surface of the hollow sealing tube includes a rigidizer or a rigidized portion, and the auxetic material positioned radially outside of the rigidizer or the rigidized portion.

In some aspects, the rigidizer or the rigidized portion includes a thread having a stiffness greater than the auxetic material.

In some aspects, the auxetic material includes auxetic foam.

In some aspects, the auxetic material is polyurethane.

In some aspects, the auxetic material is disposed on an outer edge of the seal-forming structure configured to sit adjacent to one of a nasolabial sulcus, a philtrum, a sellion, or a supramenton of a patients face.

In some aspects, the auxetic material returns to approximately its original size with removal of tension.

In some aspects, the adaptive portion is structured to increase in size over time, based on tension, heat and/or moisture, to enhance sealing between the seal-forming structure and the patient's face in use.

In some aspects, the seal-forming structure is a gasket type seal or a lip type seal.

In some aspects, the adaptive portion is configured to seal with the patient's face at a relatively low force during initial therapy, and increases to a relatively higher force with increased heat, moisture, and/or tension.

In some aspects, the seal-forming structure includes at least one fold forming a bellows.

In some aspects, the bellows folds or expands in a predetermined manner based on the application of a predetermined tension, heat or moisture.

In some aspects, the positioning and stabilizing structure includes the adaptive portion, and the usage conditions include tension, heat, and moisture.

In some aspects, the positioning and stabilizing structure includes side straps configured to extend from the seal-forming structure to a position between the patient's eye and ear.

In some aspects, each said side strap comprises a hollow tube structured to convey the flow of air to the seal-forming structure, at least a portion of each side strap includes the adaptive portion.

In some aspects, each side strap includes an auxetic material.

In some aspects, the hollow tube includes an interior surface and is adapted to receive the flow of air, the interior surface of the hollow tube including a rigid material, and the auxetic material positioned radially outside of the rigid material.

In some aspects, the adaptive portion on the positioning and stabilizing structure is configured to be located proximate to a cheek of a patient's head.

In some aspects, the adaptive portion of the positioning and stabilizing structure is coupled directly to the seal-forming portion.

In some aspects, a first port is disposed on the positioning and stabilizing structure, a perimeter of the first port includes the adaptive portion.

In some aspects, a first plug or an elbow are selectively received within the first port, the adaptive portion configured to seal around the first plug or the elbow with application of heat, moisture, and/or tension.

In some aspects, the first plug and the elbow are coupled to the positioning and stabilizing structure with a mechanical fastener and/or a magnet.

In some aspects, the positioning and stabilizing structure includes a tie removably coupled to the seal-forming structure.

In some aspects, one of the positioning and stabilizing structure and the seal-forming structure includes a catch, the adaptive portion configured to expand about the catch.

In some aspects, the seal-forming structure is an under the nose mask, with a mouth seal removably coupled to the under the nose mask.

In some aspects, the under the nose mask and the mouth seal are coupled together with a mechanical fastener and/or a magnet, and further include the adaptive portion at an interface between the nose mask and the mouth seal.

In some aspects, the plenum chamber includes a second port, the perimeter of the second port includes the adaptive portion.

In some aspects, a second plug or the elbow are selectively received within the second port, the adaptive portion configured to seal around the second plug or the elbow with the application of heat, moisture, and/or tension.

In some aspects, the second plug and the elbow are coupled to the plenum chamber with a mechanical fastener and/or a magnet.

Another aspect of the present technology is directed to a face-mounted interface comprising: a facial interface; a cushion constructed and arranged to contact at least a portion of a user's face in use; and a positioning and stabilizing structure configured to hold the cushion and/or the facial interface in an effective position on the user's head, wherein the cushion and/or the positioning and stabilizing structure includes an adaptive portion that adjusts based on usage conditions.

In some forms, the adaptive portion may be an auxetic material, a swellable material, a heat activated material, or any similar material.

Another aspect of the present technology is directed to a positioning and stabilizing structure constructed and arranged to be used with a face-mounted interface and is adapted to hold the face-mounted interface in an effective position on a user's face, the positioning and stabilizing structure comprising headgear having at least one strap that includes an adaptive portion that adjusts based on usage conditions.

Another aspect of the present technology is directed to a patient interface comprising: a plenum chamber pressurisable to a therapeutic pressure of at least 4 cm H2O above ambient air pressure; a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use; and a positioning and stabilizing structure configured to hold the seal-forming structure in a therapeutically effective position on a patient's head, wherein the patient interface is configured to leave a patient's mouth uncovered, or if the seal-forming structure is configured to seal around a patient's nose and mouth, the patient interface is configured to allow the patient to breathe from ambient in the absence of a flow of pressurized air, wherein the positioning and stabilizing structure, the seal-forming structure and/or the plenum chamber includes and/or is formed of a textile material, wherein the textile material includes at least one magnetic thread constructed of magnetic material to provide a magnetic interaction between a first part of the patient interface and a second part of the patient interface.

In some aspects, the first part is the plenum chamber and the second part is the positioning and stabilizing structure, the first part magnetically attracted to the second part.

In some aspects, the positioning and stabilizing structure further includes a third part of the patient interface magnetically attracted to at least one of the first part and the second part.

In some aspects, one of the side straps and the plenum chamber includes a first material, and the other of the side straps and the plenum chamber includes the at least one magnetic thread attracted to the first material.

In some aspects, each of the side straps having a first end and a second end that are connected in length adjustable fashion (e.g., the position of the first end with respect to the second end may change in order to adjust the overall length of the at least one strap), the first end being the first part and having the at least one magnetic thread.

In some aspects, the plenum chamber includes a sleeve though which one of the side straps can be inserted and double-backed on itself for length adjustment.

In some aspects, a section of at least one of the side straps is spaced apart from the first end includes a second magnetic material attracted to the first part in order to retain the length adjustment from the one of the side straps.

In some aspects, the second end has a plurality of slots and the first end has a catch that can be fit in the slots to allow for adjustability.

In some aspects, the catch includes a hook.

In some aspects, the second part is magnetically coupled to the third part when the one of the side straps is doubled back on itself.

In some aspects, the third part is magnetically connected to both the first part and the second part.

In some aspects, the positioning and stabilizing structure includes a strap with the at least one magnetic thread, and a clip structure through which the strap is threaded, and the plenum chamber includes a projection that releasably attaches to the clip structure.

In some aspects, the seal-forming structure includes a fourth part that is magnetically coupled to at least one of the first part and the second part.

In some aspects, the first part is the plenum chamber and the second part is the seal-forming structure, the first part magnetically attracted to the second part.

In some aspects, a third part in the positioning and stabilizing structure is magnetically coupled to at least one of the first part and the second part.

In some aspects, one of the seal-forming structure and the plenum chamber includes a first material, and the other of the seal-forming structure and the plenum chamber includes the at least one magnetic thread attracted to the first material.

In some aspects, the first material is a magnet or a second magnetic thread.

In some aspects, the at least one magnetic thread is sewn around at least a portion of a perimeter of the plenum chamber.

In some aspects, the at least one magnetic thread is sewn entirely around the plenum chamber.

In some aspects, a fourth part on the plenum chamber is spaced apart from the first part, the first part and the fourth part having opposite polarities.

In some aspects, the fourth part is repelled by the second part.

In some aspects, the plenum chamber is at least partially fixed to the seal-forming structure.

In some aspects, the positioning and stabilizing structure includes first and second side straps extending from lateral sides of the seal-forming structure, and magnetically coupled to the seal-forming structure.

In some aspects, the plenum chamber includes a port with a magnetic material defining at least a portion of a port diameter, the port configured to receive and magnetically couple with an elbow.

In some aspects, the plenum chamber further includes a flap with a magnetic portion, the magnetic portion of the flap having an opposite polarity as an inner diameter of the port.

In some aspects, the first part is the positioning and stabilizing structure and the second part is the seal-forming structure, the first part magnetically attracted to the second part.

In some aspects, the positioning and stabilizing structure includes first and second side straps extending from lateral sides of the seal-forming structure, and the first part of the patient interface includes the first and second side straps, and the second part includes seal-forming structure.

In some aspects, the positioning and stabilizing structure further includes a third part of the patient interface magnetically attracted to at least one of the first part and the second part.

In some aspects, one of the first and second side straps and the seal-forming structure includes a first material, and the other of the first end second side straps and the seal-forming structure includes the at least one magnetic thread attracted to the first material.

In some aspects, each of the first and second side straps having a first end and a second end that are connected in length adjustable fashion, the first end being the first part and having the at least one magnetic thread.

In some aspects, the plenum chamber includes sleeve though which one of the side straps can be inserted and double-backed on itself for length adjustment.

In some aspects, a section of the side strap spaced apart from the first end includes a second magnetic material attracted to the first part in order to retain the length adjustment from the one of the side straps.

In some aspects, the second end has a plurality of slots and the first end has a catch that can be fit in the slots to allow for adjustability.

In some aspects, the catch includes a hook.

In some aspects, the second part is magnetically coupled to the third part when the one of the side straps is doubled back on itself.

In some aspects, the third part is magnetically connected to both the first part and the second part.

In some aspects, the positioning and stabilizing structure includes a strap with the at least one magnetic thread, and a clip structure through which the strap is threaded, and the plenum chamber includes a projection that releasably attaches to the clip structure.

In some aspects, the first part is an inlet port and the second part is a flap, the first part magnetically repelling the second part.

In some aspects, the inlet port and the flap are disposed in the positioning and stabilizing structure.

In some aspects, the inlet port and the flap are disposed in the plenum chamber.

In some aspects, a force of air at the therapeutic pressure is greater than a force of magnetic repulsion between the first part and the second part.

In some aspects, a third part is a second inlet port and a fourth part is a second flap, the third part magnetically repelling the fourth part.

In some aspects, one of the inlet port and the flap includes a first material, and the other of the inlet port and the flap includes the at least one magnetic thread having an identical polarity as the first material.

In some aspects, the flap includes a first half and a second half.

In some aspects, the inlet port is configured to receive a decoupling structure that is magnetically attracted to the inlet port.

In some aspects, the seal-forming structure includes the first part and the second part, the first part is an under the nose mask and the second part is a mouth seal, the first part magnetically attracted to the second part.

In some aspects, the plenum chamber is removably coupled to the seal-forming structure when the first part is coupled to the second part.

In some aspects, one of the first part and the second part includes a third part that is magnetically attracted to a fourth part of the positioning and stabilizing structure.

In some aspects, the fourth part is a side strap that extends from a lateral side of the seal-forming structure when the third part is coupled to the fourth part.

In some aspects, an interface between the under the nose mask and the mouth seal is sealed when the first part is magnetically coupled to the second part.

In some aspects, an adaptive material is included in one of the under the nose mask and the mouth seal, the adaptive seal portion adjusts based on usage conditions to seal the interface.

In some forms, magnetic thread may be used to form a decoupling structure, the magnetic thread may assist with the engagement between the decoupling structure and the tubes of the positioning and stabilizing structure or the plenum chamber.

In some forms, a sleeve may be positioned over at least a portion of the positioning and stabilizing structure; wherein the sleeve is formed from a comfortable material; and wherein the sleeve includes a magnetic portion (e.g., a magnetic thread) in order to connect to the positioning and stabilizing structure.

Another aspect of the present technology is directed to a face-mounted interface comprising: a facial interface; a cushion constructed and arranged to contact a region of a user's face in use; and a positioning and stabilizing structure configured to hold the facial interface and/or the cushion in an effective position on the user's head, wherein the positioning and stabilizing structure, the cushion, and/or the facial interface includes and/or is at least partially formed of textile material, the textile material including at least one magnetic thread constructed of magnetic material to provide a magnetic interaction between a first part of the face-mounted interface and a second part of the face-mounted interface.

Another aspect of the present technology is directed to a positioning and stabilizing structure constructed and arranged to be used with a face-mounted interface and is adapted to hold the face-mounted interface in an effective position on a user's face, the positioning and stabilizing structure comprising headgear having at least one strap that includes at least one magnetic thread constructed of magnetic material adapted to provide a magnetic interaction.

Another aspect of the present technology is directed to a patient interface structured to receive a flow of air for breathing by a patient, the patient interface comprising: a plenum chamber pressurisable to a therapeutic pressure of at least 4 cm H2O above ambient air pressure; a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use; a positioning and stabilizing structure configured to hold the seal-forming structure in a therapeutically effective position on a patient's head; and a stiffener coupled to the plenum chamber, the seal-forming structure, and/or the positioning and stabilizing structure, wherein the patient interface is configured to leave a patient's mouth uncovered, or if the seal-forming structure is configured to seal around a patient's nose and mouth, the patient interface is configured to allow the patient to breathe from ambient in the absence of a flow of pressurized air, wherein the seal-forming structure and/or the positioning and stabilizing structure is constructed from a first textile material, and wherein the stiffener is constructed from a second textile material configured, upon application of treatment, to have a treatment-induced stiffness that is greater than a stiffness of the first textile material.

In some aspects, the second textile material is a rigidized thread.

In some aspects, the stiffness of the first textile material is not affected by the application of the treatment.

In some aspects, the second textile material is configured to increase in stiffness with the application of a laser treatment, a heat treatment, and/or a pressure treatment.

In some aspects, the second textile material has a stiffness greater than the stiffness of the first textile material before the application of the treatment.

In some aspects, the second textile material is a thermoplastic material.

In some aspects, the positioning and stabilizing structure includes a left side strap coupled to the seal-forming structure, the second textile material positioned along a length of the left side strap.

In some aspects, a right side strap is coupled to an opposite side of the seal-forming structure than the left side strap, the second textile material positioned along a length of the right side strap substantially equivalent to the length of the left side strap.

In some aspects, the second textile material extends from the seal-forming structure and is configured, once treated, to limit deformation along the length of the left side strap.

In some aspects, the second textile material includes a first portion and a second portion, the first portion extends from the seal-forming structure, and the second portion is spaced apart from the first portion, the left side strap configured to deform in locations without the second textile material.

In some aspects, the positioning and stabilizing structure includes ear pieces that define a hole, wherein each ear piece configured to receive a patient's ear in use, the second textile material positioned around at least a portion of each ear piece.

In some aspects, each ear piece includes a first section of the second textile material and a second section of the second textile material spaced apart from the first section, so that, in use, each ear piece is configured to deform in a first direction with an application of a force, and is configured to remain static in a second direction with the application of the force.

In some aspects, each side strap extends between the plenum chamber and one of the ear pieces.

In some aspects, the positioning and stabilizing structure includes a rear strap configured to be positioned on a posterior of the patient's head in use, the second textile material positioned along a length of the rear strap.

In some aspects, the rear strap is connected between the ear pieces, and wherein the second textile material on the rear strap is spaced apart from each of the ear pieces.

In some aspects, the seal-forming structure includes the second textile material that is positioned around at least a portion of a seal-forming structure perimeter.

In some aspects, a first thread of the second textile material extends between the seal-forming structure and the left side strap, and a second thread of the second textile material extending between the seal-forming structure and the right side strap.

In some aspects, the second textile material is configured to be a tie that is coupled to the first textile material and is configured to assist the first textile material in retaining its shape under application of a force.

Another aspect of the present technology is directed to a face-mounted interface comprising: a facial interface; a cushion constructed and arranged to contact a region of a user's face in use; a positioning and stabilizing structure configured to hold the facial interface and/or the cushion in an effective position on a patient's head; and a stiffener coupled to the facial interface, the cushion, and/or the positioning and stabilizing structure, wherein the cushion and/or the positioning and stabilizing structure is constructed from a first textile material, and wherein the stiffener is constructed from a second textile material configured, upon application of treatment, to have a treatment-induced stiffness that is greater than a stiffness of the first textile material.

Another aspect of the present technology is directed to a positioning and stabilizing structure configured to hold a facial interface in an effective position against a user's head, the positioning and stabilizing structure comprising: a left side strap including a first end configured to be coupled to the facial interface and a second end opposite the first end; a right side strap including a first end configured to be coupled to the facial interface and a second end opposite the first end, wherein the left side strap and the right side strap are at least partially constructed from a first textile material, and wherein at least one of the left and right side straps includes a stiffener constructed from second textile material configured, upon application of a treatment, to have a treatment-induced stiffness that is greater than a stiffness of the first textile material.

Another aspect of the present technology is directed to a positioning and stabilizing structure configured to hold a facial interface, like a seal-forming structure, in an effective position on a head of a patient, the effective position may be a therapeutically effective position or any other effective position conducive to use, the facial interface being constructed and arranged to contact a user's face, for example the seal-forming structure being constructed and arranged to form a seal with a region of a patient's face surrounding an entrance to a patient's airways for sealed delivery of a flow of air at a therapeutic pressure of at least 4 cm H2O with respect to ambient air pressure throughout a patient's respiratory cycle in use, the positioning and stabilizing structure comprising: a left side strap including a first end configured to be coupled to the facial interface, like the seal-forming structure, and a second end opposite the first end; a first stiffener extending along a length of the left side strap; a right side strap including a first end configured to be coupled to the facial interface, like the seal-forming structure, and a second end opposite the first end; a second stiffener extending along a length of the right side strap; a left ear piece coupled to the second end of the left side strap and defining an opening that is configured to receive a patient's left ear; a left ear stiffener extending along a length of the left ear piece; a right ear piece coupled to the second end of the right side strap and defining an opening that is configured to receive a patient's right ear; a right ear stiffener extending along a length of the right ear piece; a rear strap extending between the left ear strap and the right ear strap; and a rear stiffener extending along a length of the rear strap; wherein at least one of the left and right side straps, the left and right ear pieces, and the rear strap include a first textile material; and wherein at least one of the first stiffener, second stiffener, left ear stiffener, right ear stiffener, and rear stiffener includes a second textile material configured, upon application of a treatment, to have a treatment-induced stiffness that is greater than a stiffness of the first textile material.

In some aspects, the left and right side straps, the left and right ear pieces, and the rear strap each include the first textile material.

In some aspects, the first stiffener, second stiffener, left ear stiffener, right ear stiffener, and rear stiffener each includes the second textile material.

In some aspects, the second textile material is a rigidized thread sewn into the first textile material.

In some aspects, the first stiffener includes a first portion, a second portion, and a discontinuity therebetween, where the left side strap configured to deform.

In some aspects, the right side strap mirrors the left side strap.

In some aspects, the left ear stiffener includes a first sub-section and a second sub-section spaced apart from the first sub-section, the left ear stiffener configured to limit deformation left ear hole with an application of a force.

In some aspects, the right ear piece mirrors the left ear piece.

In some aspects, the rear stiffener is spaced apart from the left ear piece and from the right ear piece.

In some aspects, the left and right side straps, the left and right ear pieces, and the rear strap each include a single piece of the first textile material.

In some aspects, the left and right side straps define fluid conduits configured to convey air at the therapeutic pressure toward the seal-forming structure.

In some aspects, the second textile material is a thermoplastic material.

Another aspect of the present technology is directed to a patient interface structured to receive a flow of air for breathing by a patient, the patient interface comprising: a plenum chamber pressurisable to a therapeutic pressure of at least 4 cm H2O above ambient air pressure; a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use; a first stiffener extending around a superior portion of the seal-forming structure and configured to assist the seal-forming structure in retaining its shape under application of a force; a second stiffener extending around an inferior portion of the seal-forming structure and spaced apart from the first stiffener, the second stiffener configured to assist the seal-forming structure in retaining its shape under application of a force; a positioning and stabilizing structure configured to hold the seal-forming structure in a therapeutically effective position on a patient's head; and wherein the patient interface is configured to leave a patient's mouth uncovered, or if the seal-forming structure is configured to seal around a patient's nose and mouth, the patient interface is configured to allow the patient to breathe from ambient in the absence of a flow of pressurized air, wherein the seal-forming structure is constructed from a first textile material, and wherein the first and the second stiffeners are constructed from a second textile material configured, upon application of treatment, to have a treatment-induced stiffness that is greater than a stiffness of the first textile material.

In some aspects, the positioning and stabilizing structure is constructed from the first textile material.

In some aspects, the positioning and stabilizing structure includes a left side strap coupled to the seal-forming structure and a right side strap coupled to the seal-forming structure.

In some aspects, the first stiffener extends between the left side strap and the right side strap, and the second stiffener extends between the left side strap and the right side strap.

In some aspects, a left side stiffener is coupled to the left side strap and a right side stiffener coupled to the right side strap, the left side stiffener and the right side stiffener constructed from the second textile material, and the left side stiffener spaced apart from the first stiffener and the right side stiffener spaced apart from the second stiffener.

In some aspects, the positioning and stabilizing structure includes a left ear piece connected to the left side strap and a right ear right connected to the right side strap, a left ring stiffener constructed of the second textile material extending around a portion of the left ear piece and a right ring stiffener constructed of the second textile material extending around the right ear piece.

In some aspects, the positioning and stabilizing includes a rear strap that is configured to be positioned on a posterior portion of the patient's head in use, a rear stiffener constructed of the second textile material is coupled to the rear strap.

In some aspects, the positioning and stabilizing structure includes a top strap that is configured to be positioned on a superior portion of the patients head in use, a top stiffener constructed of the second textile material is coupled to the top strap.

In some aspects, the first stiffener and the second stiffener are rigidized threads.

In some aspects, the second textile material is configured to increase in stiffness with the application of a laser treatment.

In some aspects, the second textile material is a thermoplastic material.

In some aspects, the length of time the treatment is applied affects the resulting stiffness of the second textile material.

Another aspect of the present technology is directed to a method of manufacturing a seal-forming structure configured to be held in a therapeutically effective position on a head of a patient by a positioning and stabilizing structure, the seal-forming structure constructed and arranged to seal with a region of a patient's face surrounding an entrance to a patient's airways, the seal-forming structure constructed and arranged to maintain a therapeutic pressure of at least 4 cm $H_2O$ with respect to ambient air pressure in a plenum chamber coupled to the seal-forming structure throughout a patient's respiratory cycle in use; the method comprising: constructing a body from a first textile material, the body having an opening configured to receive a patient's nose and/or a patient's mouth; connecting a first stiffener to a superior portion of a perimeter of the body, the first stiffener constructed from a second textile material configured, upon application of a treatment, to have a treatment-induced stiffness that is greater than a stiffness of the first textile material; connecting a second stiffener to an inferior portion of the perimeter of the body, the second stiffener being spaced apart from the first stiffener, the second stiffener constructed from the second textile material; selectively applying the treatment to the second textile material, wherein the second textile material reaches the treatment-induced stiffness; and wherein subsequent the applying the treatment, the first stiffener and/or the second stiffener configured to maintain a shape of the opening when a force is applied to the seal forming structure.

In some aspects, the treatment is a laser treatment, a pressure treatment, a chemical treatment, and/or a heat treatment.

In some aspects, the method includes scanning the patient's face to determine locations of the seal-forming structure to stiffen, and selectively applying the treatment to stiffen the determined locations.

In some aspects, scanning also determines how long to apply the treatment to the determine locations.

In some aspects, constructing further comprises forming a hollow tube configured to receive airflow at the therapeutic pressure.

In some aspects, connecting further comprises sewing the first stiffener and the second stiffener into the body.

Another aspect of the present disclosure is a patient interface structured to receive a flow of air for breathing by a patient, the patient interface comprising: a plenum chamber pressurisable to a therapeutic pressure of at least 4 cm H2O above ambient air pressure; a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use; and a positioning and stabilizing structure configured to hold the seal-forming structure in a therapeutically effective position on a patient's head, wherein the patient interface is configured to leave a patient's mouth uncovered, or if the seal-forming structure is configured to seal around a patient's nose and mouth, the patient interface is configured to allow the patient to breathe from ambient in the absence of a flow of pressurized air, and wherein at least one of the plenum chamber and the seal-forming structure include a self-cleaning textile material; and wherein the textile material includes a surface structure that limits adhesion of debris.

In one form, the surface structure includes a microstructure.

In one form, the textile material includes a hydrophilic surface.

In one form, the textile material is configured to allow water to lift the debris off of the textile material, and remove the debris as the water moves off of the textile material.

In one form, the surface structure is rough and is configured to prevent adhesion of debris.

In one form, the textile material is coated with a layer of silver that contributes to the microstructure and increases surface roughness, the layer of silver interfering with a formation of a biofilm on the textile material.

In one form, the surface structure is smooth and limits a formation of a biofilm.

In one form, a photocatalytic layer is formed on the textile material.

In one form, the photocatalytic layer is made of titanium dioxide.

In one form, the photocatalytic layer is configured to be activated when exposed to UV light.

In one form, the plenum chamber and the seal-forming structure include the surface structure.

In one form, the positioning and stabilizing structure includes the textile material with the surface structure.

In one form, the textile material includes a nano-membrane.

In one form, the seal-forming structure and/or the positioning and stabilizing structure includes an exterior surface configured to face a patient's skin or ambient; an interior surface positioned opposite the exterior surface and at least partially isolated from the patient's skin and the ambient; and wherein the exterior surface and/or the interior surface include the self-cleaning textile material.

In another aspect, a cleaning receptacle comprising: a housing defining an interior cavity configured to house the patient interface; a lid selectively enclosing the interior cavity; and an inactivation agent configured to inactivate biofilm from the textile material.

In one form, the cleaning module is a UV light source and the inactivation agent is UV light.

In one form, the inactivation agent is configured to interact with the photocatalytic layer on the textile material.

Another aspect of the present disclosure is a face-mounted interface comprising: a facial interface; a cushion constructed and arranged to contact a region of a user's face in use; and a positioning and stabilizing structure configured to hold the facial interface and/or the cushion in an effective position on the user's head, and wherein at least one of the facial interface, the cushion, and/or the positioning and stabilizing structure include a self-cleaning textile material; and wherein the textile material includes a surface structure that limits adhesion of debris.

Another aspect of the present technology is directed to a positioning and stabilizing structure constructed and arranged to be used with a face-mounted interface and is adapted to hold the face-mounted interface in an effective position on a user's face, the positioning and stabilizing structure comprising headgear having at least one strap that includes a self-cleaning textile material; and wherein the textile material includes a surface structure that limits adhesion of debris.

In another aspect, a cleaning receptacle comprises: a housing defining an internal cavity and configured to house a patient interface usable with a respiratory pressure therapy (RPT) device; a lid for selectively enclosing the internal cavity; and a cleaning module selectively provides an inactivation agent to the internal cavity and clean the patient interface; wherein the housing is independent from the RPT device; and wherein the cleaning module is configured to provide the inactivation agent whether the housing is connected or disconnected to the RPT device.

In one form, the cleaning module is a UV light source and the inactivation agent is UV light.

In one form, the inactivation agent is configured to interact with the photocatalytic material within the internal cavity.

In one form, the inactivation agent is configured to inactivate biofilm from the internal cavity.

In one form, the cleaning receptacle includes a sensor.

In one form, the sensor determines a quantity of inactivation agent to release into the interior cavity.

In one form, the sensor is configured to detect imperfections in the patient interface.

In one form, the imperfections include a micro-tear or tear in the textile material.

In one form, the sensor is configured to communicate with the RPT device.

In one form, the sensor is coupled to the lid.

In one form, the inactivation agent is a liquid cleaning solution.

In one form, a fluid spray nozzle is configured to deliver the liquid cleaning solution to the interior cavity.

In one form, a reservoir is configured to store the liquid cleaning solution, and the reservoir in communication with the interior cavity via a fluid conduit.

In one form, the reservoir is removably coupled to the housing.

In one form, a collection chamber is configured to store waste, and the collection chamber in communication with the interior cavity via a drain.

In one form, the collection chamber is removably coupled to the housing.

In one form, the housing further includes a control configured to operate the cleaning module at a desired control pattern.

In one form, the housing further includes a button to allow for user input, the button configured to allow the patient to select the desired control pattern.

In one form, the control is configured to communicate with the RPT device and/or a communication device.

In one form, the housing includes a connection port for selectively receiving a communication cable, the control configured to transmit and/or receive data through the connection port.

In one form, the lid includes an open position configured to allow ingress to the internal cavity, and a closed position configured to prevent ingress to the internal cavity.

In one form, the housing includes a conduit aperture, and wherein the lid includes an open position and a closed position, the conduit aperture configured to receive an air circuit from the RPT device when the lid is in either the open position or the closed position.

In one form, the cleaning module is configured to release negative air ions to assist with the removal of biofilm from the patient interface.

In another aspect, a patient interface structured to receive a flow of air for breathing by a patient, the patient interface comprising: a plenum chamber pressurisable to a therapeutic pressure of at least 4 cm H2O above ambient air pressure; a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use; and a positioning and stabilizing structure configured to hold the seal-forming structure in a therapeutically effective position on a patient's head, wherein the patient interface is configured to leave a patient's mouth uncovered, or if the seal-forming structure is configured to seal around a patient's nose and mouth, the patient interface is configured to allow the patient to breathe from ambient in the absence of a flow of pressurized air, and wherein at least one of the plenum chamber and the seal-forming structure includes a textile material with a surface structure including, a first peak, a second peak spaced apart from the first peak, and a valley disposed between the first peak and the second peak; wherein a width of the valley limits debris from settling in the valley and limits adhesion of debris to the textile.

In one form, the first peak and/or the second peak include a hydrophilic material.

In one form, the valley includes a hydrophobic material.

In one form, silver is coupled to the first peak and/or the second peak, the silver configured to interfere with the formation of debris on the textile.

In one form, a photocatalytic material is applied to at least a portion of the surface structure.

In one form, the photocatalytic material is applied to the first peak and the valley.

In one form, the valley is configured to allow water to lift debris off of the textile material, further limiting adhesion of debris.

In one form, the first peak and the second peak are different lengths (e.g., measured in a direction substantially perpendicular to a peak-to-peak direction).

In one form, the first peak overlaps at least a portion of the second peak.

Another aspect of the present disclosure is a face-mounted interface comprising: a facial interface; a cushion constructed and arranged to contact a region of a user's face in use; and a positioning and stabilizing structure configured to hold the facial interface and/or the cushion in an effective position on the user's head, and wherein at least one of the facial interface, the cushion, and/or the positioning and stabilizing structure include a textile material with a surface structure including, a first peak, a second peak spaced apart from the first peak, and a valley disposed between the first peak and the second peak; wherein a width of the valley limits debris from settling in the valley and limits adhesion of debris to the textile Another aspect of the present technology is directed to a positioning and stabilizing structure constructed and arranged to be used with a face-mounted interface and is adapted to hold the face-mounted interface in an effective position on a user's face, the positioning and stabilizing structure comprising headgear having at least one strap that includes a self-cleaning textile material; and wherein the textile material includes a textile material with a surface structure including, a first peak, a second peak spaced apart from the first peak, and a valley disposed between the first peak and the second peak; wherein a width of the valley limits debris from settling in the valley and limits adhesion of debris to the textile.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialized cleaning equipment. An aspect of one form of the present technology is a humidifier tank that may be washed in a home of a patient, e.g., in soapy water, without requiring specialized cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1 shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

FIG. 2 shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 3 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 8:
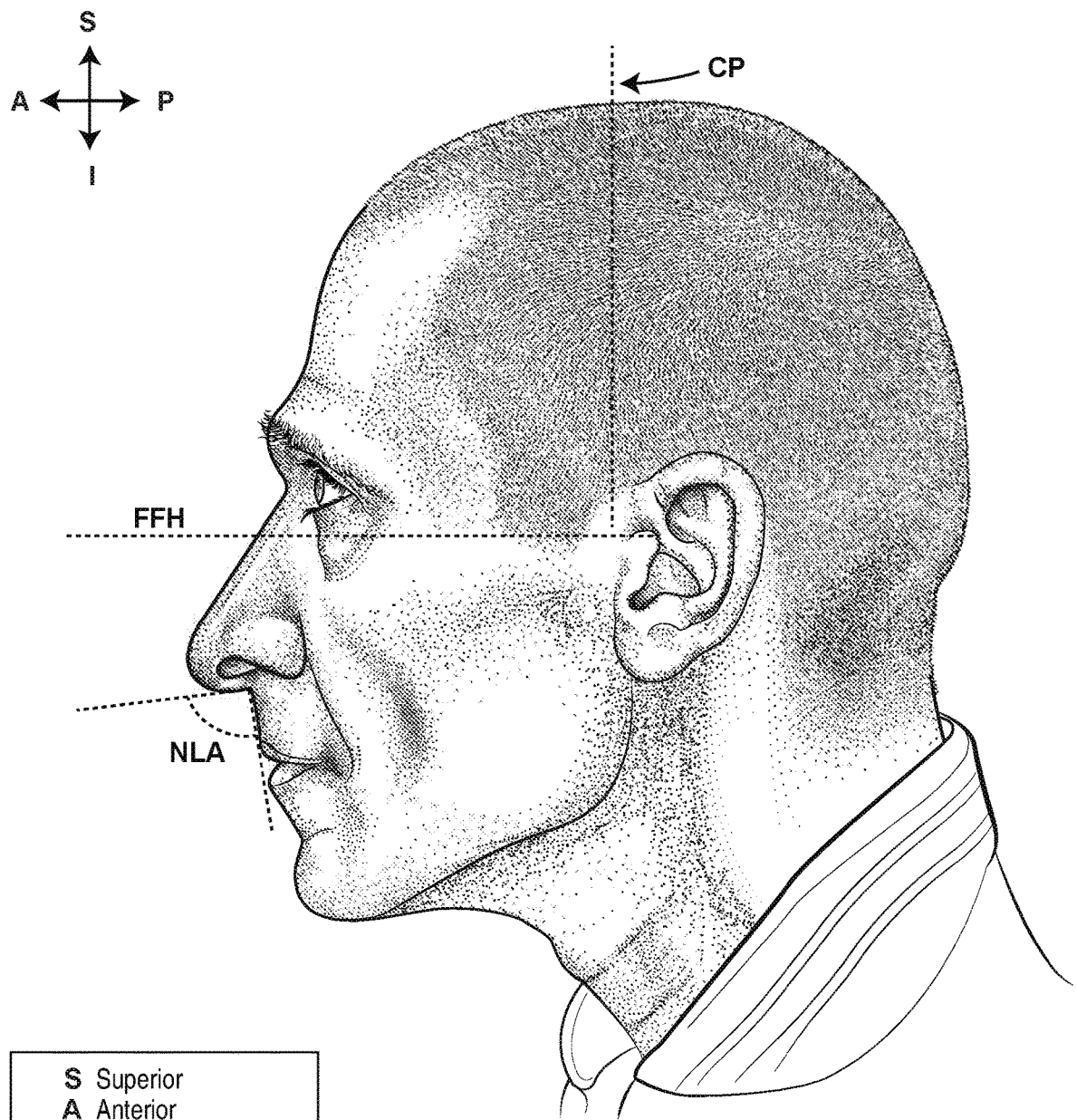

FIG. 8 is a further side view of a head. The approximate locations of the Frankfort horizontal and nasolabial angle are indicated. The coronal plane is also indicated.

Figure 9:
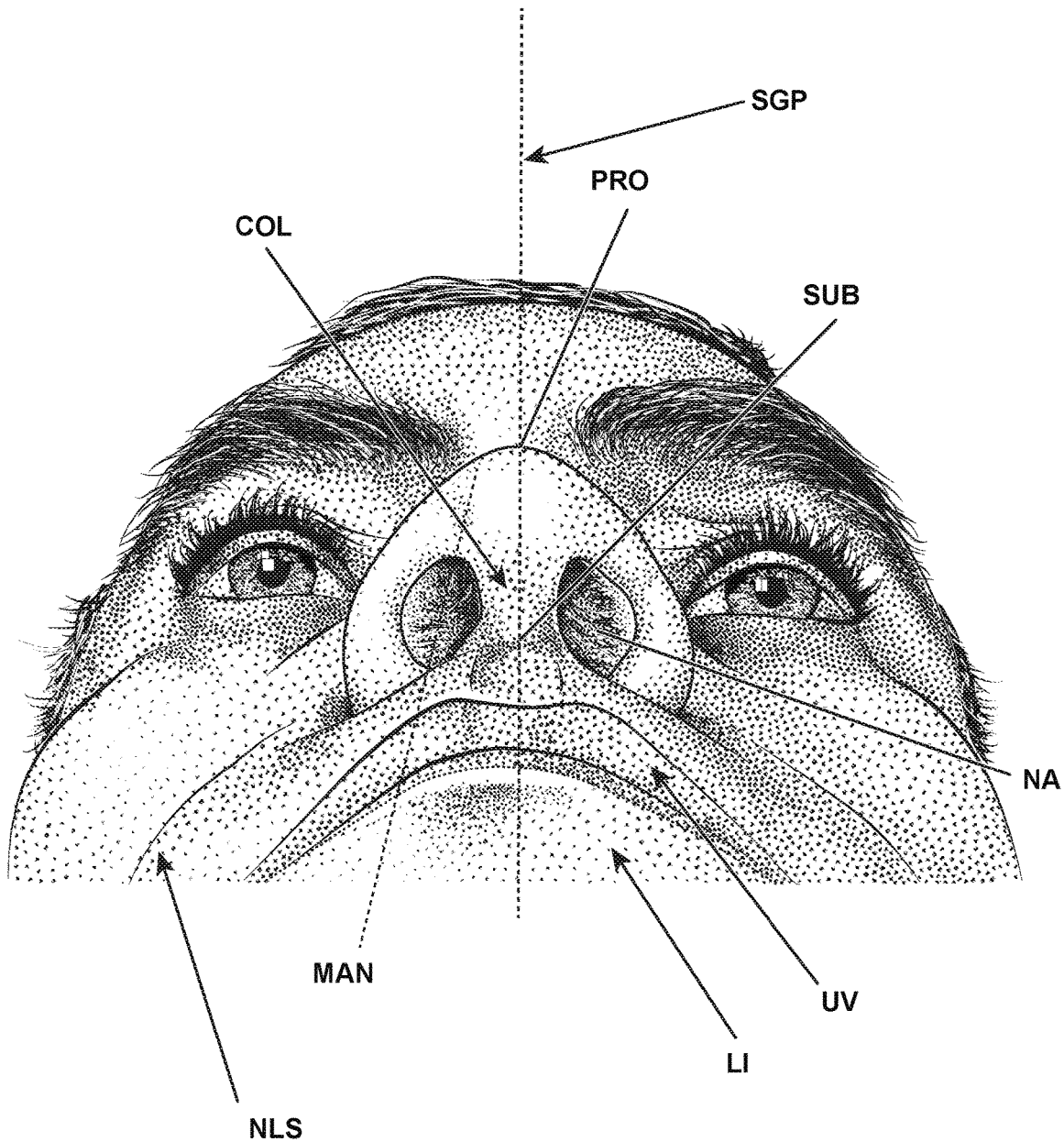

FIG. 9 shows a base view of a nose with several features identified including naso-labial sulcus, lip inferior, upper Vermilion, naris, subnasale, columella, pronasale, the major axis of a naris and the midsagittal plane.

FIG. 10 shows a side view of the superficial features of a nose.

FIG. 11 shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 12 shows a medial dissection of a nose, approximately several millimeters from the midsagittal plane, amongst other things showing the septum cartilage and medial crus of greater alar cartilage.

Figures 13, 14:
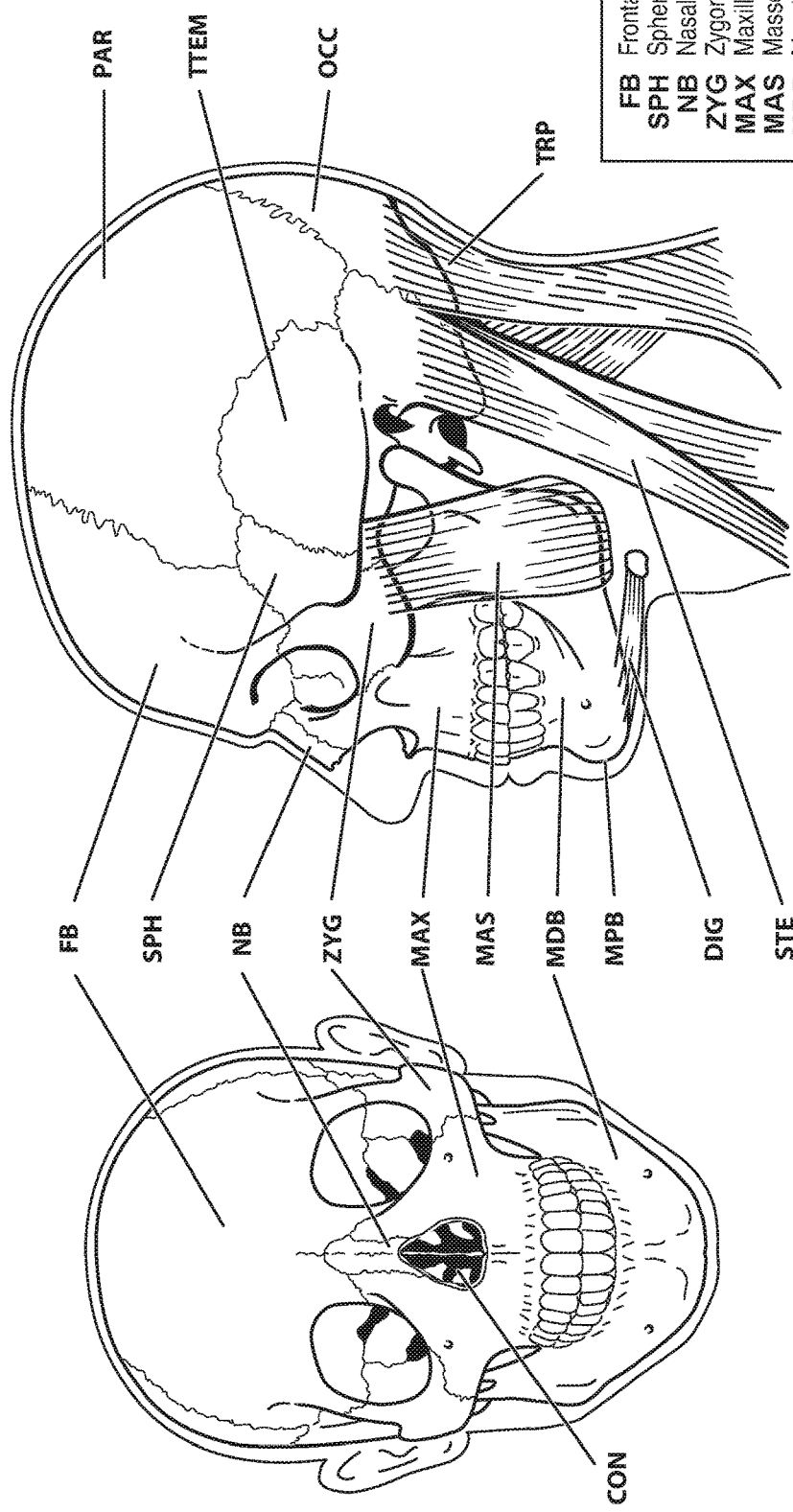

FIG. 13 shows a front view of the bones of a skull including the frontal, nasal and zygomatic bones. Nasal concha are indicated, as are the maxilla, and mandible.

FIG. 14 shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 15:
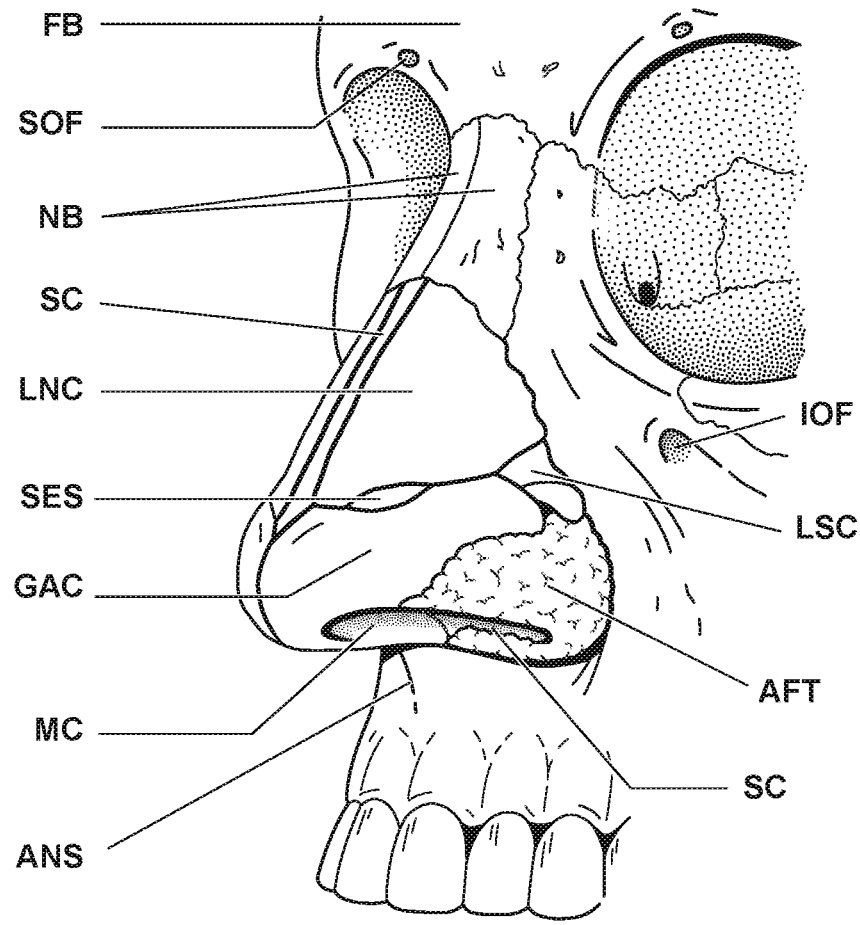

FIG. 15 shows an anterolateral view of a nose.

4.3 Patient Interface

Figure 16:
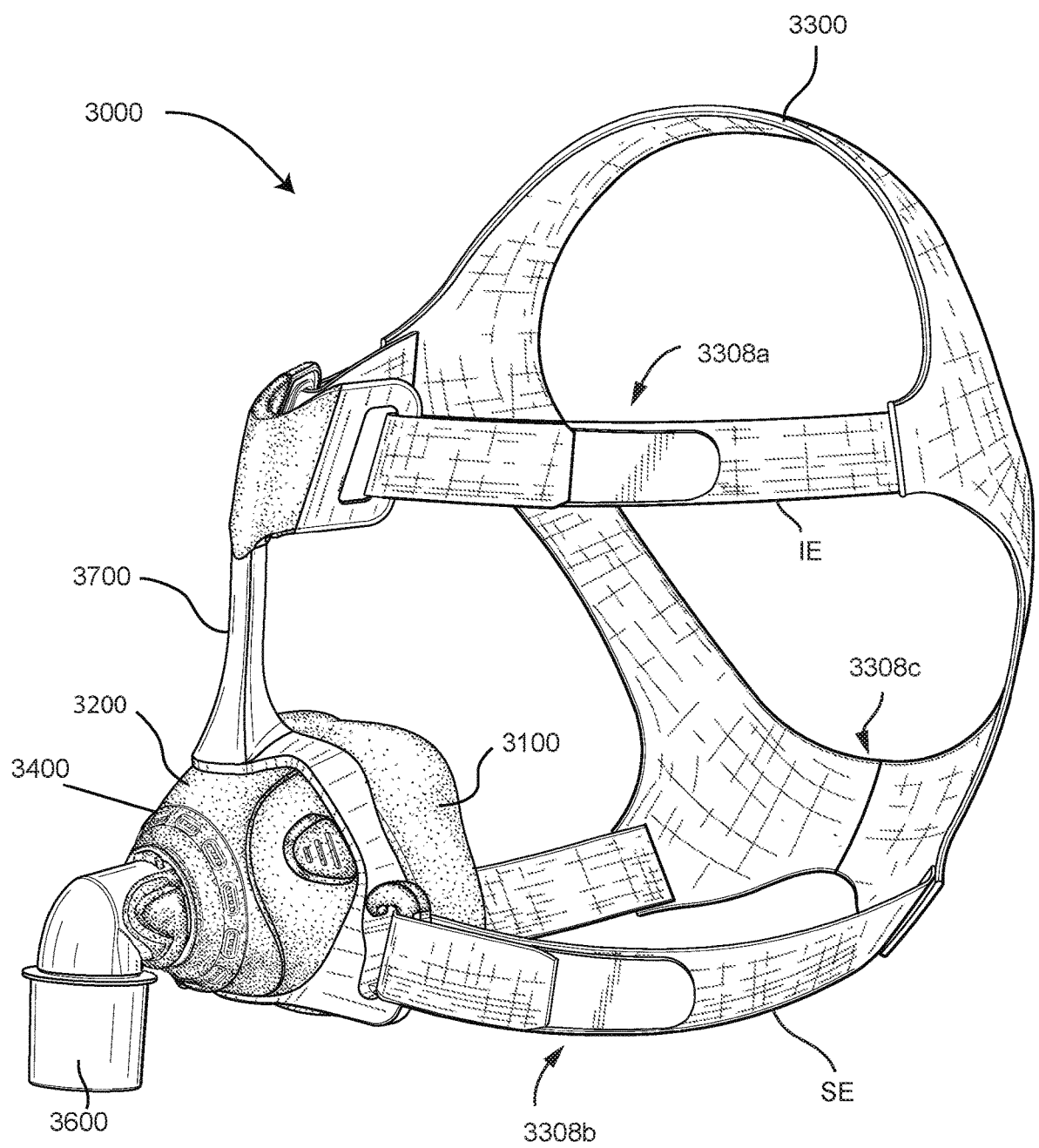

FIG. 16 shows a patient interface in the form of a nasal mask in accordance with one form of the present technology.

Figure 17:
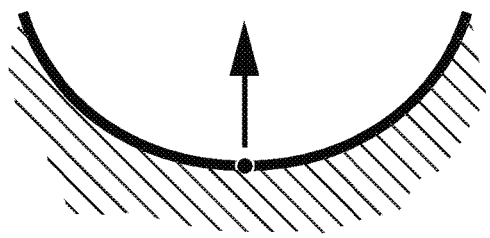

FIG. 17 shows a schematic of a cross-section through a structure at a point. An outward normal at the point is indicated. The curvature at the point has a positive sign, and a relatively large magnitude when compared to the magnitude of the curvature shown in FIG. 18.

Figure 18:
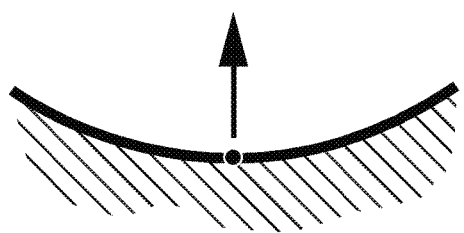

FIG. 18 shows a schematic of a cross-section through a structure at a point. An outward normal at the point is indicated. The curvature at the point has a positive sign, and a relatively small magnitude when compared to the magnitude of the curvature shown in FIG. 17.

Figure 19:
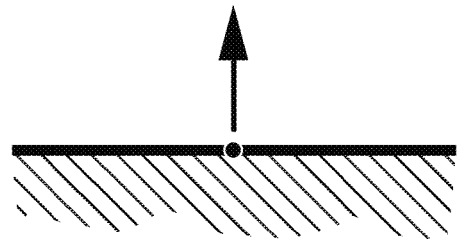

FIG. 19 shows a schematic of a cross-section through a structure at a point. An outward normal at the point is indicated. The curvature at the point has a value of zero.

Figure 20:
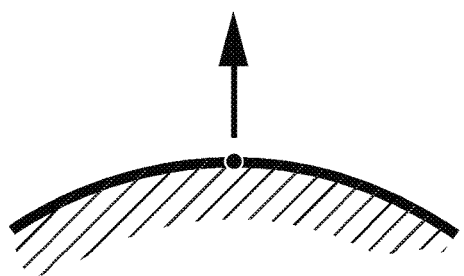

FIG. 20 shows a schematic of a cross-section through a structure at a point. An outward normal at the point is indicated. The curvature at the point has a negative sign, and a relatively small magnitude when compared to the magnitude of the curvature shown in FIG. 21.

Figure 21:
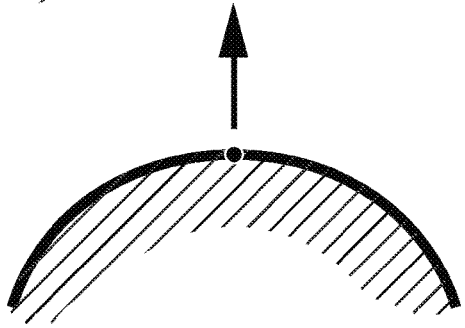

FIG. 21 shows a schematic of a cross-section through a structure at a point. An outward normal at the point is indicated. The curvature at the point has a negative sign, and a relatively large magnitude when compared to the magnitude of the curvature shown in FIG. 20.

FIG. 22 shows a cushion for a mask that includes two pillows. An exterior surface of the cushion is indicated. An edge of the surface is indicated. Dome and saddle regions are indicated.

FIG. 23 shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 24:
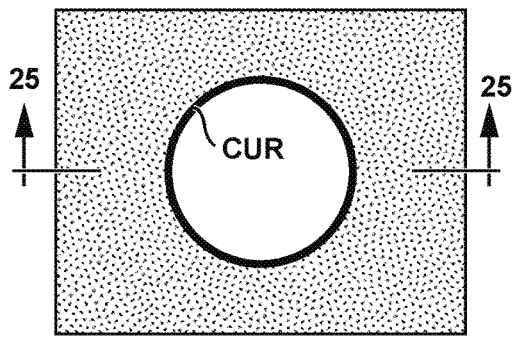

FIG. 24 shows the surface of a structure, with a one dimensional hole in the surface. The illustrated plane curve forms the boundary of a one dimensional hole.

Figure 25:
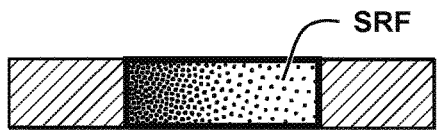

FIG. 25 shows a cross-section through the structure of FIG. 24. The illustrated surface bounds a two dimensional hole in the structure of FIG. 24.

Figure 26:
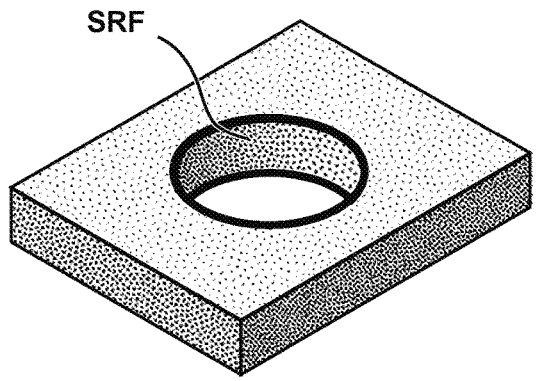

FIG. 26 shows a perspective view of the structure of FIG. 24, including the two dimensional hole and the one dimensional hole. Also shown is the surface that bounds a two dimensional hole in the structure of FIG. 24.

Figure 27:
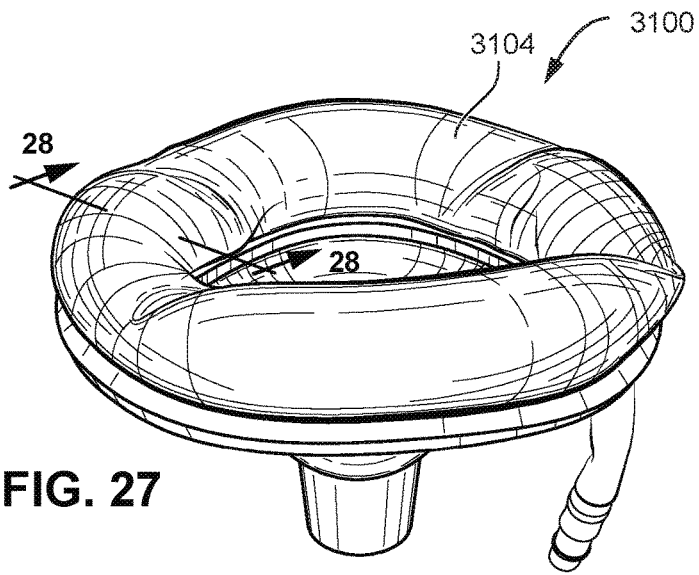

FIG. 27 shows a mask having an inflatable bladder as a cushion.

Figure 28:
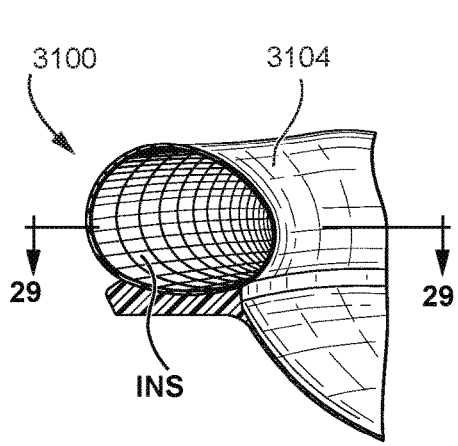

FIG. 28 shows a cross-section through the mask of FIG. 27, and shows the interior surface of the bladder. The interior surface bounds the two dimensional hole in the mask.

Figure 29:
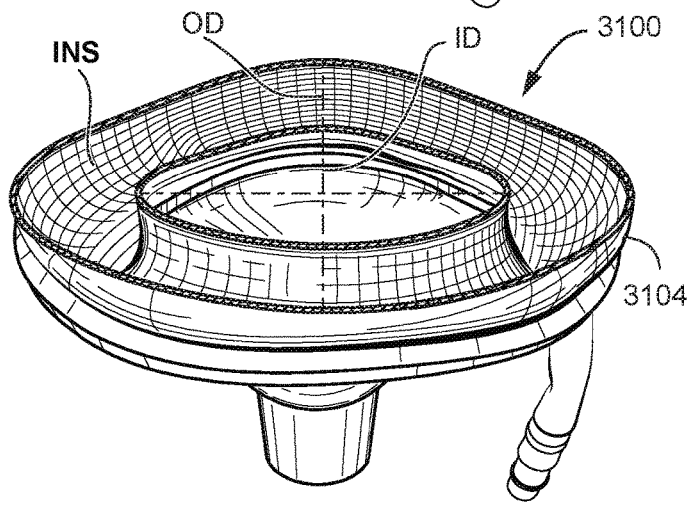

FIG. 29 shows a further cross-section through the mask of FIG. 27. The interior surface is also indicated.

Figure 30:
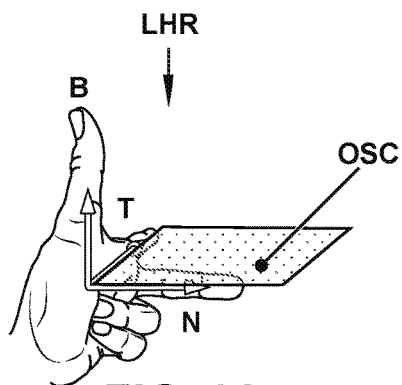

FIG. 30 illustrates a left-hand rule.

Figure 31:
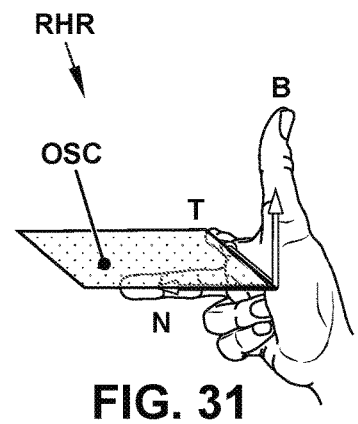

FIG. 31 illustrates a right-hand rule.

Figures 32, 33, 34:
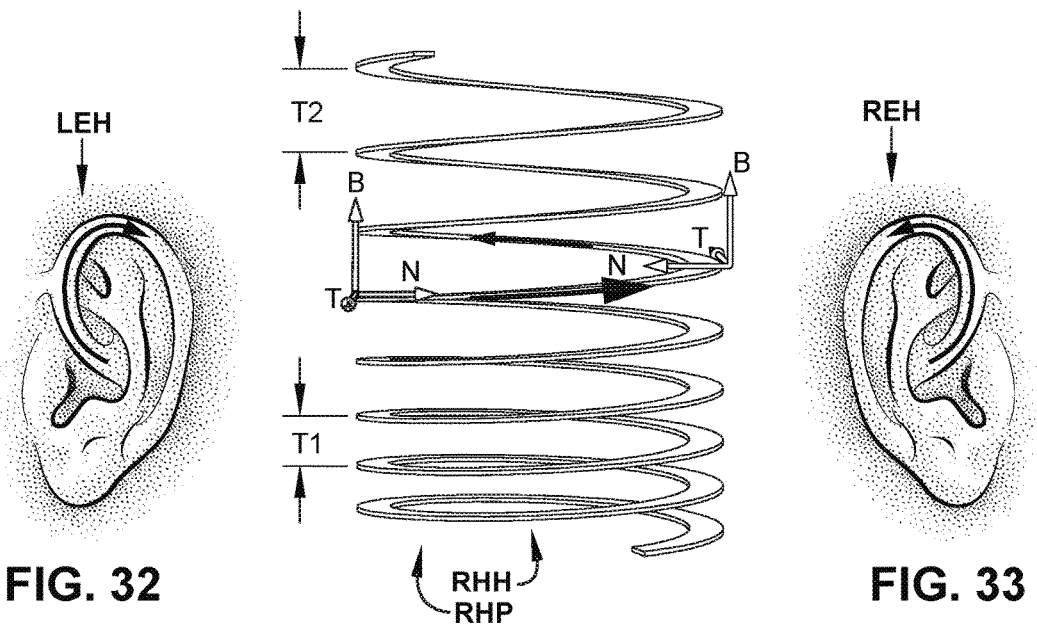

FIG. 32 shows a left ear, including the left ear helix.

FIG. 33 shows a right ear, including the right ear helix.

FIG. 34 shows a right-hand helix.

Figure 35:
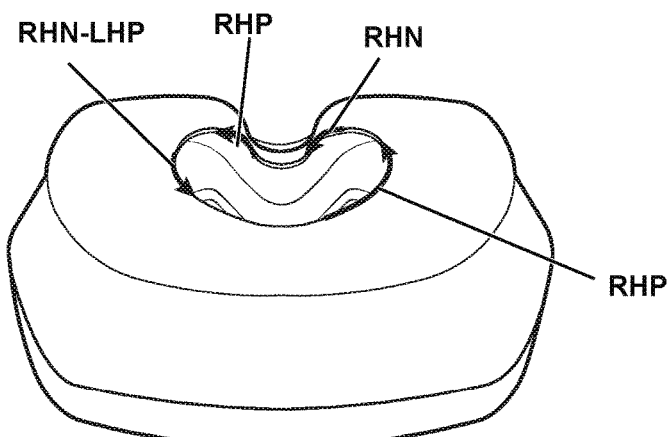

FIG. 35 shows a view of a mask, including the sign of the torsion of the space curve defined by the edge of the sealing membrane in different regions of the mask.

Figure 36:
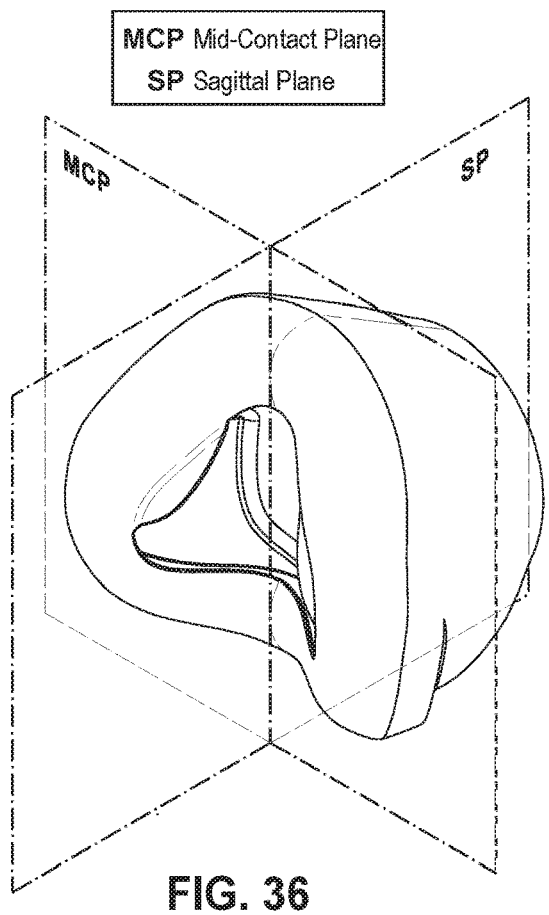

FIG. 36 shows a view of a plenum chamber 3200 showing a sagittal plane and a mid-contact plane.

Figure 37:
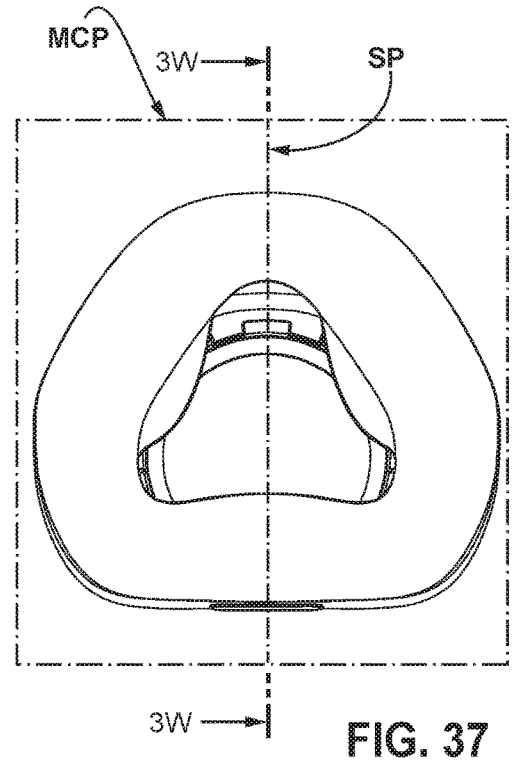

FIG. 37 shows a view of a posterior of the plenum chamber of FIG. 36. The direction of the view is normal to the mid-contact plane. The sagittal plane in FIG. 37 bisects the plenum chamber into left-hand and right-hand sides.

Figure 38:
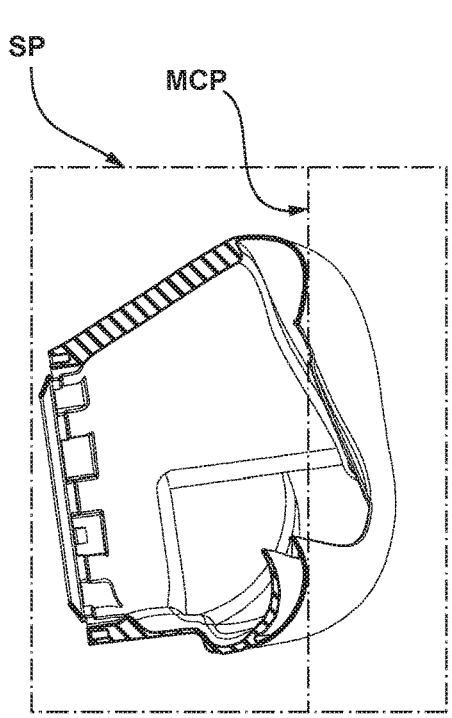

FIG. 38 shows a cross-section through the plenum chamber of FIG. 37, the cross-section being taken at the sagittal plane shown in FIG. 37. A 'mid-contact' plane is shown. The mid-contact plane is perpendicular to the sagittal plane. The orientation of the mid-contact plane corresponds to the orientation of a chord 3215 which lies on the sagittal plane and just touches the cushion of the plenum chamber at two points on the sagittal plane: a superior point 3225 and an inferior point 3235. Depending on the geometry of the cushion in this region, the mid-contact plane may be a tangent at both the superior and inferior points.

Figure 39:
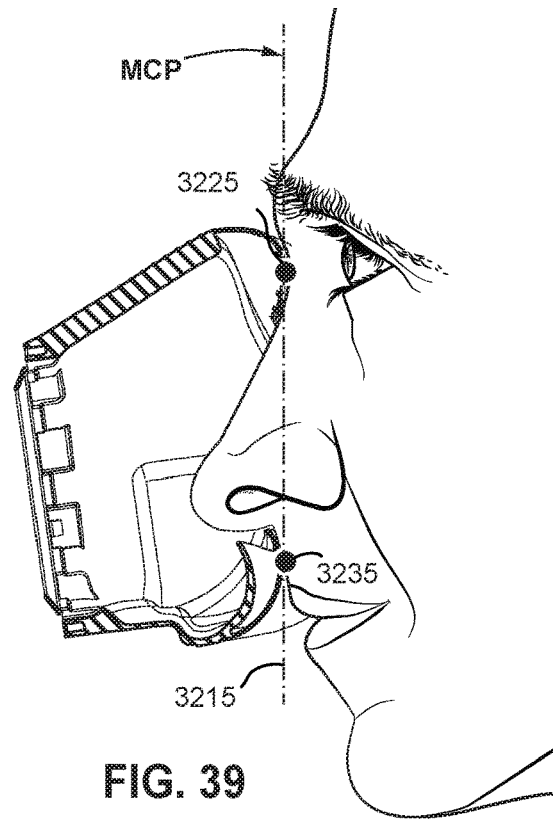

FIG. 39 shows the plenum chamber 3200 of FIG. 36 in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 39 the plenum chamber 3200 is that of a nasal mask, and the superior point 3225 sits approximately on the sellion, while the inferior point 3235 sits on the lip superior.

4.4 RPT Device

Figure 40:
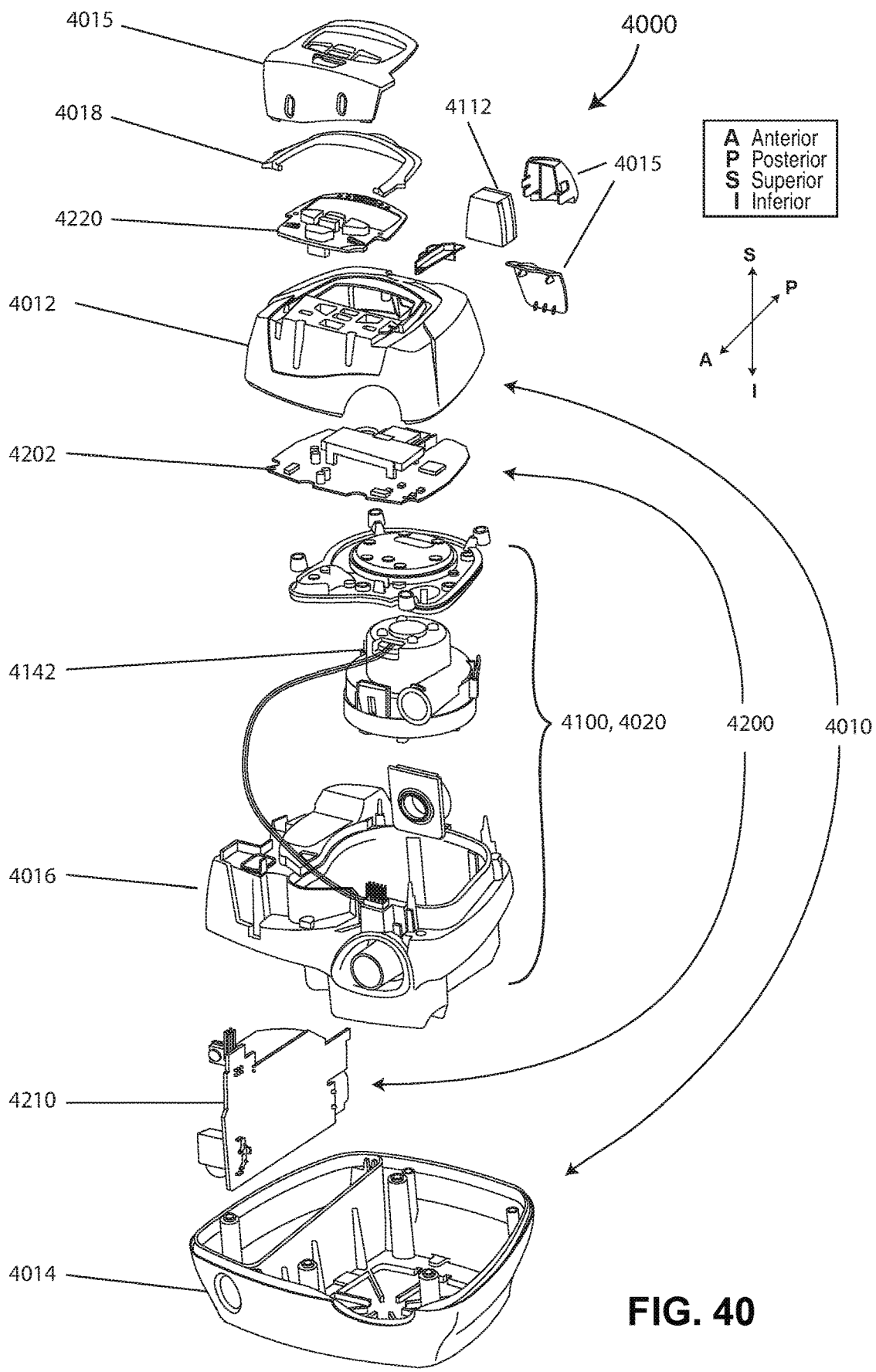

FIG. 40 shows an RPT device in accordance with one form of the present technology.

Figure 41:
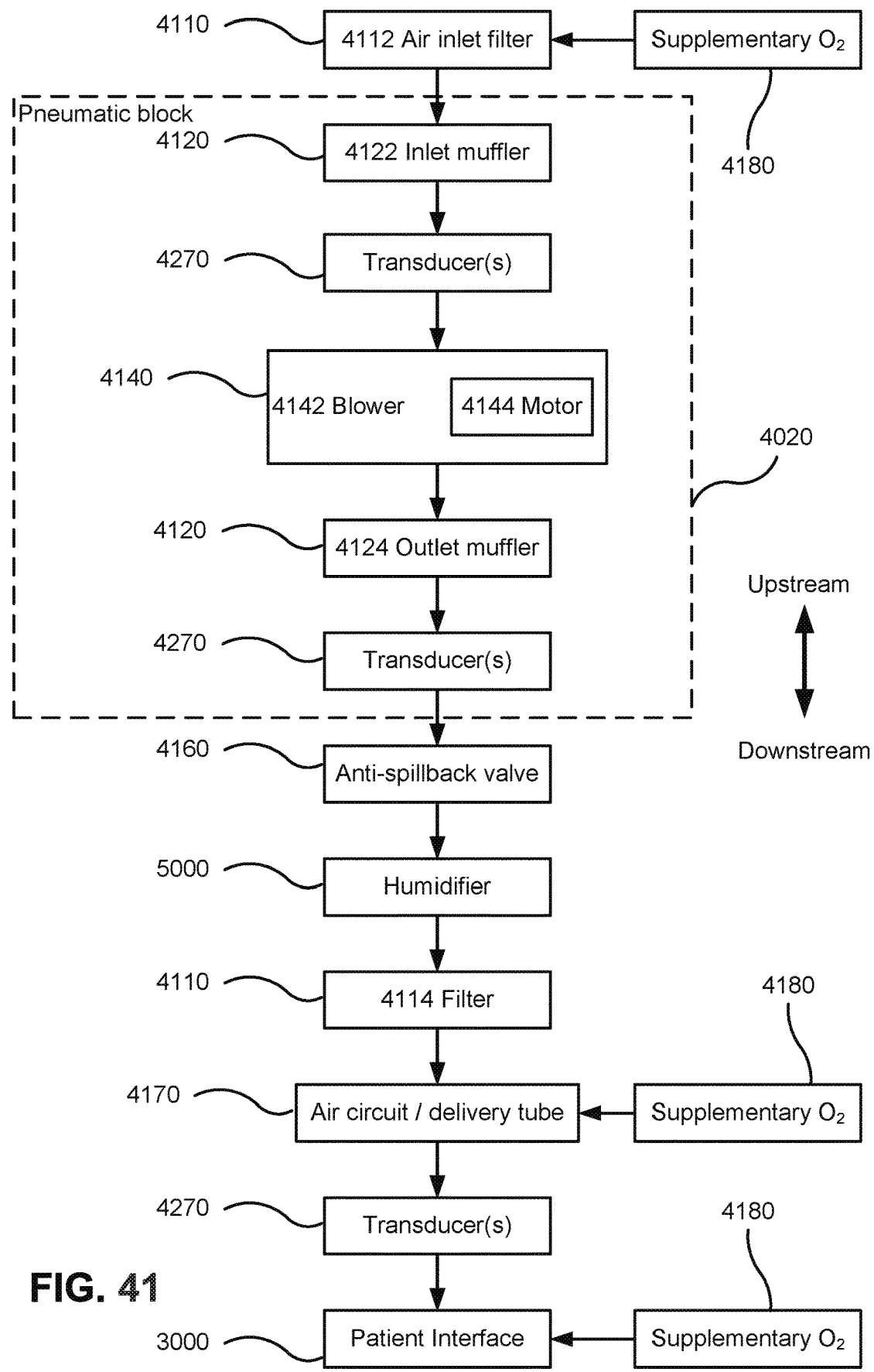

FIG. 41 is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Breathing Waveforms

Figure 42:
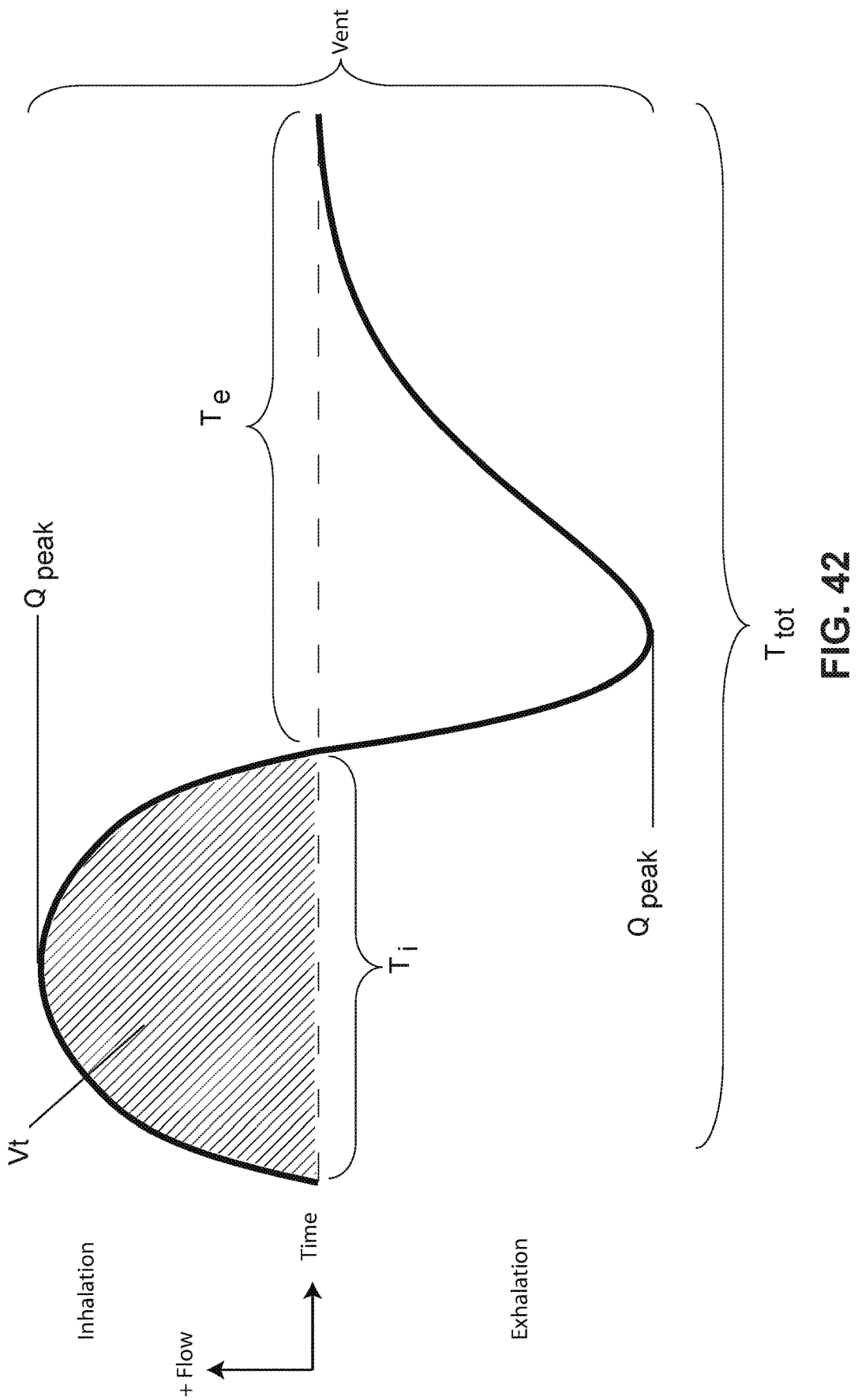

FIG. 42 shows a model typical breath waveform of a person while sleeping.

4.6 Patient Interface of the Present Technology

Figure 43:
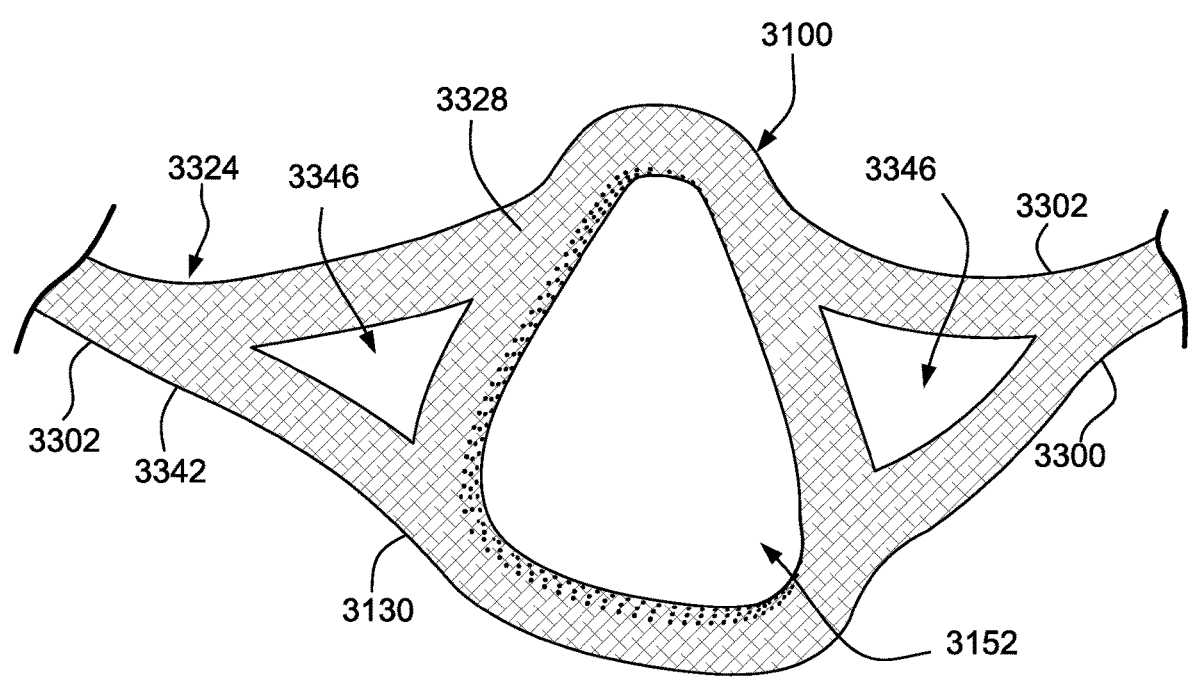

FIG. 43 shows FIG. 43 shows a one piece textile construction used to make a seal-forming structure and positioning and stabilizing structure.

Figure 44:
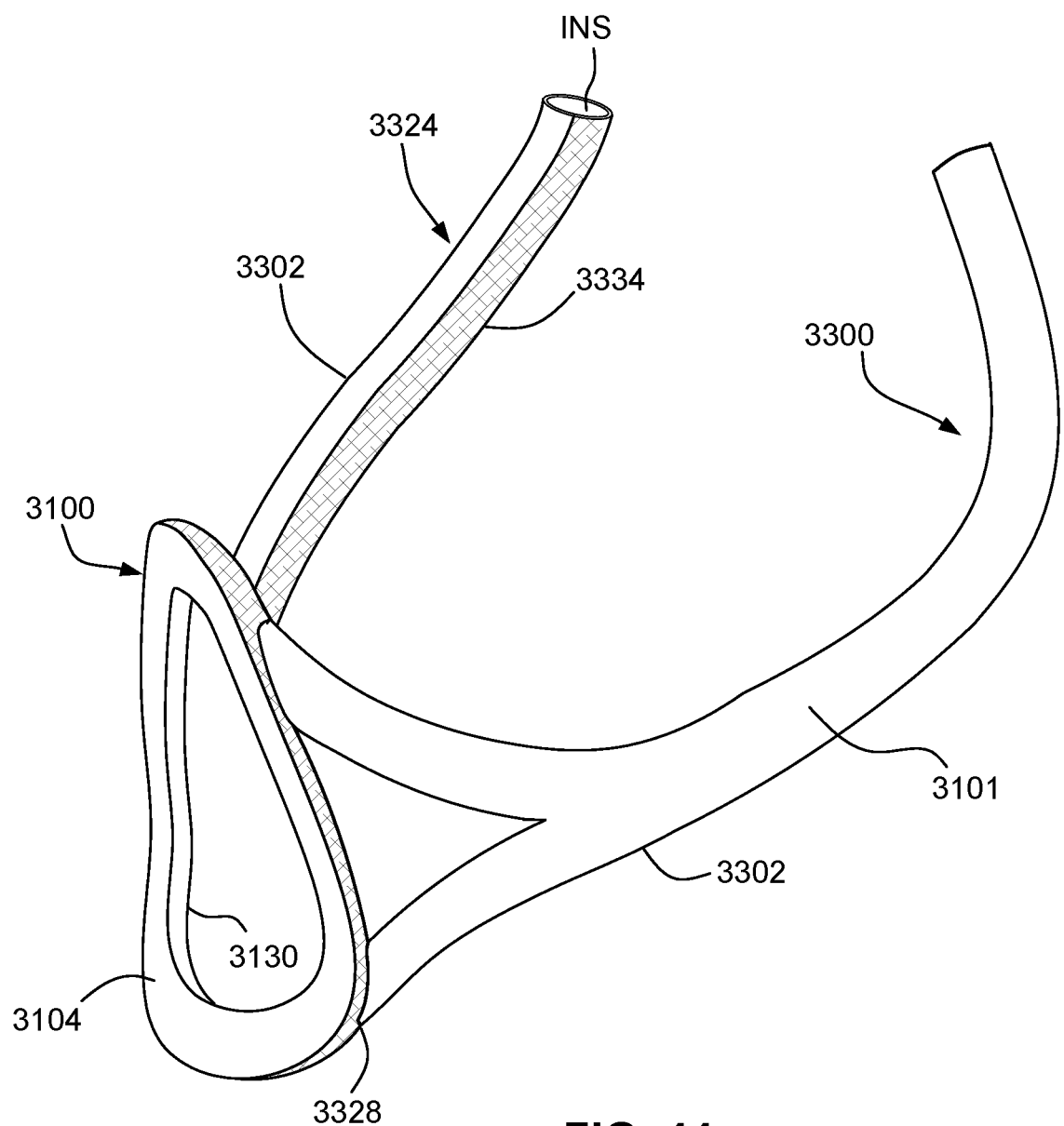

FIG. 44 shows a seal-forming structure and a positioning and stabilizing structure that are formed from a one piece fabric construction as shown in FIG. 43. The positioning and stabilizing structure is formed as a hollow tube that conveys air toward the seal-forming structure.

Figure 45:
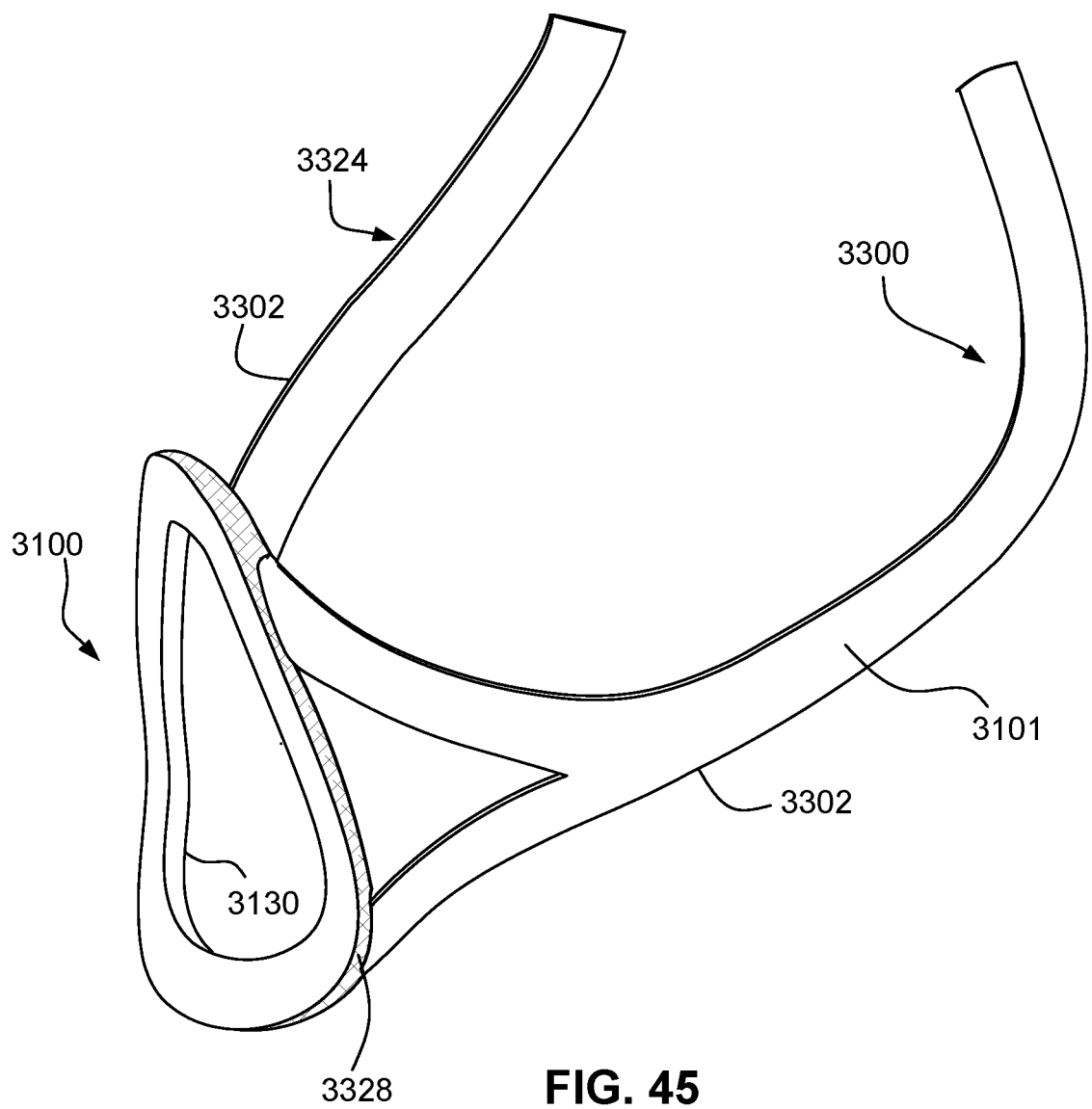

FIG. 45 shows a seal-forming structure and a positioning and stabilizing structure that are formed from a one piece fabric construction as shown in FIG. 43. The positioning and stabilizing structure is formed as flat straps.

Figure 46A:
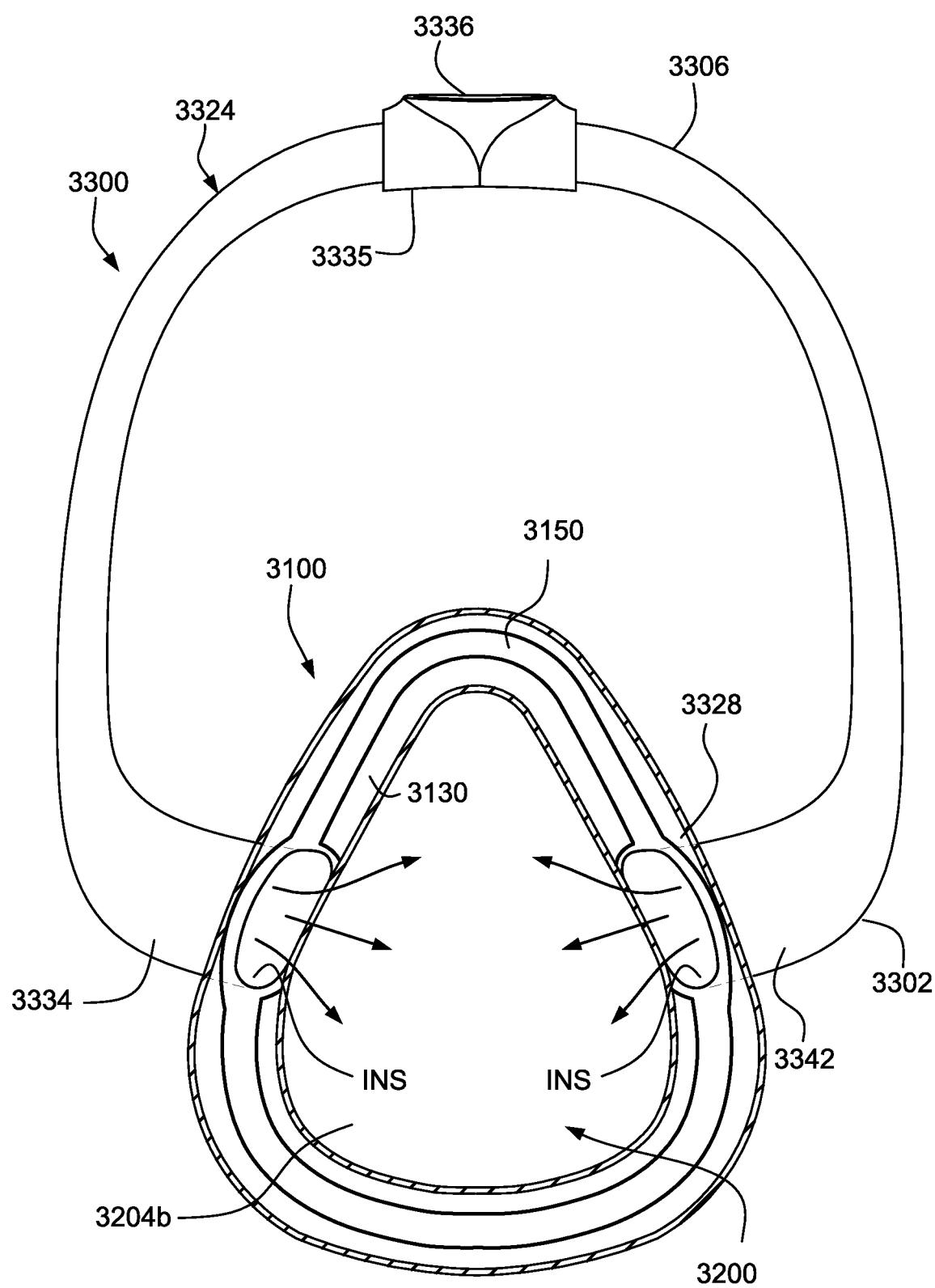

FIG. 46a shows a rear view of a patient interface formed from a one piece construction of textile material. The positioning and stabilizing structure includes hollow tubes that convey air toward the seal-forming structure. The air is conveyed directly onto a patient's face and the seal-forming structure and forms a lip type seal with the patient's face.

Figure 46B:
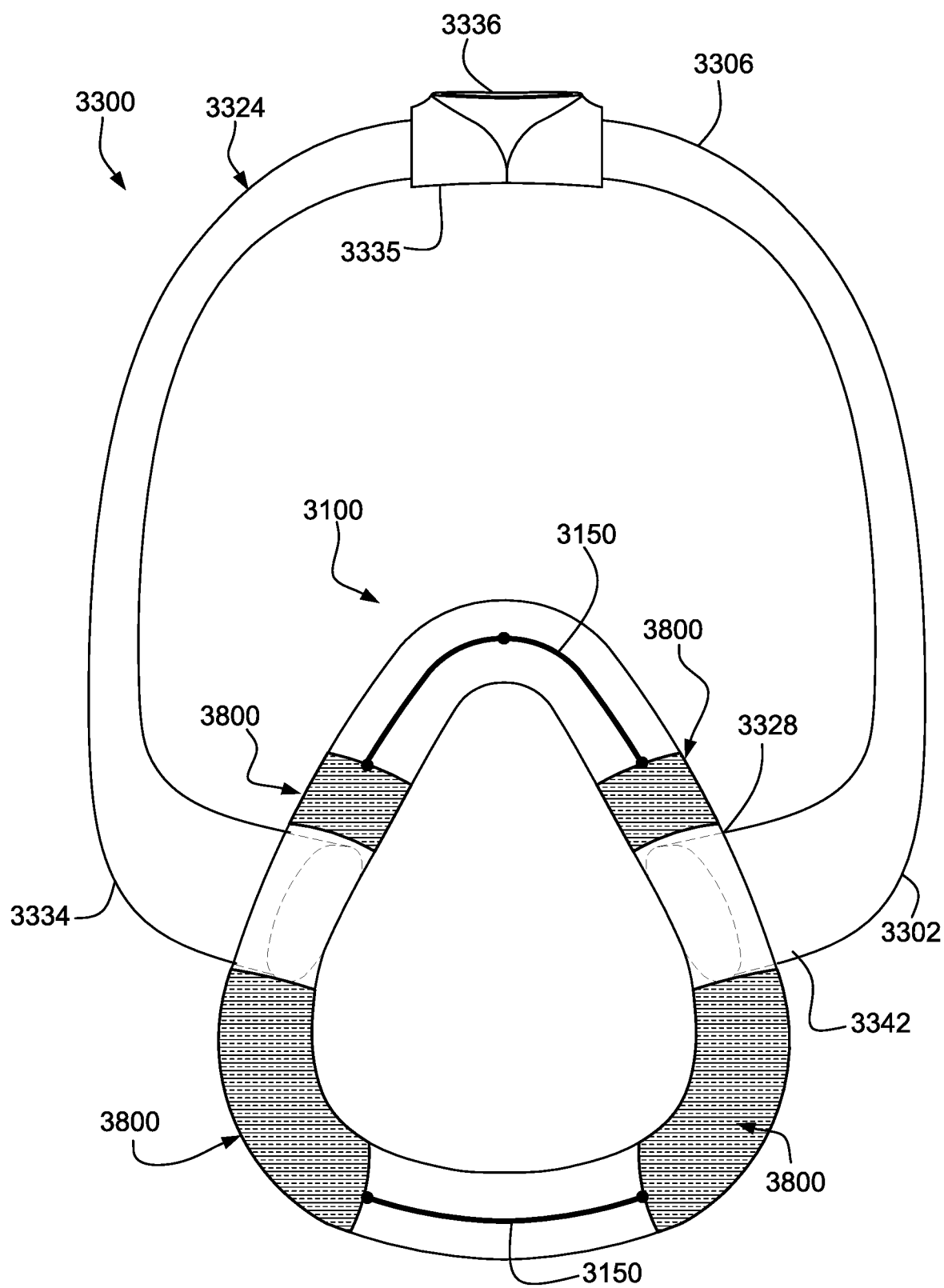

FIG. 46b shows a rear view of a patient interface formed from a one piece construction of textile material. The positioning and stabilizing structure includes hollow tubes that convey air toward the seal-forming structure. The seal-forming structure includes adaptive material and rigidizers to direct forces on the adaptive materials.

Figure 47A:
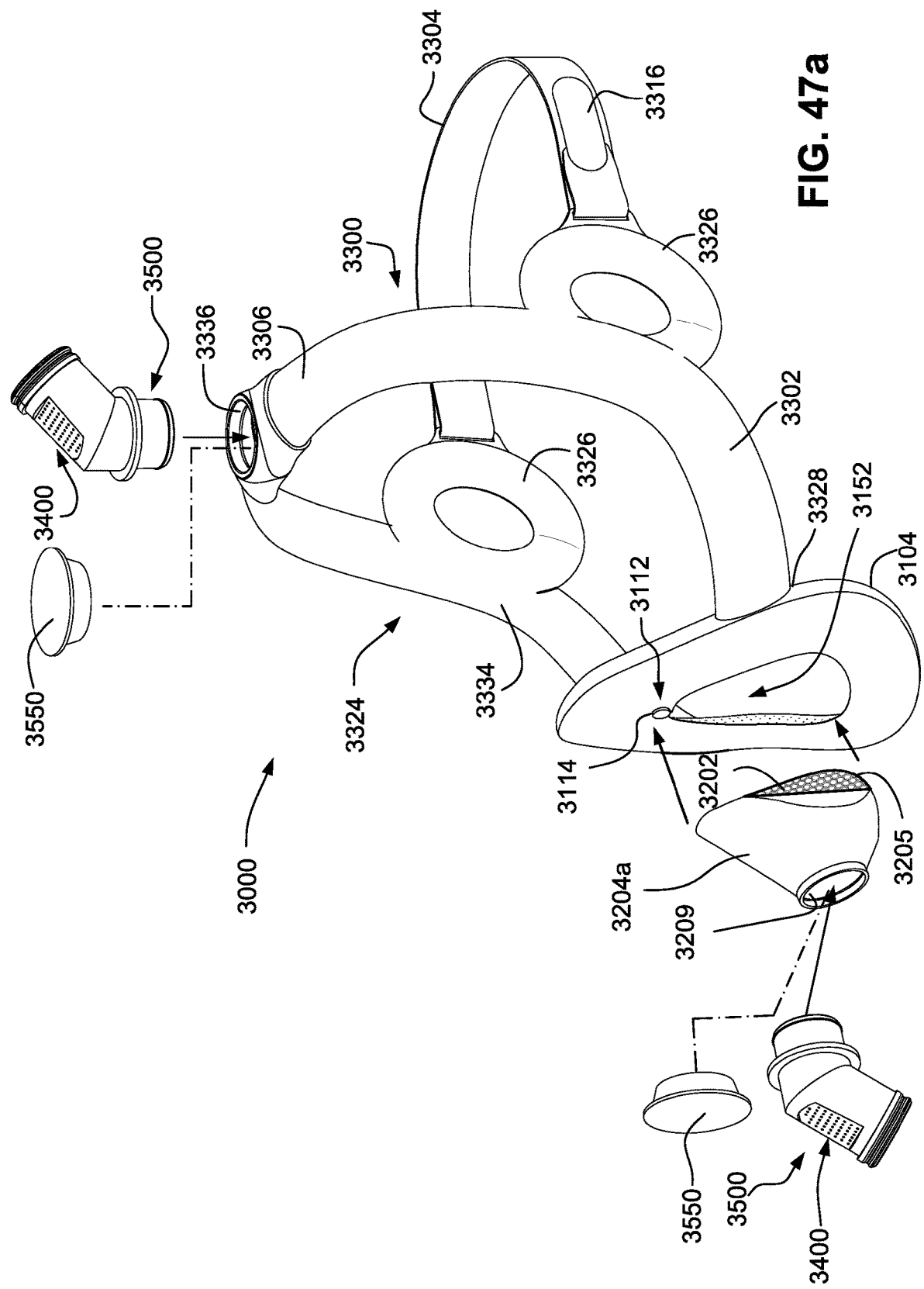

FIG. 47a shows a front perspective view of a patient interface formed from a one piece construction of textile material. The positioning and stabilizing structure includes hollow tubes that convey air toward the seal-forming structure. The air is conveyed directly into a hollow sealing tube and the seal-forming structure. A plenum chamber is removably coupled to the seal-forming structure. Air may be provided to the hollow sealing tube through a decoupling member positioned in either the positioning and stabilizing structure or the plenum chamber.

FIG. 47b shows a front perspective view of the patient interface of FIG. 47a. A rigidizer is coupled between the seal-forming structure and the positioning and stabilizing structure. The rigidizer is coupled to the seal-forming structure and the positioning and stabilizing structure with a rigid thread.

FIG. 47c shows a detail view of the patient interface of FIG. 47a. Specifically, the detail view illustrates the latticework of the plenum chamber shown in FIG. 47a.

Figure 47D:
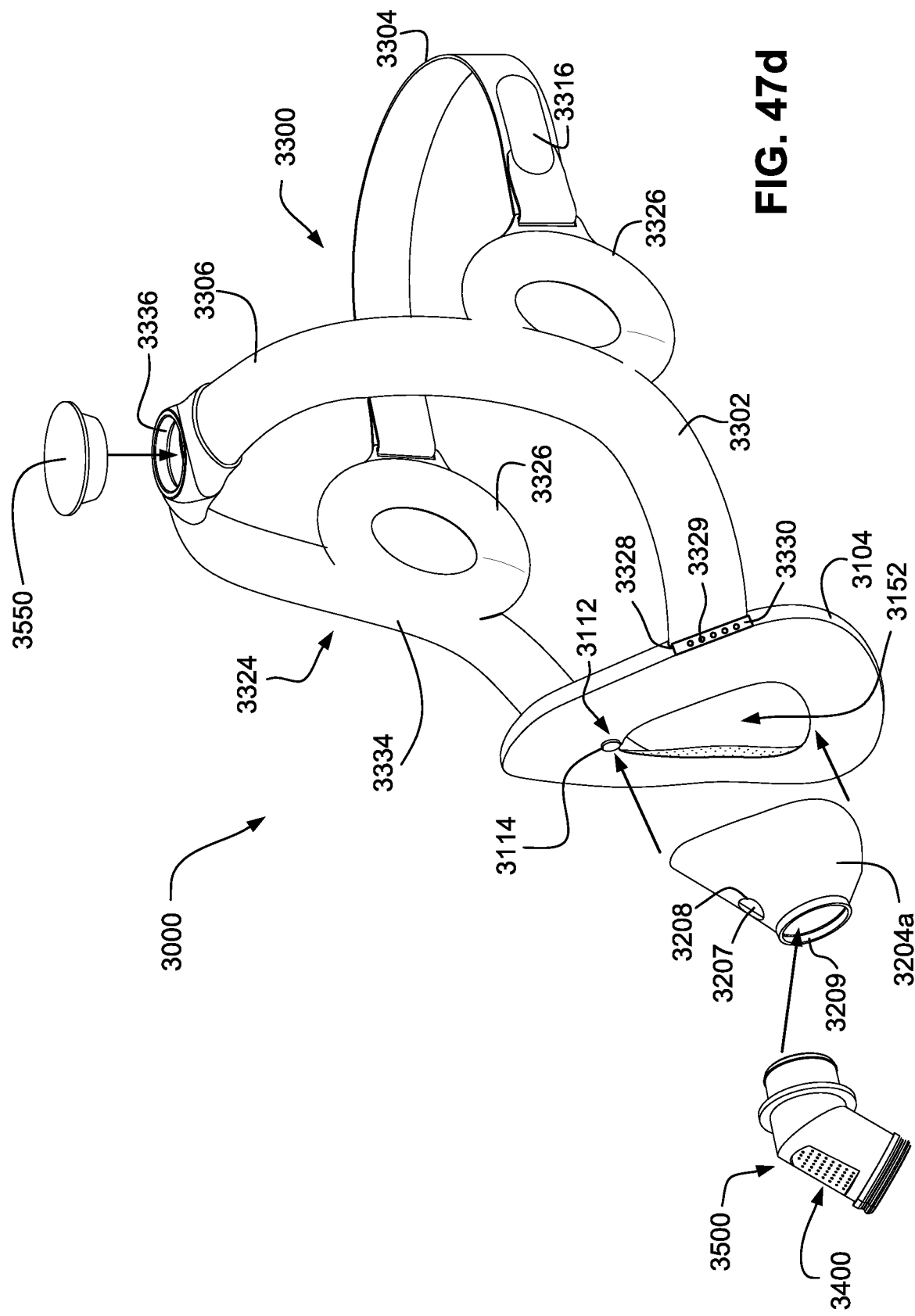

FIG. 47d shows a front perspective view of the patient interface of FIG. 47a, with a removable plenum chamber having a pair of openings.

Figure 47E:
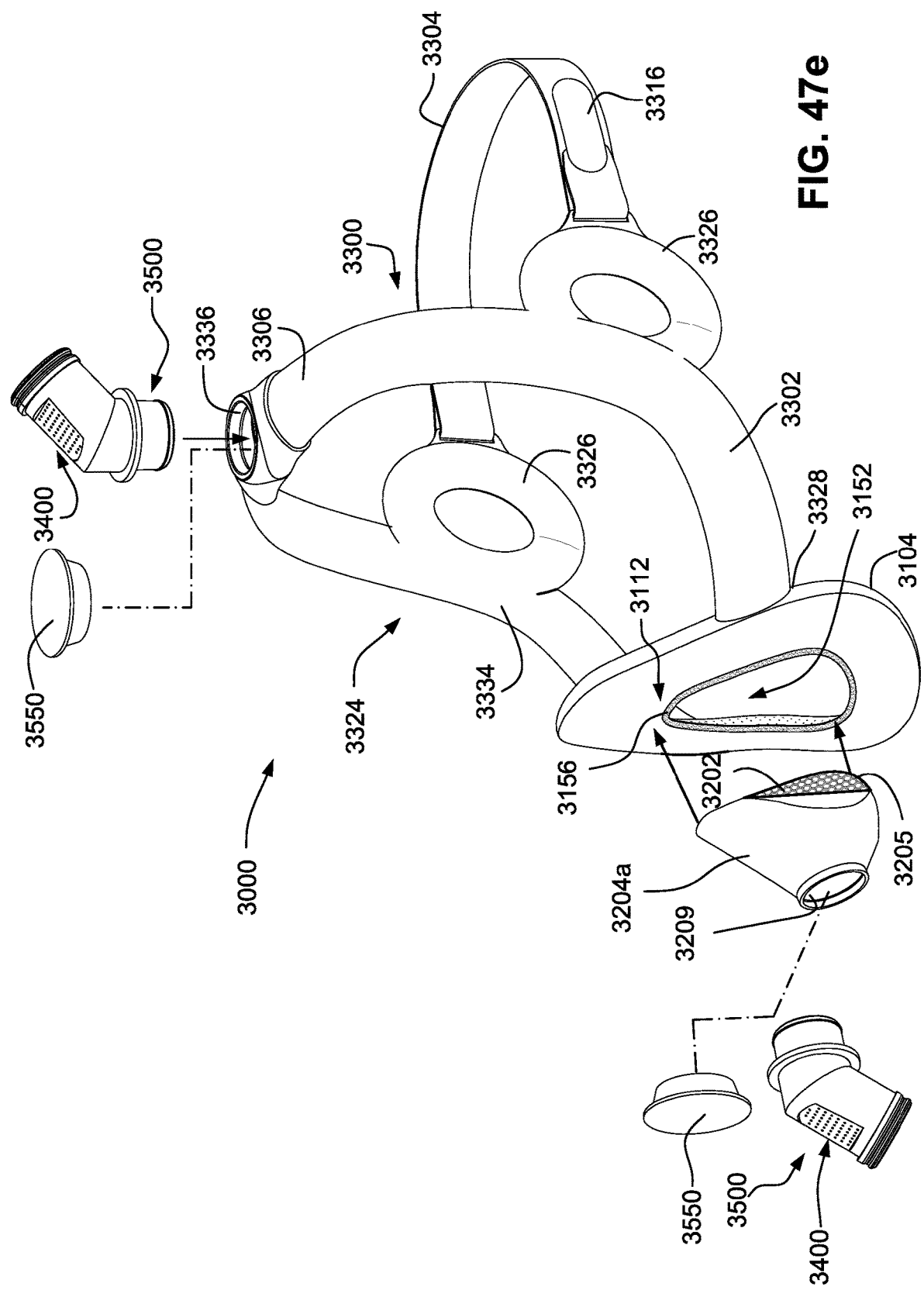

FIG. 47e shows a front perspective view of the patient interface of FIG. 47a, with a fluid layer formed on the seal-forming structure and having magnetic properties.

Figure 48:
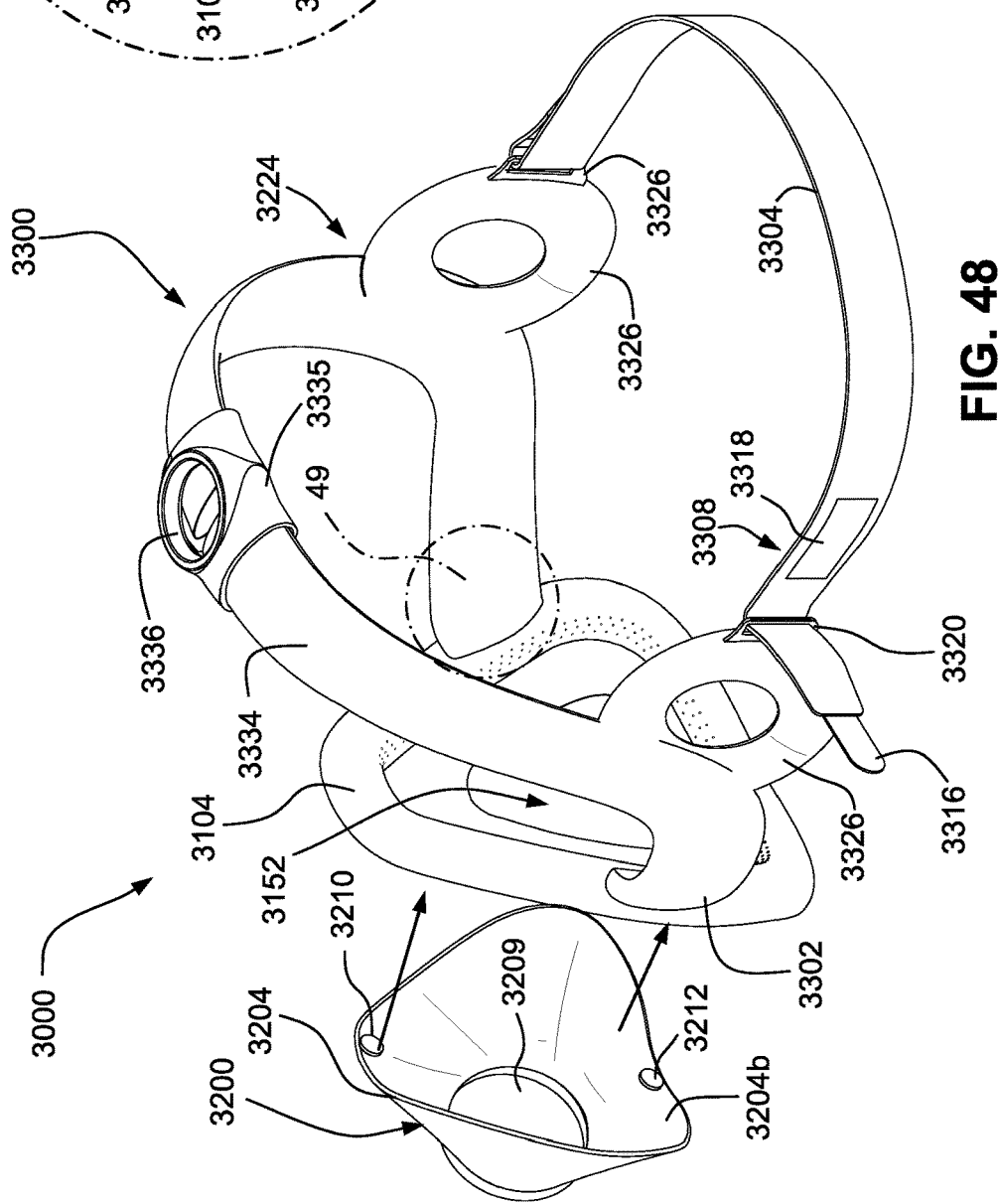

FIG. 48 shows a rear perspective view of the patient interface of FIG. 47a. The plenum chamber includes a pair of magnetic portions that assist in coupling the plenum chamber to the seal-forming structure in the proper orientation.

Figure 48A:
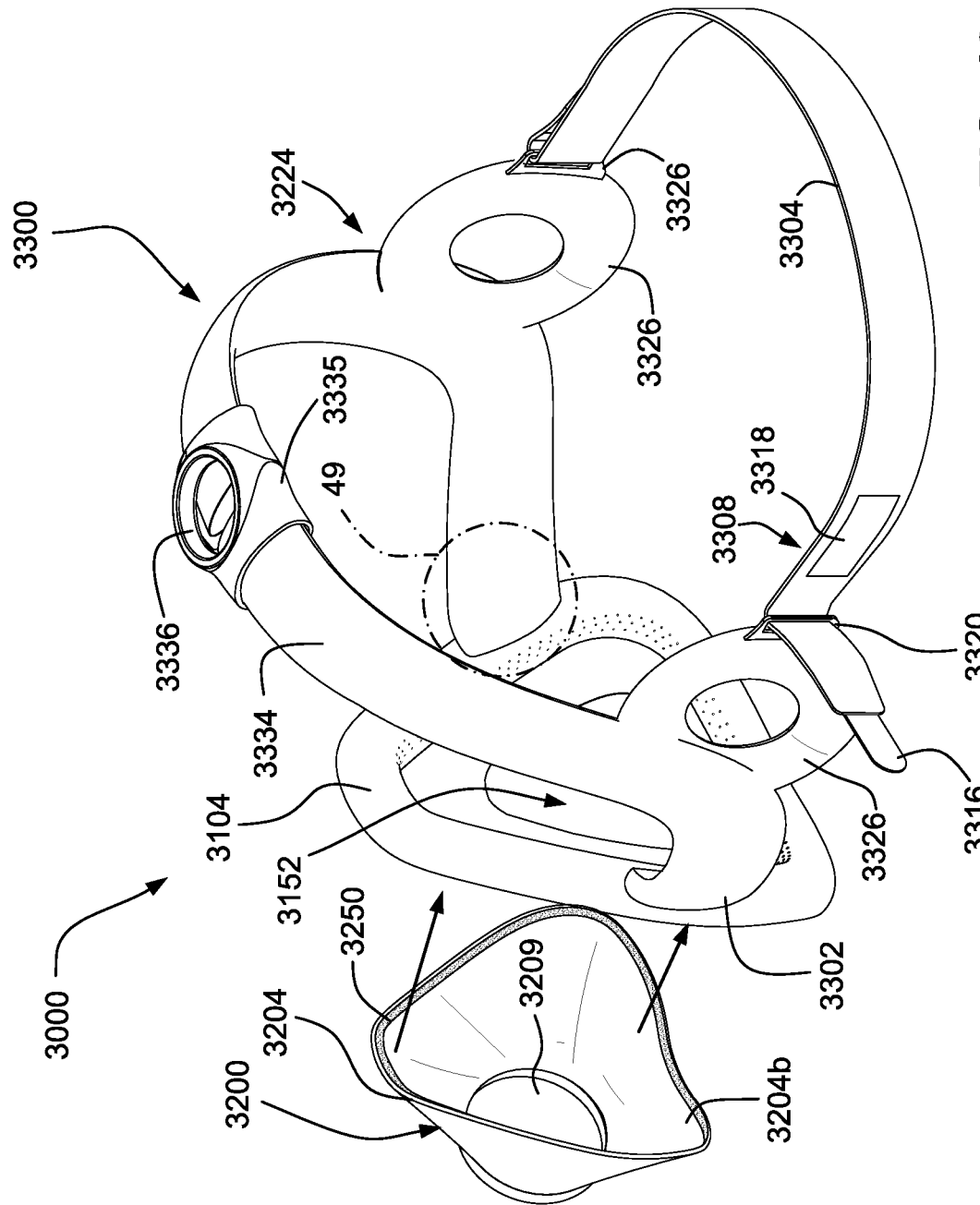

FIG. 48a shows a rear perspective view of the patient interface of FIG. 47e. The plenum chamber includes fluid layer with magnetic properties that assist in coupling the plenum chamber to the seal-forming structure in the proper orientation.

Figure 49:
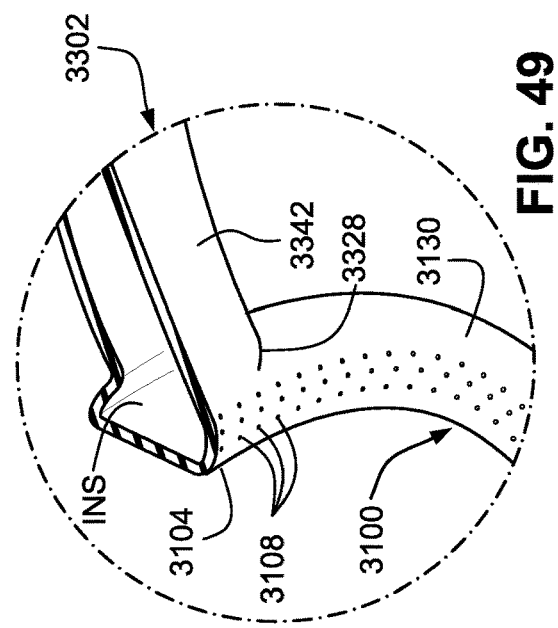

FIG. 49 shows a detail view of the patient interface of FIG. 48 that shows an interior surface of the hollow sealing tube. The seal-forming structure includes holes in communication with the hollow sealing tube. The holes allow air to be conveyed from proximate the interior surface towards the patient's face.

Figure 50:
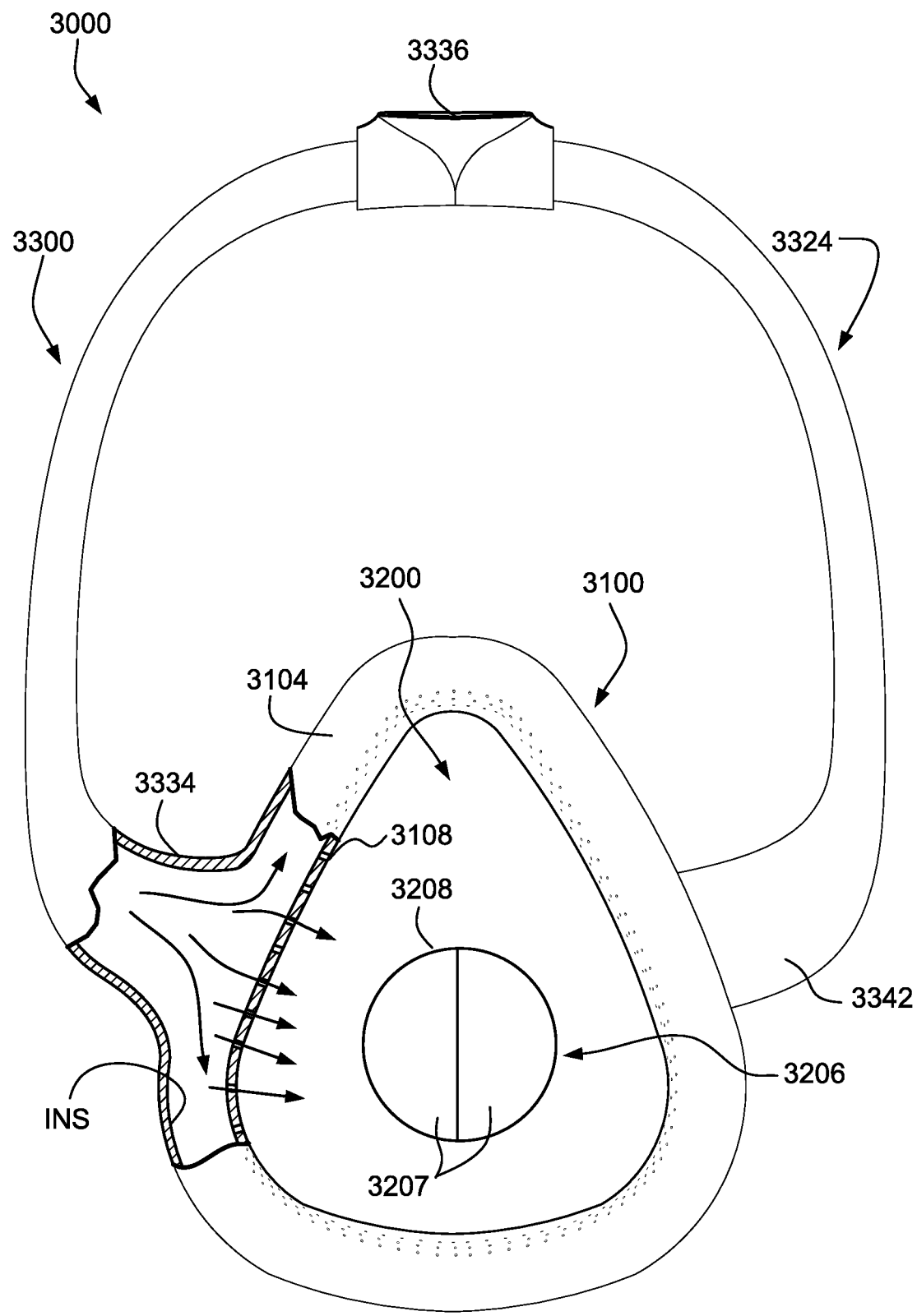
Figures 1, 50:
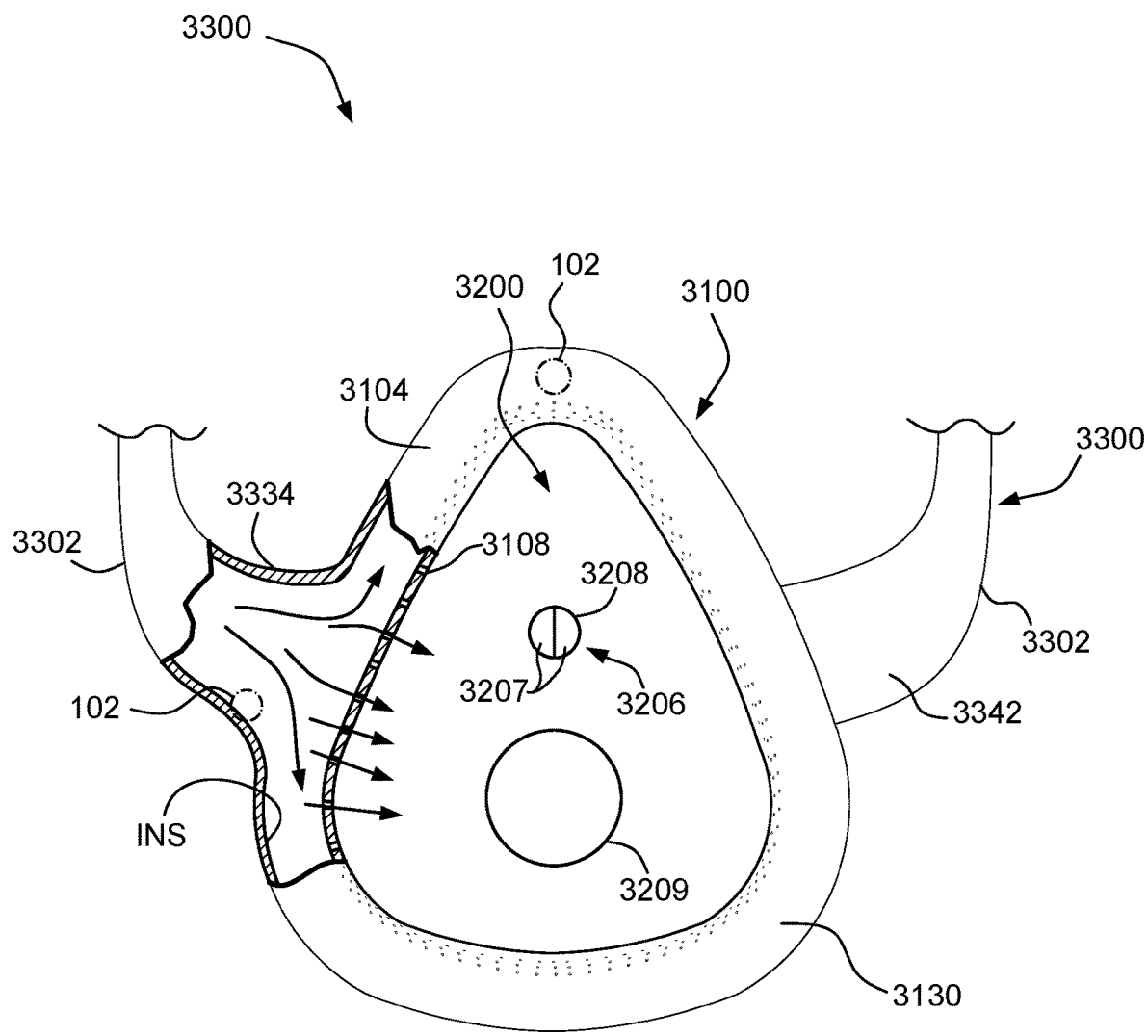

FIG. 50 shows a rear view of the patient interface of FIG. 47a. Pressurized air is conveyed from the hollow tubes, into the hollow sealing tube, and finally toward a patient's face. A flap closes off an inlet port in the plenum tube because of the force supplied by the pressurized air.

Figure 1:
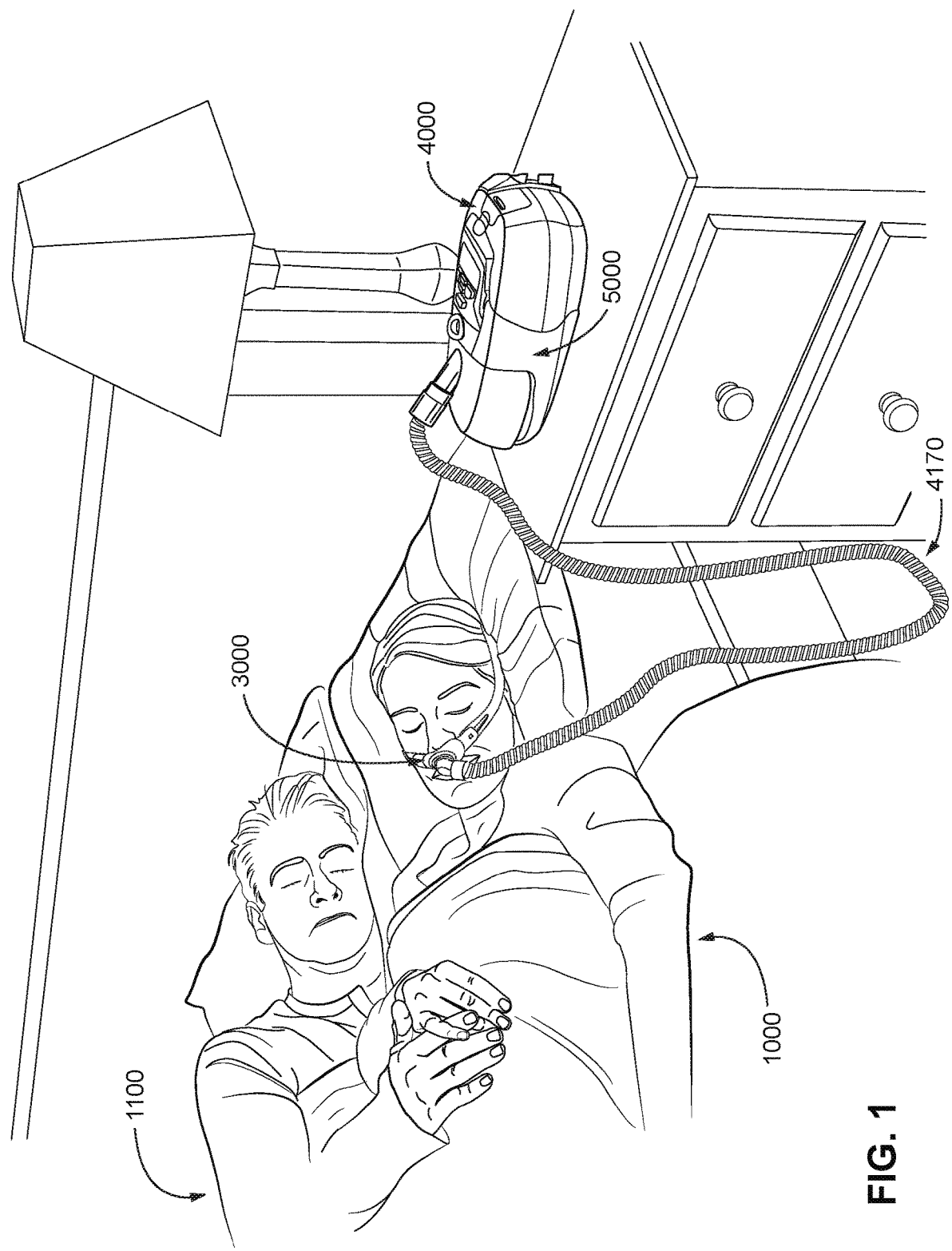
Figure 2:
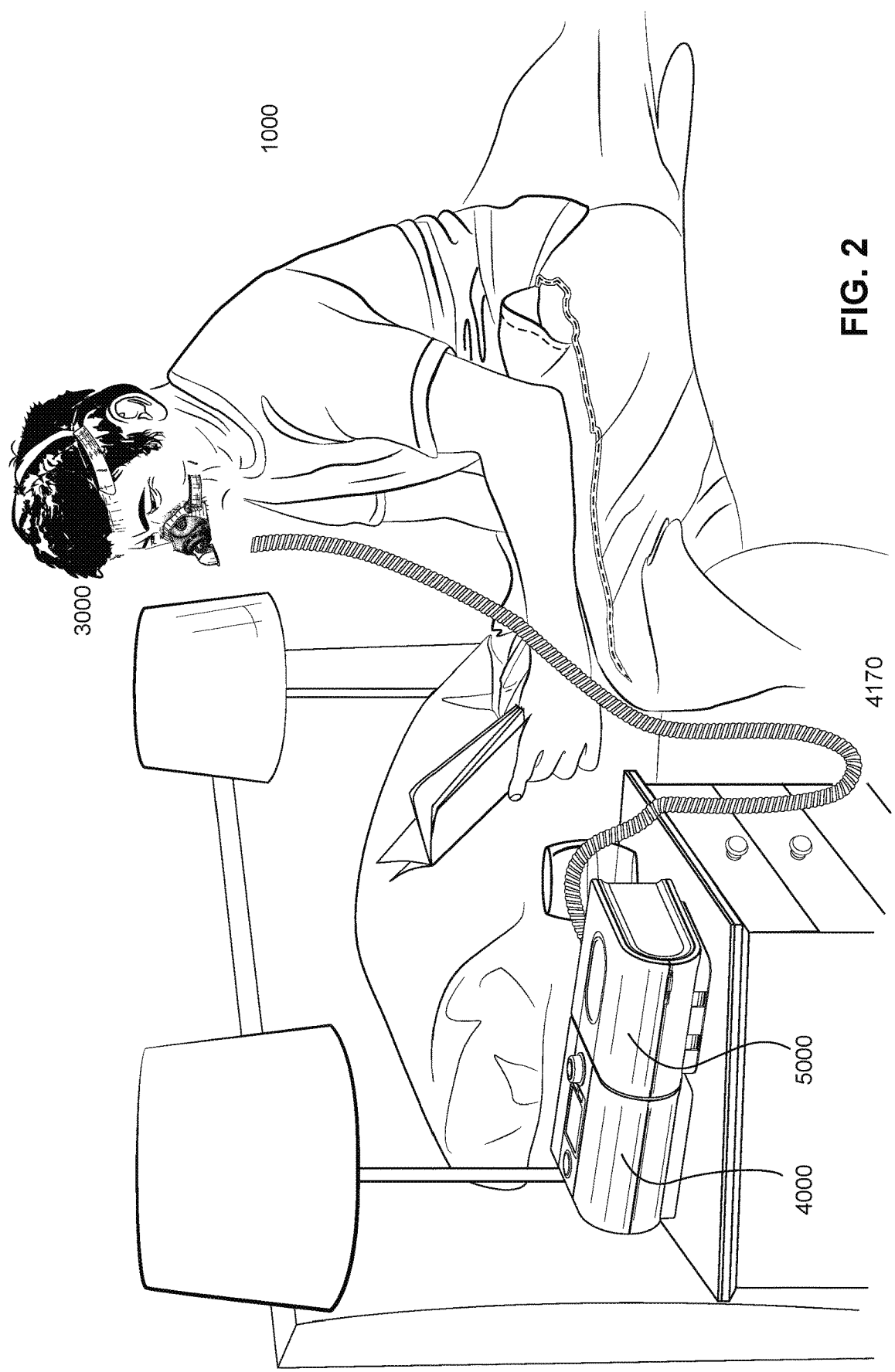
Figure 3:
Figure 4:
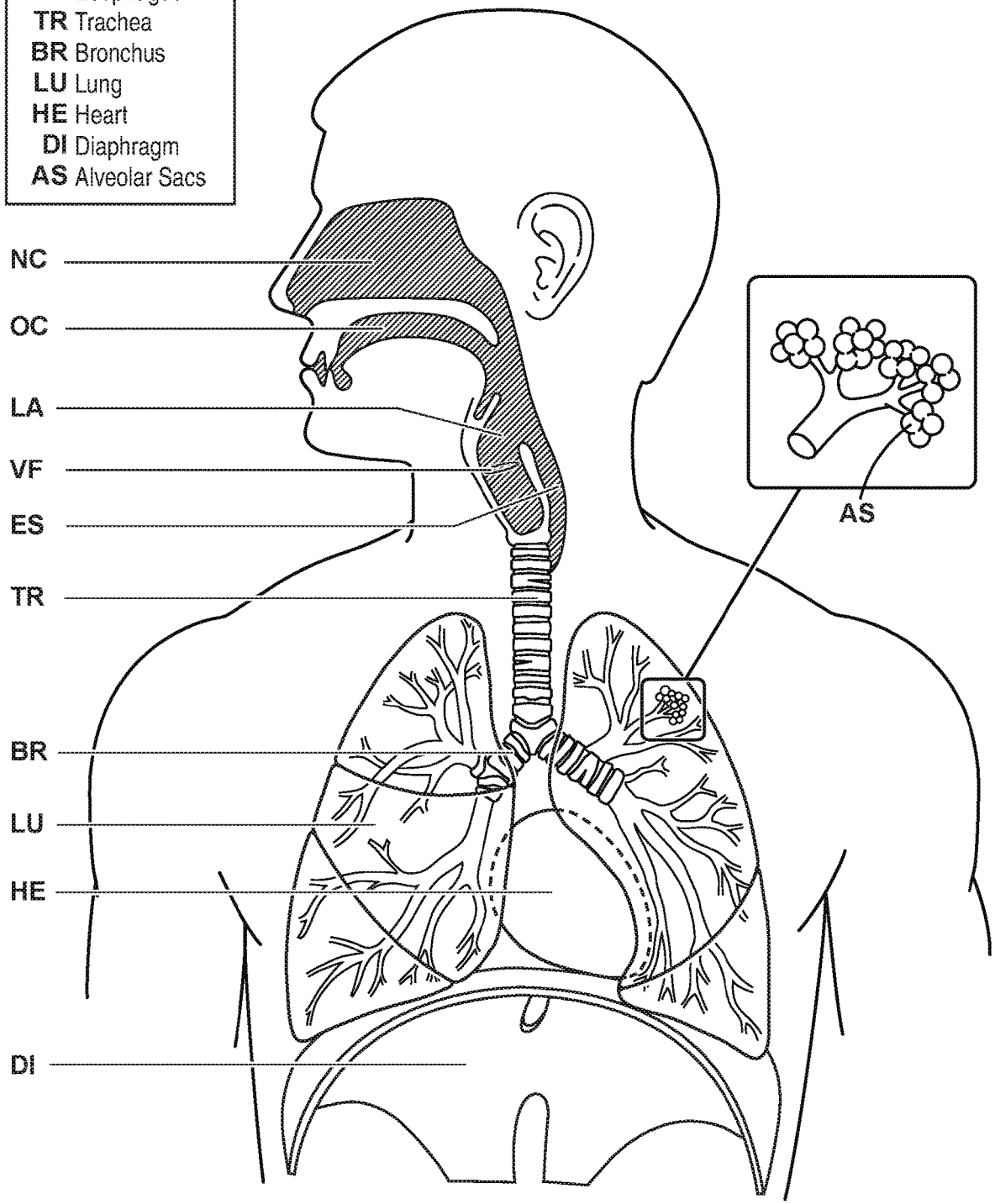
FIG. 4 shows an overview of a human respiratory system including the nasal and oral cavities, the larynx, vocal folds, oesophagus, trachea, bronchus, lung, alveolar sacs, heart and diaphragm.
Figure 5:
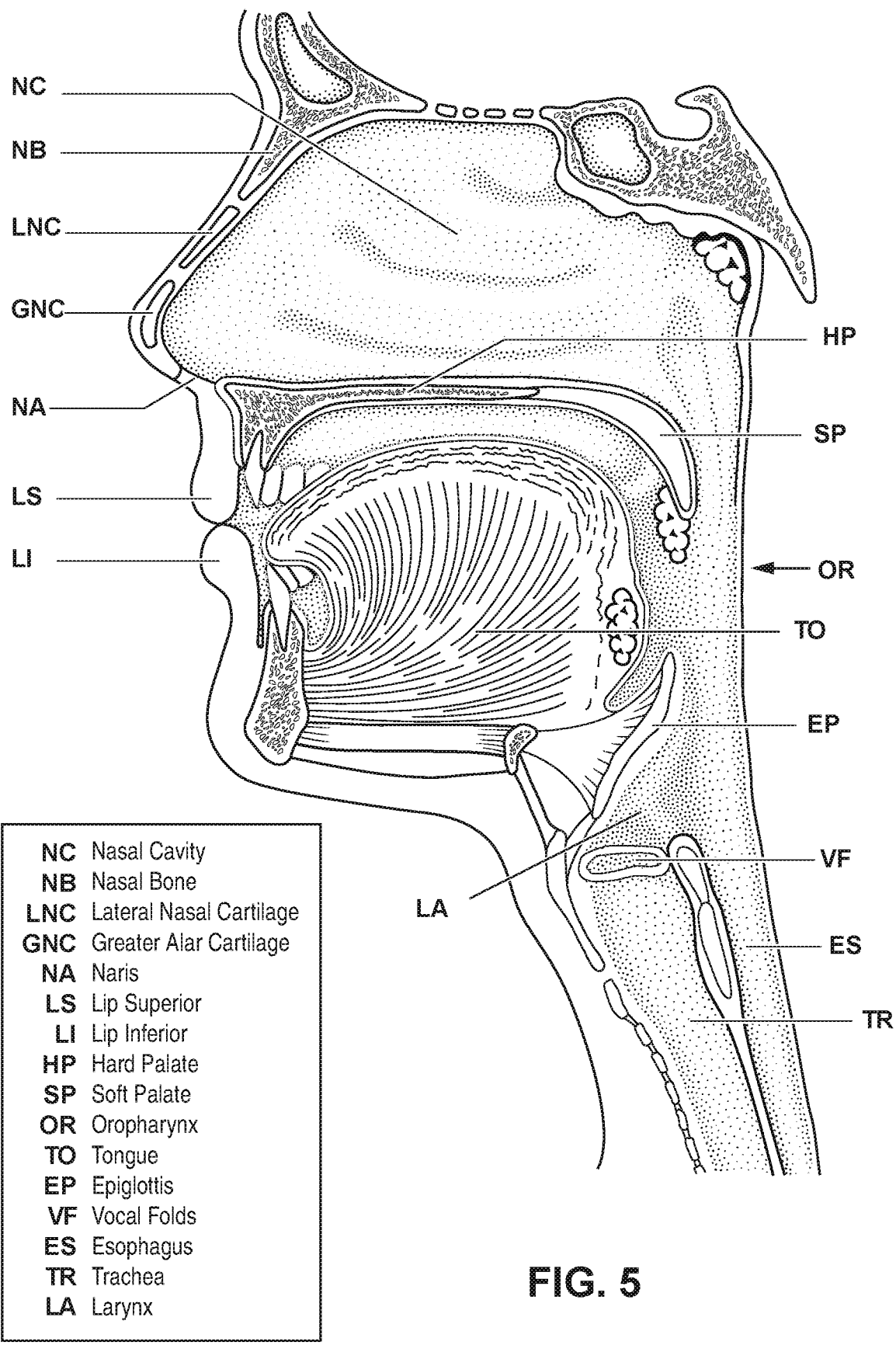
FIG. 5 shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 6:
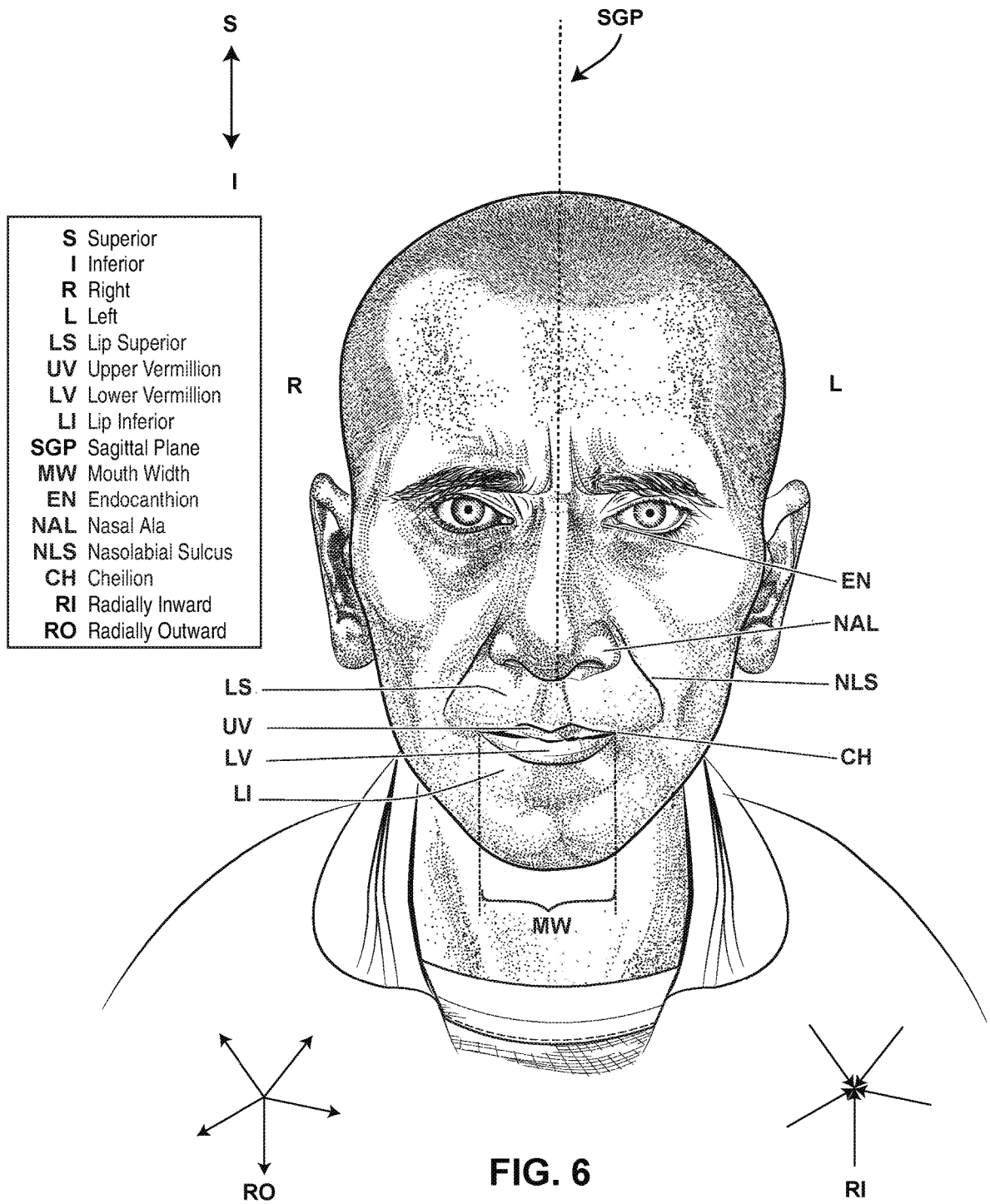
FIG. 6 is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 7:
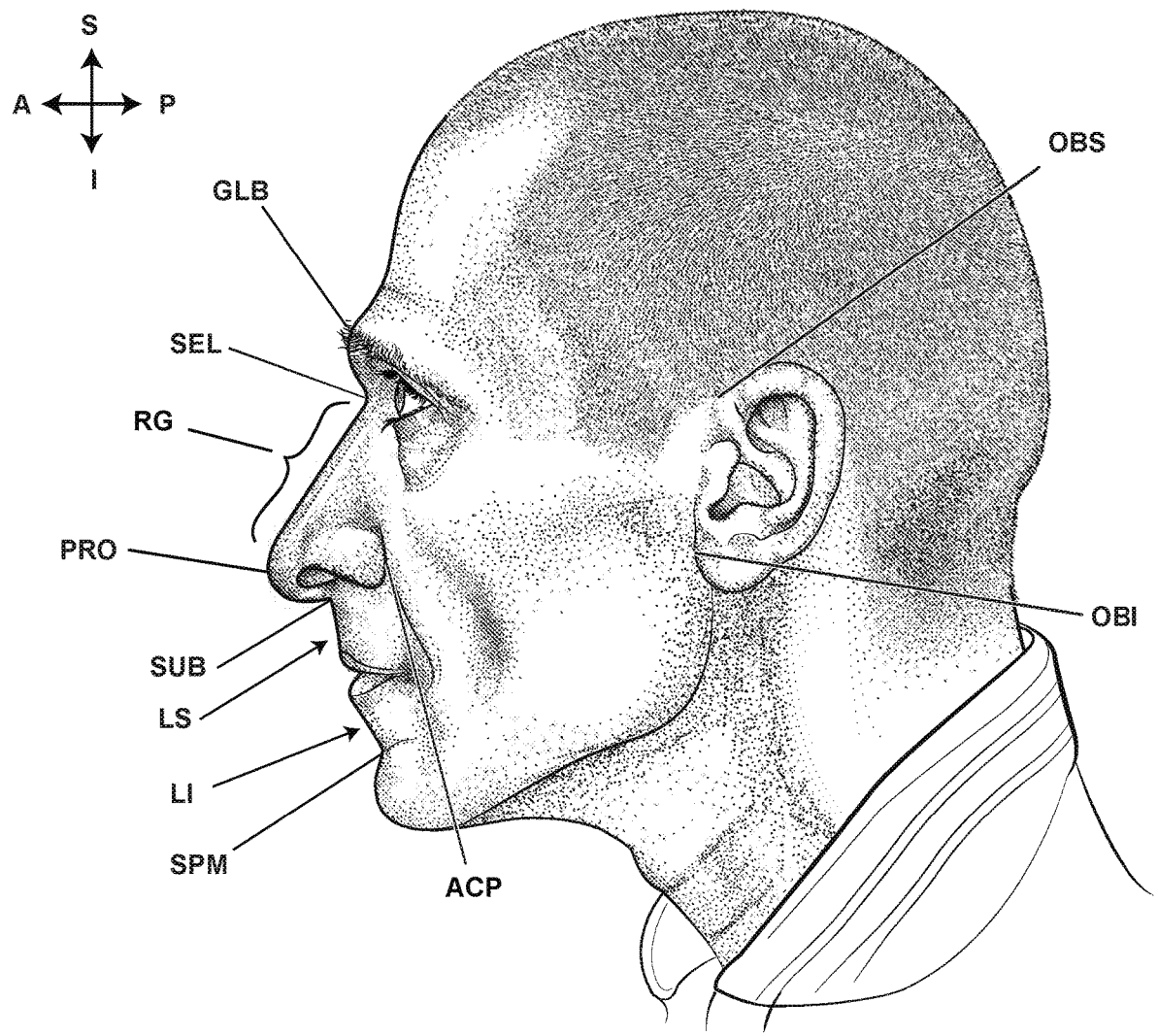
FIG. 7 is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

FIG. 50-1 shows a rear view of another example of a patient interface formed from a one piece construction of textile material. The positioning and stabilizing structure includes hollow tubes that convey air toward the seal-forming structure.

Figure 51:
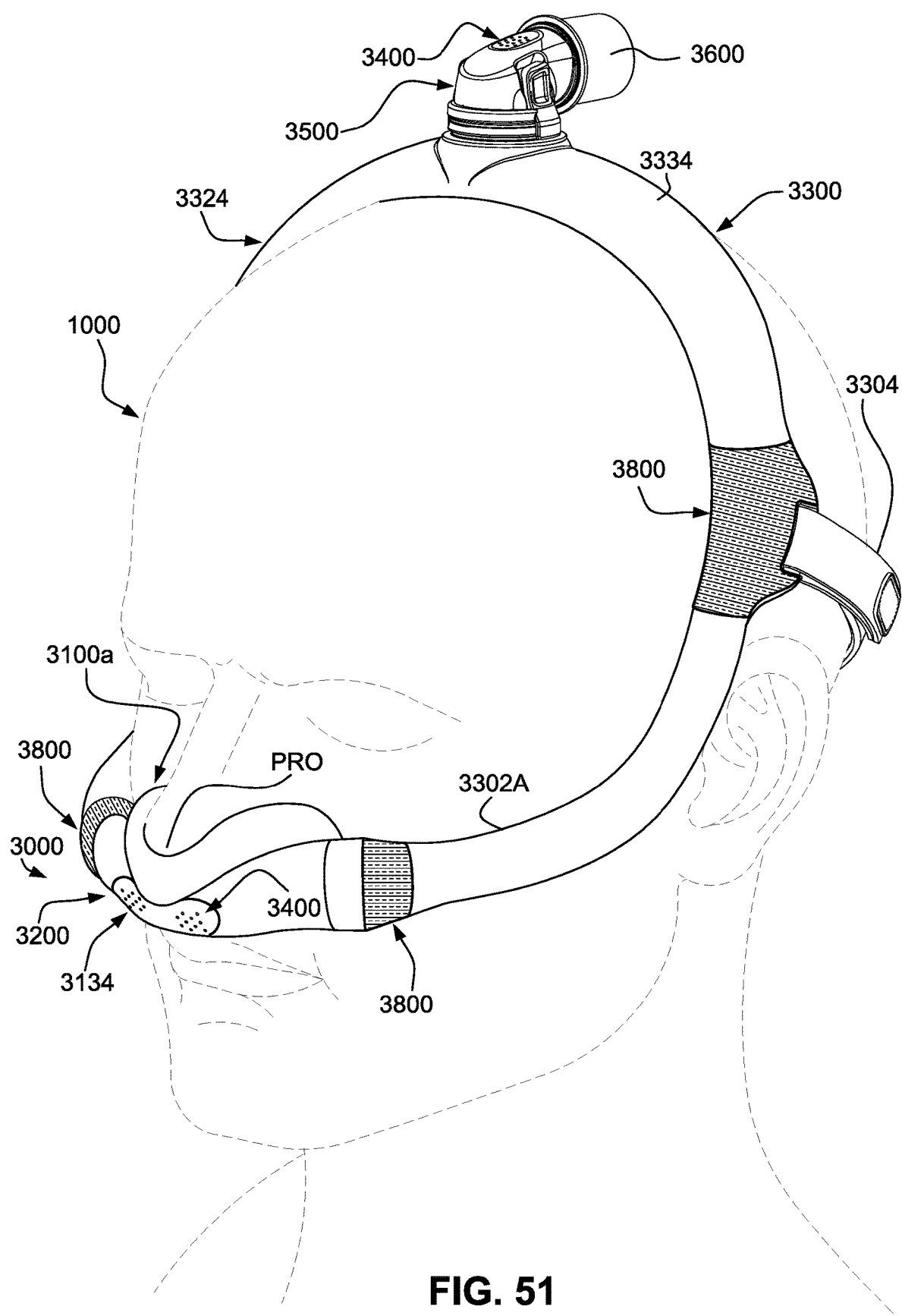

FIG. 51 shows a perspective view of an under the nose mask worn by a patient. The mask creates a seal around the patient's nares, and leaves the patient's mouth exposed to the ambient.

Figure 52:
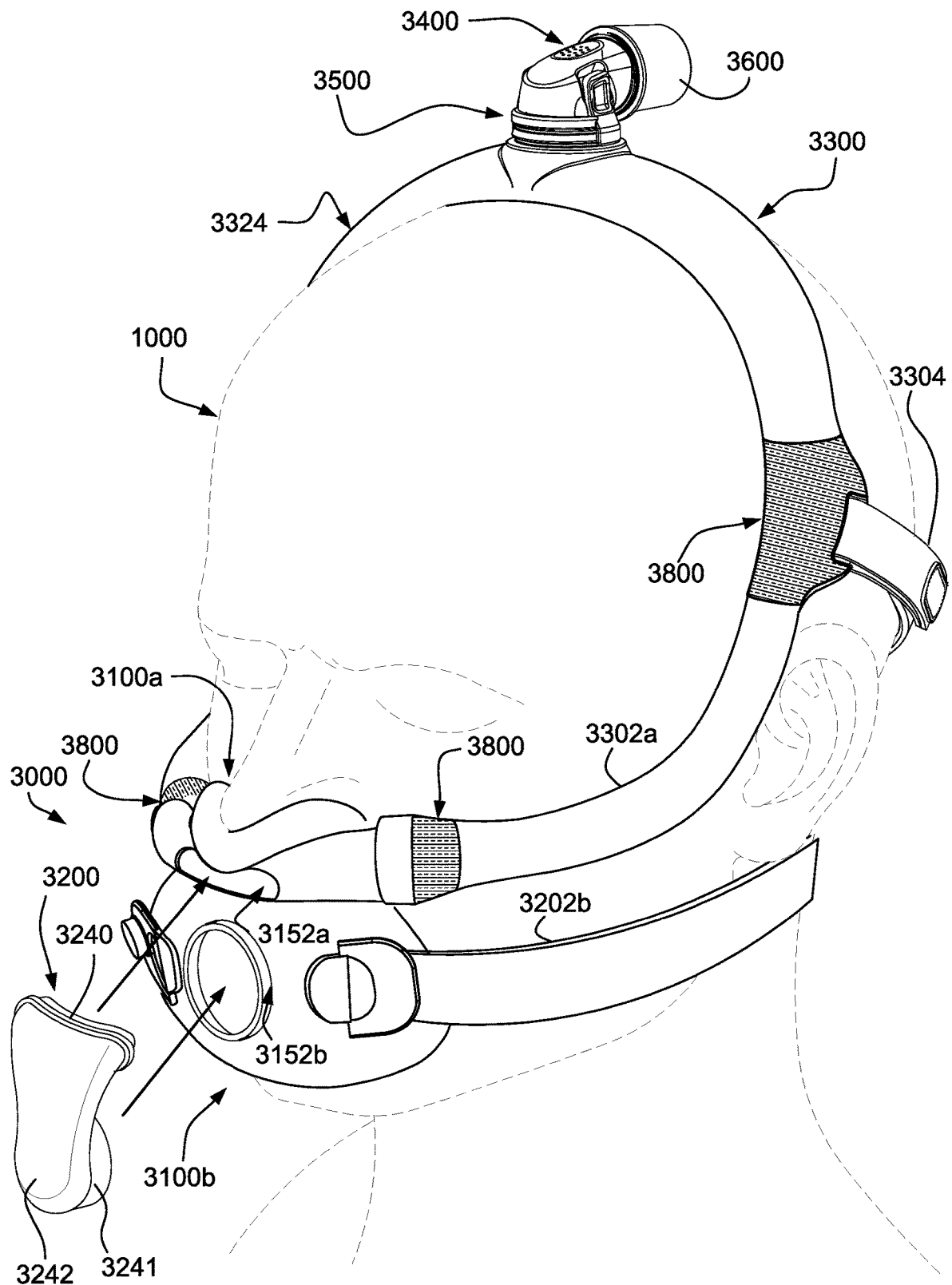

FIG. 52 shows a perspective view of the under the nose mask of FIG. 51 coupled to a mouth seal. Together, the under the nose mask and the mouth seal form a modular construction that can create a seal about the patient's nose and mouth. A plenum chamber is used with the modular configuration in order to selectively cover the patient's mouth and nose from the ambient.

FIG. 52a shows a schematic view of a lower surface of the nose mask of FIG. 51, with an interface to couple to the mouth seal.

FIG. 52b shows a schematic view of an upper surface of the mouth seal of FIG. 51, with an interface to couple to the nose mask.

FIG. 53 shows a rear view of a patient interface. The plenum chamber includes a magnetic thread sewn into an inner surface. The magnetic thread is used to couple and position the plenum chamber with respect to the seal-forming structure.

Figure 53A:
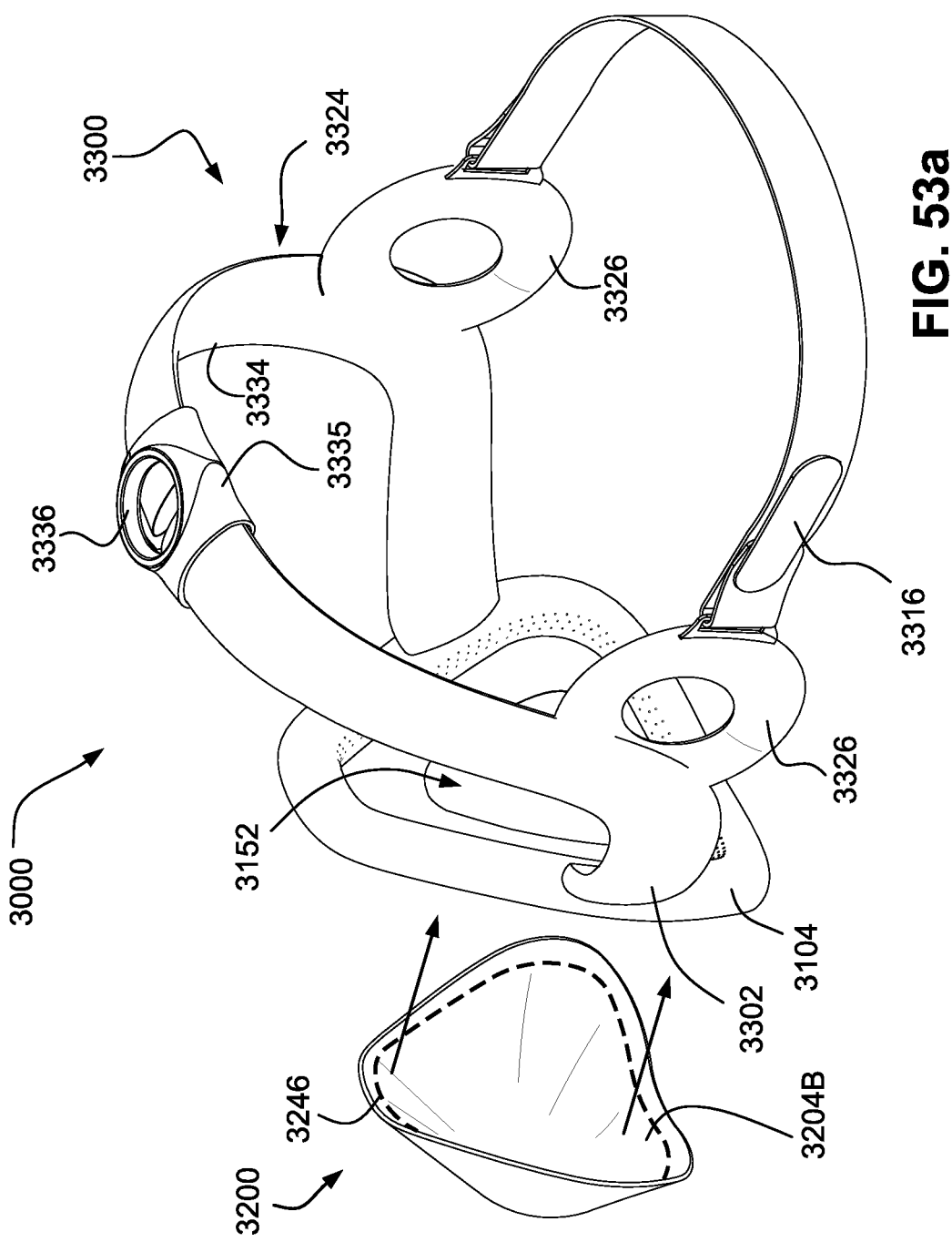

FIG. 53a shows a rear view of a patient interface. The plenum chamber includes Velcro coupled into an inner surface. The Velcro is used to couple and position the plenum chamber with respect to the seal-forming structure.

Figure 54:
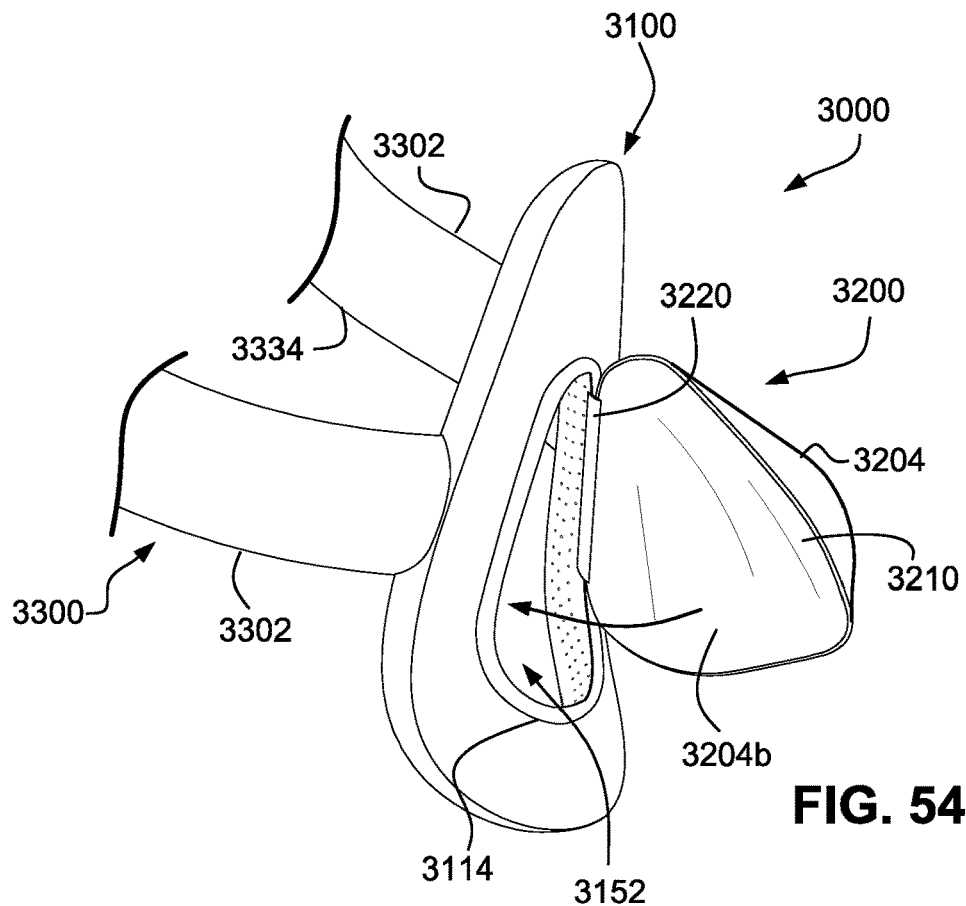

FIG. 54 shows a perspective view of a plenum chamber pivotable relative to a seal-forming structure. The plenum chamber is fixed on one side, and free on the other sides. A magnetic thread is sewn into the free sides of the plenum chamber. A magnetic thread with the opposite polarity is sewn into the seal-forming structure.

Figure 55:
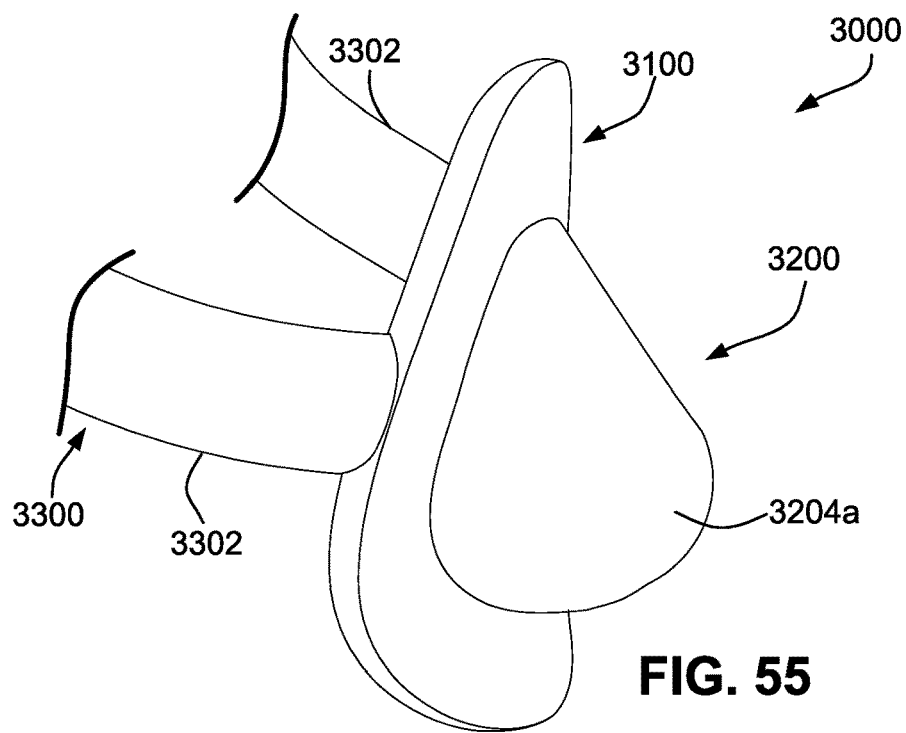
Figure 55A:
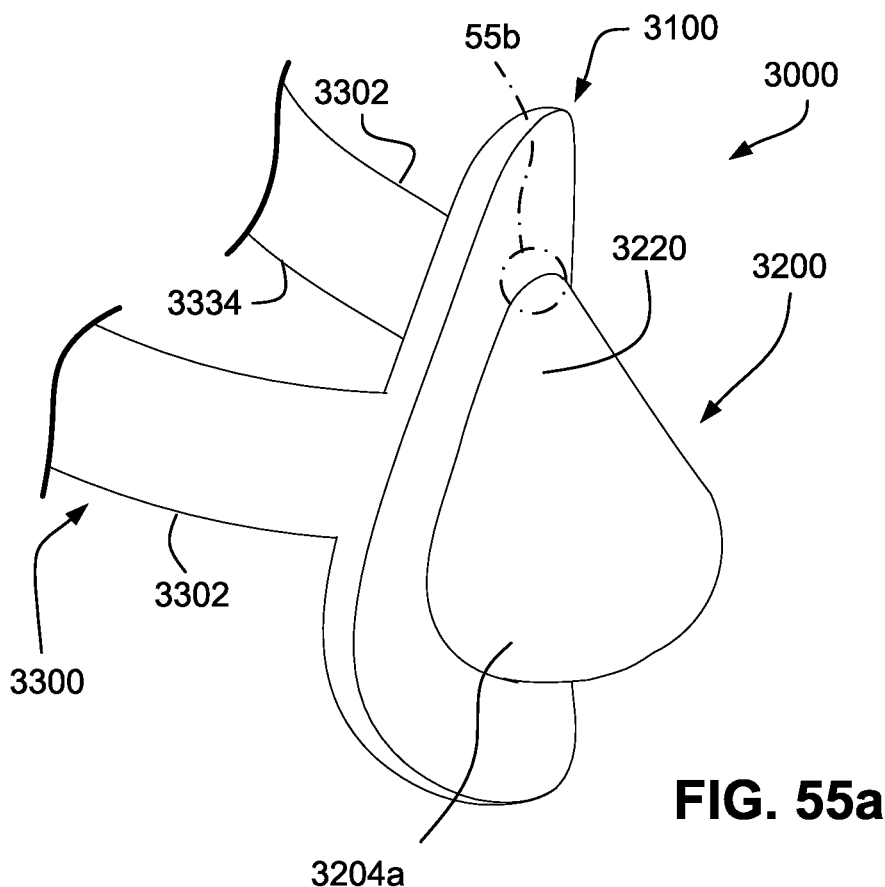

FIG. 55a shows a perspective view of a plenum chamber coupled to a seal-forming structure.

Figure 55B:
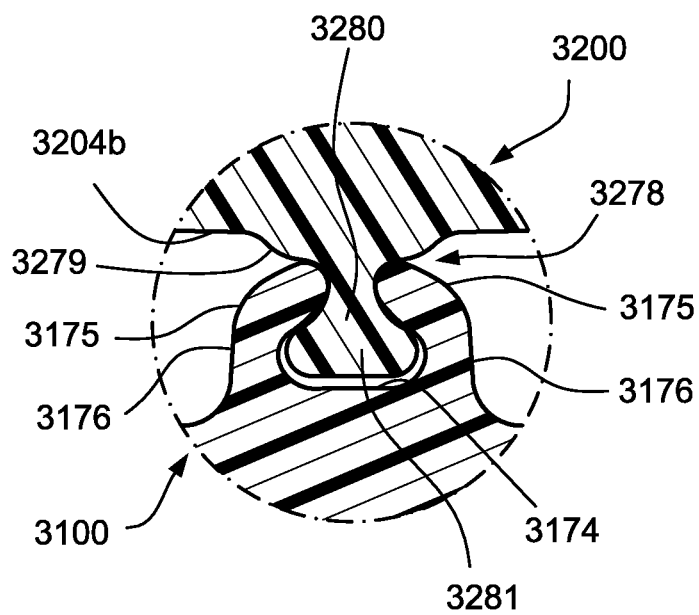

FIG. 55b shows a cross-sectional view of the patient interface of FIG. 55a, illustrating the extension engaging the groove.

Figure 55C:
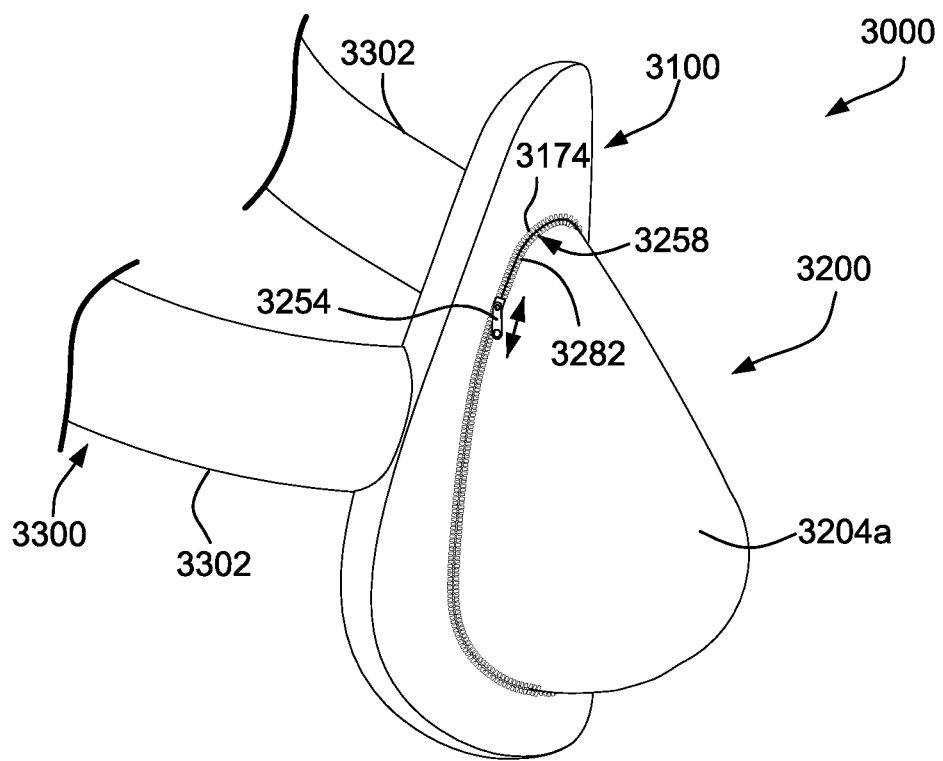

FIG. 55c shows a perspective view of a plenum chamber and a seal-forming structure coupled to one another in a sealing arrangement by a sliding zipper.

Figure 56:
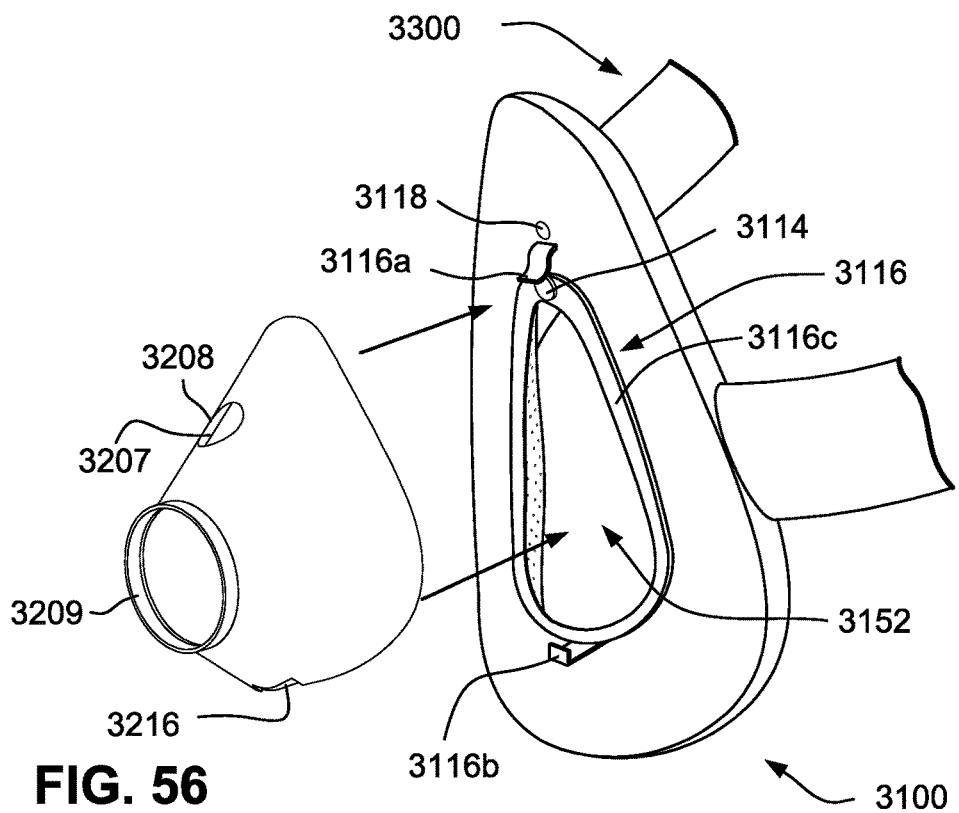

FIG. 56 shows a perspective view of a patient interface formed from a one piece construction of textile material. A seal-forming structure includes a clipping structures and a magnetic portion. A plenum chamber is received by the clipping structure and includes a magnetic portion that is complementary to the portion on the seal-forming structure. The clipping structure and the magnetic portions work together to assist in coupling the plenum chamber to the seal-forming structure.

Figure 56A:
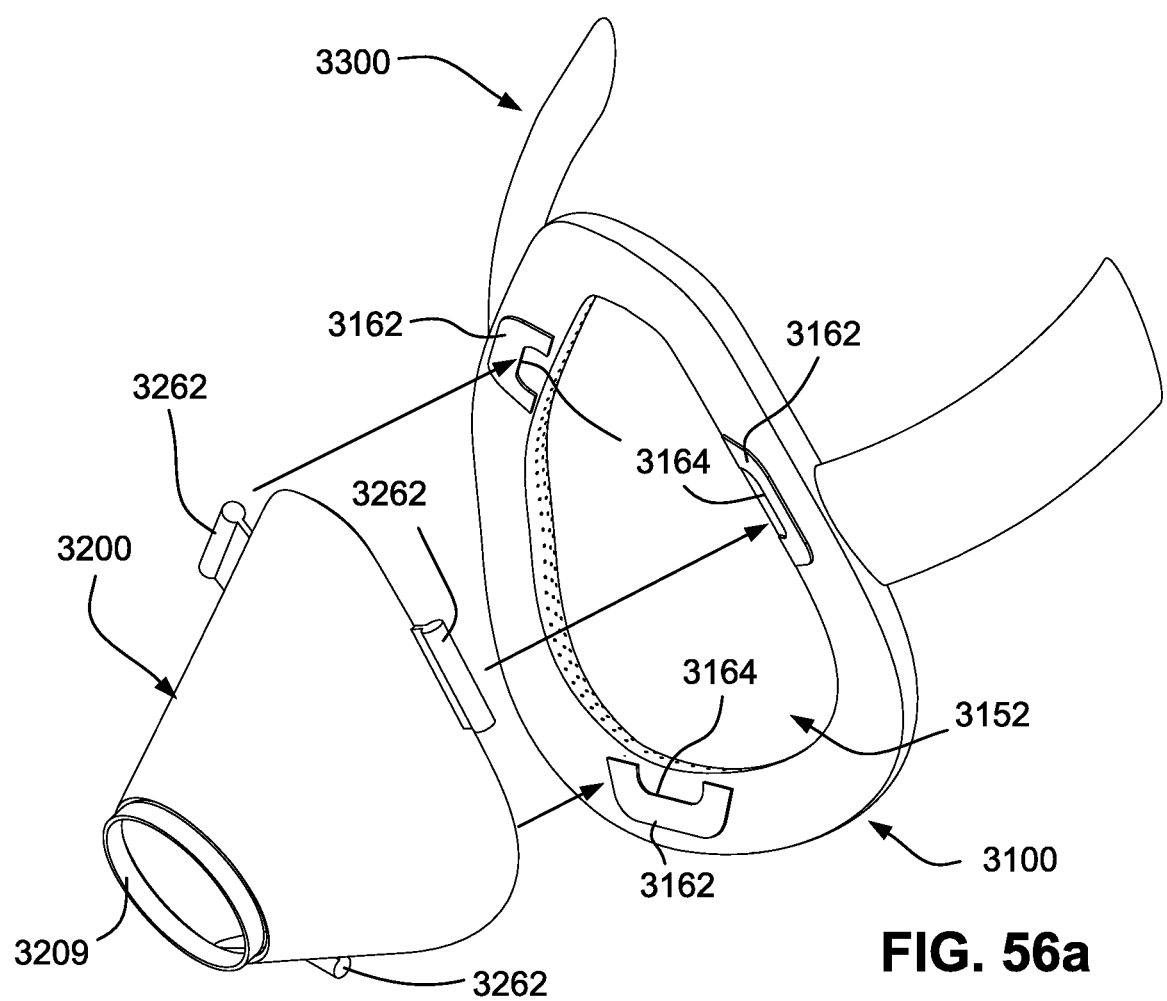

FIG. 56a shows a perspective view of a plenum chamber of a patient interface removed from a seal-forming structure. The plenum chamber includes projections and the seal-forming structure includes pivotable latches that selectively engage with the projections.

Figure 56B:
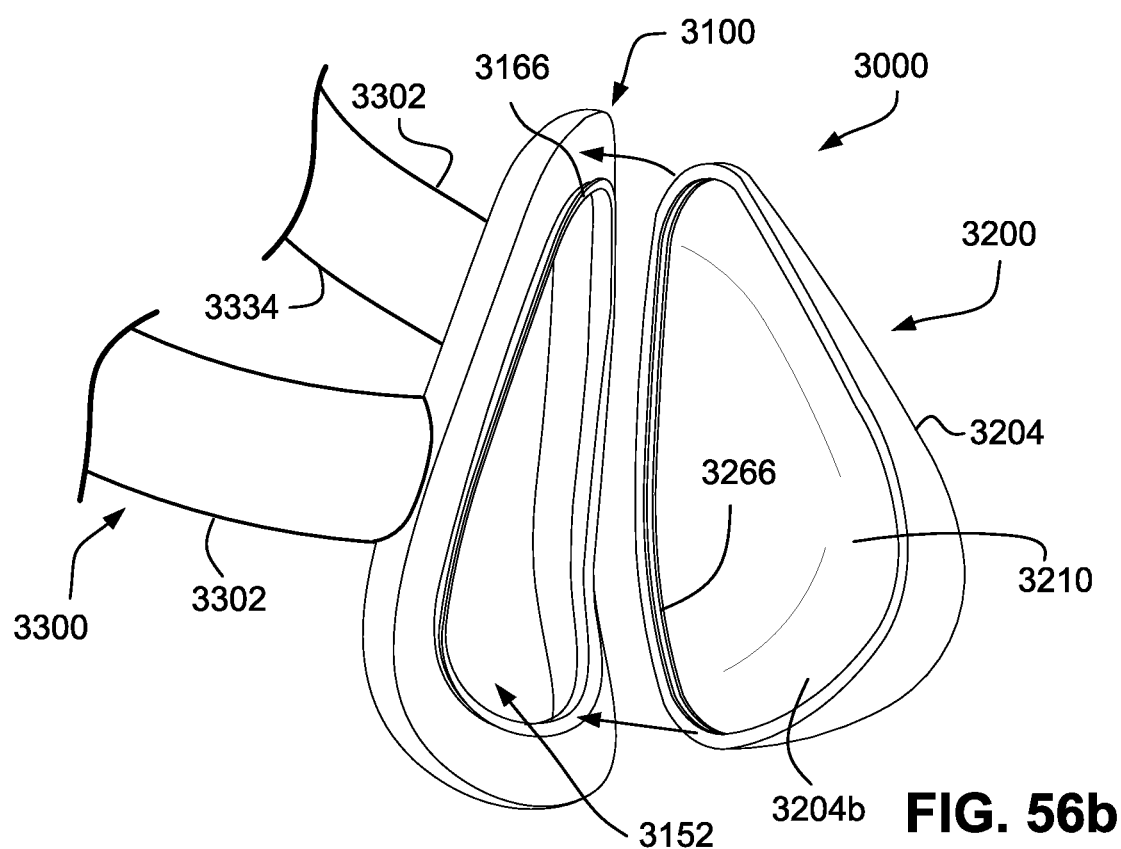

FIG. 56b shows a perspective view of a plenum chamber of a patient interface removed from a seal-forming structure. The plenum chamber includes an overhang and the seal-forming structure includes an undercut that selectively engages with the overhang.

Figure 56C:
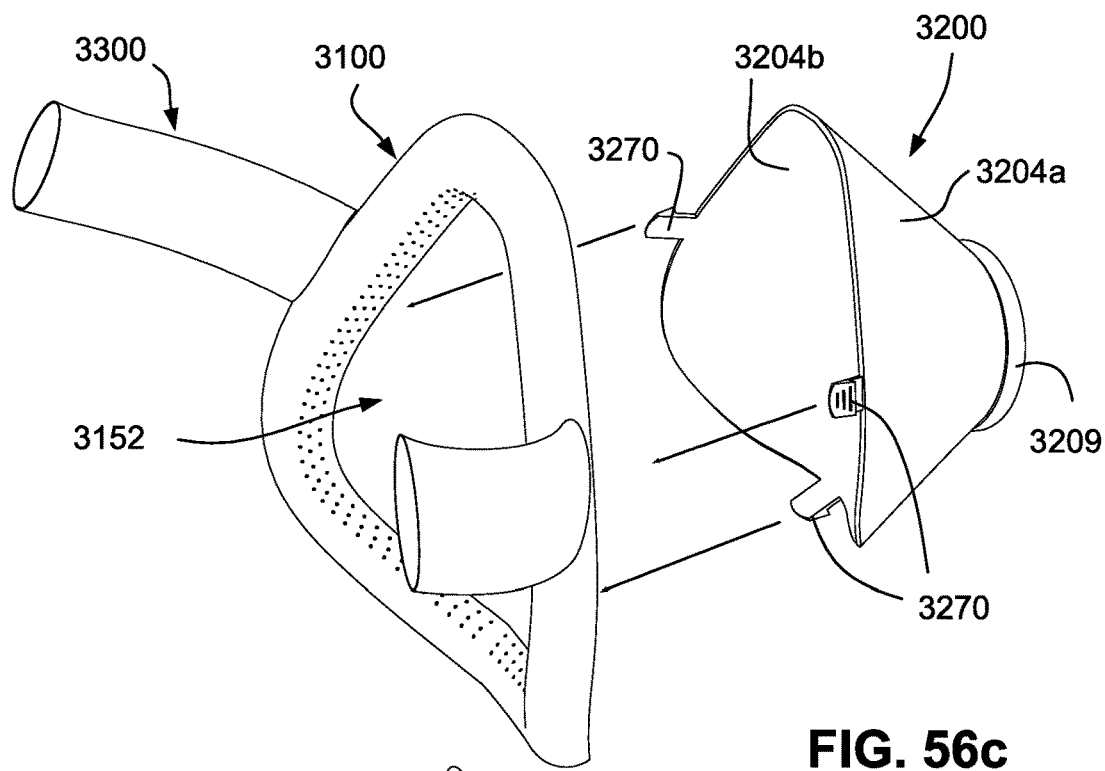
Figures 1, 56C:
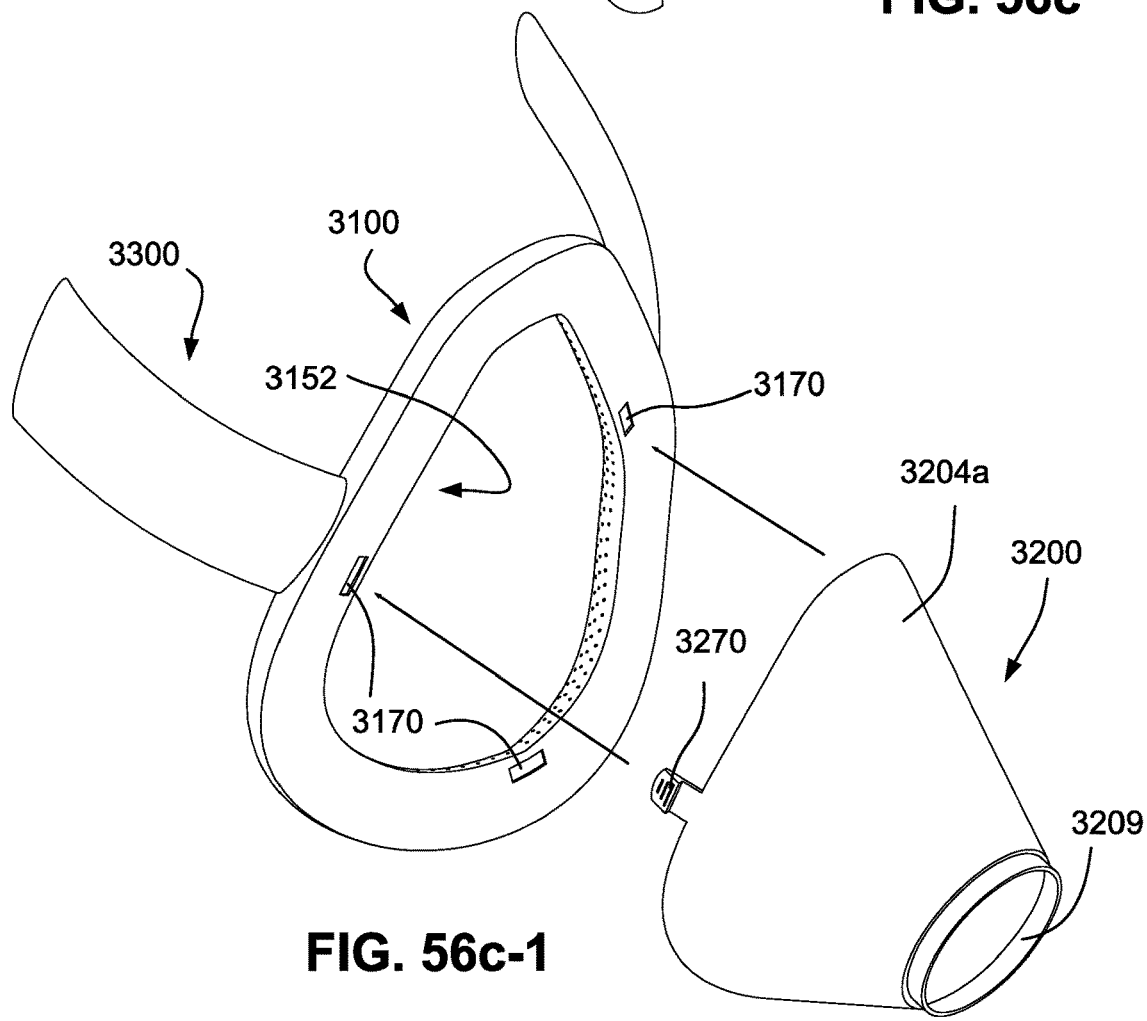

FIG. 56c shows a rear perspective view of a plenum chamber of a patient interface removed from a seal-forming structure. The plenum chamber includes a plurality of projections and the seal-forming structure includes slits that selectively receive the projections.

FIG. 56c-1 shows a front perspective view of the patient interface of FIG. 56c.

Figure 56D:
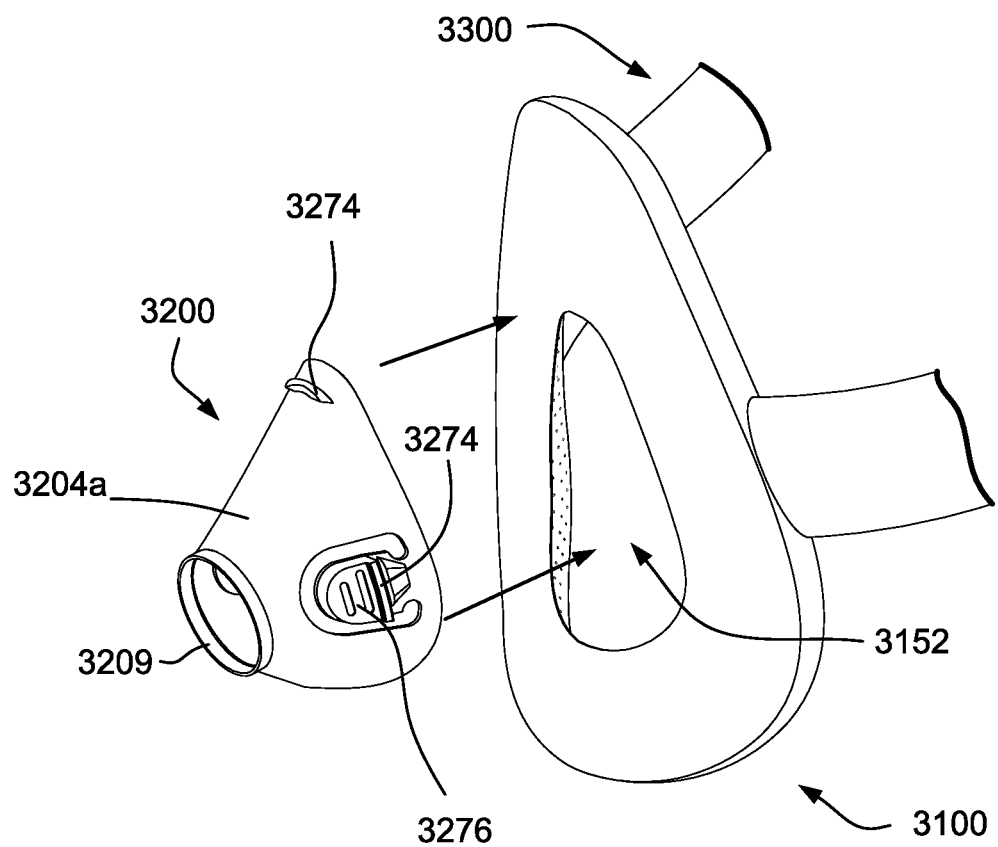

FIG. 56d shows a plenum chamber of a patient interface removed from a seal-forming structure. The plenum chamber is radially smaller than an opening of the seal-forming structure.

Figures 57A, 57B:
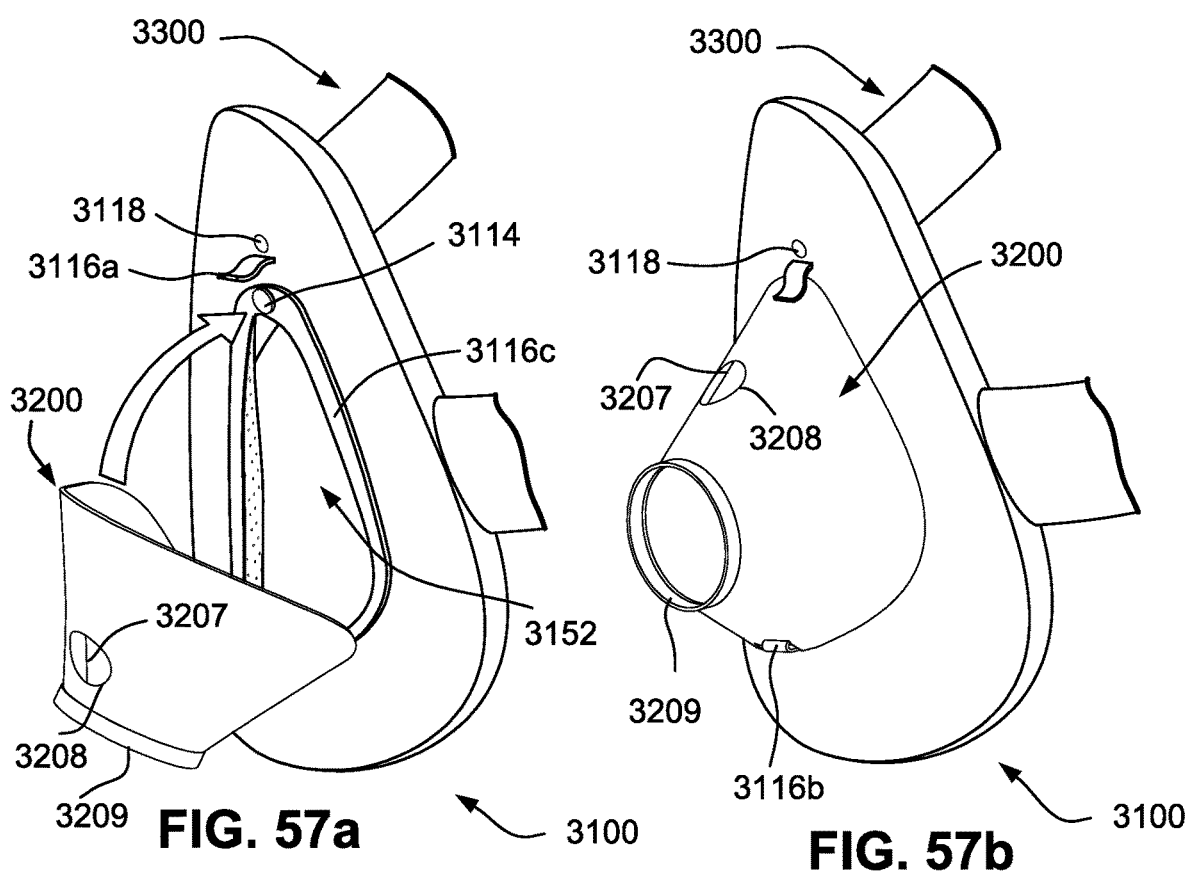

FIG. 57a shows a perspective view of the patient interface of FIG. 56. The plenum chamber is partially coupled to the seal-forming structure using the clipping structure and the magnetic portions.

FIG. 57b shows a perspective view of the patient interface of FIG. 56. The plenum chamber is fully coupled to the seal-forming structure using the clipping structure and the magnetic portions.

Figure 57C:
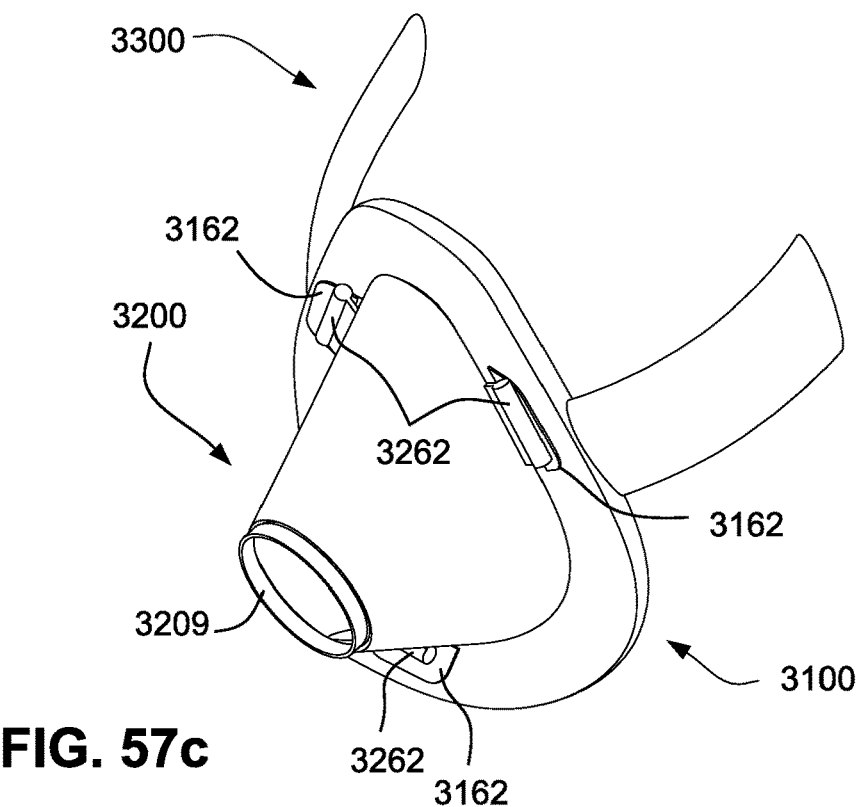

FIG. 57c shows a perspective view of the patient interface of FIG. 56a. The plenum chamber is partially coupled to the seal-forming structure and the latches remain in the rest position.

Figure 57D:
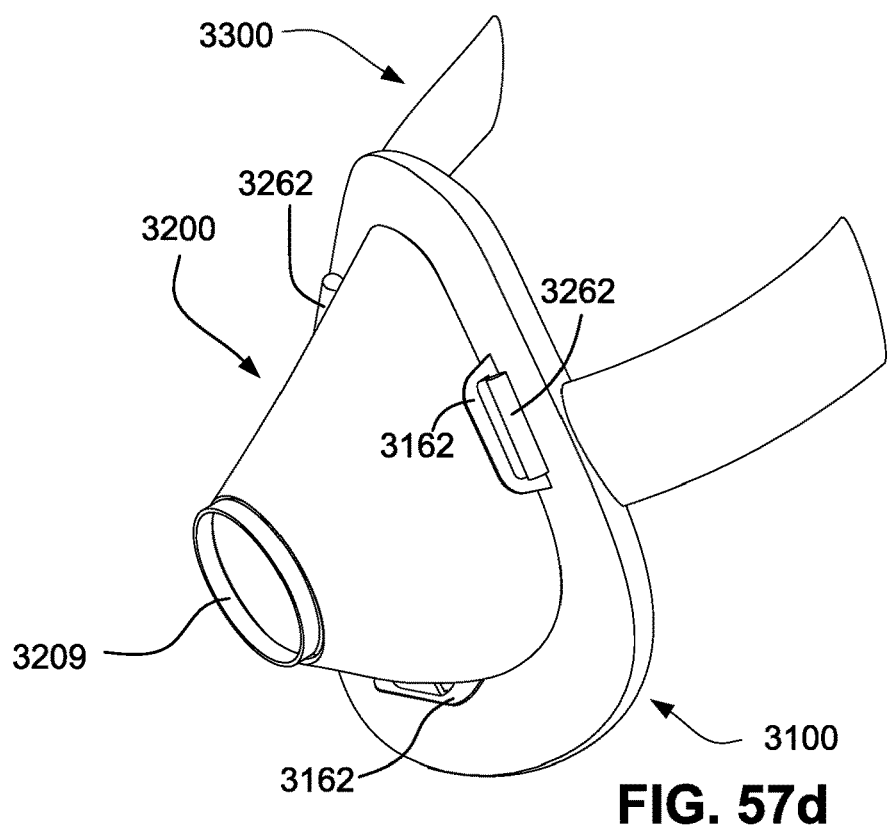

FIG. 57d shows a perspective view of the patient interface of FIG. 56a. The plenum chamber is fully coupled to the seal-forming structure and the latches are engaged with the projections.

FIG. 57e shows a perspective view of the patient interface of FIG. 56b. The plenum chamber is fully coupled to the seal-forming structure and the undercut is engaged with the overhang.

FIG. 57f is a cross-sectional view of the patient interface of FIG. 57e.

FIG. 57g shows a perspective view of the patient interface of FIG. 56d. The plenum chamber is positioned partially within the opening of the seal-forming structure in a sealing arrangement.

Figure 58:
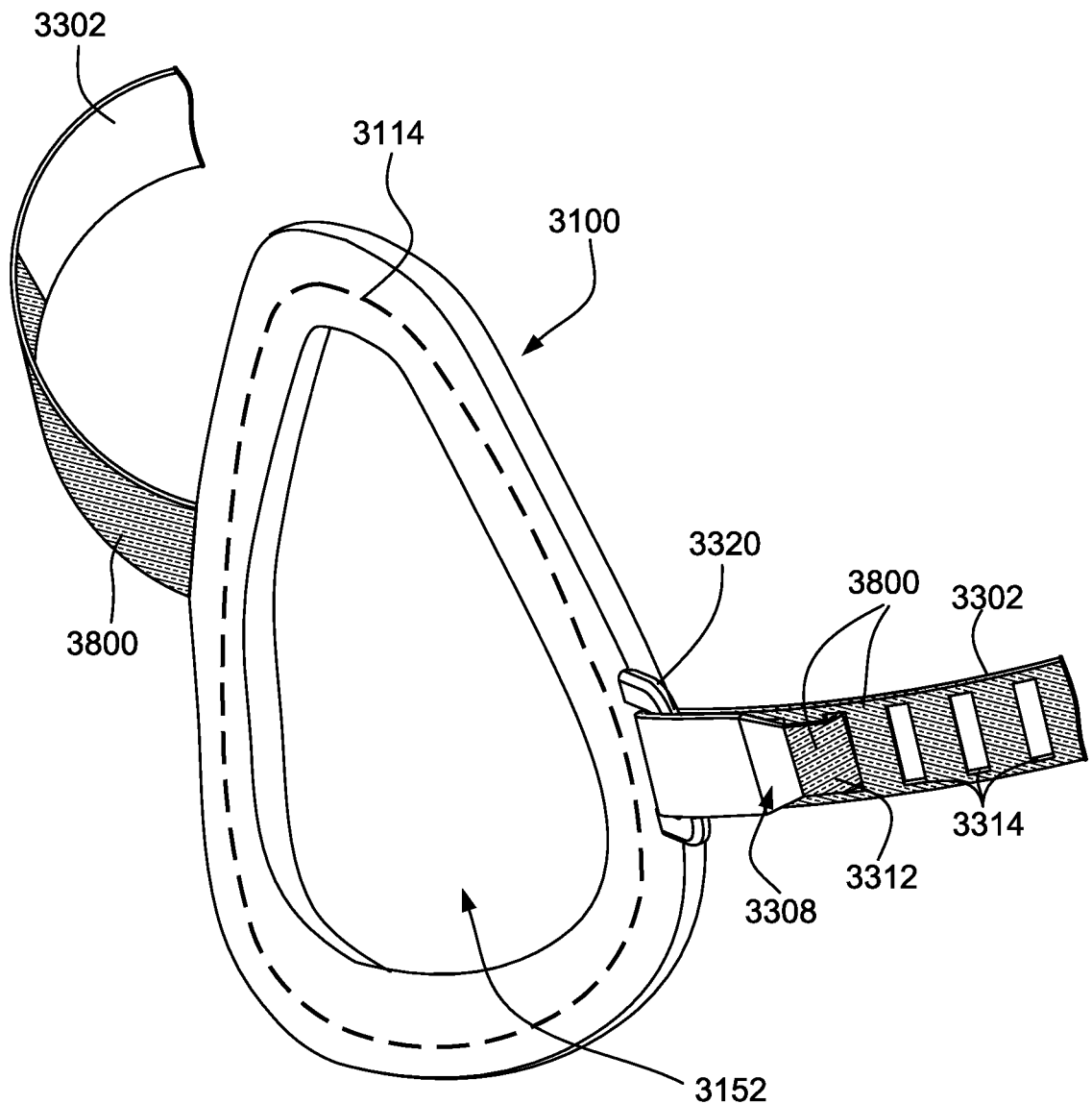

FIG. 58 shows a perspective view of a positioning and stabilizing structure coupled to a seal-forming structure. The positioning and stabilizing structure includes side straps, each with a hook and a plurality of loops. The side straps pass through the loop on the seal-forming structure, and doubles back on itself so the hook is received in one of the loops.

Figure 59:
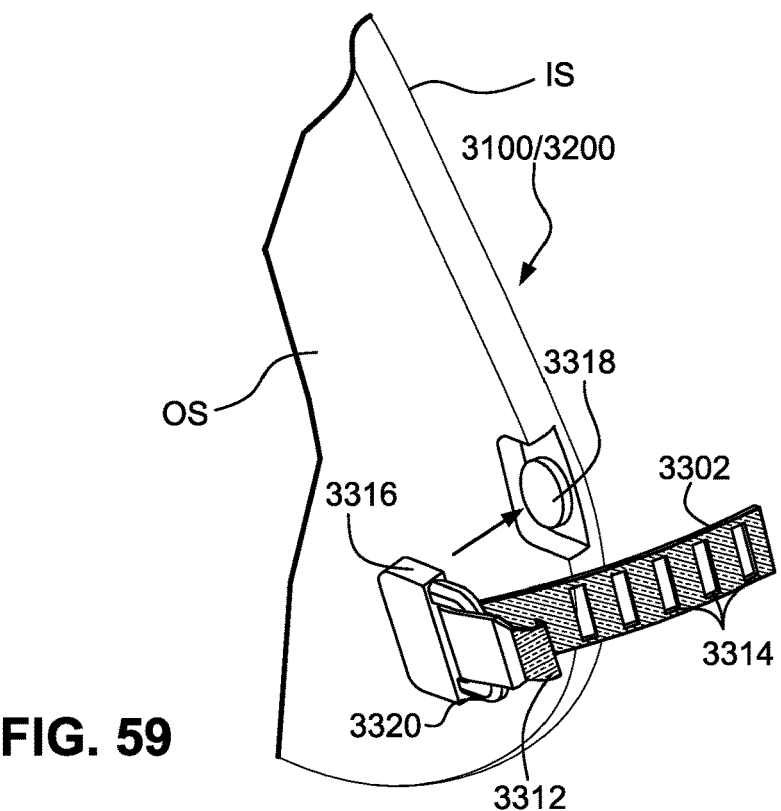

FIG. 59 shows a perspective view of a positioning and stabilizing structure that includes a side strap formed as ties, each with a hook and a plurality of loops. The tie passes through the loop on a removable magnetic section. The removable magnetic section is configured to couple to a magnetic section on either the seal-forming structure or the plenum chamber.

Figure 60:
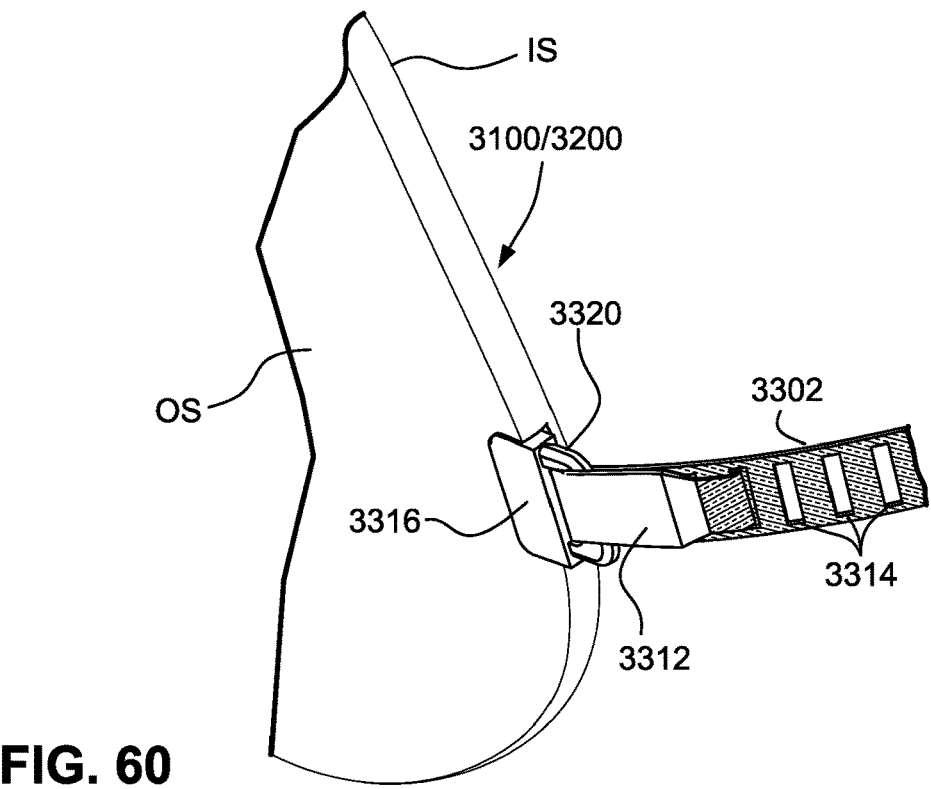

FIG. 60 shows a perspective view of the positioning and stabilizing structure of FIG. 59, with the removable magnetic section coupled to the magnetic section of either the seal-forming structure or the plenum chamber.

Figure 61:
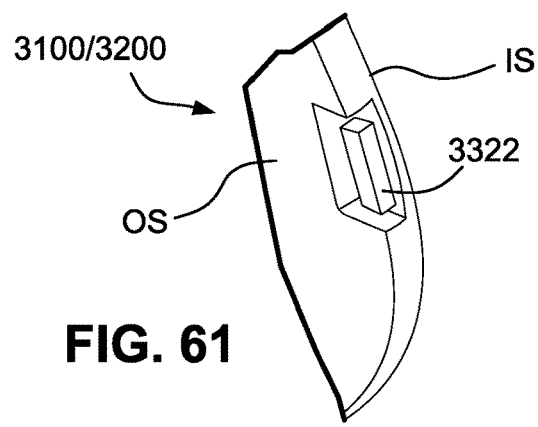

FIG. 61 shows a detail view of a projection of a seal-forming structure or a plenum chamber.

Figure 62:
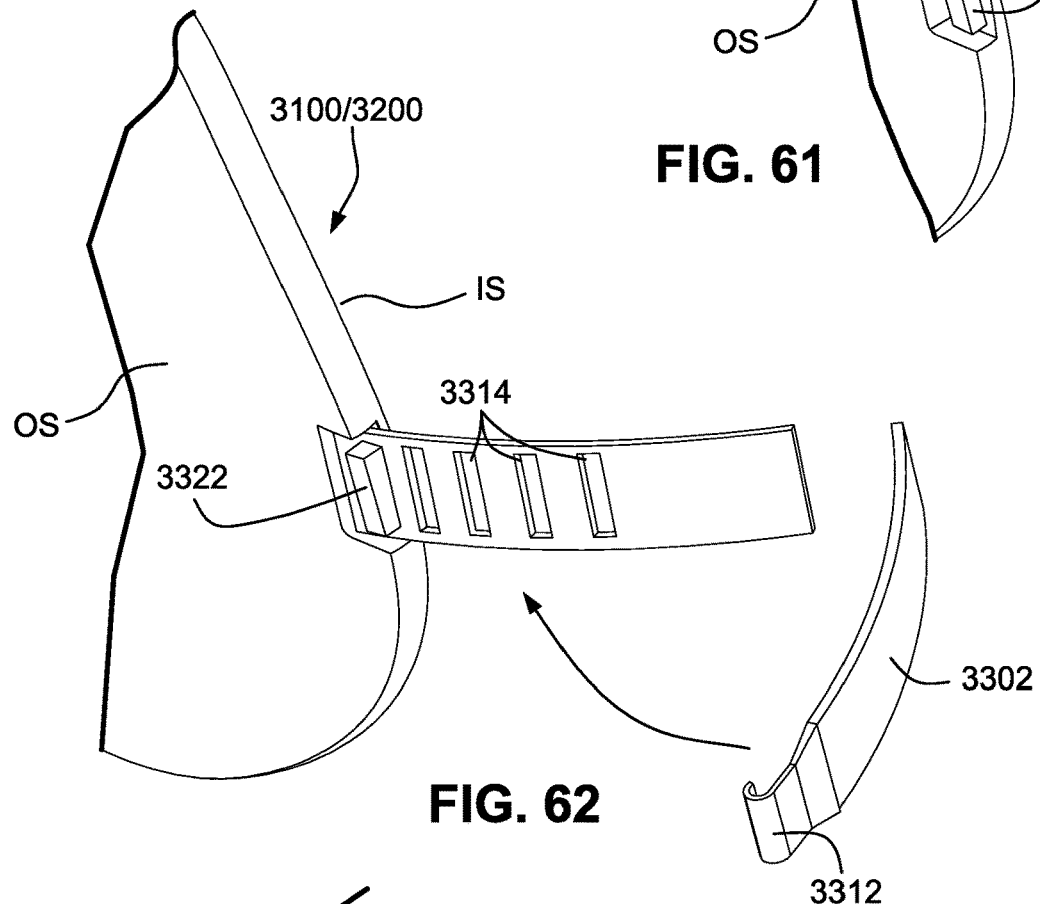

FIG. 62 shows a detail view of the projection of FIG. 61. A side strap of a positioning and stabilizing structure includes a plurality of loops at one end and a hook at the opposite end. One loops of the plurality of loops is positioned around the projection in order to couple the positioning and stabilizing structure to the seal-forming structure or the plenum chamber.

Figure 63:
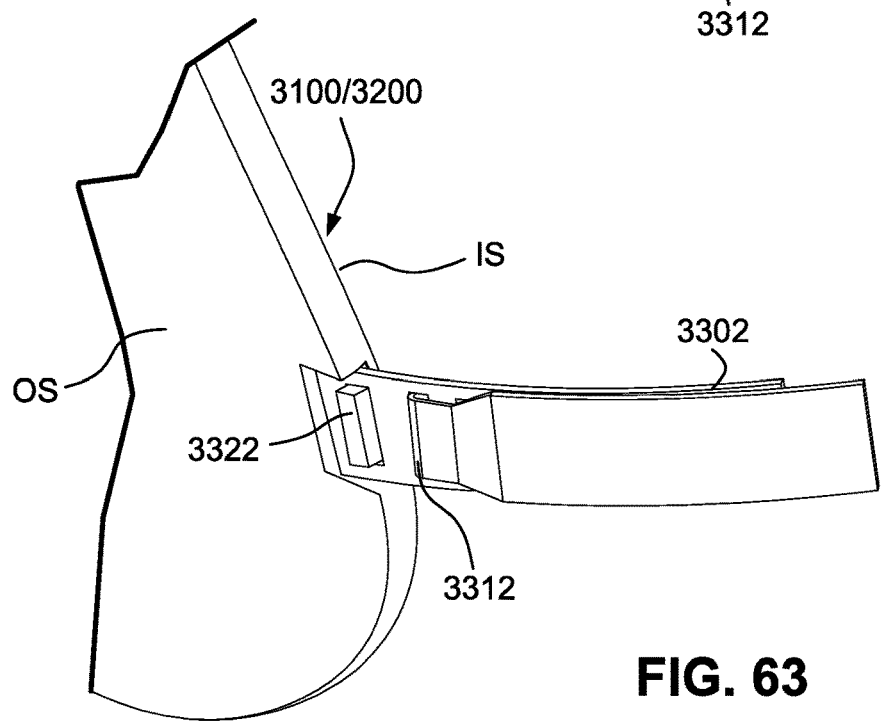

FIG. 63 shows a detail view of the projection and side strap of FIG. 62. The hook is doubled back on the side strap and is positioned in one of the loops in order to tighten the side strap against a patient's head.

FIG. 64 shows a perspective view of a patient interface. A plenum chamber is coupled to the seal-forming structure. The plenum chamber includes a flap that is biased to an open position in order to provide fluid communication through the plenum chamber. A positioning and stabilizing structure is made of hollow tubes that are configured to convey air toward the seal-forming structure. A decoupling structure is configured to connect to either the plenum chamber or the positioning and stabilizing structure in order to provide pressurized airflow to the seal-forming structure.

FIG. 65 shows a detail view of the patient interface of FIG. 64. The decoupling structure is coupled to the positioning and stabilizing structure, and is configured to provide pressurized airflow to the seal-forming structure through the hollow tubes.

FIG. 66 shows a perspective view of FIG. 65 with the decoupling structure coupled to the positioning and stabilizing structure. Flaps of the positioning and stabilizing structure are remain in an open position, even when the airflow is provided through the decoupling structure.

Figure 67:
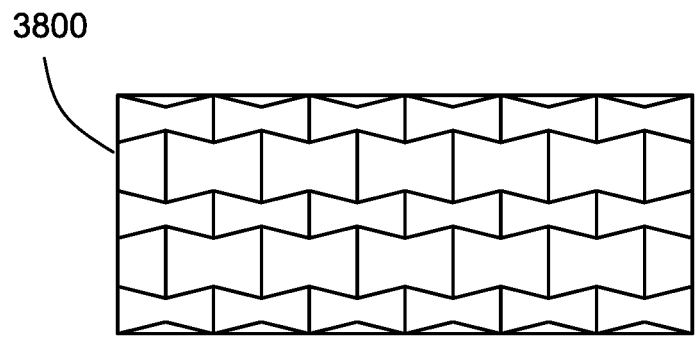

FIG. 67 shows a schematic view of auxetic material in an unstressed position.

Figure 68:
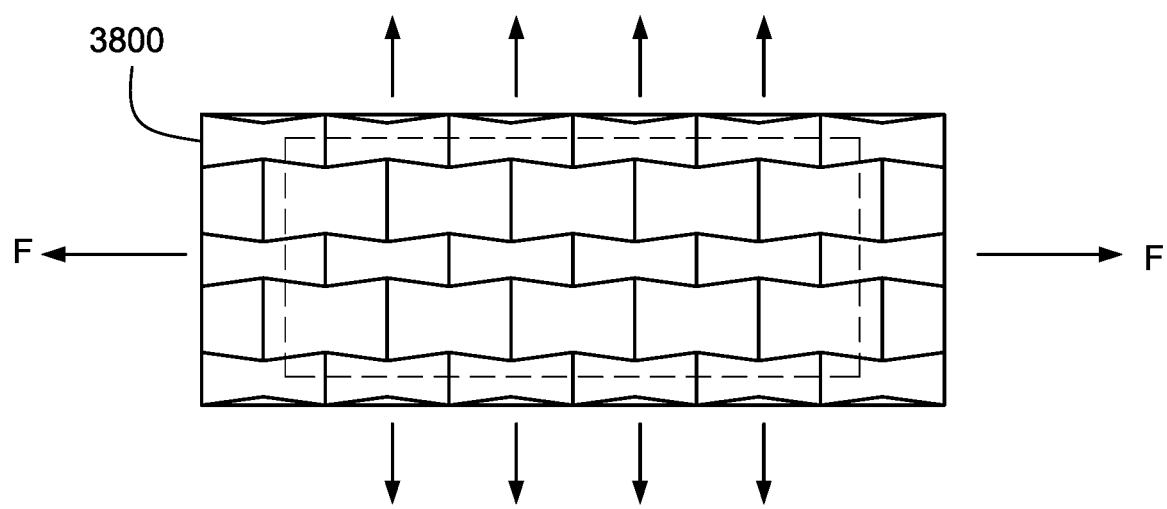

FIG. 68 shows a schematic view of the auxetic material of FIG. 67 in a stressed position. A tensile force is provided along the length of the auxetic material, and the auxetic material expands along its width.

Figures 69, 70, 71:
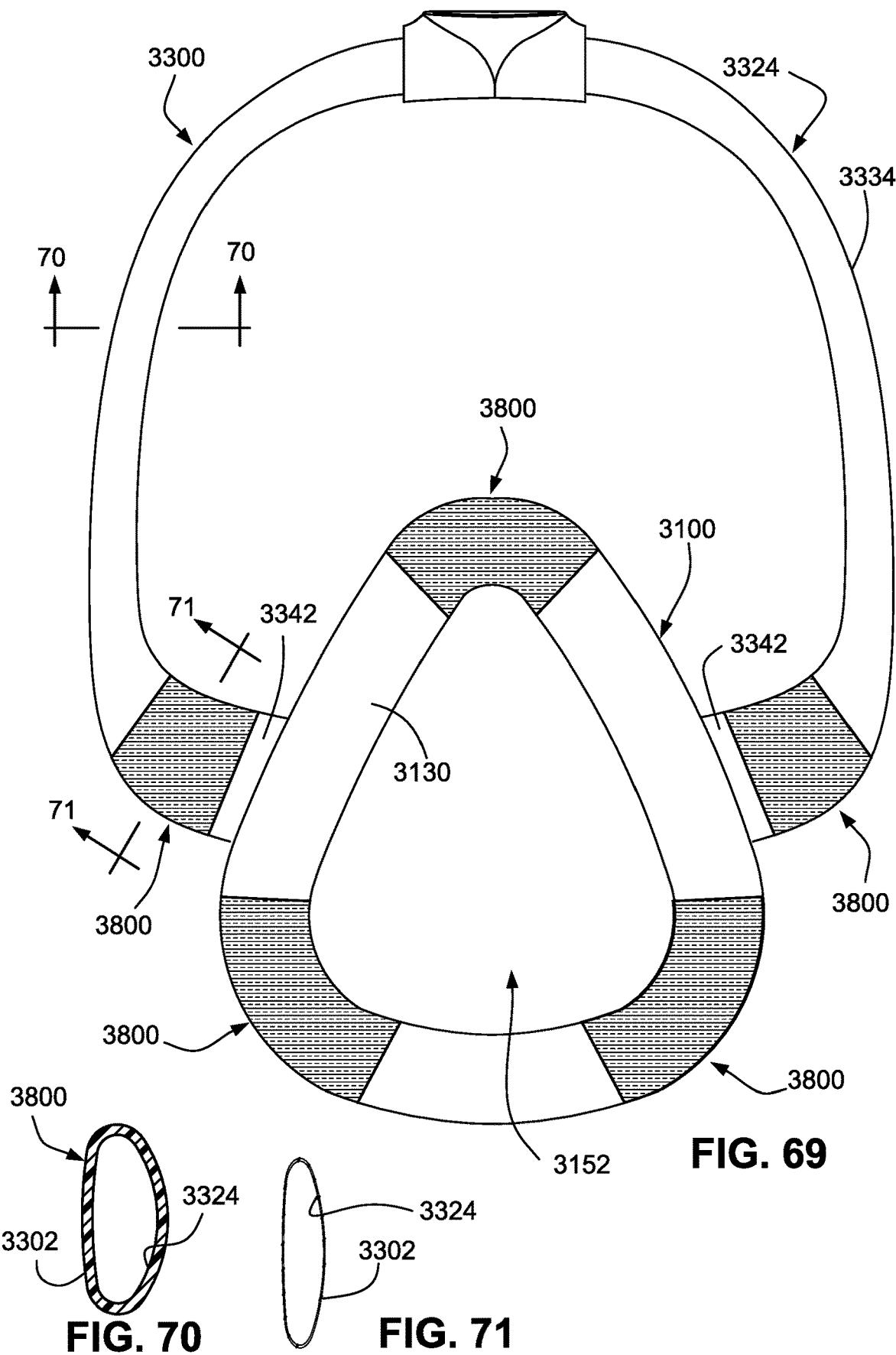

FIG. 69 shows a rear view of a patient interface that includes adaptive materials, which may include auxetic materials, moisture swellable materials, and/or heat activated materials. The adaptive materials are provided in a variety of locations around the patient interface. Multiple types of adaptive materials are used in different locations depending on specific requirements.

FIG. 70 shows a cross-sectional view of the patient interface of FIG. 69 viewed along line 70-70. The portion of the hollow tube is made of fabric and lined with an impermeable layer.

FIG. 71 shows a cross-sectional view of the patient interface of FIG. 69 viewed along line 71-71. The portion of the hollow tube is made of fabric and lined with an impermeable layer. An adaptive material, like auxetic material, is disposed between the fabric layer and the impermeable layer in order to impart adaptive properties on the hollow tube.

Figure 72:
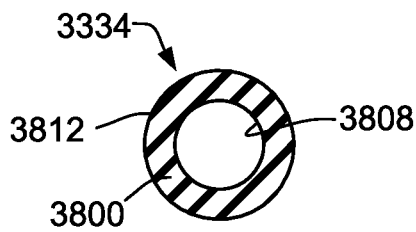

FIG. 72 shows a cross-sectional view of a hollow tube having an inner rigid layer, an outer flexible layer, and an adaptive material sandwiched in between. The adaptive material is in a relaxed position.

Figure 73:
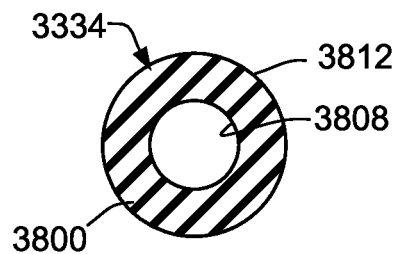

FIG. 73 shows a cross-section view of the hollow tube of FIG. 72 with the adaptive material in a stressed position. The rigid inner layer blocks inward expansion of the adaptive material, and maintains the inner diameter of the hollow tube. The flexible outer layer allows the adaptive layer to expand in some or all directions so that the outer diameter hollow tube is greater in the stressed position than in the relaxed position. This configuration is particularly useful in places where airflow is provided in order to not restrict the flow of air.

Figure 74:
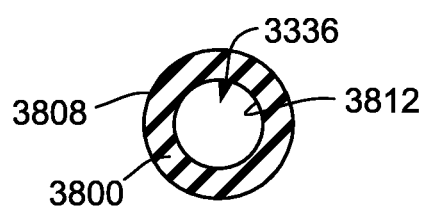

FIG. 74 shows a cross-sectional view of a hollow tube having an outer rigid layer, an inner flexible layer, and an adaptive material sandwiched in between. The adaptive material is in a relaxed position.

Figure 75:
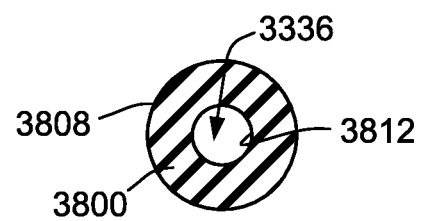

FIG. 75 shows a cross-section view of the hollow tube of FIG. 74 with the adaptive material in a stressed position. The rigid outer layer blocks outward expansion of the adaptive material, and maintains the outer diameter of the hollow tube. The flexible inner layer allows the adaptive layer to expand in some or all directions so that the inner diameter hollow tube is less in the stressed position than in the relaxed position. This configuration is particularly useful in places where the decoupling structure and/or plug is received in order to provide a better seal.

Figure 76:
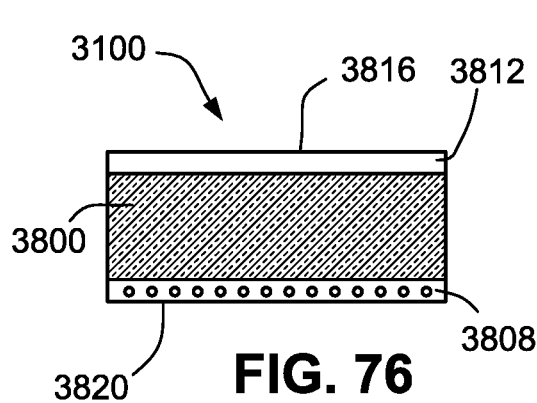

FIG. 76 shows a cross-sectional view of a seal-forming structure in a relaxed position.

Figure 77:
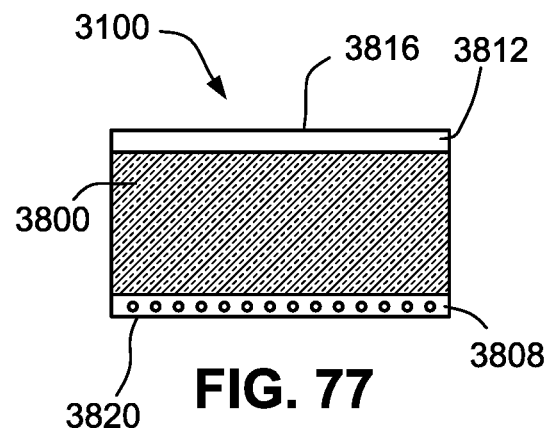

FIG. 77 shows a cross-sectional view of the seal-forming structure of FIG. 76 in a stressed position. An adaptive section of the seal-forming structure has expanded as a result in a change in conditions. A rigid section of the seal-forming structure directs the expansion on the adaptive section in one direction.

Figure 78:
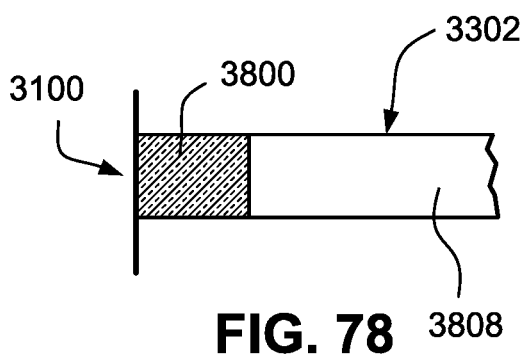

FIG. 78 shows a cross-sectional view of a strap of a positioning and stabilizing structure coupled to a seal-forming structure. The strap is in a relaxed position.

Figure 79:
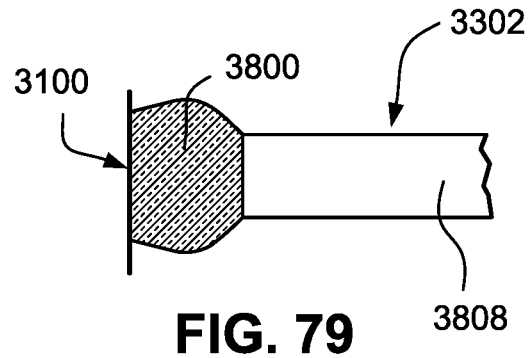

FIG. 79 shows a cross-sectional view of the strap of FIG. 78 in a stressed position. An adaptive section of the strap has expanded as a result in a change in conditions. A rigid section of the strap remains substantially the same length.

Figure 80:
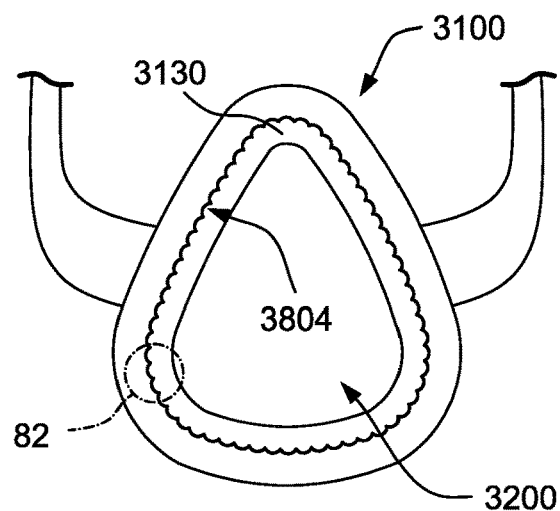

FIG. 80 shows a seal-forming structure with bellows along an inner surface. The bellows are in a relaxed position.

Figure 81:
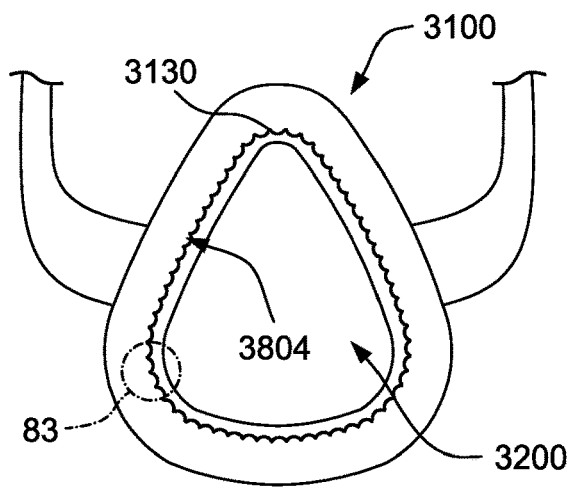

FIG. 81 shows the seal-forming structure of FIG. 80 with the bellows in a stressed position. The inner surface is closer to the patient's face and forms a better seal.

Figure 82:
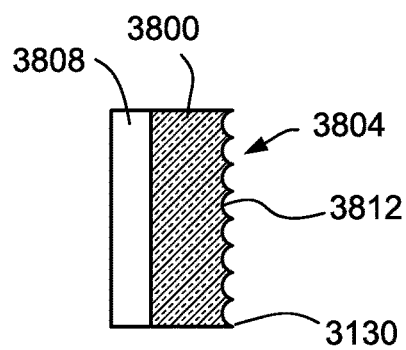

FIG. 82 shows a cross-sectional view of the seal-forming structure of FIG. 80. The bellows are made up of a rigid material, an adaptive material, and a textile material. The textile material in on the inner surface of the seal-forming structure.

Figure 83:
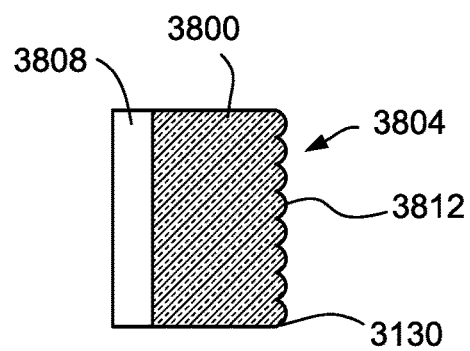

FIG. 83 shows a cross-sectional view of the seal-forming structure of FIG. 81. The adaptive material has expanded based on a change in conditions, which caused the bellows to expand.

Figure 84:
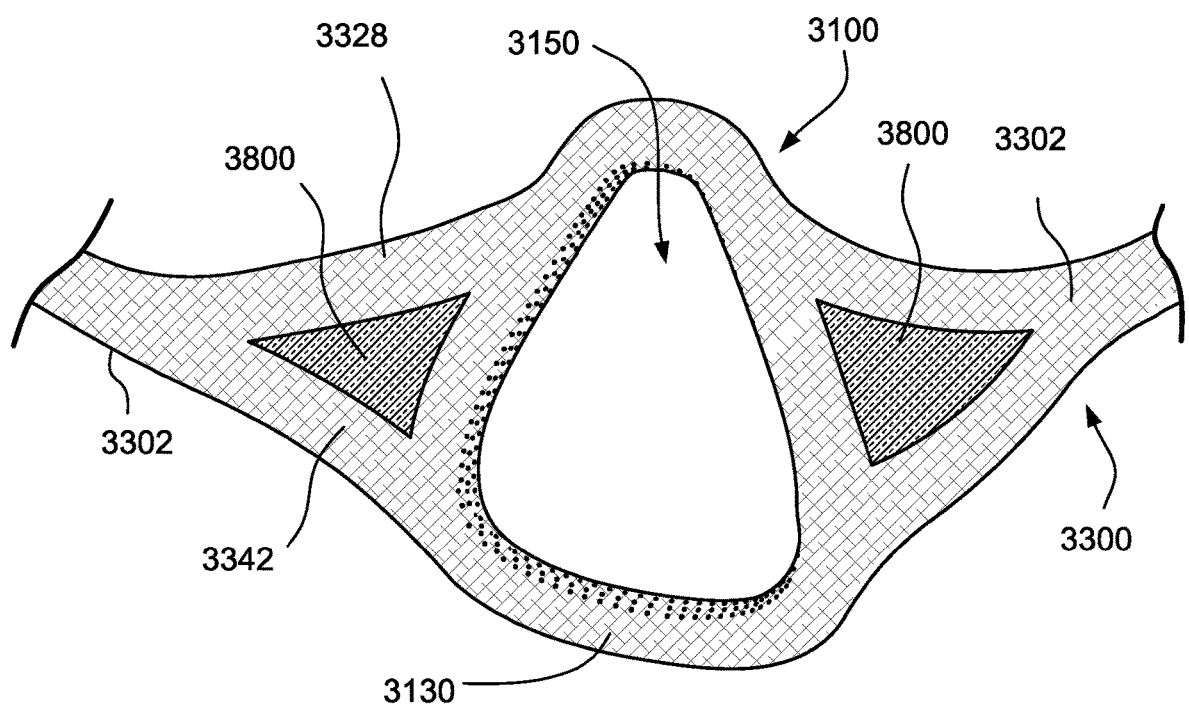

FIG. 84 shows a one piece fabric construction used to make a seal-forming structure and position and stabilizing structure. The positioning and stabilizing structure bifurcates from the seal-forming structure. An adaptive material is formed between the bifurcations.

Figure 85:
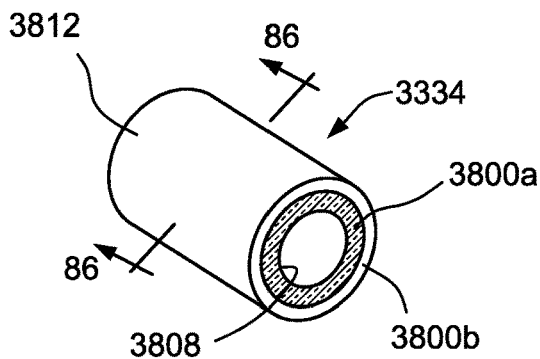

FIG. 85 shows a perspective view of a hollow tube to be used in a patient interface. The hollow tube includes a first adaptive material and a second adaptive material, both in a relaxed position.

Figure 86:
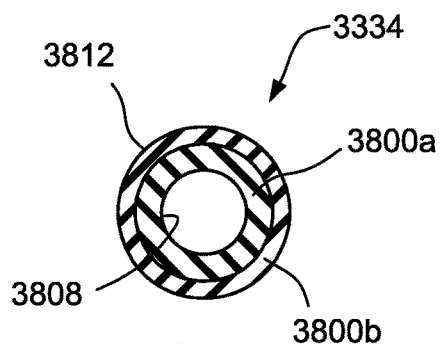

FIG. 86 shows a cross-sectional view of the hollow tube of FIG. 85, viewed along section 86-86.

Figure 87:
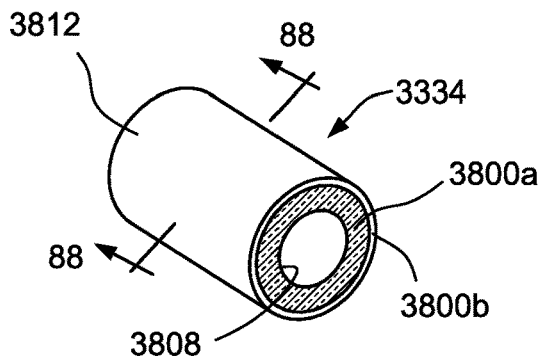

FIG. 87 shows a perspective view of the hollow tube of FIG. 85 with a force of tension applied. The first adaptive material is in an expanded position and the second adaptive material is in the relaxed position.

Figure 88:
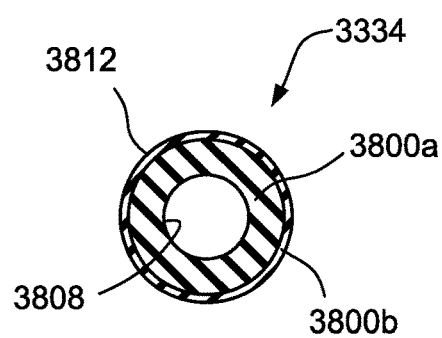

FIG. 88 shows a cross-sectional view of the hollow tube of FIG. 87, viewed along section 88-88.

Figure 89:
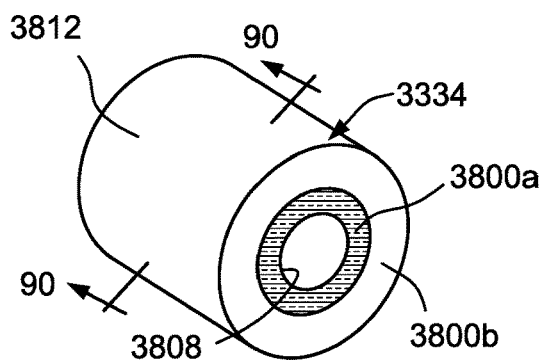

FIG. 89 shows a perspective view of the hollow tube of FIG. 85 with a force of tension applied. The first adaptive material and the second adaptive material are in the expanded position.

Figure 90:
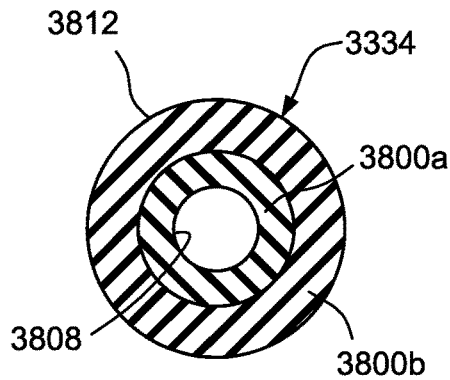

FIG. 90 shows a cross-sectional view of the hollow tube of FIG. 89, viewed along section 90-90.

Figure 91:
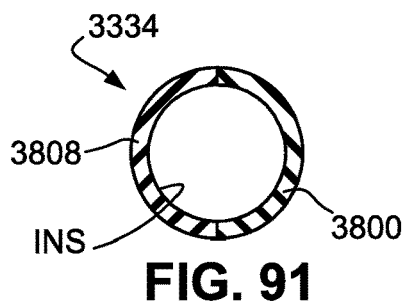

FIG. 91 shows a cross-sectional view of a hollow tube of another embodiment in a relaxed state. A portion made from an adaptive material and a portion made from another material.

Figure 92:
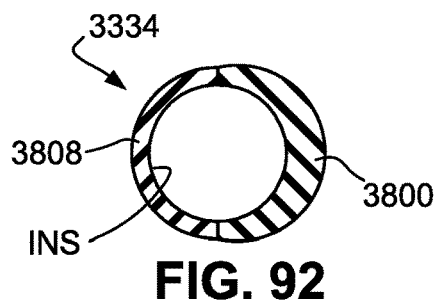

FIG. 92 shows a cross-sectional view of a hollow tube of another embodiment in an expanded state.

Figure 93:
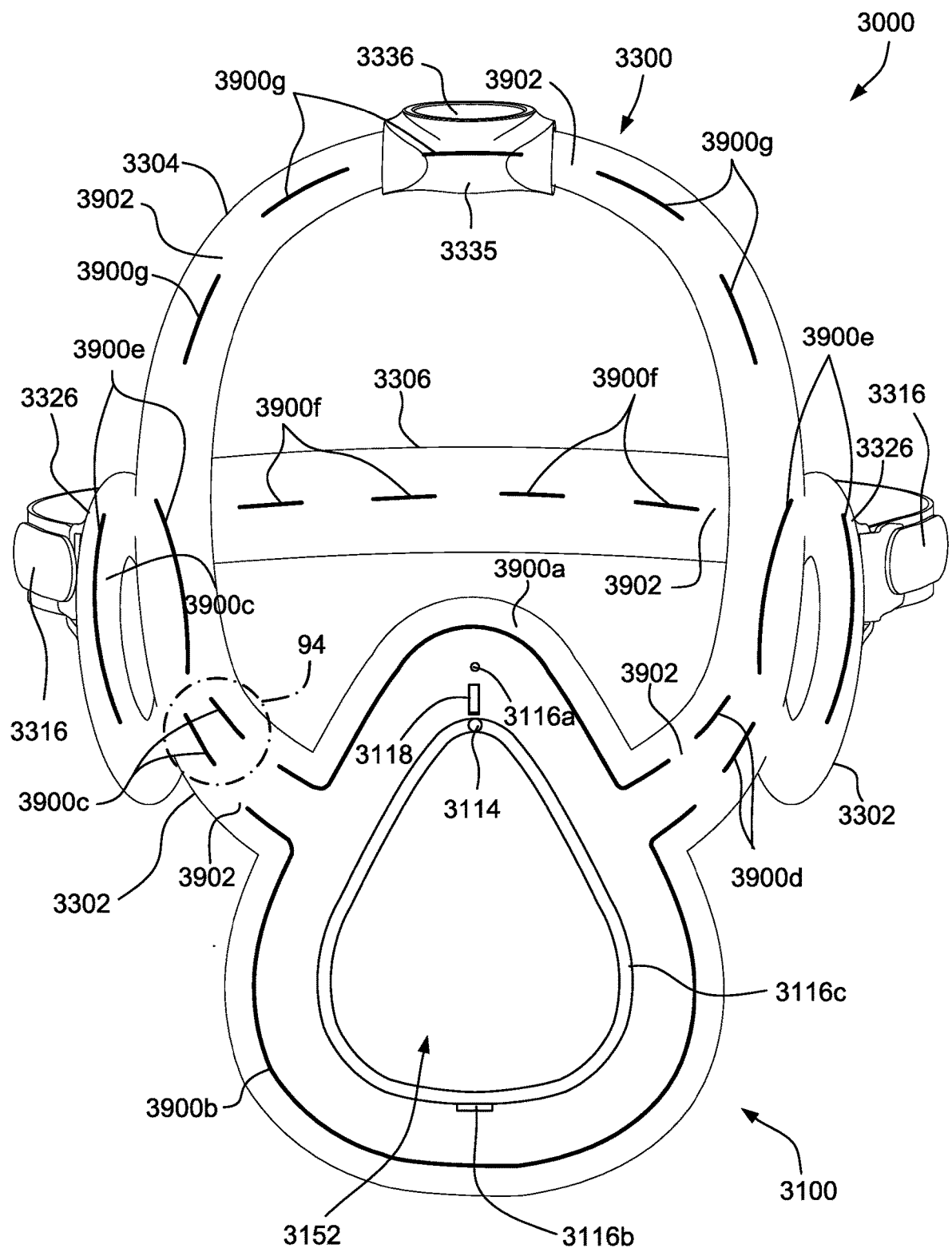

FIG. 93 shows a schematic view of stiffened portions positioned at various locations on a patient interface.

Figure 94:
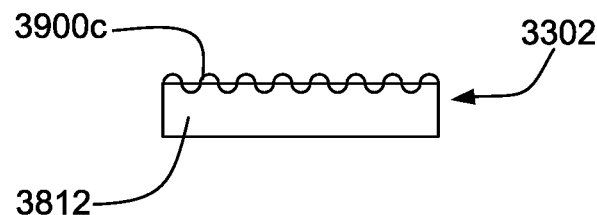

FIG. 94 shows a detail view of the stiffened portions of FIG. 93, illustrating the stiffened portions as textile threads sewn into the patient interface.

Figure 95:
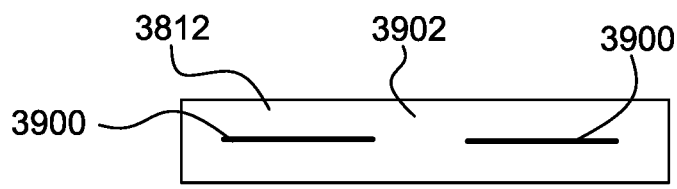

FIG. 95 shows a schematic view of a textile material in an unstressed position, with a pair of stiffened portions coupled to the textile material.

Figure 96:
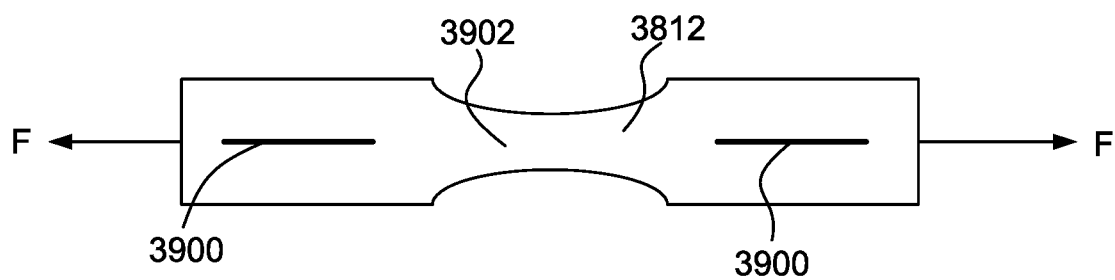

FIG. 96 shows a schematic view of the textile material of FIG. 95 in a stressed position, where the sections with stiffened portions do not deform and sections without stiffened portions deform.

Figure 97:
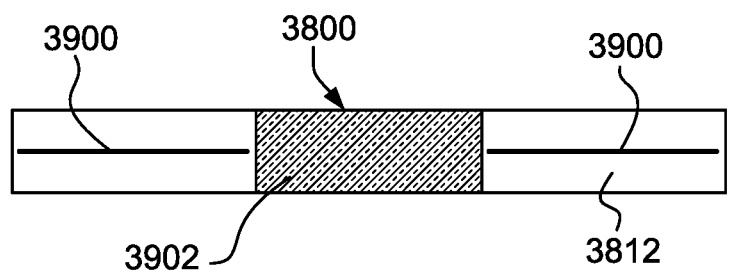

FIG. 97 shows a schematic view of a textile material in an unstressed position, with an adaptive material positioned between a pair of stiffened portions.

Figure 98:
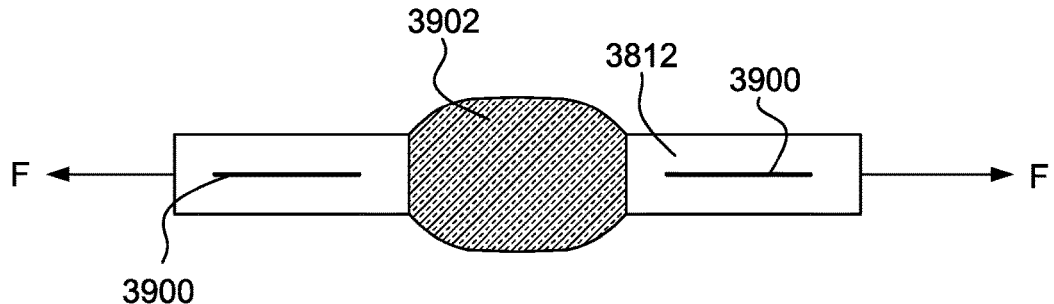

FIG. 98 shows a schematic view of the textile material of FIG. 97 in a stressed position, where the sections with stiffened portions do not deform and sections with the adaptive material deform.

Figure 99:
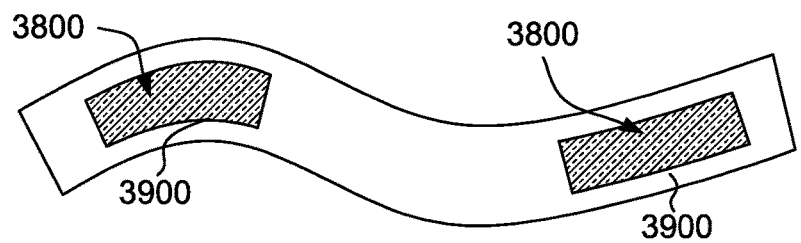

FIG. 99 shows a schematic view of a textile material in an unstressed position, with a pair of stiffened portions having adaptive properties.

Figure 100A:
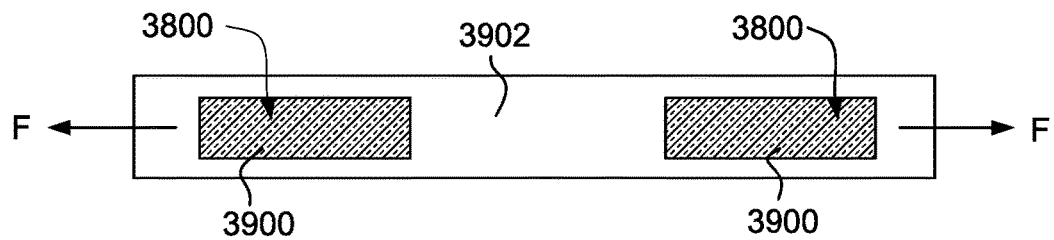

FIG. 100*a* shows a schematic view of the textile material of FIG. 99 in a first stressed position, where the stiffened portions expand and the textile material does not deform.

Figure 100B:
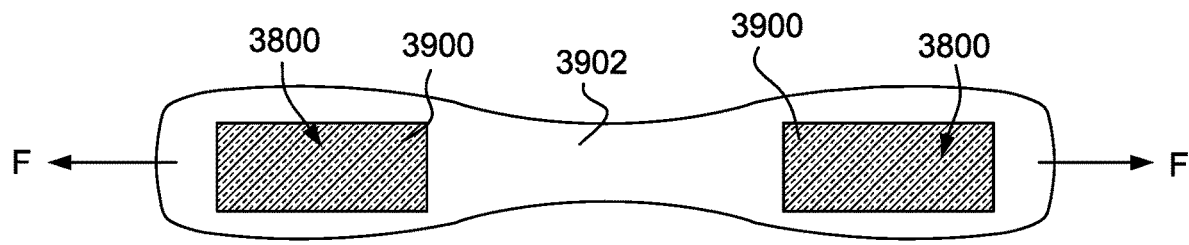

FIG. 100*b* shows a schematic view of the textile material of FIG. 99 in a second stressed position, where the stiffened portions are fully expanded and the textile material is deformed.

FIG. 101*a* shows a flow diagram illustrating a first method of selectively stiffening portions of the patient interface of FIG. 93.

FIG. 101*b* shows a flow diagram illustrating a second method of selectively stiffening portions of the patient interface of FIG. 93.

FIG. 101*c* shows a flow diagram illustrating a third method of selectively stiffening portions of the patient interface of FIG. 93.

Figure 102A:
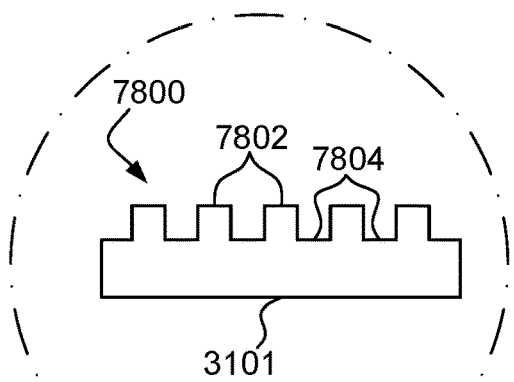

FIG. 102*a* is a detail view of the patient interface of FIG. 50-1, illustrating a rough surface.

Figure 102B:
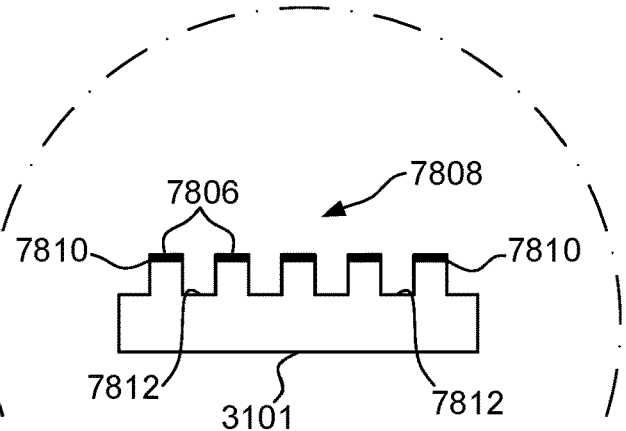

FIG. 102*b* is a detail view of the patient interface of FIG. 50-1, illustrating a rough surface having a surface infused with particles.

Figure 102C:
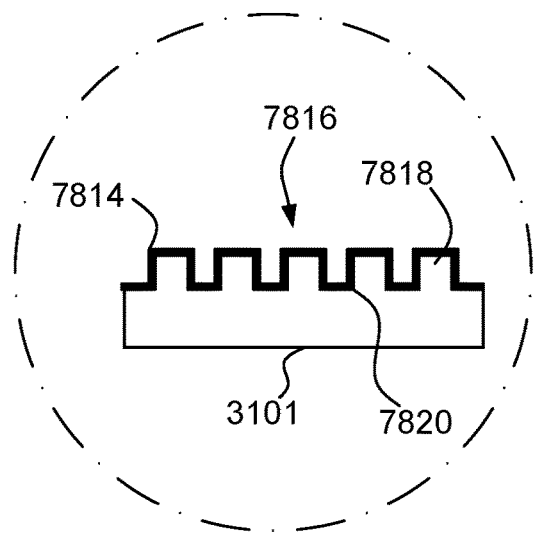

FIG. 102*c* is a detail view of the patient interface of FIG. 50-1, illustrated a rough surface coated with a material.

Figure 102D:
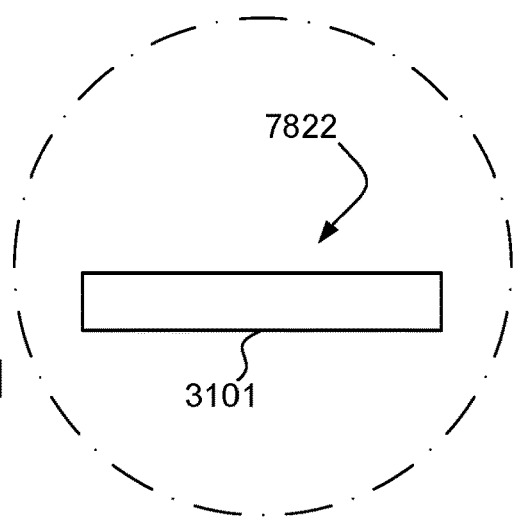

FIG. 102*d* is a detail view of the patient interface of FIG. 50-1, illustrating a smooth surface.

Figure 102E:
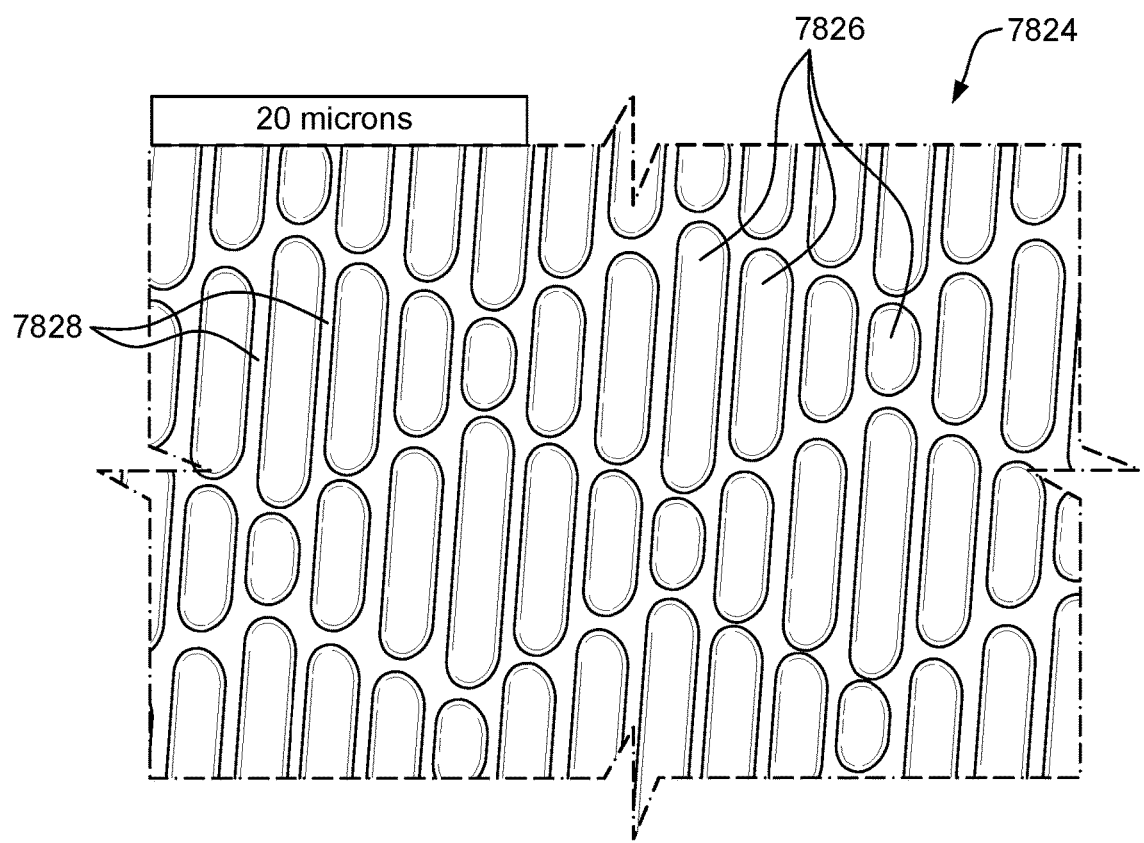

FIG. 102*e* is a detail view of the patient interface of FIG. 50-1, illustrating a rough surface with varying lengths.

Figure 102F:
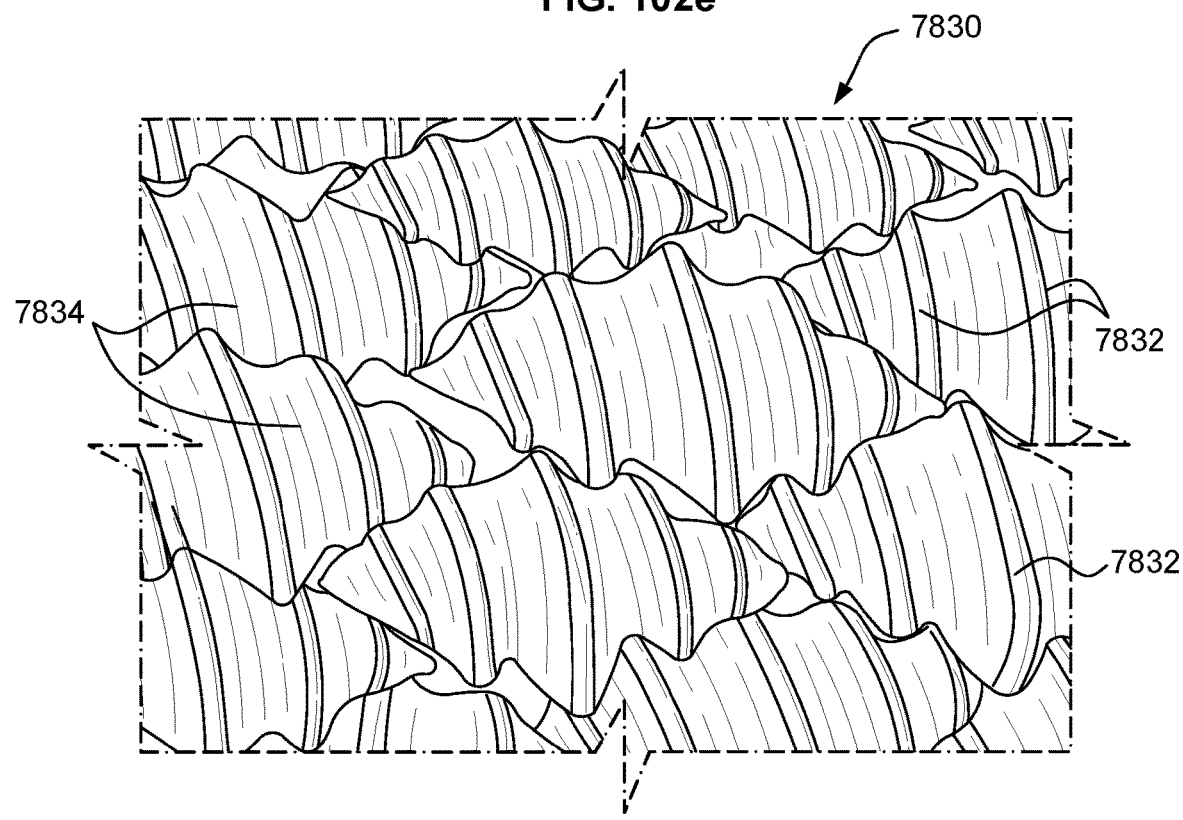

FIG. 102*f* is a detail view of the patient interface of FIG. 50-1, illustrating an overlapping rough surface.

Figure 103:
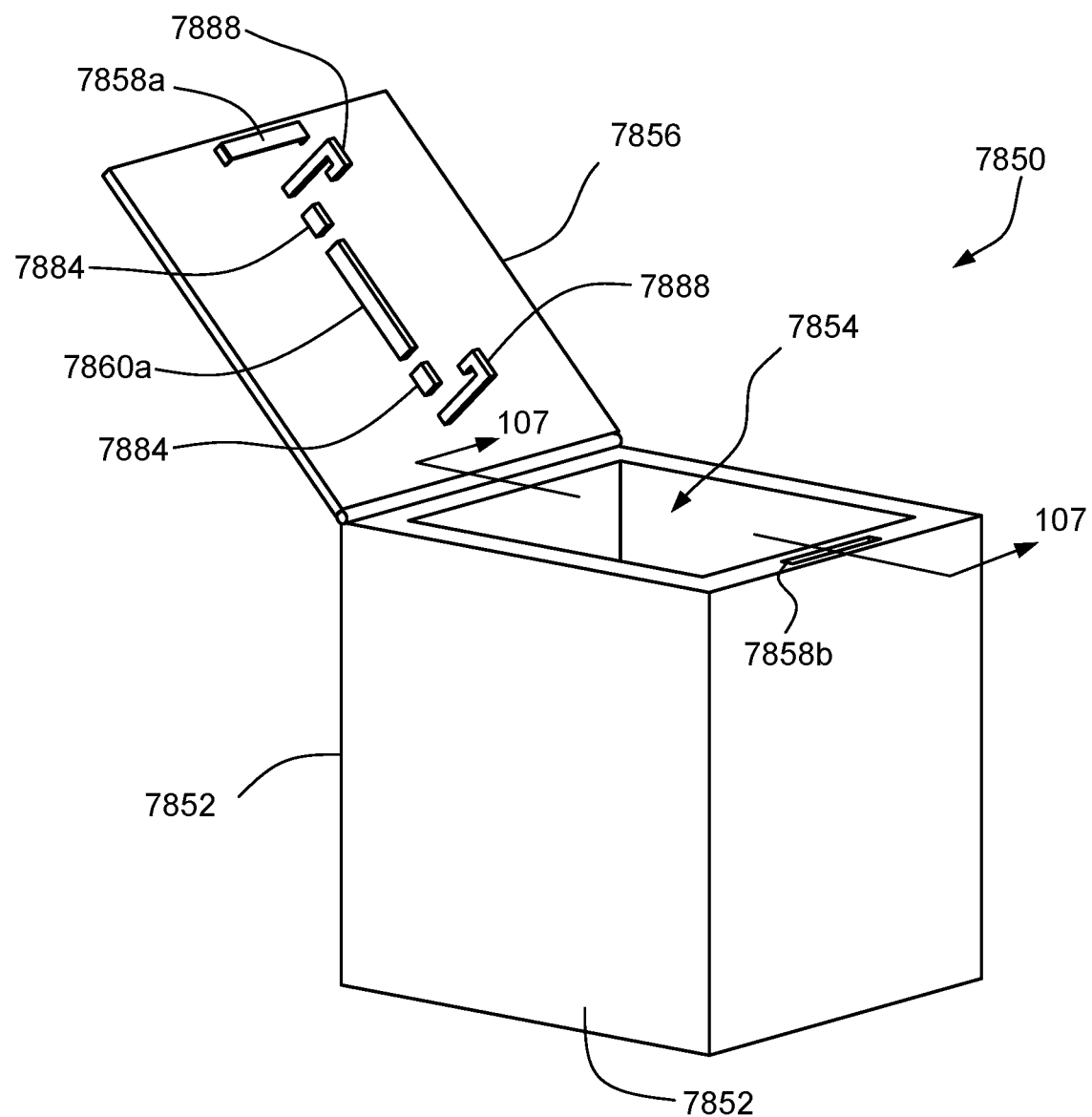

FIG. 103 is a perspective view of a cleaning box for cleaning the patient interface of FIG. 47*d*.

Figure 104:
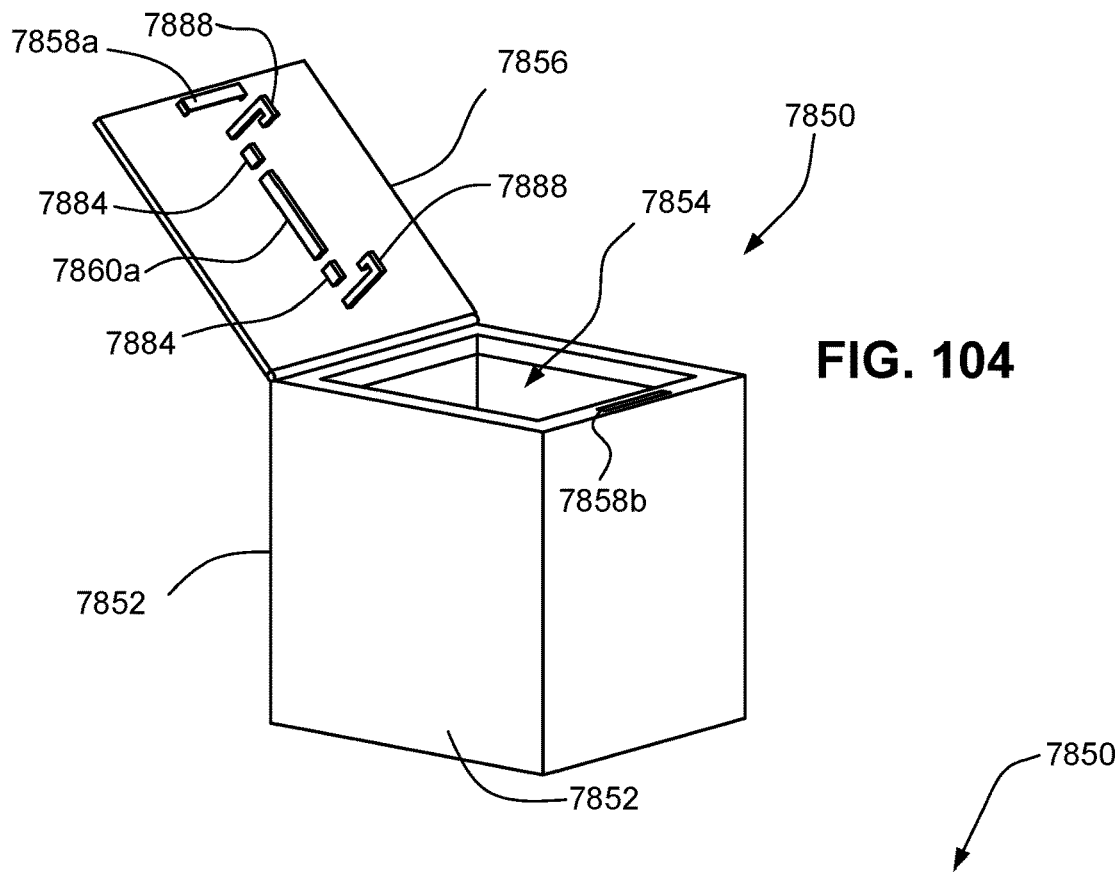

FIG. 104 is a detail view of the cleaning box of FIG. 103, illustrating a latching mechanism between a lid and a wall of the cleaning box.

Figure 105:
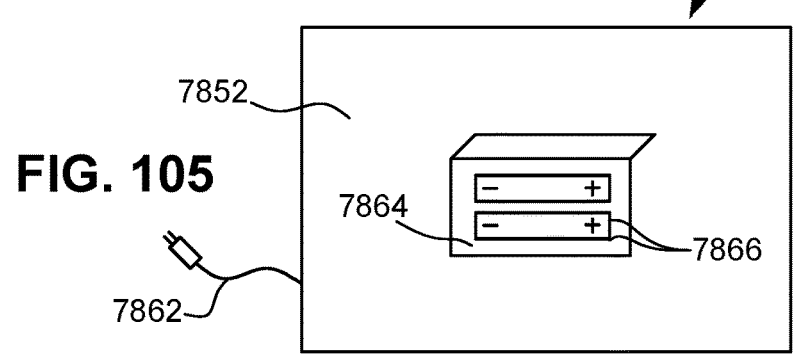

FIG. 105 is a bottom view of the cleaning box of FIG. 103, illustrating an electrical cord and battery compartment.

Figure 106:
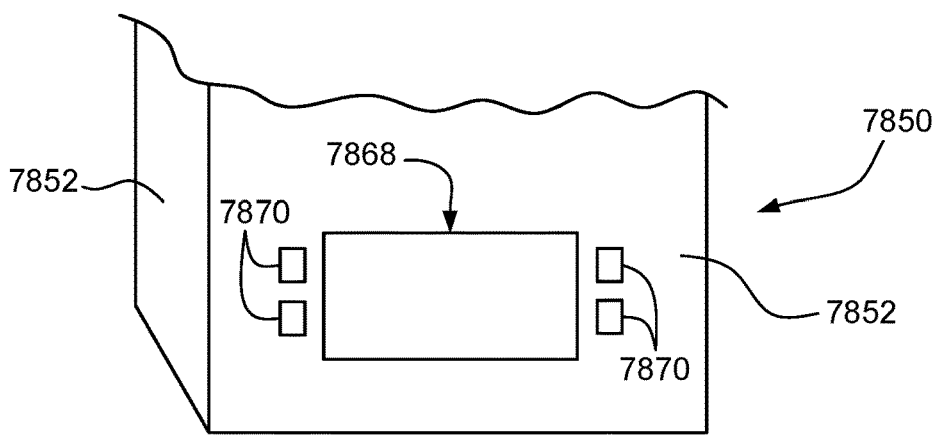

FIG. 106 is a detail view of the cleaning box of FIG. 103, illustrating a control on a wall of the cleaning box.

Figure 107:
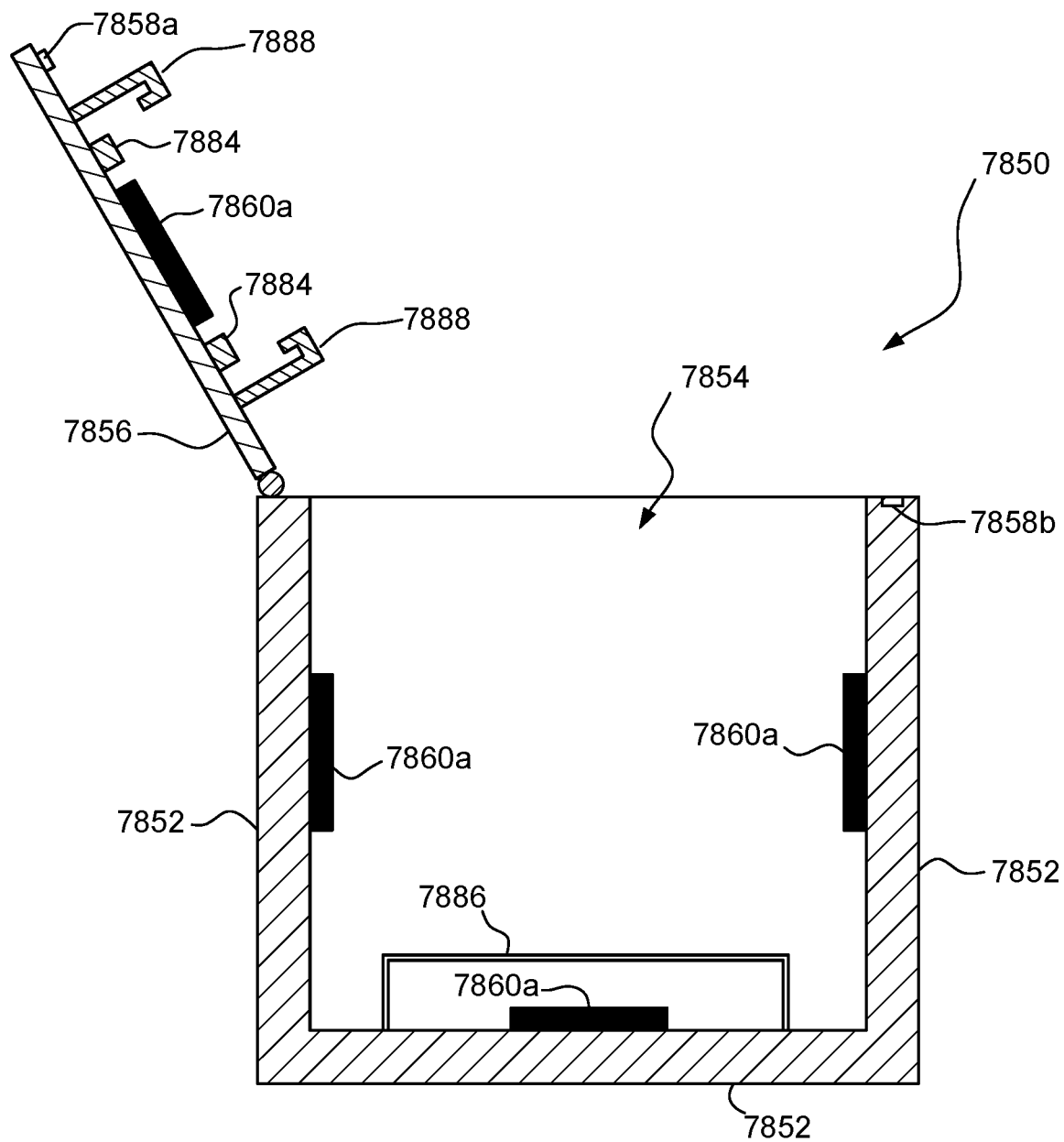

FIG. 107 is a cross-sectional view of the cleaning box of FIG. 103, viewed along line 107-107.

Figure 108:
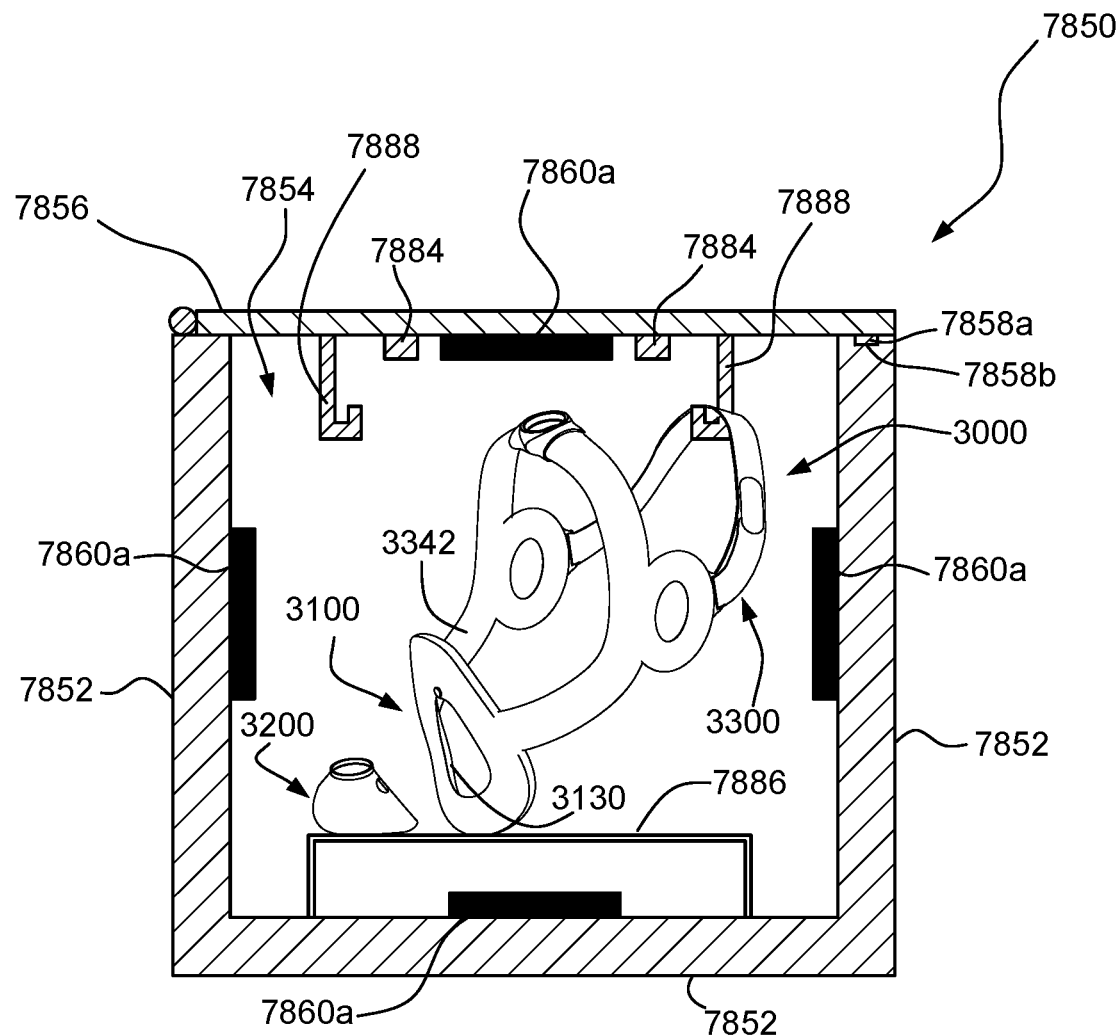

FIG. 108 is a cross-sectional view of the cleaning box of FIG. 103, housing the patient interface of FIG. 47*d* to be cleaned.

Figure 109:
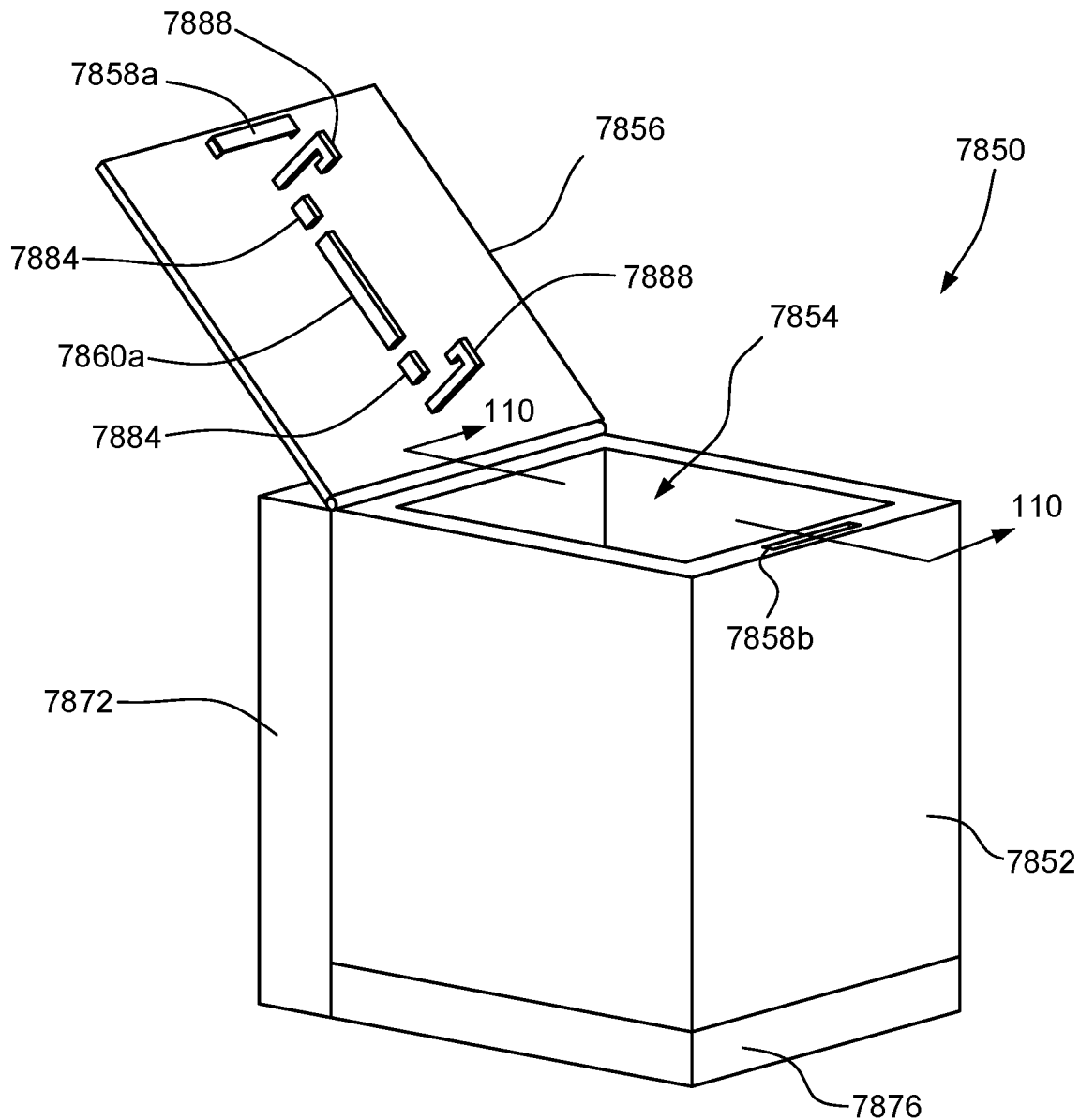

FIG. 109 is a perspective view of a cleaning box for cleaning the patient interface of FIG. 47*d* according to another embodiment.

Figure 110:
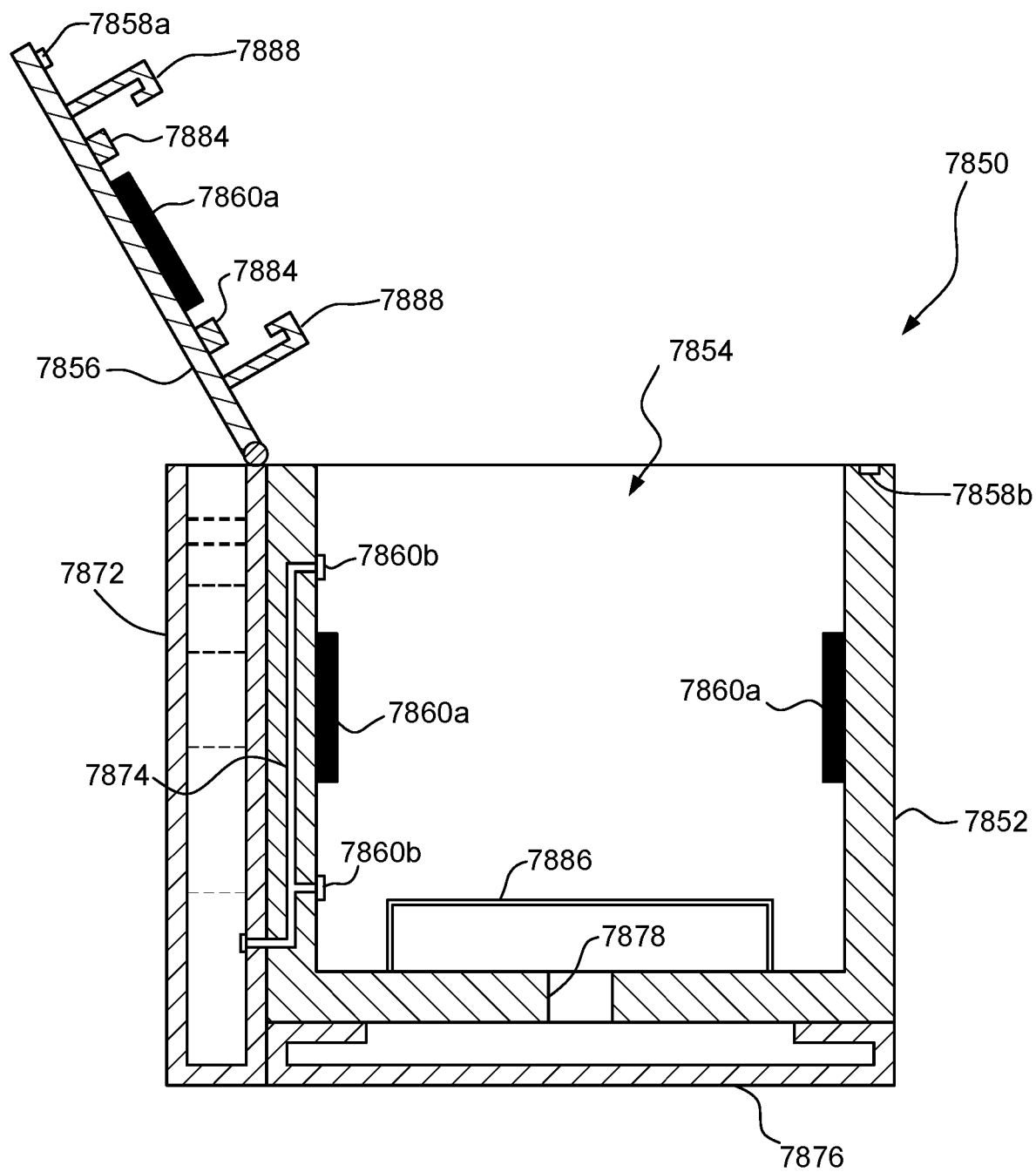

FIG. 110 is a cross-sectional view of the cleaning box of FIG. 109, viewed along line 110-110.

Figure 111:
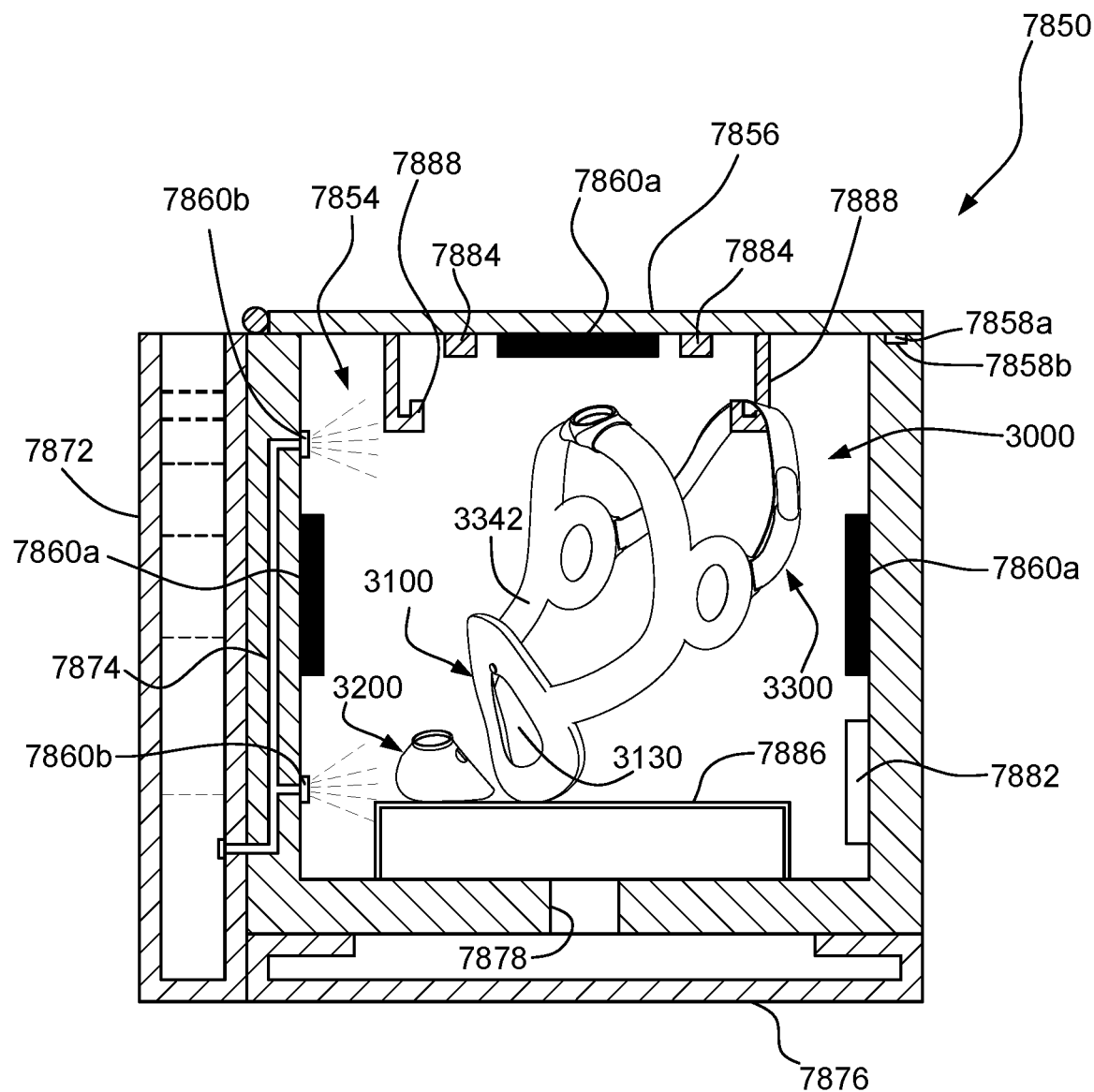

FIG. 111 is a cross-sectional view of the cleaning box of FIG. 109, housing the patient interface of FIG. 47*d* to be cleaned in a first orientation.

Figure 112:
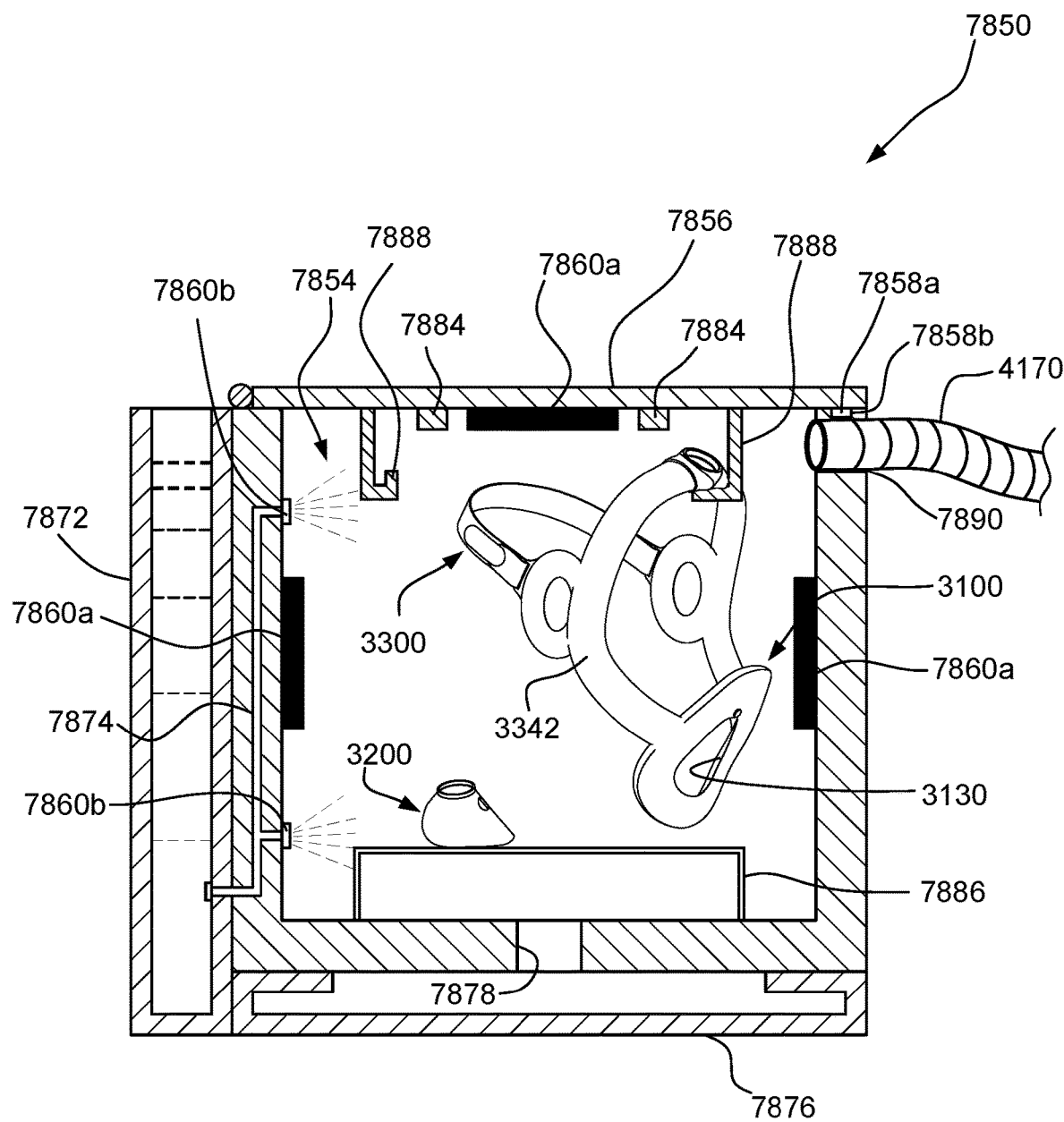

FIG. 112 is a cross-sectional view of the cleaning box of FIG. 109, housing the patient interface of FIG. 47*d* to be cleaned in a second orientation.

Figure 113:
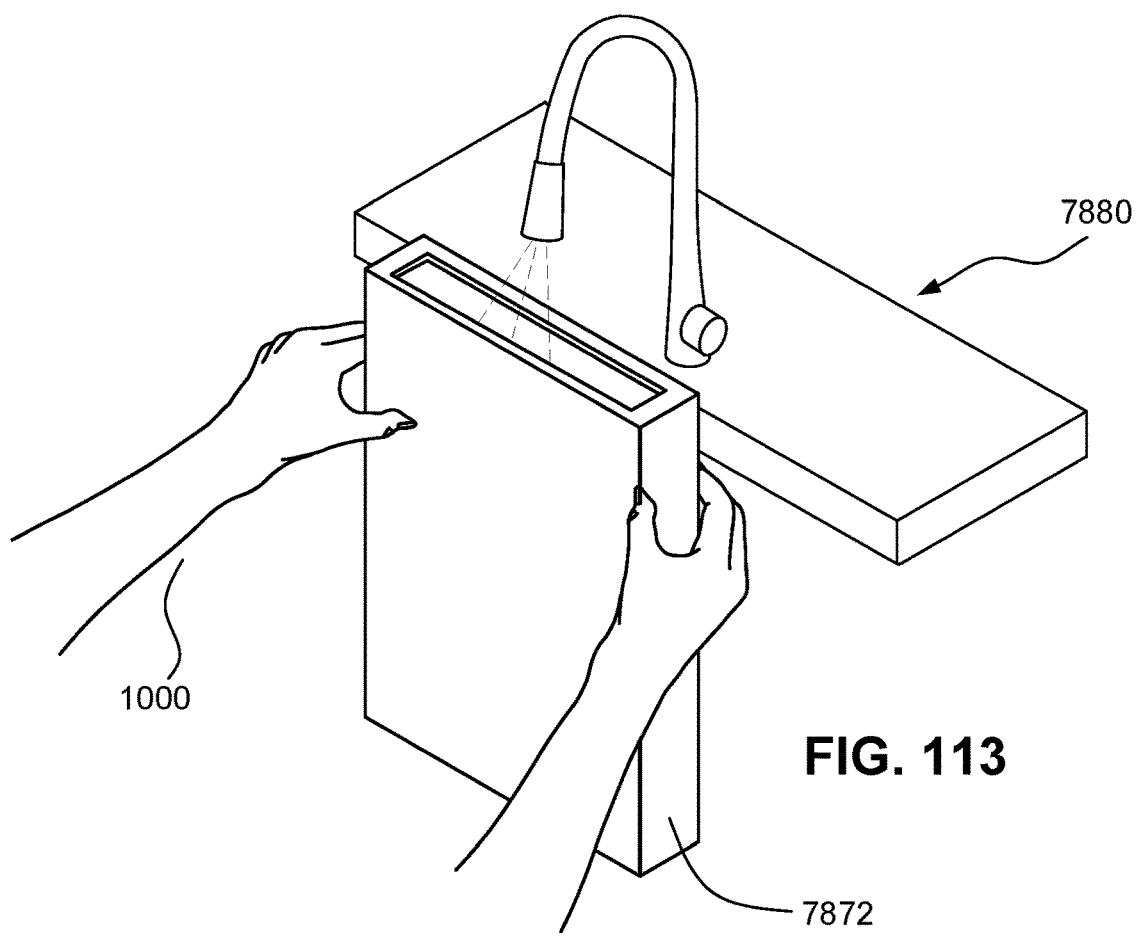

FIG. 113 is a perspective view of a patient filling a reservoir with cleaning fluid.

Figure 114:
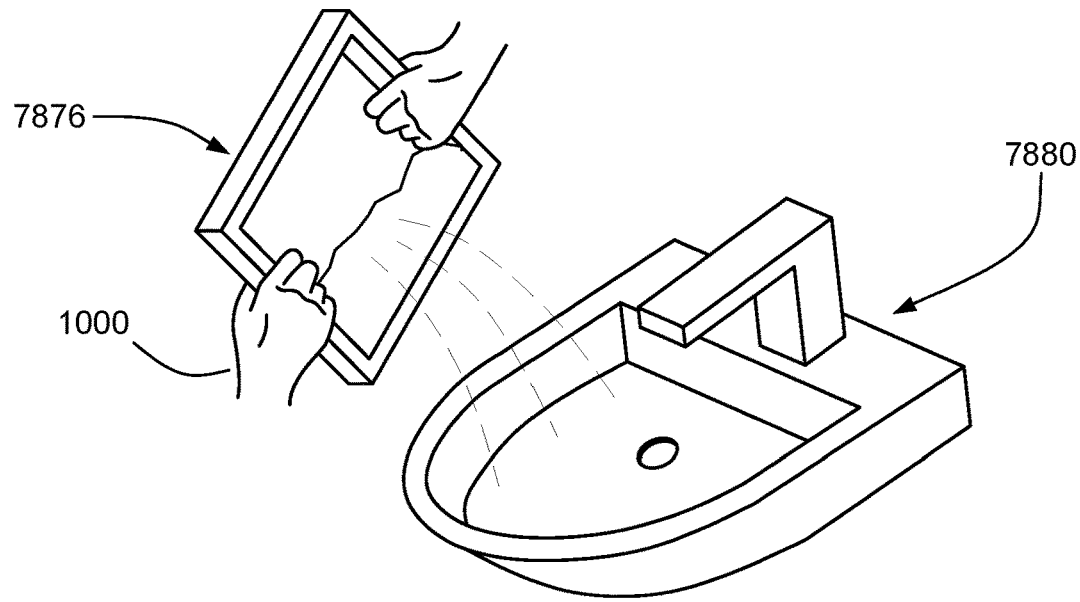

FIG. 114 is a perspective view of a patient emptying a collection chamber of waste fluid.

Figure 115:
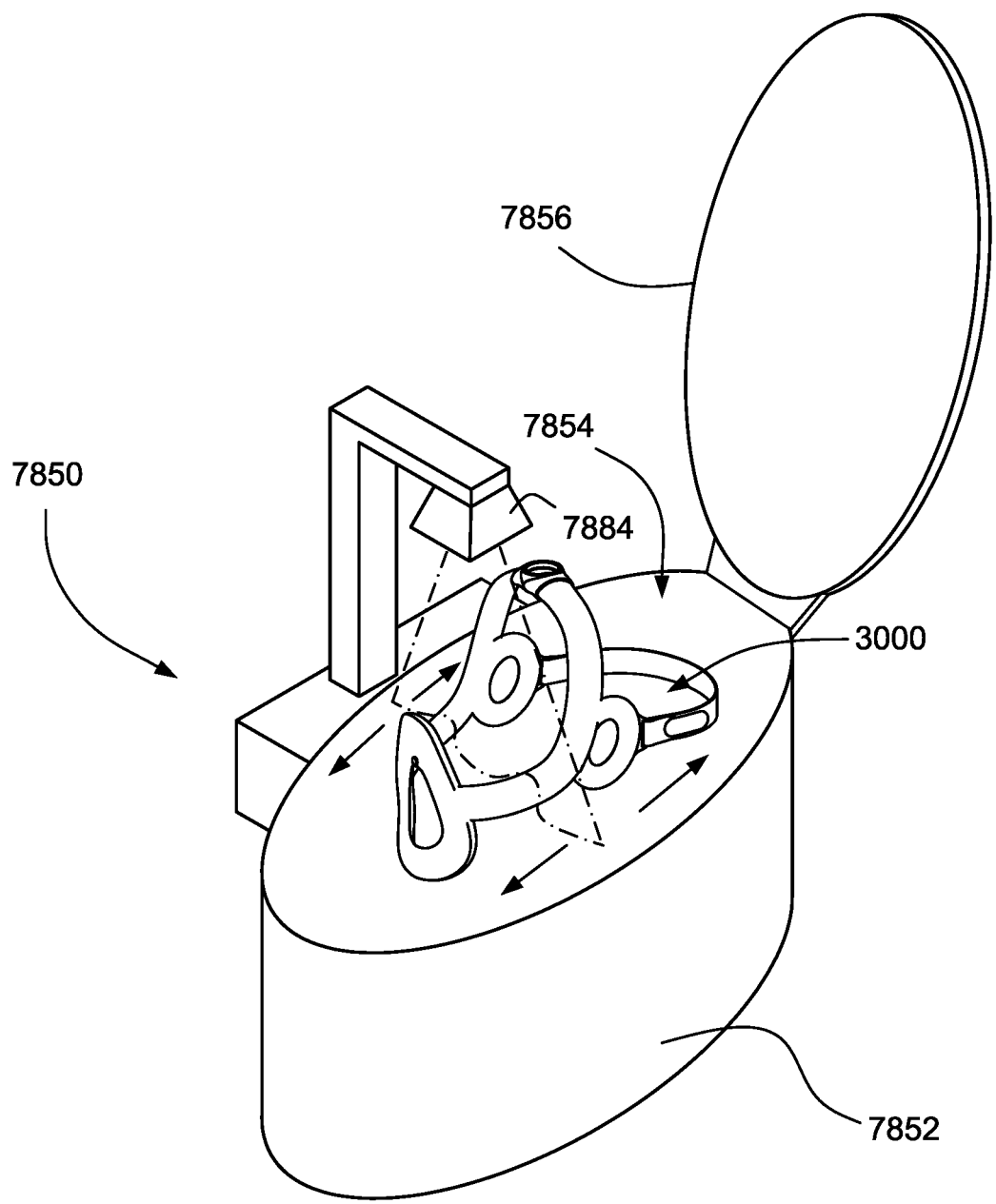

FIG. 115 is a perspective view of a cleaning box according to an alternate embodiment, which includes a sensor for detecting imperfections in a patient interface.

Figure 116:
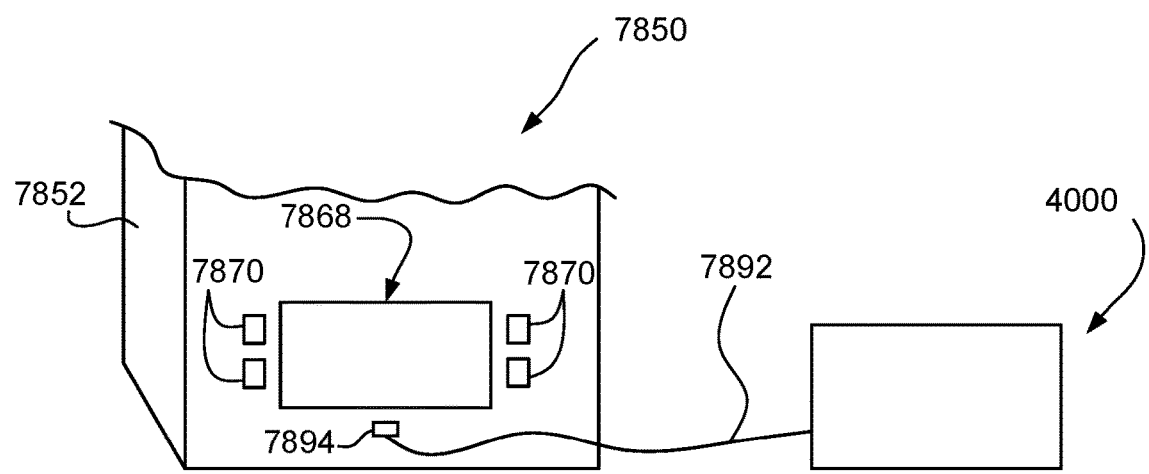

FIG. 116 is a schematic view of the cleaning box of FIG. 109 electrically connected to an RPT device.

Figure 117:
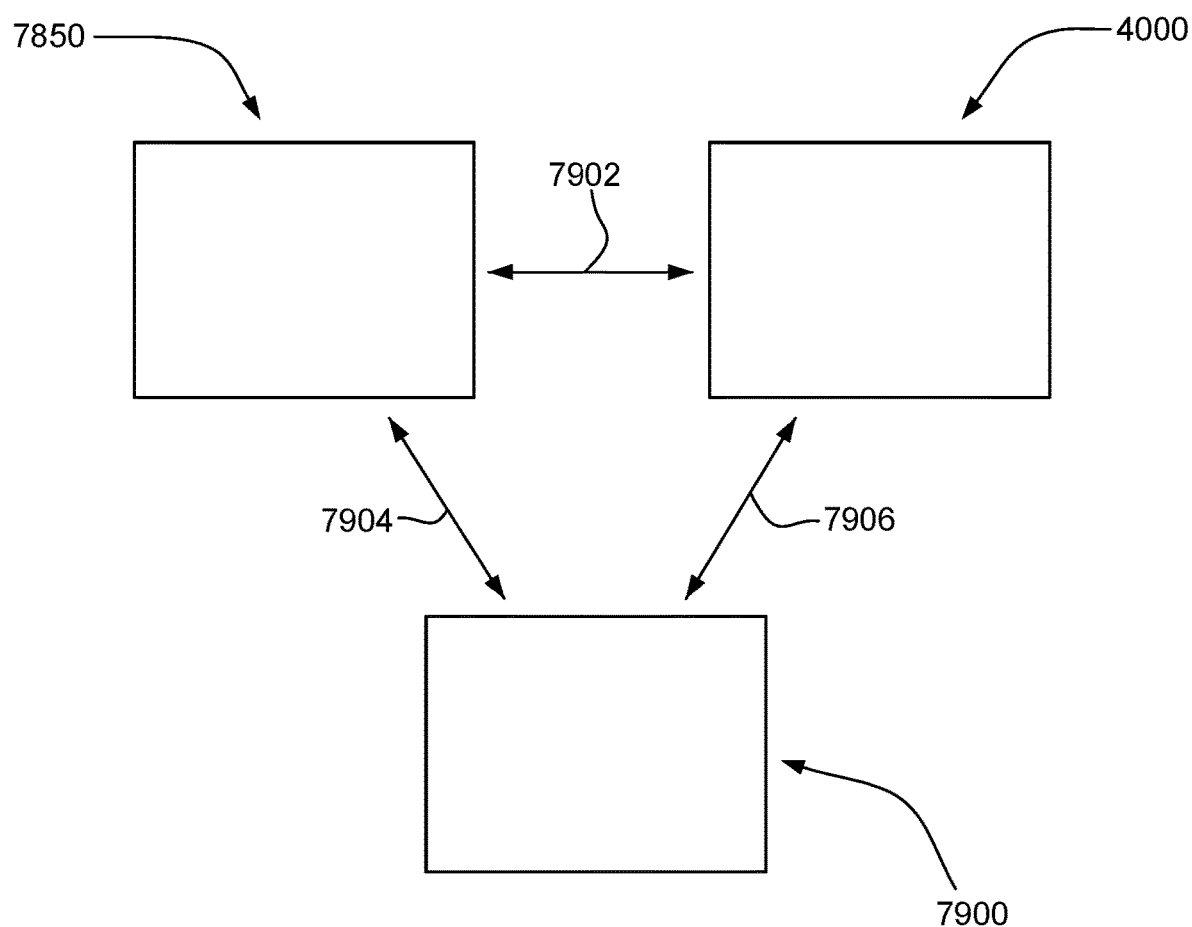

FIG. 117 is a schematic view showing commination pathways between a cleaning box, an RPT device, and a device.

Figure 118:
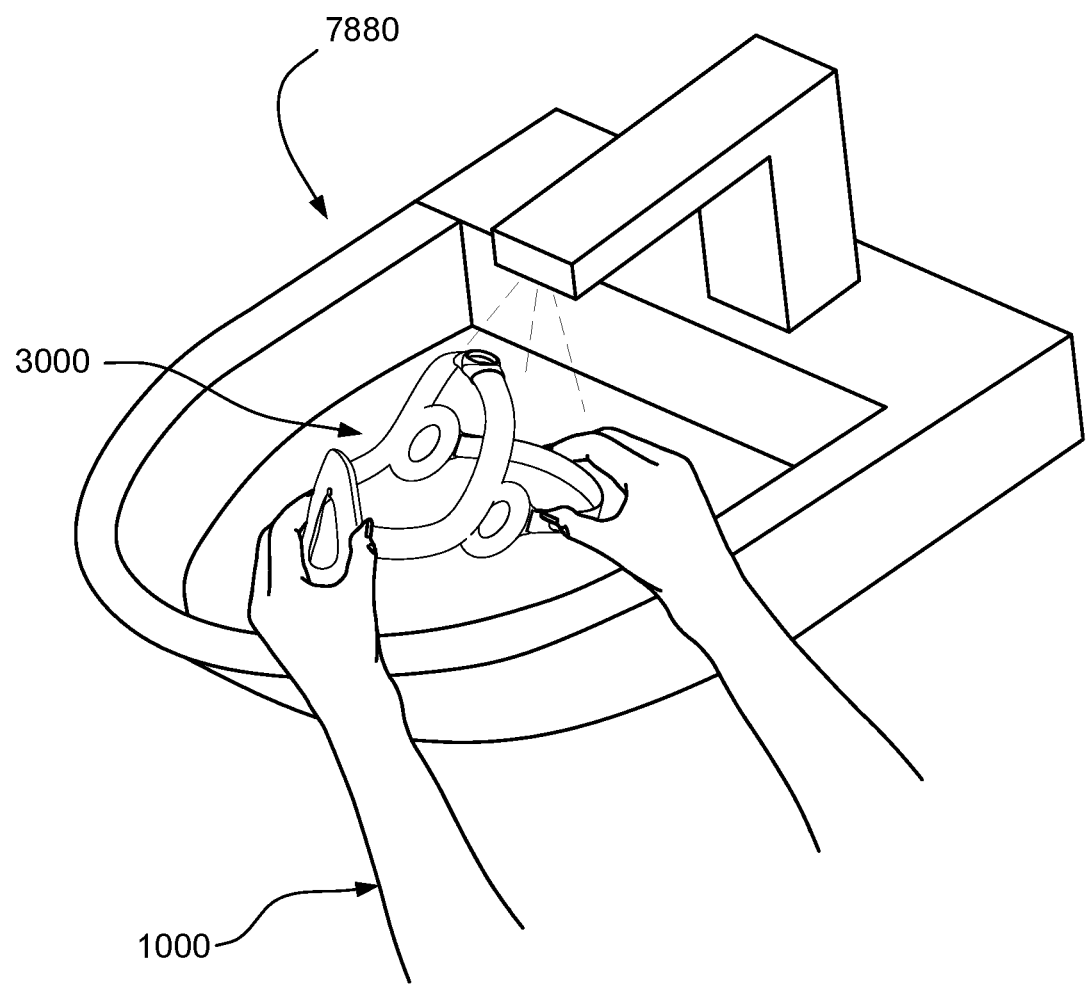

FIG. 118 is a perspective view of the patient interface of FIG. 47*d*, being cleaned by hand under running water.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising pressuring air to a positive pressure relative to ambient and directing the pressurized air to the entrance of the airways of a patient 1000.

In certain examples of the present technology, a supply of air at positive pressure relative to ambient is provided to the nasal passages of the patient via one or both nares. In further examples, the supply of air at positive pressure may be provided to the mouth, in addition to the nasal passages.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

In one form, the present technology comprises a face-contacting system for interacting a user's face. The system may comprise a facial interface that engages or contacts the user's face. The facial interface may include a patient interface 3000, or any other system that interacts with a user's face.

5.3 Patient Interface

A face-contacting system may include a facial interface that is configured to be positioned against or near a user's face. The facial interface is positioned and arranged to interact with an anatomical feature on the user's face. One example of the facial interface is a non-invasive patient interface 3000.

A non-invasive patient interface 3000 in accordance with one aspect of the present technology comprises one or more of the following functional aspects: a seal-forming structure 3100, a plenum chamber 3200, a positioning and stabilizing structure 3300, a vent 3400, one form of connection port 3600 for connection to air circuit 4170, and a forehead support 3700. In some forms, a functional aspect may be performed by one or more physical components. In some forms, one physical component may perform one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 4 cm $H_2O$ with respect to ambient.

The patient interface 3000 in accordance with one form of the present technology is constructed and arranged to be able to provide a supply of air at a positive pressure of at least 6 cm $H_2O$ with respect to ambient.

The patient interface 3000 in accordance with one form of the present technology is constructed and arranged to be able to provide a supply of air at a positive pressure of at least 10 cm $H_2O$ with respect to ambient.

The patient interface 3000 in accordance with one form of the present technology is constructed and arranged to be able to provide a supply of air at a positive pressure of at least 20 cm $H_2O$ with respect to ambient.

5.3.1 Seal-Forming Structure

In one form of the present technology, a seal-forming structure 3100 includes a target seal-forming region, and may additionally include a cushioning function. The seal-forming structure 3100 may also be referred to as a cushion. In other examples of a face-contacting system, the cushion may contact the user's face and may not seal against the user's face. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface 3000 was placed on the face, tension in the positioning and stabilizing structure 3300, and the shape of a patient's face.

In one form, the target seal-forming region is located on an outside surface of the seal-forming structure 3100.

In certain forms of the present technology, the seal-forming structure 3100 is constructed from a biocompatible material, e.g., silicone rubber.

A seal-forming structure 3100 in accordance with the present technology may be constructed from a soft, flexible, resilient material such as silicone.

A seal-forming structure 3100 in accordance with one form of the present technology may be constructed from a textile material (see e.g., FIGS. 43-84).

As shown in FIGS. 45 and 84, certain forms of the present technology may be a cover. The seal-forming structure 3100 of FIG. 45 may be positioned directly against a patient's face, and between the patient's face and a separate seal-forming structure (see e.g., FIG. 16). The seal-forming structure 3100 may provide the patient additional comfort, as the textile material would contact the patient's skin, and another material could be used in the seal-forming structure.

In certain forms of the present technology, a system comprising more than one seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head.

In other forms, a single sized seal-forming structure 3100 may be used for patients with different sized heads. The seal-forming structure 3100 may include an air bladder or inflatable section (or sections) that may include with air. For example, the inflatable section may be selectively inflated by the patient. Adding air to the inflatable section may allow a selected portion of the seal-forming structure 3100 to expand (e.g., decreasing the size of the opening of the) and create a tighter seal against the particular patient's face. In some forms, a valve may be included to selectively allow pressurized air from the RPT device 4000 to inflate the inflatable sections. In other examples, an alternate air source may provide air for the inflatable sections. Air within the inflatable section may be selectively released (e.g., by opening a valve) after each use so that the inflatable section forms tight contact with the patient's face each use, and the inflatable section is not overloaded.

5.3.1.1 Sealing Mechanisms

In one form, the seal-forming structure 3100 includes a sealing flange utilizing a pressure-assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilizing structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilizing structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

In one form of the present technology (see e.g., FIGS. 27-29), the seal-forming structure 3100 includes a hollow sealing tube 3104 that receives the flow of pressurized air. The hollow sealing tube 3104 includes an outer diameter OD in contact with the ambient, and an inner diameter ID positioned proximate the patient's oro-nasal region and not exposed to the ambient while the seal-forming structure 3100 is worn by the patient. An interior surface INS of the hollow sealing tube 3104 may be at least partially impermeable.

In one form (see e.g., FIG. 44), the interior surface INS proximate the outer diameter OD is made from and/or lined with an impermeable material (e.g., silicon, a thermoformed and/or laminate structure, etc.), and the interior surface INS proximate the inner diameter ID is made from and/or lined with a permeable material. When pressurized air fills the hollow sealing tube 3104, the impermeable material substantially prevents the air from escaping to the ambient. The air is instead directed toward the inner diameter ID, and is able to leak through the permeable material toward the patient's nose and/or mouth. The patient's nose and/or mouth may be exposed to the ambient through an opening 3152 in the seal-forming structure 3100. The mouth and/or nose may extend through the opening 3152.

In one form (see e.g., FIGS. 47-50), the hollow sealing tube 3104 is entirely made from and/or lined with the impermeable material. Holes 3108 are cut through the interior surface INS toward the inner diameter ID, and allow air to exit the hollow sealing tube 3104 toward the patient's nose and/or mouth. The holes 3108 may be evenly spaced about the inner diameter ID, or they may be concentrated in a specific area or areas along the inner diameter ID.

5.3.1.2 Nose Bridge or Nose Ridge Region

In one form, the non-invasive patient interface 3000 comprises a seal-forming structure that seals in use on a nose bridge region or on a nose-ridge region of the patient's face.

In one form, the seal-forming structure includes a saddle-shaped region constructed to seal in use on a nose bridge region or on a nose-ridge region of the patient's face.

5.3.1.3 Upper Lip Region

In one form, the non-invasive patient interface 3000 comprises a seal-forming structure that seals in use on an upper lip region (that is, the lip superior) of the patient's face.

In one form, the seal-forming structure includes a saddle-shaped region constructed to seal in use on an upper lip region of the patient's face.

5.3.1.4 Chin-Region

In one form the non-invasive patient interface 3000 comprises a seal-forming structure that seals in use on a chin-region of the patient's face.

In one form, the seal-forming structure includes a saddle-shaped region constructed to seal in use on a chin-region of the patient's face.

5.3.1.5 Forehead Region

In one form, the seal-forming structure that seals in use on a forehead region of the patient's face. In such a form, the plenum chamber may cover the eyes in use.

5.3.1.6 Retention Mechanisms

In one form of the present technology, the seal-forming structure 3100 includes at least one retention mechanism 3112 in order to couple an addition component (e.g., the plenum chamber 3200) of the patient interface 3000 to the seal-forming structure 3100.

5.3.1.6.1 Magnetic Retention

In one form of the present technology (see e.g., FIG. 47a), the seal-forming structure 3100 includes a first magnetic portion 3114. The first magnetic portion 3114 includes a first polarity.

In certain forms (see e.g., FIG. 47a), the first magnetic portion 3114 is a magnet coupled (e.g., sewn, glued, etc.) into the seal-forming structure 3100. The magnet may also be molded (e.g., in-molded, over-molded, etc.) onto the seal-forming structure 3100. The magnet may be provided in any orientation, and along any length of the seal-forming structure 3100. Multiple magnets may be provided on different sides (e.g., top/bottom, left/right, etc.) of the seal-forming structure 3100. The multiple magnets may have the same polarity as one another.

In certain forms (see e.g., FIG. 54), the first magnetic portion 3114 is a magnetic thread (e.g., thin wires with polymer yarn which have been twisted and magnetized, or magnetic material in polymer melt which have been extruded into fibres to make thread which is then magnetized) sewn into the seal-forming structure 3100. The magnetic thread may extend around or substantially around the perimeter of the seal-forming structure 3100. The magnetic thread may also extend around a portion of the perimeter of the seal-forming structure 3100.

In certain forms (see e.g., FIG. 47b), the first magnetic portion 3114 is a material attracted to magnets (e.g., a ferrous metal). The magnetic material is incorporated (e.g., sewn into, glued to, or magnetic threads added, etc.) into the material of the seal-forming structure 3100. The additional component (e.g., the plenum chamber 3200) includes a magnet and or a magnetic thread that is attracted to the first magnetic portion 3114.

In certain forms (see e.g., FIG. 47e), the first magnetic portion 3114 is a layer of fluid 3156 (e.g., magnetic ink, ferromagnetic fluid, ferro-fluid, etc.) applied to the seal-forming structure 3100. The fluid 3156 has magnetic properties (e.g., is attracted to a similar material with the opposite polarity), but does not require additional components (e.g., molded onto the seal-forming structure 3100) to form a seal.

5.3.1.6.2 Mechanical Retention

Any of these retention mechanisms described below may be used together. For example, a single seal-forming structure 3100 may have two or more of the above described magnetic and/or mechanical retention mechanisms. Including multiple retention mechanisms may assist in forming a stronger connection, and/or may provide a fail-safe in case one of the mechanisms breaks, or is otherwise unable to function. Combining the retention mechanisms together would not substantially change the operation of any of the retention mechanisms.

5.3.1.6.2.1 Clipping Structure

In certain forms of the present technology (see e.g., FIGS. 56 and 57), the seal-forming structure 3100 includes a first mechanical retainer or clip structure 3116. The first clip structure 3116 is at least partially ring shaped (e.g., defines at least a portion of a perimeter/circumference).

In certain forms, the first clip structure 3116 is made from a rigid material (e.g., plastic, rigid fabric, rigid thread, etc.), and is incorporated (e.g., sewn into) into the seal-forming structure 3100. The first clip structure 3116 includes clips (e.g., a first or movable clip 3116a, a second or fixed clip 3116b, and a gasket 3316c) that extend from the surface of the seal-forming structure 3100. The rigid material has a stiffness greater than the stiffness of at least a portion of the remaining material of the seal-forming structure 3100.

In certain forms, the first clip structure 3116 is formed as part of the seal-forming structure 3100. For example, the first clip structure 3116 may be integrally formed with the seal-forming structure 3100, or may be permanently attached to the seal-forming structure 3100.

In certain forms, the first clip structure 3116 is a male clip structure. A detachment mechanism 3118 may be included with the first clip structure 3116, and is used to uncouple the first clip 3116a from a corresponding structure. The detachment mechanism 3118 allows the first clip 3116a to move.

5.3.1.6.2.2 Hinge Lock Mechanism

In certain forms (see e.g., FIGS. 56a and 57c-57d), the seal-forming structure 3100 includes latches 3162 that are spaced around the opening 3152. Each latch 3162 is movable with respect to the other latches 3162. In the illustrated example, the seal-forming structure includes two latches 3162, although any number of latches 3162 may be used. The latches 3162 may also be used as a separate coupling mechanism as the first clip structure 3116, although in some examples, the latches 3162 and the first clip structure 3116 may both be included on the same seal-forming structure 3100.

Each latch 3162 may lay against a surface of the seal-forming structure 3100 in a rest position (see e.g., FIG. 57c).

The latches 3162 do not obstruct the opening 3152 in the rest position. The latches 3162 are pivotable away from the surface of the seal-forming structure 3300 (see e.g., FIG. 57d). The latches 3162 may be prevented from pivoting into the opening 3152 (e.g., further than 180°). The latches 3162 are configured to return to the rest position if an external force is removed.

In one form, each latch 3162 includes an opening 3164 that is formed at least partially be the latch 3162 and the seal-forming structure 3100. In other words, the opening 3164 is not completely bounded by the body of the latch 3162. In some examples, there may be an opening 3164 on each latch 3162. In other examples, only some of the latches 3162 include the openings 3164. In other examples, the opening 3164 of the latch 3162 may be completely bounded within the latch 3162.

5.3.1.6.2.3 Undercut Feature

In certain forms (see e.g., FIGS. 56b and 57e-57f), the seal-forming structure 3100 includes an undercut 3166 that may extend along at least a portion of the perimeter of the opening 3152. For example, FIG. 56b shows the undercut 3166 extending entirely around the perimeter of the opening 3152. In other words, the opening is slightly raised from the surface of the seal-forming structure 3100. The undercut 3166 is disposed apart from the surface, so that a space or gap exists between the undercut 3166 and the surface of the seal-forming structure 3100.

In one form, the undercut 3166 includes a curved or rounded edge. This may extend along the entire length of the undercut 3166, or may extend along only a portion of the undercut 3166 (e.g., some of the undercut 3166 may be rounded and some of the undercut 3166 is pointed).

5.3.1.6.2.4 Clip and Aperture Mechanism

In certain forms (see e.g., FIGS. 56c and 56c-1), the seal-forming structure 3100 includes apertures or slits 3170 (optionally reinforced with a rigid part and/or thread), which are disposed around the perimeter of the opening 3152. In other words, the slits 3170 are disposed radially outside of the opening 3152. The slits 3170 may be evenly spaced around the perimeter of the opening 3152, or the slits 3170 may be spaced at uneven intervals. The slits 3170 may have a generally rectangular profile, although any shape may be used. The slits 3170 may extend partially through the seal-forming structure 3100. In other examples, the seal-forming structure may have projections instead of slits 3170.

5.3.1.6.2.5 Zipping Mechanism

In certain forms (see e.g., FIGS. 55a and 55b), the seal-forming structure 3100 includes a groove 3174 that extends along at least a portion of the perimeter of the opening 3152. The groove 3174 is at least partially formed by a pair of overhangs 3175 that are spaced apart from the surface of the seal-forming structure 3100. For example, the overhangs 3175 may be formed on the ends of extensions 3176. The overhangs 3175 are disposed closer together than the remained of the extensions 3176, so that an entrance to the groove 3174 orthogonal to the seal-forming structure is less than the width of the groove 3174. In other words, the groove 3174 is narrower distal to the surface of the seal-forming structure 3100, than proximate to the seal-forming structure 3100.

In one form, the overhangs 3175 and/or extensions 3176 are formed from a flexible or semi-flexible material. The extensions 3176 are therefore able to move (e.g., pivot) relative to one another and change the width of the groove 3174. The overhangs 3175 may also be capable of compressing, so that the opening to the groove 3174 distal to the surface of the seal-forming structure 3100 may expand.

5.3.1.6.2.6 Zipper Mechanism

In one form (see e.g., FIG. 55c), the groove 3174 may partially around the perimeter of the opening 3152 to define a track. In other words, the groove 3174 does not completely connect, and there is a gap between sections of the groove 3174.

5.3.1.7 Nasal Pillows

In one form (see e.g., FIG. 22), the seal-forming structure of the non-invasive patient interface 3000 comprises a pair of nasal puffs, or nasal pillows, each nasal puff or nasal pillow being constructed and arranged to seal with a respective naris of the nose of a patient.

Nasal pillows in accordance with an aspect of the present technology include: a frusto-cone, at least a portion of which seals on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.8 Modular Construction

In one form of the present technology (see e.g., FIGS. 51-52b), the seal-forming structure 3100 is an under the nose mask 3100a that is adapted to engage the patient's upper lip LS and seal against the nares NA while leaving the nasal tip PRO free. The patient's mouth remains exposed to the ambient regardless of the position of the seal-forming structure 3100.

In one form, the plenum chamber 3200 (described below) is incorporated into the seal-forming structure 3100 as an integral or unitary construction. The plenum chamber 3200 includes an insert 3134 with a vent 3400 to assist with the removal of $CO_2$.

In one form, the insert 3134 of the plenum chamber 3200 is at least partially removable from the seal-forming structure 3100, and a mouth seal 3100b is further attached to the under the nose mask 3100a. The mouth seal 3100b covers the patient's mouth from the ambient.

In one form, the mouth seal 3100b is removably coupled to the under the nose mask 3100a using magnetic and/or mechanical coupling. The mouth seal 3100b may include a magnet or a magnetic thread 3142 that is magnetically attracted to a magnet or a magnetic thread 3140 in the under the nose mask 3100a. The mouth seal 3100b may also, or in addition, include a feature (e.g., a tab 3144) that mates with a complementary feature (e.g., a recess 3146) on the under the nose mask 3100a (e.g., via a snap-fit, a press fit, etc.). The tab 3144 may be a rigidized portion (e.g., a rigid fabric, a rigid thread, etc.) form (e.g., integrally) with the mouth seal 3100b. Any combination of the magnetic and mechanical coupling may seal the interface between the under the nose mask 3100a and the face mask, to substantially prevent pressurized air from escaping the seal-forming structure 3100 to the ambient.

In one form, a separate plenum chamber 3200 is removably coupled to both the under the nose mask 3100a and the mouth seal 3100b after the insert has been removed from the under the nose mask 3100a. The plenum chamber 3200 includes a first end 3240 that covers a nose opening 3152a of the nose mask 3100a and a second end 3241 that covers a mouth opening 3152b of the mouth seal 3100b in order to seal the patient's nose and mouth. A conduit 3242 connects the first end 3240 to the second end 3241 in order to provide fluid communication between the patient's nose and mouth. The conduit 3242 may include one or more holes for washout gas.

5.3.2 Plenum Chamber

The plenum chamber 3200 may have a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurized volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g., polycarbonate. The use of a transparent material can reduce the obtrusive appearance of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusive appearance of the patient interface, and help improve compliance with therapy.

In certain forms of the present technology (see e.g., FIGS. 47-84), the plenum chamber 3200 is constructed from a textile material 3101. The textile material 3101 can reduce the weight experienced by the patient's face, and help improve compliance with therapy.

The plenum chamber 3200 may be formed with a skeletal support 3202 sandwiched between a textile cover 3204 (see e.g., FIGS. 47a-47c). The skeletal support 3202 includes a greater stiffness than the textile cover 3204, and provides the plenum chamber 3200 with rigidity. The skeletal support 3202 also imparts a predefined shape (e.g., a concave shape) on the plenum chamber 3200. In certain forms, the skeletal support 3202 includes a framework with a polygonal latticework 3205 (e.g., triangular, rectangular, pentagonal, hexagonal, etc.). The polygonal latticework 3205 may increase the strength of the skeletal support 3202, while also reducing the weight. At least a portion of the textile cover 3204 (e.g., an outer surface 3204a, an inner surface 3204b, or both) may include a thermoformed and/or laminate structure, which may provide additional rigidity and impermeability to the plenum chamber 3200.

In certain forms, the polygonal latticework 3205 includes some elasticity and is able to bend as the result of an applied force, but is biased back to its original position when the force is removed. The elasticity of the polygonal latticework 3205 gives the plenum chamber 3200 both flexibility and rigidity (e.g., the plenum chamber 3200 is able to bend to a new shape, but is biased back to its original shape).

In certain forms of the present technology (see e.g., FIGS. 47b and 47d), the plenum chamber 3200 includes a valve 3206 (e.g., an anti-asphyxia valve (AAV)). The AAV 3206 includes a flap 3207 of textile material 3101 on the plenum chamber 3200 that selectively provides fluid communication through a first inlet port 3208 the plenum chamber 3200. The AAV 3206 is biased to an open position, which allows a patient to breathe from the ambient in the absence of a flow of pressurized air. The bias may be a mechanical bias (e.g., a spring), or may be through magnetic repulsion (e.g., two sections with identical polarities). The AAV 3206 closes and blocks communication through the first inlet port 3208 with the ambient when pressurized air is supplied.

5.3.2.1 Removable Plenum Chamber

In certain forms of the present technology (see e.g., FIGS. 47a-48, 52, and 53), the plenum chamber 3200 is selectively removable from the seal-forming structure 3100. The plenum chamber 3200 includes a first or decoupled position where the patient's nose and/or mouth is uncovered and exposed to the ambient. The plenum chamber 3200 also includes a second or coupled position where the patient's nose and/or mouth is covered by the plenum chamber 3200. The plenum chamber 3200 is movable between the decoupled and coupled positions independently of the seal-forming structure 3100. The seal-forming structure 3100 may remain in position (e.g., sealed against a patient's face) regardless of the position of the plenum chamber 3200. In the decoupled position, a patient's nose and/or mouth is exposed to the ambient through the opening 3152.

5.3.2.1.1 Magnetic Retention

In certain forms of the present technology (see e.g., FIGS. 48 and 53), the plenum chamber 3200 includes a second magnetic portion 3210 with an opposite polarity than the first magnetic portion 3114 of the seal-forming structure 3100. The magnetic portions 3114, 3210 provide the patient with a haptic response to indicate that the plenum chamber 3200 is properly aligned with the seal-forming structure 3100. In some embodiments, a third magnetic portion 3212 is also included in the plenum chamber 3200. The third magnetic portion 3212 includes the same polarity as the first magnetic portion 3114 (i.e., an opposite polarity than the second magnetic portion 3210).

In certain forms (see e.g. FIG. 48), the second magnetic portion 3210 is a magnet sewn into the textile cover 3204. The magnet may be provided in any orientation, and along any length of the textile cover 3204. Where the third magnetic portion 3212 is included, the second and third magnetic portions 3210, 3212 are disposed on opposite sides of the plenum chamber 3200 (e.g., left/right, top/bottom, etc.). The plenum chamber 3200 couples to the seal-forming structure 3100 when aligned correctly (i.e., the second magnet is adjacent to the first magnetic portion 3114), and is prevented from coupling to the seal-forming structure 3100 when aligned improperly (i.e., the second magnet is distal to the first magnetic portion 3114).

In certain forms (see e.g., FIG. 53), the second magnetic portion 3210 is a magnetic thread (e.g., thin wires with polymer yarn which have been twisted and magnetized, or magnetic material in polymer melt which have been extruded into fibres to make thread which is then magnetized) sewn into the plenum chamber 3200. The magnetic thread may extend around or substantially around the perimeter of the plenum chamber 3200, and may be used to retain the textile cover 3204 around the skeletal support 3202. The magnetic thread may also extend around a portion of the perimeter of the plenum chamber 3200. Where the third magnetic portion 3212 is included, the second and third magnetic threads are sewn into opposite sides of the plenum chamber 3200 (e.g., left/right, top/bottom, etc.). The plenum chamber 3200 couples to the seal-forming structure 3100 when aligned correctly (i.e., the second magnetic thread is adjacent to the first magnetic portion 3114), and is prevented from coupling to the seal-forming structure 3100 when aligned improperly (i.e., the second magnetic thread is distal to the first magnetic portion 3114).

In certain forms, the second magnetic portion 3210 and/or the third magnetic portion 3212 is a material attracted to magnets (e.g., a ferrous metal). The first magnetic portion 3114 includes a magnet and or a magnetic thread that is attracted to the second magnetic portion 3210, and repels the third magnetic portion 3212 (e.g., the patient receives haptic feedback in the form of magnetic resistance indicating the improper alignment of the plenum chamber 3200).

When aligned properly (e.g., the first magnetic portion 3114 adjacent to the second magnetic portion 3210), the seal-forming structure 3100 and the plenum chamber 3200 are coupled together and relatively fixed in place. In some forms, the magnetic force is greater than the force of pressurized air, and forms a seal between the seal-forming structure 3100 and the plenum chamber 3200. No additional structure is required in order to retain the plenum chamber 3200 in place and prevent the escape of pressurized air when the patient interface 3000 is in use. In some forms, the magnetic force is less than the force of pressurized air, and an additional structure (e.g., a mechanical fastener—discussed below) helps to retain the plenum chamber 3200 in place and prevent the escape of pressurized air when the patient interface 3000 is in use. In either form, the magnetic force is less than a force applied by a patient's hand (e.g., when moving the plenum chamber 3200 to the decoupled position).

In certain forms of the present technology (see e.g., FIG. 48a), the second magnetic portion 3210 is a layer of fluid 3250 (e.g., magnetic ink, ferromagnetic fluid, ferrofluid, etc.) applied to the plenum chamber 3200. The fluid 3156 has magnetic properties (e.g., is attracted to a similar material with the opposite polarity), but does not require additional components (e.g., molded onto the plenum chamber 3200) to form a seal.

In one form, when the fluid layer 3250 of the plenum chamber 3200 is positioned proximate to the fluid layer 3156 of the seal-forming structure 3100, the fluid layers 3156, 3250 interact with one another in order to form a magnetic connection. This connection may be used to secure the plenum chamber 3200 to the seal-forming structure 3100.

In one form, the magnetic interactions between the fluid layers 3156, 3250 is not sufficient to establish a seal between the seal-forming structure 3100 and the plenum chamber 3200. Thus, the fluid layers 3156, 3250 may assist in properly positioning the plenum chamber 3200, and may provide a loose coupling between the plenum chamber 3200 and the seal-forming structure 3100. An additional retention mechanism (e.g., magnetic and/or mechanical) may be used with the fluid layers 3156, 3250 in order to secure the plenum chamber 3200 to the seal-forming structure 3100, and seal the interface between them.

The loose coupling may help hold the plenum chamber 3200 in place against the seal-forming structure 3100 prior to further coupling the plenum chamber 3200 to the seal-forming structure 3100. For example, the fluid layers 3156, 3250 may hold the plenum chamber 3200 in place so the patient may have both hands free to engage the additional retention mechanism. In other words, the patient may use both hands to interact with the additional retention mechanisms (e.g., move clips), as opposed to having to keep one hand holding the plenum chamber 3200, and having only a single hand free to interact with the additional retention mechanism.

In one form, the second magnetic portion 3212 (e.g., in the form of a magnetic thread) may be formed on the outer surface 3204a of the plenum chamber 3200. The first magnetic portion 3114 (e.g., in the form of magnetic thread) may be proximate the inner surface 3130. The plenum chamber 3200 may be coupled to the seal-forming structure 3100 in the opposite direction as the plenum chamber 3200 shown in FIG. 48. In other words, connection direction for the plenum chamber 3200 may be in the same direction as the patient moves their face into the patient interface 3000. The first and second magnetic portions 3114, 3212 may engage one another as the plenum chamber 3200 is moved toward its engaged position. In some forms, the plenum chamber may also be held in place with a press fit or friction fit, or with a mechanical retention, as described below.

5.3.2.1.2 Mechanical Retention

Any of the below described retention mechanisms may be used with a one piece plenum chamber 3200 (described below). In other words, these retention mechanisms may similarly be used if the plenum chamber 3200 is not completely separable from the seal-forming structure 3100. The method of operating each retention mechanism would remain substantially the same.

5.3.2.1.2.1 Clipping Structure

In certain forms of the present technology (see e.g., FIGS. 56 and 57), the plenum chamber 3200 includes a second mechanical retainer or clip structure 3216 with a complementary shape as the first clip structure 3116. The second clip structure 3216 removably mates with the first clip structure 3116 and secures the plenum chamber 3200 in place relative to the seal-forming structure 3100.

In certain forms, the second clip structure 3216 is a made from a rigid material (e.g., plastic, rigid fabric, rigid thread, etc.), and is incorporated (e.g., sewn into) into the textile cover 3204. The second clip structure 3216 extends from the surface of the textile cover 3204 in order to mate with the first clip structure 3116. The rigid material has a stiffness greater than the stiffness of at least a portion of the textile cover 3204 and/or the skeletal support 3202.

In certain forms, the second clip structure 3216 is formed as part of the textile cover 3204 and/or the skeletal support 3202. For example, the second clip structure 3216 may be integrally formed with the textile cover 3204 and/or the skeletal support 3202, or may be permanently attached to the textile cover 3204 and/or the skeletal support 3202.

In certain forms, the second clip structure 3216 is a female clip structure and mates with a male clip structure of the first clip structure 3116; although these may be reversed. A patient aligns the first and second clip structures 3116, 3216 and couples the plenum chamber 3200 to the seal-forming structure 3100 with a snap-fit that provides a seal between the plenum chamber 3200 and the seal-forming structure 3100. Specifically, the patient aligns the second clip structure 3216 with the second clip 3216 (see e.g., FIG. 57a). The patient then actuates the detachment mechanism 3118 to pivot the first clip 3116a away from the magnetic portion 3114. The patient then positions the plenum chamber 3200 proximate the magnetic portion 3114 and releases the detachment mechanism 3118 so that the first clip 3116a contacts the outer surface 3204a (see e.g., FIG. 57b). The gasket 3116c provides a seal between the seal-forming structure 3100 and the plenum chamber 3200 to prevent the flow of fluid between the interface of the seal-forming structure 3100 and the plenum chamber 3200. The female clip portion 3216 may be oriented to complement the second magnetic portion 3210. In other words, the female clip portion 3216 is oriented to couple to the male clip portion 3116 in a single orientation (e.g., which corresponds to the orientation where the first and second magnetic portions 3114, 3210 attract).

In certain forms, the magnetic force between the first magnetic portion 3114 and the second magnetic portion 3210 is insufficient to retain the plenum chamber 3200 to the seal-forming structure 3100 (e.g., the weight of the plenum chamber 3200 exceeds a vertical component of magnetic force). In this case, the magnetic portions 3114, 3210 only provide the patient with a haptic response that the plenum chamber 3200 is properly aligned. The plenum chamber 3200 is retained entirely by the first and second clipping structures 3116, 3216.

In certain forms, the detachment mechanism 3118 is used to uncouple the first and second clip structures 3116, 3216. The detachment mechanism 3118 separates the first clip structure 3116 from the second clip structure 3216 so that the plenum chamber 3200 is movable to the decoupled position. The detachment mechanism 3118 may be a finger activated detachment mechanism 3118 (e.g., a push button) that separates the first clip structure 3116 from the second clip structure 3216.

5.3.2.1.2.2 Hinge Lock Mechanism

In certain forms of the present technology (see e.g., FIGS. 56a and 57c-57d), the plenum chamber 3200 includes projections 3262 on the outer surface 3204a. The projections 3262 are spaced around the plenum chamber 3200, and have a generally complementary shape to the latches 3162. In the illustrated example, the projections 3262 include a rounded free end, although in other examples, the projections 3262 may have any shape.

The latches 3162 do not block the opening 3152 while they are in the rest position (see e.g., FIGS. 56a and 57c). The plenum chamber 3200 can be positioned above the opening 3152, and moved into position against the surface of the seal-forming structure 3100. In some examples, a gasket may be disposed on the plenum chamber 3200 and/or the seal-forming structure 3100, and may assist in providing a sealed connection.

Once the plenum chamber 3200 is positioned against the seal-forming structure 3100, the patient may pivot the latches 3162 into engagement with the projections 3262. As the latches engage the projections (see e.g., FIG. 57d), the plenum chamber 3200 is pulled into the seal-forming structure 3100, and seals the interface between the two bodies 3100, 3200. If the patient interface 3000 includes a gasket (e.g., on the seal-forming structure 3100 and/or the plenum chamber 3200), the engagement between the latch 3162 and the projection 3262 compresses the gasket to create the seal.

In one form, the latches 3162 include the openings 3164, which have a substantially complementary shape to the projections 3262. As the latches 3162 rotate from the rest position toward the plenum chamber 3200, the latches 3162 receive the projections 3262. For example, the openings 3164 of the latches 3162 may engage the respective projection 3262 with a snap-fit, friction fit, or similar engagement. The openings 3164 of the latches 3162 may not be aligned with the projections 3262, and may be formed at different angles. In other words, the angle between the opening 3164 when the latch 3162 is pivoted, and the angle of the projection with respect to the seal-forming structure 3100 may not exactly match. This may allow the projection 3262 to be received within the opening 3164, but can also force a wall of the opening 3164 into the projection 3262, thereby providing a force directed into the seal-forming structure 3100.

In one form, an end of each latch 3162 engages a respective projection 3262. The latch 3162 may pivot over the projection 3262, and engage the projection 3262 with a snap-fit, friction fit, or similar engagement Similar to when the latches 3162 included the openings 3164, each respective latch 3162 may engage the projection 3262 at an angle so that the latch 3162 provides a force against the projection 3262 directed into the seal-forming structure 3100.

In either form, the patient may pivot the latches 3162 out of engagement with the projections 3262 (e.g., one at a time), so that the force directed into the seal-forming structure 3100 is lessened (e.g., a full seal between the seal-forming structure 3100 and the plenum chamber 3200 may no longer exist). The force provided by the patient may overcome the engagement between the projection 3262 and the opening 3164, so that the latches 3162 are again capable of moving freely. The plenum chamber 3200 can then be removed from the seal-forming structure 3100 (or an additional retention mechanism can be uncoupled) in order to re-expose the opening 3152. The latches 3162 return to the rest position when they have been uncoupled from the respective projection 3262.

In one form, the patient interface 3000 includes magnets that hold the plenum chamber 3200 in place prior to pivoting the latches 3162 from the rest position. In other words, the magnets have sufficient magnetic force to overcome the force of gravity and keep the plenum chamber 3200 properly positioned, so that the patient may use both hand to actuate the latches 3162.

5.3.2.1.2.3 Undercut Feature

In certain forms of the present technology (see e.g., FIGS. 56b and 57e-57f), the plenum chamber 3200 includes an overhang 3266. For example, an outer edge of the inner surface 3204b of the plenum chamber 3200 may extend beyond the remainder of the plenum chamber 3200. The overhang 3266 extends along at least a portion of the perimeter of the inner surface 3204b. In the illustrated example, the overhang 3266 extends entirely around the inner surface 3204b. In other words, the overhang 3266 extends a complementary distance around the plenum chamber 3200, as the undercut 3166 extends around the seal-forming structure 3100.

The overhang 3266 may be constructed from a rigidized piece of textile. In other words, the overhang 3266 may have a greater stiffness than the remainder of the textile used to construct the plenum chamber 3200. The overhang 3266 therefore cannot move (e.g., flex) as much as the remainder of the plenum chamber 3200 can.

In one form, the overhang 3266 includes a rounded or curved edge. This may extend along the entire length of the overhang 3266, or may extend along only portion of the overhang 3266. In the illustrated example, the rounded portion of the overhang 3266 substantially matches the rounded portion of the undercut 3166 (e.g., extend the same distance).

In one form (see e.g., FIGS. 57e and 57f), the plenum chamber 3200 is disposed over the opening 3152, and is pressed into the seal-forming structure 3100. The plenum chamber 3200 may be capable of flexing (e.g., changing its shape) in order to extend around the undercut 3166. In other words, the undercut 3166 of the seal-forming structure 3100 is slightly wider than the overhang 3266. The plenum chamber 3200 must flex in order to fit around the undercut 3166. However, once the plenum chamber 3200 is around the undercut 3166, the plenum chamber 3200 may return to its original shape (e.g., because of the skeletal support 3202).

When the plenum chamber 3200 returns to its original shape, the overhang 3266 is able to engage the underside of the undercut 3166. Since the overhang 3266 is smaller (e.g., has a smaller diameter) than the undercut 3166, the two are engaged (i.e., the overhang 3266 engages the undercut 3166). This engagement may provide a seal between the plenum chamber 3200 and the seal-forming structure 3100. Since the overhang 3266 is wrapped around the undercut 3166, the patient is unable to simply pull the plenum chamber 3200 off of the seal-forming structure 3100. Instead, the patient must flex the plenum chamber 3200 again, so that its shape changes and it can be removed. The rounded edges may make removing the plenum chamber 3200 from the seal-forming structure 3100 easier (e.g., because the curved surfaces allow the overhang 3266 to more easily slide along the undercut 3166).

In certain forms, the undercut 3166 and the overhang 3266 are both generally rigid members (e.g., formed from or reinforced with rigidized textile). This may provide a generally snap-fit connection, and may provide the user with a tactile or haptic response to the engagement between the plenum chamber 3200 and the seal-forming structure 3100. In other forms, one of the undercut 3166 and the overhang 3266 may be flexible (e.g., not rigidized). This may assist the patient in more easily flexing the overhang 3266 into engagement with the undercut 3166.

5.3.2.1.2.4 Clip and Aperture Mechanism

In certain forms of the present technology (e.g., FIGS. 56c and 56c-1), projections 3270 that extend through the plenum chamber 3200. The projections 3270 are spaced apart, and may be disposed at equal intervals.

In the illustrated example, the projections 3270 are longer in a first direction then in a second, orthogonal direction. In other words, the projections 3270 may be longer than they are wide (or vice versa). For example, a projection 3270 disposed along a side of the plenum chamber may have its long dimension extend generally along the height of the plenum chamber (e.g., the vertical direction), and its short dimension generally along the width of the plenum chamber (e.g., the horizontal direction). These would be reversed for a projection 3270 disposed along an end (e.g., top of bottom) of the plenum chamber 3200.

In one form, the plenum chamber 3200 is positioned so that it is aligned with the opening 3152 of the seal-forming structure 3100. In other words, the plenum chamber 3200 is positioned so that it can cover the opening 3152, and therefore enclose the patient's nose and/or mouth. The plenum chamber 3200 is aligned so that each projection 3270 matches a respective slit 3170. For example, the plenum chamber 3200 is positioned so that similarly shaped slits 3170 and projections 3270 have substantially the same orientation.

Once the orientation of the projections 3270 and slits 3170 match, the patient may move the plenum chamber 3200 toward the seal-forming structure 3100 so that the projections 3270 extend through the slits 3170. The projections 3270 may be flexible members that have a rest position radially outside of the position of the slits 3170. As the plenum chamber 3200 is being coupled to the plenum chamber 3200, the projections 3270 may flex radially inward (e.g., because of a force applied by the user) in order to be received within the respective slit 3170. Alternatively, or in addition, the plenum chamber 3200 may couple to the seal-forming structure 3100 by receiving one projection at a time. Each individual projection 3270 is pulled radially inward as it is received within the respective slit 3170. In either case, the projections 3270 move radially inward in order to extend through the slit 3170, but move radially outward after passing through the respective slit 3170 (e.g., in the direction of the rest position). This movement of the projections 3270 locks or secures the plenum chamber 3200 to the seal-forming structure 3100. In addition, this may create a seal between the interfaces of the plenum chamber 3200 and the seal-forming structure 3100. The coupled plenum chamber 3200 and seal-forming structure 3100 will have a similar appearance as that of FIG. 55a.

To remove the plenum chamber 3200, the patient may actuate the projections 3270. For example, the patient may move at least one of the projections 3270 radially inwards (i.e., away from the rest position) so that it is fully aligned with the slit 3170 by flexing the plenum chamber 3200. The plenum chamber 3200 may then be lifted away from the seal-forming structure 3100 so that the projection 3270 may pass through the slit 3170. The patient may repeat this for every projection 3270, or the patient may be able to remove the plenum chamber 3200 after actuating less than all of the projections 3270 (e.g., by pivoting the plenum chamber 3200).

In one form, the projections 3270 and slits 3170 may be used in conjunction with a magnetic retention mechanism (e.g., magnetic thread, magnetic fluid, etc.). For example, the plenum chamber 3200 and the seal-forming structure 3100 may magnetically interact in order to assist the patient in properly positioning the slits 3170 with respect to the projections 3270. In other words, the magnetic field may assist in helping the patient identify the proper alignment of the plenum chamber 3200 with respect to the seal-forming structure 3100.

5.3.2.1.2.5 Friction-Fit Mechanism

In certain forms of the present technology (see e.g., FIGS. 56d and 57g), at least a portion of the plenum chamber 3200 is radially smaller than the opening 3152 of the seal-forming structure 3100. The plenum chamber 3200 can thus be inserted partially through the opening 3152 so that the outer surface 3204a is adjacent to the opening 3152. The plenum chamber 3200 itself may act as a plug, and limit fluid from passing through the opening 3152 and escaping to the environment (e.g., as opposed to entering the patients airways).

In one form, the outer surface 3204a of the plenum chamber 3200 includes a protrusion 3274 that projects away from the outer surface 3204a. The protrusion 3274 may extend around the entire perimeter of the plenum chamber 3200, or the protrusion 3274 may extend only partially around the plenum chamber 3200. Additionally, the protrusion 3274 may extend continuously, or may a series of discontinuities.

The patient positions the plenum chamber 3200 so that it is aligned with the opening 3152, and moves the plenum chamber 3200 toward the seal-forming structure 3100 (e.g., in a similar manner as was done in FIGS. 56c, 56c-1 and 57e with the projections 3270 and slits 3170). The plenum chamber 3200 translates (e.g., slides) through the opening 3152 in the direction toward the patient's face. The protrusion 3274 is positioned on the outer surface 3204a in order to limit translational movement of the plenum chamber 3200. In other words, the protrusion 3274 is radially wider than the opening 3152 of the seal-forming structure 3100. Thus, the protrusion 3274 is unable to pass through the opening 3152, and limits further movement of the plenum chamber 3200 toward the patient's face.

In one form, the protrusion 3274 rests against the surface of the seal-forming structure 3100 when the plenum chamber 3200 has been fully inserted. The plenum chamber 3200 may be coupled to the seal-forming structure 3100 via a friction fit. The protrusion 3274 may be a positioning mechanism so that the plenum chamber 3200 does not extend too far through the opening 3152 (e.g., and be too close to the patient's face). The protrusion 3274 therefore does not lock the plenum chamber 3200 to the seal-forming structure 3100. The outer surface 3204a of the plenum chamber 3200 may also engage the opening 3152 (e.g., via a friction fit), so that there are two means of securing the plenum chamber 3200 to the seal-forming structure 3100.

In one form, a groove may be positioned on a surface of the seal-forming structure 3100 in order to receive the protrusion 3274. This may assist the patient in properly positioning the plenum chamber 3200 with respect to the seal-forming structure 3100 (e.g., because there is only one orientation of the plenum chamber 3200 that will allow the protrusion 3274 to fit within the groove). The groove could also assists in limiting rotational movement of the plenum chamber 3200 once it is coupled to the seal-forming structure 3100, which would loosen the plenum chamber 3200 and cause leaks.

In one form, the plenum chamber 3200 includes a button 3276 on the outer surface 3204a. The button may be selectively actuated (e.g., pressed inwardly) by the patient in order to assist in decoupling the plenum chamber 3200 from the seal-forming structure 3100. For example, actuating the button 3276 may alter the shape of the plenum chamber 3200 and assist in removing the protrusion 3274.

The patient pulls the plenum chamber 3200 away from their face in order to remove the plenum chamber 3200, and expose their mouth and/or nose through the opening 3152. The force provided by the patient is sufficient to overcome the friction-fit and/or press-fit, so that the plenum chamber 3200 may be pulled away.

In certain forms, the plenum chamber 3200 and seal-forming structure 3100 may be coupled together using an additional retention mechanism (e.g., a separate mechanical retention mechanism, a magnetic retention mechanism, etc.). The patient may have to uncouple this retention mechanism prior to pulling the plenum chamber 3200 away from the seal-forming structure 3100. Or, the pulling force provided by the patient may be sufficient to remove all the retention mechanisms at once.

5.3.2.1.2.6 Zipping Mechanism

In certain forms of the present technology (see e.g., FIGS. 55a and 55b), the plenum chamber 3200 includes an extension 3278 that extends from a surface of the plenum chamber 3200. The extension 3278 may extend from the inner surface 3204b of the plenum chamber 3200, or it may extend from the edge between the outer and inner surfaces 3204a, 3204b of the plenum chamber 3200.

The extension 3278 includes a base 3279, a shaft 3280, and a head 3281. The base 3279 is formed on the surface of the plenum chamber 3200. The shaft 3280 is directly connected to the base 3279, and extends in a direction away from the base 3279. In the illustrated example, the shaft 3280 is approximately orthogonal with respect to the base 3279, although any angle may be used. The shaft 3280 may be constructed from a rigidized textile (or include rigidizers) so that it is able to maintain its angle with respect to the base 3279. However, the shaft 3280 may be capable of flexing (e.g., pivoting slightly) relative to the base 3279 under the application of a force, and returning to its neutral position (e.g., orthogonal to the base 3279).

The head 3281 is directly connected to the shaft 3280 and forms the free end of the extension 3278. The head 3281 and the base 3279 are both wider than the shaft 3280 (although not necessarily the same width). For example, the base 3279 may be wider than both the shaft 3280 and the head 3281, while the head 3281 is only wider than the shaft 3280.

The plenum chamber 3200 is aligned with the opening 3152 of the seal-forming structure 3100, and the patient translates the plenum chamber 3200 toward the seal-forming structure 3100 so that it covers the opening 3152. As the plenum chamber 3200 reaches the seal-forming structure 3100, the head 3281 contacts the overhangs 3175. The head 3281 may be slightly larger than the overhang 3175, so that it cannot pass directly into the groove 3174. As the patient applies more force (e.g., generally directed toward the patient's face), the head 3281 may compress, the overhangs 3175 may compress, and/or the extensions 3176 may flex outwardly. This allows the head to pass into the groove 3174. Once this has occurred, the head 3281 and/or the extension 3176 returns to its original position (e.g., unflexed or uncompressed).

The overhangs 3175 sit adjacent to the shaft 3280, and between the base 3279 and the head 3281. In other words, the overhangs 3175 extend adjacent to the narrower width of the shaft 3280. The distance between the base 3279 and the head 3281 (i.e., the length of the shaft 3280) may be approximately equal to the length of the overhang 3175. This limits the ability for the overhangs 3175 to translate relative to the seal-forming structure 3100 (e.g., in a direction into or away from the seal-forming structure 3100).

The overhang 3175 and extension 3278 may extend entirely around there respective perimeters, so that this engagement occurs along the entire perimeter of the opening 3152. While engaged, the overhangs 3175 may seal around the shaft 3280, and substantially limit fluid flow through the opening 3152.

The patient applies a sufficient force to the plenum chamber 3200 (e.g., directed generally away from the patient's face) in order to uncouple the plenum chamber 3200 from the seal-forming structure 3100. The force provided by the patient is sufficient to cause the extensions 3176 and/or the extension 3278 to deflect, thereby increasing the width of the groove 3174. In this scenario, the overhangs 3175 are no longer adjacent to the shaft 3280, and are wider than the head 3281, so that the head 3281 can move out of the groove 3174.

5.3.2.1.2.7 Velcro

In certain forms of the present technology (see e.g., FIG. 53a), Velcro 3246 may be connected to the inner surface 3204b of the plenum chamber 3200. The Velcro 3246 may extend around any portion of the perimeter (e.g., completely around the perimeter or partially around the perimeter). When the plenum chamber 3200 is moved toward the seal-forming structure 3100, the Velcro 3246 may connect to the Velcro on the seal-forming structure 3100, in order to secure the two pieces together. The patient may provide a force directed generally away from their face in order to uncouple the plenum chamber 3200 from the seal-forming structure 3100. In some forms, the Velcro 3246 may be replaced with a different connection mechanism (e.g., a magnet, magnetic thread, friction fit, mechanical engagement (e.g., snap fit), etc.).

5.3.2.2 One Piece Plenum Chamber

In certain forms of the present technology (see e.g., FIGS. 54 and 55), the plenum chamber 3200 and the seal-forming structure 3100 are formed from a single piece of textile. Using a single piece of material reduces manufacturing costs and provides for an easier assembly of the patient interface 3000.

5.3.2.2.1 Movable One-Piece Construction

In certain forms of the present technology (see e.g., FIG. 54), the plenum chamber 3200 is movable relative to the seal-forming structure 3100, but not separable from the seal-forming structure 3100. In other words, the plenum chamber 3200 may be fixed along at least one edge 3220, and pivotable relative to the seal-forming structure 3100. The plenum chamber 3200 and the seal-forming structure 3100 may be connected along the edge 3220 with a seamless joint.

The plenum chamber 3200 includes a first or decoupled position where the plenum chamber 3200 is pivoted so the patient's nose and/or mouth is uncovered and exposed to the ambient. The plenum chamber 3200 also includes a second or coupled position where the patient's nose and/or mouth is covered by the plenum chamber 3200. The plenum chamber 3200 is movable between the decoupled and coupled positions independently of the seal-forming structure 3100. The seal-forming structure 3100 may remain in position (e.g., sealed against a patient's face) regardless of the position of the plenum chamber 3200.

In the illustrated example, the edge 3220 is along the side (e.g., the patient's left side) of the patient interface 3000. In other embodiments, the edge 3220 may be disposed elsewhere along the perimeter of the opening 3152. For example, the edge 3220 may be positioned proximate to the bottom of the opening 3152. This would allow the plenum chamber 3200 to pivot away from the opening 3152 and toward the patient's chest (while being worn). This may be useful to the patient in the event that they walk around while wearing the patient interface 3000 (e.g., to use the bath-room), so that they continue to wear the patient interface 3000. Having the edge 3220 proximate to the lower portion of the opening 3152 would allow the plenum chamber 3200 to remain in the decoupled position (e.g., because of the force of gravity).

5.3.2.2.1.1 Magnetic Retention

In certain forms of the present technology, the plenum chamber 3200 includes a second magnetic portion 3210 with an opposite polarity than the first magnetic portion 3114 of the seal-forming structure 3100.

In certain forms, the second magnetic portion 3210 is a magnet sewn into the textile cover 3204. The magnet may be provided in any orientation, and along any length of the textile cover 3204. The plenum chamber 3200 couples to the seal-forming structure 3100 when the second magnet 3210 is pivoted proximate to the first magnetic portion 3114.

In certain forms, the second magnetic portion 3210 is a magnetic thread (e.g., thin wires with polymer yarn which have been twisted and magnetized, or magnetic material in polymer melt which have been extruded into fibres to make thread which is then magnetized) sewn into the plenum chamber 3200. The magnetic thread 3210 may extend around or substantially around the perimeter of the plenum chamber 3200, and may be used to retain the textile cover 3204 around the skeletal support 3202. The magnetic thread 3210 may also extend around a portion of the perimeter of the plenum chamber 3200. The plenum chamber 3200 couples to the seal-forming structure 3100 when the second magnetic thread 3210 is positioned proximate to the first magnetic portion 3114.

In certain forms, the second magnetic portion 3210 is a material attracted to magnets (e.g., a ferrous metal). The first magnetic portion 3114 includes a magnet and or a magnetic thread that is attracted to the second magnetic portion 3210.

When positioned proximate to one another, the seal-forming structure 3100 and the plenum chamber 3200 are coupled together and relatively fixed in place (e.g., the plenum chamber 3200 is retained from freely pivoting). In some forms, the magnetic force is greater than the force of pressurized air, and forms a seal between the seal-forming structure 3100 and the plenum chamber 3200. No additional structure is required in order to retain the plenum chamber 3200 in place and prevent pressurized air from escaping when the patient interface 3000 is in use. In some forms, the magnetic force is less than the force of pressurized air and/or is included around only a portion of the perimeter, and an additional structure (e.g., a mechanical fastener—discussed below) is required to retain the plenum chamber 3200 in place and prevent the escape of pressurized air when the patient interface 3000 is in use. In either form, the magnetic force is less than a force applied by a patient's hand (e.g., when moving the plenum chamber 3200 to the decoupled position).

5.3.2.2.1.2 Mechanical Retention

In certain forms of the present technology, the plenum chamber 3200 includes a second mechanical retainer or clip structure with a complementary shape as the first clip structure 3116. The second clip structure 3216 removably mates with the first clip structure 3116 and secures the plenum chamber 3200 in place relative to the seal-forming structure 3100.

In certain forms, the second clip structure 3216 is a made from a rigid material (e.g., plastic, rigid fabric, rigid thread, etc.), and is incorporated (e.g., sewn into) into the textile cover 3204. The second clip structure 3216 extends from the surface of the textile cover 3204 in order to mate with the first clip structure 3116. The rigid material has a stiffness greater than the stiffness of at least a portion of the textile cover 3204 and/or the skeletal support 3202.

In certain forms, the second clip structure 3216 is formed as part of the textile cover 3204 and/or the skeletal support 3202. For example, the second clip structure 3216 may be integrally formed with the textile cover 3204 and/or the skeletal support 3202, or may be permanently attached to the textile cover 3204 and/or the skeletal support 3202.

In certain forms, the second clip structure 3216 is a female clip structure and mates with a male clip structure of the first clip structure 3116; although these may be reversed. A patient aligns the first and second clip structures 3116, 3216 and couples the plenum chamber 3200 to the seal-forming structure 3100 with a snap-fit that provides a seal between the plenum chamber 3200 and the seal-forming structure 3100. Specifically, the patient aligns the second clip structure 3216 with the second clip 3216 (see e.g., FIG. 57a). The patient then actuates the detachment mechanism 3118 to pivot the first clip 3116a away from the magnetic portion 3114. The patient then positions the plenum chamber 3200 proximate the magnetic portion 3114 and releases the detachment mechanism 3118 so that the first clip 3116a contacts the outer surface 3204a (see e.g., FIG. 57b). The gasket 3116c provides a seal between the seal-forming structure 3100 and the plenum chamber 3200 to prevent the flow of fluid between the interface of the seal-forming structure 3100 and the plenum chamber 3200.

In certain forms, the detachment mechanism 3118 is used to uncouple the first and second clip structures 3116, 3216. The detachment mechanism 3118 separates the first clip structure 3116 from the second clip structure 3216 so that the plenum chamber 3200 is movable to the decoupled position. The detachment mechanism 3118 may be a finger activated detachment mechanism 3118 (e.g., a push button) that separates the first clip structure 3116 from the second clip structure 3216. This allows clip structures 3116, 3216 to break their snap-fit and release from one another.

In certain forms of the present technology (see e.g., FIG. 55c), the plenum chamber 3200 includes a groove 3282 that defines a second portion of the track 3258 to that of the seal-forming structure 3100. The groove 3282 of the plenum chamber 3200 also is not formed as a continuous path (e.g., it does not connect with itself). The groove 3282 may not extend along the edge 3220, so as not to impede the movement (e.g., pivoting) of the plenum chamber 3200. Similarly, the groove 3174 of the seal-forming structure 3100 may not intersect the edge 3220.

A zipper 3254 is connected to each of the two grooves 3174, 3282, and is configured to slide along the track 3258. The zipper 3254 is movable along the entire length of the track 3258. When moving in a first direction (e.g., clockwise with respect to the patient), the zipper 3254 couples the two grooves 3174, 3282 together. In other words, the grooves 3174, 3282 are separated, and the zipper 3254 connects them as it slides past. A seal is formed between the grooves 3174, 3282 when they are connected in order to substantially limit fluid from passing through the grooves 3174, 3282.

When moving the zipper 3254 in the second, opposite direction (e.g., counter clockwise with respect to the patient), the zipper 3254 uncouples the groove 3282 of the plenum chamber 3200 from the groove 3174 of the seal-forming structure 3100. In other words, the grooves 3174, 3282 are connected, and the movement of the zipper 3254 uncouples them, and allows the plenum chamber 3200 to again move with respect to the seal-forming structure 3100. Fluid is then able to move between the plenum chamber 3200 and the seal-forming structure 3100 (e.g., into the environment).

In other forms, the plenum chamber 3200 and the seal-forming structure 3100 may be separate pieces (i.e., not formed as one-piece). The zipper 3254 may be connected to the plenum chamber 3200, and the groove 3174 may be threaded into the zipper 3254 when the plenum chamber 3200 is connected to the seal-forming structure 3100. The zipper 3254 may then operate in the same way as described above in order to seal and unseal the plenum chamber 3200 to the seal-forming structure 3100.

5.3.2.2.2 Fixed One-Piece Construction

In certain forms of the present technology (see e.g., FIG. 55*a*), the plenum chamber 3200 is fixed relative to the seal-forming structure 3100. The plenum chamber 3200 substantially covers the patient's mouth and/or nose at all times while the patient is wearing the patient interface 3000. The fixed one-piece construction would have substantially the same appearance as the zipping mechanism in the assembled form (see e.g., FIG. 55*a*). The difference between these two examples would be than in the fixed one-piece construction, the interface between the plenum chamber 3200 and the seal-forming structure 3100 would be a single piece of material.

In certain forms, the plenum chamber 3200 includes a first inlet port 3208 that allows the patient to breathe from the ambient in the absence of pressurized air. The plenum chamber 3200 may include the AAV 3206 adjacent to the first inlet port 3208. Pressurized air may also be provided to the patient interface 3000 through the first inlet port 3208.

5.3.3 Positioning and Stabilizing Structure

The positioning and stabilizing structure 3300 may be generally referred to as a structure that maintains the position of the facial interface in a desired position on the user's face.

In some forms, a single positioning and stabilizing structure 3300 may be usable with multiple types of facial interfaces. Other forms of positioning and stabilizing structures may be usable only with a single type of facial interface.

The seal-forming structure 3100 of the patient interface 3000 of the present technology may be held in sealing position in use by the positioning and stabilizing structure 3300.

In one form the positioning and stabilizing structure 3300 retains the patient interface 3000 on the patient's head with a force at least sufficient to overcome the effect of the positive pressure in the plenum chamber 3200 urging the seal-forming structure 3100 to lift off the face.

In one form the positioning and stabilizing structure 3300 retains the patient interface 3000 on the patient's head with a force sufficient to overcome the effect of the gravitational force on the patient interface 3000.

In one form the positioning and stabilizing structure 3300 retains the patient interface 3000 on the patient's head with a force as a safety margin to overcome the potential effect of disrupting forces on the patient interface 3000, such as from tube drag, or accidental interference with the patient interface.

In one form of the present technology, a positioning and stabilizing structure 3300 is configured in a manner consistent with being worn by a patient while sleeping. In one example the positioning and stabilizing structure 3300 has a low profile, or cross-sectional thickness, to reduce the perceived or actual bulk of the apparatus. In one example, the positioning and stabilizing structure 3300 comprises at least one strap (e.g., a side strap 3302, a rear strap 3304, and/or a top strap 3306) having a rectangular cross-section. In one example the positioning and stabilizing structure 3300 comprises at least one flat strap.

In one form of the present technology, a positioning and stabilizing structure 3300 is configured so as not to be too large and bulky to prevent the patient from lying in a supine sleeping position with a back region of the patient's head on a pillow.

In one form of the present technology, a positioning and stabilizing structure 3300 is configured so as not to be too large and bulky to prevent the patient from lying in a side sleeping position with a side region of the patient's head on a pillow.

In one form of the present technology, a positioning and stabilizing structure 3300 includes a decoupling portion located between an anterior portion of the positioning and stabilizing structure 3300, and a posterior portion of the positioning and stabilizing structure 3300. The decoupling portion does not resist compression and may be a flexible or floppy strap. The decoupling portion is constructed and arranged so that when the patient lies with their head on a pillow, the presence of the decoupling portion prevents a force on the posterior portion from being transmitted along the positioning and stabilizing structure 3300 and disrupting the seal.

In one form of the present technology, a positioning and stabilizing structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material 3314 to engage with a hook material portion 3312.

In certain forms (see e.g., FIGS. 58-65), an end of the strap 3302, 3304, 3306 includes the hook 3312, and the plurality of loops 3314 are spaced from the end of the strap 3302, 3304, 3306. The hook 3312 is selectively receivable within the different loops 3314 in order to adjust the tightness of the strap 3302, 3304, 3306 (e.g., in a length adjustable fashion). The hook 3312 and the loops 3314 may include magnetic portions (e.g., a magnet, a magnetic thread, etc.) with opposite polarities. The hook 3312 and loops 3314 magnetically and mechanically couple in order to provide additional retention between the hook 3312 and the respective loop 3314.

In certain forms of the present technology, a positioning and stabilizing structure 3300 comprises a strap that is extensible, e.g. resiliently extensible. For example the straps 3302, 3304, 3306 may be configured in use to be in tension, and to direct a force to draw a seal-forming structure 3100 into sealing contact with a portion of a patient's face. In an example the straps 3302, 3304, 3306 may be configured as a tie.

In one form of the present technology, the positioning and stabilizing structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilizing structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilizing structure includes a third tie that is constructed and arranged to interconnect the first tie and the second tie to reduce a tendency of the first tie and the second tie to move apart from one another.

In one form of the present technology (see e.g., FIGS. 59 and 60), the side strap 3302 of the positioning and stabilizing structure 3300 includes a first magnetic section 3316 (e.g., a magnet, a magnetic thread, etc.). The first magnetic section 3316 is disposed proximate an end of the side strap 3302. A second magnetic section 3318 (e.g., a magnet, a magnetic thread) with an opposite polarity from the first magnetic section 3316 is disposed on an outer surface OS of the seal-forming structure 3100 and/or the plenum chamber 3200. This allows the second magnetic structure 3318 to remain exposed while the inner surface IS is proximate the patient's face. The first magnetic section 3316 of the side strap 3302 is removably coupled to the second magnetic section 3318. The patient may uncouple the side strap 3302 and remove the positioning and stabilizing structure 3300 without adjusting the length (i.e., tightness) of the side strap 3302.

In one form of the present technology (see e.g., FIG. 48), the positioning and stabilizing structure 3300 includes a side strap 3302 with a pair of magnetic sections (e.g., a magnet, a magnetic thread, etc.). The first magnetic section 3316 is disposed proximate an end of the side strap 3302. The second magnetic section 3318 is spaced apart from the first magnetic section 3316 and includes the opposite polarity from the first magnetic section 3316. Using magnetic sections 3316, 3318 (e.g., magnetic thread) in a length adjustable fashion may reduce pilling or snagging when connecting and disconnecting the magnetic sections 3316, 3318 from one another. In some embodiments, the magnetic sections may be replaced with another coupling means (e.g., Velcro).

In certain forms, the seal-forming structure 3100 (see e.g., FIGS. 58-60), the plenum chamber 3200, and/or the positioning and stabilizing structure 3300 include a sleeve or loop 3320 that selectively receives the side strap 3302. The side strap 3302 is threaded through the loop 3320 and doubled back on itself in order to allow the first magnetic section 3316 to couple to the second magnetic section 3318. The second magnetic section 3318 may be larger (i.e., include a larger area on the side strap 3302) than the first magnetic section 3316, so that the first magnetic section 3316 can couple to the second magnetic section 3318 in a variety of positions (e.g., corresponding with a different tightness).

In one form (see e.g., FIGS. 61-63), projection 3322 is disposed on the outer surface OS of the seal-forming structure 3100 and/or the plenum chamber 3200. The side strap 3302 includes a hook 3312 on one end and a plurality of loops 3314 on an opposite end. One loop is coupled to the projection 3322 to retain the side strap 3302 to the seal-forming structure and/or the plenum chamber 3200. The hook 3312 is doubled back and coupled to one of the loops 3314 in order to tighten the side strap 3302 to the patient's head.

In certain forms of the present technology, a positioning and stabilizing structure 3300 comprises a strap (e.g., the side strap 3302, the rear strap 3304, and/or the top strap 3306) that is bendable and non-rigid. An advantage of this aspect is that the strap 3302, 3304, 3306 is more comfortable for a patient to lie upon while the patient is sleeping.

In certain forms of the present technology, a positioning and stabilizing structure 3300 comprises a strap (e.g., the side strap 3302, the rear strap 3304, and/or the top strap 3306) constructed to be breathable to allow water vapour to be transmitted through the strap 3302, 3304, 3306.

In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another. Suitable for a small sized head, but not a large sized head.

In one form of the present technology (see e.g., FIGS. 43-84), a positioning and stabilizing structure 3300 includes headgear 3324 formed from a textile material 3101. The headgear 3324 is coupled to the seal-forming structure 3100, and at least a portion of the headgear 3324 and the seal-forming structure 3100 are formed from a one-piece construction of the textile material 3101. Although, in other forms, the headgear 3324 and the seal-forming structure 3100 may each be formed from individual pieces of textile and coupled together (e.g., by sewing, gluing, etc.)

In one form (see e.g., FIGS. 47a-53), the headgear 3324 of the positioning and stabilizing structure 3300 includes side straps 3302 that are coupled to the seal-forming structure 3100, and extend to a position between the patient's ear and eye when worn by the patient. Specifically, the side straps 3302 extend from a lateral sides of the seal-forming structure 3100, inferior to the patient's eyes and along the patient's cheeks. The side straps 3302 are formed from the textile material 3101.

In one form (see e.g., FIGS. 47a-53), the headgear 3324 of the positioning and stabilizing structure 3300 includes a rear strap 3304 that is coupled to the seal forming structure 3100, and engages the occiput of the patient's head when worn by the patient. The rear strap 3304 is formed from a textile material 3101.

In one form (see e.g., FIGS. 47a-53), the headgear 3324 of the positioning and stabilizing structure 3300 includes a top strap 3306 that is coupled to the seal forming structure 3100, and engages the top of the patient's head when worn by the patient. The top strap 3306 is formed from a textile material 3101.

In one form (see e.g., FIGS. 47a-48 and 53), the positioning and stabilizing structure 3300 includes ear pieces 3326 that is coupled to the seal forming structure 3100, and partially or completely surrounds the patient's ears when worn by the patient. The ear pieces 3326 are formed from a textile material 3101.

In some forms, the textile material may be flexible (e.g., not rigidized). In other forms, the textile material may be at least partially rigidized (e.g., in at least some locations along the headgear). In some examples, the textile material may be stretchable (e.g., constructed from an elastic material). In other examples, the textile material may be at least partially inextensible (e.g., along at least some locations).

In certain forms (see e.g., FIGS. 47a-53), at least a portion of the position and stabilizing structure 3300 and the seal-forming structure 3100 is a one-piece construction. That is, one or both side straps 3302, the top strap 3306, the rear strap 3304, and/or the ear pieces 3326 are formed as a one-piece construction with the seal-forming structure 3100. For example, at least one of the side straps 3302 is integrally formed with the seal-forming structure 3100, and is not removable from the seal-forming structure 3100. The interface between the side strap and the seal-forming structure 3100 may be a seamless transition 3328.

In certain forms, transition 3328 may be visible to an observer (e.g., the bed partner 1100) as a result of bending or flexing of the side strap 3302 relative to the seal-forming structure 3100. In other words, the transition 3328 may be a crease that delineates the transition between the headgear 3324 and the seal-forming structure 3100 (e.g., the side straps 3302 may bend outwardly or away from the patient as they follow the contours of the patient). The transition 3328 may also be the result of pressurized air expanding the seal-forming structure 3100 and/or the side straps 3302 (e.g., the seal-forming structure 3100 and/or the side straps 3302 inflate to different shapes on either side of the transition 3328).

In certain forms (see e.g., FIGS. 47a-48 and 53), the ear pieces 3326 are formed with the side straps 3302 as a single piece of textile material 3101, and coupled to the seal-forming structure 3100 indirectly through the respective side strap. The top strap 3306 is formed with either the side straps 3302 or the ear straps as a single piece of textile material 3101, and coupled to the seal-forming structure 3100 indirectly through the side straps 3302. The rear strap 3304 is formed directly with the seal-forming structure 3100, or is formed directly with the side straps 3302 and coupled to the seal-forming structure 3100 indirectly through the side straps 3302.

In one form (see e.g., FIG. 47b), the transition or joint 3328 between each side strap and the seal-forming structure 3100 is strengthened. The joint 3328 is rigidized and/or reinforced in order to impart additional strength to the joint 3328, and allow the joint 3328 to receive additional tension without failing (e.g., the side strap and the seal-forming structure 3100 separating).

In certain forms, the joint 3328 is rigidized and/or reinforced with a rigidized thread 3329 sewn into the textile material of the side strap and/or the seal-forming structure 3100. The rigidized thread 3329 has a stiffness that is greater than the stiffness of a least a portion of the fabric material used in the joint 3328.

In certain forms, the joint 3328 is rigidized and/or reinforced with a rigidized piece of material 3330 coupled to the side strap and/or seal-forming structure 3100. The rigidized piece of material 3330 is a textile material that has a stiffness greater than the stiffness of the joint 3328. The rigidized piece of material 3330 may be attached with rigidized threads 3329.

In certain forms, the textile material of the joint 3328 is heat treated and/or lased in order to impart rigidity on the joint 3328. Heat treating and/or lasing does not require additional pieces of material be added to the joint 3328, and may simplify the manufacturing steps. Heat treating and/or lasing may also be incorporated in addition to rigidized material 3330 and/or rigidized thread 3329 in order to further increase the strength and rigidity of the joint 3328.

In some forms, a sleeve may be connected to at least a portion of the positioning and stabilizing structure 3300. The sleeve may be constructed from a comfortable material (e.g., soft, smooth, etc.). For example, the sleeve may be constructed from a textile material and/or a foam material. In some examples, the sleeve may be constructed from an adaptive material 3800 (described below).

In one form, at least a portion of the inner surface of the sleeve may be magnetic. For example, the sleeve may be constructed at least partially from magnetic thread. The side straps 3302 may also be constructed at least partially with a magnetic material (e.g., a magnetic thread). The sleeve may be wider (e.g., slightly wider) than the side strap 3302 and may slide along the side strap 3302 without significant resistance (e.g., from friction). When the sleeve is properly positioned, the magnetic materials in the sleeve and the side strap 3302 may retain the sleeve in position.

5.3.3.1 Used for Airflow

In one form of the present technology (see e.g., FIGS. 45-53), the side straps 3302 are at least a portion of hollow tubes 3334 that convey pressurized air toward the seal-forming structure 3100. The hollow tubes 3334 made from and/or lined with an impermeable material (e.g., silicon, a thermoformed and/or laminate structure, etc.). The hollow tubes 3334 couple to the seal-forming structure 3100 with a seamless or substantially seamless transition (e.g., at joint 3328) in order to prevent or substantially prevent the escape of pressurized air toward the ambient. In one example, the hollow tubes 3334 are dual lumen tubes.

In certain forms (see e.g., FIGS. 43 and 84), a single piece of textile is used to make the side straps 3302 and the seal-forming structure 3100. As the patient interface 3000 is constructed (e.g., to give the seal-forming structure 3100 depth and form the side straps 3302 as hollow tubes 3334), the side straps 3302 transition to the seal-forming structure 3100 at a substantially smooth joint 3328 (see e.g., FIGS. 44 and 46). For example, while a visible transition exists at the joint 3328 as a result of the different shapes of the seal-forming structure 3100 and the side straps 3302, the same piece of textile is used on either side of the joint 3328. Particularly, the inner surface 3130 of the seal-forming structure 3100 and an inner surface 3342 of the side straps 33a02 both rest against the patient's face while the patient interface 3000 is in use. The side strap extends to the seal-forming structure 3100, so that as viewed by the patient, there is almost no visible joint 3328 between the inner surfaces 3130, 3342.

In certain forms (see e.g., FIG. 46a), the seal-forming structure 3100 is a lip type seal. The hollow tubes 3334 extend to an inner surface 3130 of the seal-forming structure 3100, and openings of the hollow tubes 3334 are disposed proximate to the patient's face. Pressurized air is conveyed directly onto the patient's face. A rigidizer 3150 may extend around the seal-forming structure 3100. The hollow tubes 3334 extend through the rigidizer 3150, which provides support to the hollow tubes 3334 (e.g., limit minimizing of a diameter of the hollow tube 3334)

In certain forms (see e.g., FIGS. 47a-50), the seal-forming structure 3100 is a gasket type seal. The seal-forming structure 3100 forms a hollow sealing tube 3104, and the hollow tubes 3334 extend to an interior surface INS of the hollow sealing tube 3104. Pressurized air is conveyed into the interior (e.g., adjacent to the interior surface INS) of the hollow sealing tube 3104, and inflates the hollow sealing tube 3104. The air then exits the hollow sealing tube 3104 in order to reach the patient's face.

In one form (see e.g., FIGS. 46-53), a connector 3335 is used to couple the two hollow tubes 3334 of the side straps 3302 together. The connector 3335 includes a second inlet port 3336, although the second inlet port 3336 may also be positioned on the positioning and stabilizing structure 3300 (e.g., on the side straps 3302, on the top strap 3306, etc.).

The second inlet port 3336 provides communication between the ambient and the hollow tubes 3334 of the side straps 3302. The second inlet port 3336 may allow the patient to breathe from the ambient in the absence of pressurized air.

The positioning and stabilizing structure 3300 may include a valve 3339 with flap 3338 that is adjacent to the second inlet port 3336 (see e.g., FIGS. 64 and 66). The flap 3338 is biased (e.g., magnetically, mechanically, etc.) to an open position (i.e., to allow airflow through the second inlet port 3336), and may move to a closed position (i.e., substantially limiting airflow through the second inlet port 3336) as the result of pressurized air being provided (e.g., through the first inlet of the plenum chamber 3200).

In one form (see e.g., FIGS. 51 and 52), the under the nose mask 3100*a* and the mouth seal 3100*b* each include side straps 3302 so that tension is applied to both the under the nose mask 3100*a* and the mouth seal 3100*b*. The side strap 3302*a* of the under the nose mask 3100*a* may be part of the hollow tube 3334. The side strap 3302*b* of the mouth seal 3100*b* may be only a strip of fabric that does not convey pressurized air toward the mouth seal 3100*b*.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes 3404, for example, about 20 to about 80 holes 3404, or about 40 to about 60 holes 3404, or about 45 to about 55 holes 3404.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure 3500, for example, a swivel or a ball and socket.

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes 3404, for example, about 20 to about 80 holes 3404, or about 40 to about 60 holes 3404, or about 45 to about 55 holes 3404.

The vent 3400 may be located in the plenum chamber 3200. Alternatively, the vent 3400 is located in a decoupling structure, e.g., a swivel.

In one form (see e.g., FIGS. 64-66), the decoupling structure 3500 is inserted through the first inlet port 3208. The decoupling structure 3500 retains the flap 3338 in the open position, and prevents the flap 3338 from moving to the closed position. In some forms, the decoupling structure 3500 may be press fit and/or snap fit into the first inlet port 3208. In some forms, the decoupling structure 3500 may have a magnetic portion (e.g., via a magnetic thread), and may magnetically couple to the flap 3338 or another structure proximate to the first inlet port 3208.

In certain forms (see e.g., FIGS. 47*a* and 47*b*), the decoupling structure 3500 is movable from the first inlet port 3208 to the second inlet port 3336. The flap 3207 of the first inlet port 3208 is then free to move. For example, when pressurized air is supplied through the decoupling structure 3500 and the second inlet port 3336, the force of the air is greater than the bias (e.g., mechanical, magnetic, etc.) of the flap 3207. The flap 3207 moves to the closed position and substantially prevents air from escaping through the first inlet port 3208.

In certain forms (see e.g., FIG. 47*d*), the decoupling structure 3500 is movable from the first inlet port 3208 to a third inlet port 3209 on the plenum chamber 3200 that is spaced apart from the second inlet port 3336. Unlike the second inlet port 3336, the third inlet port 3209 does not include a flap.

5.3.6 Plug

In one form (see e.g., FIGS. 47*a*, 47*b*, and 47*d*), the patient interface 3000 includes a plug 3550. The plug 3550 is inserted through one of the ports 3208, 3336 to substantially prevent airflow through the port 3208, 3336. For example, the plug 3550 may be coupled to the port 3208, 3336 when not receiving the decoupling structure 3500.

In certain forms, the plug 3550 may be used with ports 3208, 3336 that include a valve 3206, 3339. The plug 3550 retains the valve 3206, 3339 in the open position, while providing the seal itself.

5.3.7 Connection Port

Connection port 3600 allows for connection to the air circuit 4170.

5.3.8 Forehead Support

In one form, the patient interface 3000 includes a forehead support 3700. In another form, the patient interface 3000 does not include a forehead support 3700.

5.3.9 Anti-Asphyxia Valve

In one form, the patient interface 3000 includes an anti-asphyxia valve (AAV) (e.g., flap 3207 and flap 3338).

In certain forms (see e.g., FIG. 64), the flap 3207, 3338 proximate the first and/or second ports 3208, 3336 respectively act as AAV 3206, 3339 when a decoupling structure 3500 is not coupled to the respective port 3208, 3336. The decoupling structure 3500 may include an additional AAV 3206, 3339 to allow airflow through the port that the decoupling structure 3500 is coupled to.

In certain forms, an AAV (not shown) may be included on the decoupling structure 3500 and either the plenum chamber 3200 or the positioning and stabilizing structure 3300 may not include the respective flap 3207, 3338 (see e.g., FIG. 47a). The plug 3550 is inserted into the port 3208, 3336 that does not include the decoupling structure 3500.

In certain forms (see e.g., FIG. 66), the AAV 3206, 3339 is made of a pair of flaps (e.g., 3338a, 3338b) that each cover a portion of the respective port (e.g., 3208). A first half 3338a may have a first polarity and the second half 3338b may have also have the first polarity. The halves 3338a, 3338b repel one another because they have a common polarity, and are biased to a normally open position. The magnetic repulsion between the two halves 3338a, 3338b can be overcome by the force of pressurized air (i.e., the force of the pressurized air exceeds the force of magnetic repulsion). Supplying pressurized air to the patient interface 3000 moves the halves 3338a, 3338b to the closed position (e.g., pivoted proximate one another in order to close the AAV 3206, 3339). The halves 3338, 3338b remain in the closed position until the flow of pressurized air ceases.

5.3.10 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.3.11 Adaptive Material

In one form of the present technology (see e.g., FIGS. 67-90), the patient interface 3000 includes adaptive materials 3800 that change based on a variety of usage conditions.

In certain forms (see e.g., FIG. 69), the adaptive materials 3800 provide an adaptive seal. A property of the adaptive material (e.g., rigidity, size, strength, etc.) changes with the presence of the specific usage conditions.

In one form (see e.g., FIGS. 67 and 68), the adaptive material 3800 increases in size or expands over time with additional presence of the usage conditions. The adaptive material 3800 may provide a stronger seal as it expands. For example, the sealant force from the adaptive material(s) 3800 is low or non-existent when the patient interface 3000 is first worn, and increases with increased presence of the conditions.

In one form (see e.g., 72-79), the adaptive material 3800 experiences substantially elastic deformation through cycles of usage conditions. For example, the adaptive material 3800 is capable of expanding and contracting (e.g., depending on conditions) to approximately the same maximums with each successive cycle.

In certain forms (see e.g., FIGS. 76 and 77), the adaptive material 3800 is sandwiched between a rigidized material 3808 (e.g., rigidized textile) and a textile material 3812 (e.g., flexible textile). The textile material be substantially similar or the same as the textile material 3101. The rigidized material 3808 can bias and direct the expansion of the adaptive material 3800 (e.g., toward a patient's face). The rigidized material 3808 may include other properties (e.g., impermeability) to block particles from reaching the adaptive material 3800 and/or the patient's face. The textile material 3812 can be flexible and stretch as the adaptive material 3800 expands. The textile material 3812 can also be elastic so that it returns to its original shape after the adaptive material 3812 contracts. The textile material 3812 is generally soft in order to provide comfort to the patient's face. The textile material 3812 may also be coated with a slightly adhesive material in order to increase the frictional force between the textile material 3812 and the patient's face.

In one form (see e.g., FIGS. 69-71), locations along the patient interface 3000 that do not include adaptive material 3800 may be formed from rigidized material 3808. This controls where the expansion occurs (i.e., expansion occurs where the adaptive material 3800 is located and is limited from expanding in other locations by the rigidized material 3808). Textile material 3812 may be included instead of or in addition to the rigidized material 3808 at locations that do not include the adaptive material 3800. The textile material 3812 may allow some expansion to occur, but would not expand on its own independent of the adaptive material 3800.

In one form (see e.g., FIGS. 80-83), a portion of the patient interface 3000 (e.g., the seal-forming structure 3100) includes at least one fold to form a bellows 3804. The bellows 3804 are formed from a combination of adaptive material 3800, rigidized material 3808, and textile material 3812. The adaptive material 3800 may cause the bellows 3804 to expand. The rigidized material 3808 direct the expansion of the adaptive material 3800 in a predetermined manner or pattern. Both the rigidized material 3808 and the textile material 3812 may not react to the conditions that cause the adaptive material to expand.

In some forms, the patient interface 3000 may be constructed using injection molding. In some forms, various types of adaptive materials 3800 may be molded into various sections of the patient interface 3000. These may all be the same type of adaptive material 3800 with various properties (e.g., expand from the same force but expand different amounts), different types of adaptive material (e.g., swellable, heat activated, and/or auextic materials, described below), or a combination of both.

5.3.11.1 Moisture Swellable Material

In one form of the present technology, the adaptive material 3800 is a swellable material. The adaptive material 3800 expands as it absorbs liquid or moisture. The swellable material 3800 returns to substantially its original size when the moisture evaporates.

In one form, the swellable material 3800 is a swellable foam that increases in size with the absorption of moisture. For example, the swellable foam may be a polyurethane foam. In other embodiments, the swellable material 3800 includes sodium acrylamide or nylon.

In one form, the swellable material 3800 is disposed around a perimeter of an opening of the seal-forming structure 3100. The swellable material 3800 may extend around the entire perimeter of the seal-forming structure 3100. The swellable material 3800 may also extend around only a portion of the seal-forming structure 3100. For example, the swellable material 3800 may be positioned in order to contact at least one of the patient's nasolabial sulcus, the philtrum, the sellion, and the supramenton. The swellable material 3800 may expand at any of these regions as the result of the patient sweating or due to moisture in the air (e.g., moisture in exhaled air or in supplied humidified air). The expansion of the swellable material 3800 may provide a better seal (e.g., a greater sealing force) and/or may provide the patient with added comfort (e.g., because there is more padding).

In one form, the swellable material 3800 is disposed on the positioning and stabilizing structure 3300 (e.g., on the headgear 3324). The swellable material 3800 may be included throughout the headgear 3324, or may be included only in specific locations (e.g., proximate to the patient's temple) along the headgear 3324. For example, the swellable material 3800 may be included only on the side straps 3302 (e.g., against the patient's cheek) and/or only on the rear strap 3304 (e.g., against the patient's occiput). The swellable material 3800 may expand at any of these regions as the result of the patient sweating. The expansion of the swellable material 3800 may provide the patient with added comfort (e.g., because there is more padding) for side and back sleepers respectively. In other forms, the entire positioning and stabilizing structure 3300 may include the swellable material, instead of only discrete locations.

In one form, a rigid support 3808 is provided proximate to the swellable material 3800. The rigid support 3808 may be rigid material added to the patient interface 3000, rigid threads sewn into the patient interface 3000, and/or a heat treated and/or lased section of the patient interface 3000. The rigid support 3808 is substantially fixed (i.e., does not expand) with respect to the swellable material 3800. The rigid support 3808 is able to bias or direct the direction of expansion of the swellable material 3800.

In certain forms, the rigid support 3808 may be positioned only partially around the swellable material 3800. For example, the swellable material 3800 may be positioned proximate an inner surface 3816 and the rigid support 3808 may be positioned proximate an outer surface 3820. The inner surface 3816 is proximate the patient's face and the outer surface 3820 is distal to the patient's face. The rigid support 3808 is therefore able to direct the expansion of the swellable material 3800 into the patient's face (e.g., to provide a stronger seal).

In certain forms, the swellable material 3800 may surround the rigid support 3808. For example, the swellable material 3800 may surround the hollow tube 3334 of the headgear 3324. The rigid support 3808 of the hollow tube 3334 limits the inwardly expansion of the swellable material 3800, which prevents the diameter of the hollow tube 3334 from shrinking as a result of the absorption of moisture.

In certain forms, the swellable material 3800 may be positioned within at least one of the inlet ports 3208, 3336. The outer periphery of the respective inlet port 3208, 3336 provides a rigid support 3808 and directs the expansion of the swellable material 3800 toward a center of the inlet 3208, 3336. The swellable material 3800 may expand to provide a better seal with a decoupling structure or provide a better seal around the flap when the decoupling structure is not coupled to the respective inlet 3208, 3336. For example, the swellable material 3800 may expand when the pressurized air is humidified.

In one form (see e.g., FIG. 58), the positioning and stabilizing structure 3300 includes hooks 3312 and loops 3314 that are selectively coupled together in order to retain the headgear 3324 in place. The hooks 3312 and/or loops 3314 are made from the swellable material 3800 in order to provide additional assistance in retaining the hook 3312 in the loop.

In one form, the seal-forming portion 3100 includes an under the nose mask 3100a and a modular mouth seal 3100b that can be selectively coupled to the under the nose mask 3100a and provide pressurized air to both the patient's nose and mouth. As shown in FIGS. 52a and 52b, swellable material 3800 may be included at the interface between the under the nose mask 3100a and the mouth seal 3100b in order to provide additional sealing between the two pieces.

5.3.11.2 Heat Activated Material

In one form of the present technology, the adaptive material 3800 is a heat activated material 3800. The adaptive material 3800 expands as it absorbs heat. The heat activated material 3800 returns to substantially its original size when the heat dissipates.

In one form, the heat activated material 3800 is a heat activated foam that increases in size with the absorption of heat. For example, the heat activated foam has a close cell foam structure where gas is entrapped and expands when the temperature exceeds a pre-determined value. For example, the heat activated material 3800 includes shape memory alloys or polymers such as polyurethane In certain forms, the heat activated material 3800 is activated between 70° F. and 120° F. Preferably, the heat activated material 3800 is activated around body temperature e.g. between 32° C.-34° C. (89.6° F.-93.2° F.) to 38° C.-39° C. (100.4° F.-102.2° F.). In certain forms, the heat activated material 3800 is activated between 75° F. and 115° F. In certain forms, the heat activated material 3800 is activated between 85° F. and 110° F. In certain forms, the heat activated material 3800 is activated between 90° F. and 110° F.

In one form, the heat activated material 3800 is disposed around a perimeter of an opening of the seal-forming structure 3100. The heat activated material 3800 may extend around the entire perimeter of the seal-forming structure 3100. The heat activated material 3800 may also extend around only a portion of the seal-forming structure 3100. For example, the heat activated material 3800 may be positioned in order to contact at least one of the patient's nasolabial sulcus, the philtrum, the sellion, and the supramenton. The heat activated material 3800 may expand at any of these regions as the result of the patient sweating or being sandwiched between the patient's bed and the patient's face. The heat activate material may also expand because conduction from the patient's skin and/or convection from the patient's exhaled air. The expansion of the heat activated material 3800 may provide a better seal (e.g., a greater sealing force) and/or may provide the patient with added comfort (e.g., because there is more padding). In other forms, the heat activated material 3800 may be on the patient interface 3000 and may expand to make contact with the patient's face, but may not provide a sealing effect. In other words, the heat activated material may assist in cushioning the patient's face, without sealing against the patient's face.

In one form, the heat activated material 3800 is disposed on the positioning and stabilizing structure 3300 (e.g., on the headgear 3324). The heat activated material 3800 may be included throughout the headgear 3324, or may be included only in specific locations (e.g., proximate a patient's temple) along the headgear 3324. For example, the heat activated material 3800 may be included only on the side straps 3302 (e.g., against the patient's cheek) and/or only on the rear strap 3304 (e.g., against the patient's occiput). The heat activated material 3800 may expand at any of these regions as the result of the patient sweating. The heat activated material may also expand because of conduction from the patient's skin. The expansion of the heat activated material 3800 may provide the patient with added comfort (e.g., because there is more padding) for side and back sleepers respectively. In other forms, the entire positioning and stabilizing structure 3300 may include the heat activated material, instead of only discrete locations.

In certain forms, the textile material 3812 is a partially insulated material, which may slow the heat transfer to the adaptive material 3800. The adaptive material would not expand as soon as the seal-forming structure was applied. Instead, the adaptive material 3800 may not reach the necessary expansion temperature for a period of time (e.g., 30 minutes, one hour, two hours, etc.) after the patient interface 3000 is applied. For example, this may not occur until the patient has fallen asleep, and the muscles in their face relax causing their skin to hang flaccid. The expansion of the adaptive material 3800 provides a better seal against the flaccid skin.

In one form, a rigid support 3808 is provided proximate to the heat activated material 3800. The rigid support 3808 may be a rigid material added to the patient interface 3000, rigid threads sewn into the patient interface 3000, and/or a heat treated and/or lased section of the patient interface 3000. The rigid support 3808 is substantially fixed (i.e., does not expand) with respect to the heat activated material 3800. The rigid support 3808 is able to bias or direct the direction of expansion of the heat activated material 3800.

In certain forms, the rigid support 3808 may be positioned only partially around the heat activated material 3800. For example, the heat activated material 3800 may be positioned proximate an inner surface 3816 and the rigid support 3808 may be positioned proximate an outer surface 3820. The inner surface 3816 is proximate the patient's face and the outer surface 3820 is distal to the patient's face. The rigid support 3808 is therefore able to direct the expansion of the heat activated material 3800 into the patient's face (e.g., to provide a stronger seal).

In certain forms, the heat activated material 3800 may surround the rigid support 3808. For example, the heat activated material 3800 may surround the hollow tube 3334 of the headgear 3324. The rigid support 3808 of the hollow tube 3334 limits the inwardly expansion of the heat activated material 3800, which prevents the diameter of the hollow tube 3334 from shrinking as a result of the absorption of moisture. A similar construction may be used in other parts of the headgear 3324 that do not include the hollow tubes 3334.

In certain forms, the heat activated material 3800 may be positioned within at least one of the inlet ports 3208, 3336. The outer periphery of the respective inlet port 3208, 3336 provides a rigid support 3808 and directs the expansion of the heat activated material 3800 toward a center of the inlet port 3208, 3336. The heat activated material 3800 may expand to provide a better seal with a decoupling structure or provide a better seal around the flap when the decoupling structure is not coupled to the respective inlet port 3208, 3336. For example, the heat activated material 3800 may expand when the pressurized air is heated.

In one form, the positioning and stabilizing structure 3300 includes hooks 3312 and loops 3314 that are selectively coupled together in order to retain the headgear 3324 in place. The hooks 3312 and/or loops 3314 are made from the heat activated material 3800 in order to provide additional assistance in retaining the hook 3312 in the loop.

In one form, the seal-forming portion 3100 includes an under the nose mask 3100a and a modular mouth seal 3100b that can be selectively coupled to the under the nose mask 3100a and provide pressurized air to both the patient's nose and mouth. As shown in FIGS. 52a and 52b, heat activated material 3800 may be included at the interface between the under the nose mask 3100a and the mouth seal 3100b in order to provide additional sealing between the two pieces.

5.3.11.3 Auxetic Material

In one form of the present technology (see e.g., FIGS. 67 and 68), the adaptive material 3800 is an auxetic material. The adaptive material 3800 expands as it receives a tensile force F (e.g., in a direction perpendicular, parallel, and/or oblique with respect to the force vector). The auxetic material 3800 returns to substantially its original size when the tensile force F is removed. The auxetic material 3800 is generally aligned with the tensile force. If the tensile force and the auxetic material 3800 are not aligned, the force may not cause the auxetic material 3800 to expand.

In one form, the auxetic material 3800 is an auxetic foam that increases in size (e.g., width) with the application of tension. For example, the auxetic foam may be a polyurethane foam. In other embodiments, the auxetic material 3800 may include silicon or polyurethane.

In one form, the auxetic material 3800 is an auxetic thread that increases in size (e.g., diameter) with the application of tension. For example, the auxetic thread may be thermal yarns.

In one form, the auxetic material 3800 is disposed around a perimeter of an opening of the seal-forming structure 3100. The auxetic material 3800 may extend around the entire perimeter of the seal-forming structure 3100. The auxetic material 3800 may also extend around only a portion of the seal-forming structure 3100. For example, the auxetic material 3800 may be positioned in order to contact at least one of the patient's nasolabial sulcus, the philtrum, the sellion, and the supramenton. The auxetic material 3800 may expand at any of these regions as the result of tension applied by the positioning and stabilizing structure (e.g., tightening the side straps 3302). The expansion of the auxetic material 3800 may provide a better seal (e.g., a greater sealing force F) and/or may provide the patient with added comfort (e.g., because there is more padding). In other forms, the auextic material 3800 may be on the patient interface 3000 and may expand to make contact with the patient's face, but may not provide a sealing effect. In other words, the heat activated material may assist in cushioning the patient's face, without sealing against the patient's face.

In one form, the auxetic material 3800 is disposed on the positioning and stabilizing structure 3300 (e.g., on the headgear 3324). The auxetic material 3800 may be included throughout the headgear 3324, or may be included only in specific locations (e.g., proximate the patient's temple) along the headgear 3324. For example, the auxetic material 3800 may be included only on the side straps 3302 (e.g., against the patient's cheek) and/or only on the rear strap 3304 (e.g., against the patient's occiput). The auxetic material 3800 may expand at any of these regions as the result of tension applied to the headgear 3324. The expansion of the auxetic material 3800 may provide the patient with added comfort (e.g., because there is more padding) for side and back sleepers respectively.

In one form, a rigid support 3808 is provided proximate to the auxetic material 3800. The rigid support 3808 may be rigid material added to the patient interface 3000, rigid threads sewn into the patient interface 3000, and/or a heat treated and/or lased section of the patient interface 3000. The rigid support 3808 is substantially fixed (i.e., does not expand) with respect to the auxetic material 3800. The rigid support 3808 is able to bias or direct the direction of expansion of the auxetic material 3800. The rigid support 3808 is also able to transfer tension to areas of the patient interface 3000 not aligned with the tensile force F, that otherwise would not expand when tension was applied to the patient interface 3000.

In certain forms, the rigid support 3808 may be positioned only partially around the auxetic material 3800. For example, the auxetic material 3800 may be positioned proximate an inner surface 3816 and the rigid support 3808 may be positioned proximate an outer surface 3820. The inner surface 3816 is proximate the patient's face and the outer surface 3820 is distal to the patient's face. The rigid support 3808 is therefore able to direct the expansion of the auxetic material 3800 into the patient's face (e.g., to provide a stronger seal).

In certain forms, the auxetic material 3800 may surround the rigid support 3808. For example, the auxetic material 3800 may surround the hollow tube 3334 of the headgear 3324. The rigid support 3808 of the hollow tube 3334 limits the inwardly expansion of the auxetic material 3800, which prevents the diameter of the hollow tube 3334 from shrinking as a result of the application of tension.

In certain forms, the auxetic material 3800 may be positioned within at least one of the inlet ports 3208, 3336. The outer periphery of the respective inlet port 3208, 3336 provides a rigid support 3808 and directs the expansion of the auxetic material 3800 toward a center of the inlet port 3208, 3336. The auxetic material 3800 may expand to provide a better seal with a decoupling structure or provide a better seal around the flap when the decoupling structure is not coupled to the respective inlet port 3208, 3336. For example, the auxetic material 3800 may expand when the pressurized air is humidified.

In one form, the positioning and stabilizing structure 3300 includes hooks 3312 and loops 3314 that are selectively coupled together in order to retain the headgear 3324 in place. The hooks 3312 and/or loops 3314 are made from the auxetic material 3800 in order to provide additional assistance in retaining the hook 3312 in the loop.

In one form, the seal-forming portion 3100 includes an under the nose mask 3100a and a modular mouth seal 3100b that can be selectively coupled to the under the nose mask 3100a and provide pressurized air to both the patient's nose and mouth. As shown in FIGS. 52a and 52b, auxetic material 3800 may be included at the interface between the under the nose mask 3100a and the mouth seal 3100b in order to provide additional sealing between the two pieces.

In one form (see e.g., FIG. 46b), the inner surface 3130 of the seal-forming structure 3100 (e.g., the surface resting positioned against the patient's face) includes auxetic materials 3800 around anchoring points of the patient's face (e.g., the nasolabial sulcus). Rigidizers 3150 are positioned in locations lacking auxetic material 3800 (e.g., the sellion, the lip superior, etc.). When tension is applied to the seal-forming structure 3100, the rigidizers 3150 direct all tension into the auxetic material 3800, causing the material 3800 to expand. The rigidizers 3150 limit tensile forces applied to locations lacking the auxetics, which could be uncomfortable for the patient.

5.3.11.4 Combination of Adaptive Materials

In one form of the present technology (see e.g., FIGS. 85-90), multiple adaptive materials 3800 may be used together in order to act in concert. For example, the hollow tube 3334 of the headgear 3324 may include an innermost layer made of rigidized material 3808 and an outermost payer made of textile material 3812. Between the rigidized and textile materials 3808, 3812 are a pair of adaptive materials 3800a, 3800b.

In certain forms, the adaptive materials 3800a, 3800b have the same adaptive properties. For example, both adaptive materials 3800a, 3800b may have auxetic properties. The first adaptive material 3800a may expand while under a first range of tensions, and the second adaptive material 3800b may expand while under a second range of tensions (i.e., the adaptive materials 3800a, 3800b are staged).

In certain forms, the first adaptive material 3800a has a different adaptive property than the second adaptive material 3800b. For example, the first adaptive material 3800a may have auxetic properties and expand when tension T is applied to the hollow tube 3334 (see e.g., FIGS. 87 and 88). As the first adaptive material 3800a expands, the outer diameter of the hollow tube 3334 expands (e.g., because the textile material 3812 is flexible) and the inner diameter remains substantially the same. The second adaptive material 3800b may not expand, and may actually compress as the first adaptive material 3800a expands into the second adaptive material 3800b.

The second adaptive material 3800b may expand because of moisture and/or heat, in addition to the expansion of the first adaptive material 3800a (see e.g., FIGS. 89 and 90). The first adaptive material 3800a may limit the inward expansion of the second adaptive material 3800b (e.g., because the applied tension T causes the first adaptive material 3800a to maintain its outer shape). The second adaptive material 3800b expands outwardly, further increasing the outer diameter of the hollow tube 3334.

The staged expansion may be useful to create a better seal and/or provide additional comfort as a patient sleeps. For example, the first adaptive material 3800a (e.g., an auxetic material) may expand when the headgear 3324 is tightened on the patients head. The hollow tube 3334 may then be taut against the patient's face. As the patient falls asleep, the skin droops and becomes flaccid. The hollow tube 3334 may no longer be taut against the patient's face (e.g., the hollow tube may be able to move). To prevent this movement, the second adaptive material 3800b slowly expands as the patient wears the headgear 3324 (e.g., as heat transfer and/or liquid absorption occur). As the skin begins to droop, the second adaptive material 3800b fills in the space and maintains the hollow tube 3334 taut against the patient's face. The second adaptive material 3800b may also expand more slowly than the first adaptive material 3800a so that the headgear 3324 is not too tight (e.g., uncomfortable to wear) while the patient is awake.

In one form, the first adaptive material 3800a and the second adaptive material 3800b may be reversed (e.g., the first adaptive material 3800a is moisture and/or heat activated, and the second adaptive material 3800b is an auxetic material). The first adaptive material may expand first (e.g., as a result of heat transfer and/or liquid absorption). The first adaptive material 3800a applies tension T to the second adaptive material 3800b as the first adaptive material 3800a expands. The tension T produced as a result of the first adaptive material 3800a expanding causes the auxetic second adaptive material 3800b to expand.

In one form (see e.g., FIG. 84), the side straps 3302 bifurcate from the seal-forming structure 3100 on each respective side. An opening 3346 is formed between the bifurcated side straps 3302 on the respective side. In some embodiments, an adaptive material 3800 (e.g., a moisture and/or heat activated material) is disposed in the opening 3346. As the adaptive material 3800 expands, the side straps 3302 receive a tensile force. The side straps 3302 may include an additional adaptive material 3800 (see e.g., FIGS. 72 and 73) which may have auxetic properties. As the adaptive material 3800 in the bifurcated region expands, the adaptive material 3800 lining the side straps 3302 may also expand.

In certain forms, the seal-forming structure 3100 illustrated in FIG. 84 may be used as a liner in combination with another seal-forming structure (see e.g., FIG. 16). The seal-forming structure 3100 of FIG. 84 may be positioned directly against a patient's face, and between the patient's face and a separate seal-forming structure (see e.g., FIG. 16). The adaptive material 3800 is in direct contact with the patient's skin, and can provide benefits of additional comfort to the user as compared to a liner without the adaptive materials 3800 (see e.g., FIG. 45). For example, the adaptive material 3800 may be used to limit the amount that the separate seal-forming structure (see e.g., FIG. 16) digs into the patient's face and creates markings on the skin.

As shown in FIGS. 91 and 92, the hollow tubes 3334 of the side straps 3302 may include a combination of materials around a perimeter. For example, a portion of the perimeter may be made from an adaptive material 3800, and a portion may be made from another material (e.g., a rigidized material 3808). As the adaptive material 3800 expands, only a portion of the hollow tube 3334 expands. The rigidized material 3808 retains the shape of a portion of the perimeter (e.g., the left side as viewed in FIG. 92), and only another portion of the perimeter expands (e.g., the right side as viewed in FIG. 92). This can be used to direct the expansion toward the patient's face, as only the adaptive material expands 3800. The rigidized material 3808 is positioned away from the patient's face, so expansion in that section is not necessary.

In some forms, the weight of the patient's head may exceed the strength of the rigidized material 3808. For example, a side sleeper may compress a hollow tube 3334 while sleeping. In some forms, the adaptive materials 3800 may allow the other hollow tube 3334 (e.g., the hollow tube 3334 not being compressed) may be able to open wider than normal in order to compensate for the decreased airflow through the other hollow tube 3334.

In some forms, the seal-forming structure 3100 may also move as a result of the patient sleeping on their side. The adaptive materials 3800 may similarly work to maintain a sufficient level of seal when the seal-forming structure shifts as a result of the different sleeping position. For example, expansion of the adaptive material may create a larger surface area in order to maintain the seal, while also providing cushioning in order to avoid disturbing the patient.

In some forms, a stiffened or rigid member may be connected in the same location as the adaptive material 3800. For example, the stiffened or rigid member may be threaded through the adaptive material 3800 and/or may be imbedded within the adaptive material 3800. In some forms, the stiffened or rigid member may be a metal wire or metal thread, or may be a stiffening portion 3900 (described below).

In some forms, the stiffened or rigid member may limit the expanded and/or compressed shape of the adaptive material 3800. For example, the stiffened or rigid member may provide a maximum compressed shape for the adaptive material 3800. This shape may conform to a particular patient's face buy may not allow the adaptive material 3800 to completely compress (e.g., so that the adaptive material 3800 does not completely compress if the patient is a side sleeper).

In some forms, the seal-forming structure 3100 may be at least partially inflatable in order to provide a snug fit to a variety of sized patient's faces (e.g., as described above). In some forms, the inflatable portions may be constructed at least partially from the adaptive material 3800. The adaptive material 3800 may assist the inflatable portion expand (e.g., when the patient falls asleep). In other examples, the adaptive portion 3800 may be used instead of the partially inflatable portion.

In certain forms, having adaptive materials 3800 that expand under different environmental conditions (e.g., heat activated materials that expand at different temperatures) may assist in providing the snug fit.

Although described above in certain examples, any combination of the adaptive materials 3800 could be incorporated in any location through the patient interface 3000 (or more generally, the face-mounted interface).

5.3.12 Stiffening Portions

As shown in FIGS. 93-101*c*, one form of the present technology includes a patient interface 3000 with stiffening portions 3900 that include material properties adapted to resist an external force (e.g., a tensile force and/or a compressive force).

In some embodiments, the stiffening portions 3900 are mouldable or capable of being formed into a shape so as to provide a better fit with the patient's face for improved comfort or to form a better seal. For example, the material of the stiffening portions 3900 may include thermoplastic or thermosoftening plastic which have activation agent dependent material properties e.g. its material properties such as stiffness is altered when its temperature is within a predetermined range. In this embodiment, the stiffening portions 3900 may include phase change materials which are activated when it is around body temperature i.e. the phase of the stiffening portions 3900 shift from solid to liquid or vice versa thereby altering its stiffness depending on the temperature range.

In some embodiments, elevated temperatures result in the stiffening portions 3900 becoming more pliable (e.g. the stiffening portions phase change into liquid or semi-liquid) which allows some sections to be made (or moulded or formed) into a specific shape or form. Upon cooling, the stiffening portions 3900 stiffen or solidify thereby forming the patient interface 3000 into a shape which conforms to the patient's face contour(s) better.

In some embodiments, the stiffening portions 3900 have an altered stiffness upon application of a treatment. In some embodiments, the stiffening portions 3900 alter its material properties, for example stiffness, upon other activation agents (other than temperature). For example, the stiffening portions 3900 are activated by pressure or force which allows the patient to form the patient interface 3000 whilst it is being worn to ensure that a good fit and/or seal is achieved. In another embodiment, the activation agent may be liquid or a particular chemical. In other embodiments, the activation agent may be an electrical charge. In this embodiment, the stiffening portions 3900 may be a liquid crystal polymer which stiffens when an electrical charge passes through it. In another example, resistance or electrical tracks are embedded within the stiffening portions which allow electrical current to pass, thereby resulting in a change in temperature.

In certain forms, the patient interface 3000 is constructed at least partially from a textile material 3812. As described above, the illustrated embodiments of the patient interface 3000 is formed from a one-piece construction of textile, although the patient interface may be constructed in a different fashion using the textile material 3812.

As shown in FIG. 94, the stiffening portions 3900*c* (e.g., a second material) may be a thread that is sewn into the textile material 3812 (e.g., a first or base material). In some embodiments, the thread 3900 may be sewn into the textile material 3812 after the patient interface 3000 is assembled. In other embodiments, the thread 3900 may be sewn into the textile material 3812 while the patient interface 3000 is being assembled. The thread 3900 may be used to couple different layers of the patient interface 3000 together. The thread 3900 used in the stiffening portions may be identical to the rigidized thread 3329.

In certain forms, the thread 3900 is a different material than the textile material 3812. The thread 3900 has different material properties than the textile material 3812, including an increased stiffness as compared to the textile material 3812. In the illustrated embodiment, the thread 3900 is a textile thread; although in other embodiments, the thread 3900 may be another material (e.g., a metal, a plastic, etc.).

In certain forms, the thread 3900 is a different material than the textile material 3812, and includes different material properties after an application of a treatment. For example, the material properties (e.g., stiffness) of the thread 3900 and the textile material 3812 may be substantially the same prior to the application of the treatment. With the application of the treatment, the material properties of the thread 3900 change (e.g., a treatment-induced increase in stiffness). In other embodiments, material properties between the pre-treated thread 3900 and the textile material 3812 may be different, but the treatment still alters the material properties of the thread 3900 (e.g., increases its stiffness).

In certain forms, the treatment may consist of applying heat, pressure, a chemical, or a laser to the thread 3900 (e.g., specific areas or its entire length). Application of one of these treatments causes the stiffness (or other material properties) to alter, and enables the thread 3900 to act as a stiffened portion. These treatments may be applied before or after the thread 3900 is coupled to the textile material 3812. The treatment may also be in the form of an external force applied after the patient interface 3000 is constructed. For example, the thread 3900 may be made from an adaptive material 3800 (e.g., an auxetic material), and would increase in stiffness when the usage conditions changed (e.g., a tensile force was applied). In some embodiments, the treatment may include a combination of applying heat, pressure, a chemical, or a laser, as well as an external force.

In other forms, the stiffened portion 3900 may not be a thread and/or the stiffened portion 3900 may be coupled to the textile material 3812 in a different manner This may include adhesives (e.g., glue), fasteners (mechanical, magnetic, etc.), or any other suitable means.

In certain forms, the textile material 3812 is unaffected by the application of the treatment to the thread 3900. In other words, the textile material 3812 includes no treatment-induced properties that change as a result of the application of the treatment. Thus, the treatment may be applied while the thread 3900 is coupled to the textile material 3812, without changing the material properties of the textile material 3812.

5.3.12.1 Locations

As shown in FIG. 93, the stiffening portions (or stiffeners) 3900 are coupled to the patient interface 3000 in a variety of locations. Specifically, the stiffening portions 3900 are coupled to the seal-forming structure 3100 and the positioning and stabilizing structure 3300. In other words, at least one stiffening portion 3900 may be coupled to the positioning and stabilizing structure 3300, to the seal-forming structure 3100, or both the positioning and stabilizing structure 3300 and the seal-forming structure 3100. A stiffening portion 3900 may also be coupled to any other portion of the patient interface 3000 (e.g., the plenum chamber 3200) without departing from the scope of the present technology.

In one form of the present technology, the seal-forming structure 3100 includes a first or upper stiffener 3900a and a second or lower stiffener 3900b. In the illustrated embodiment, the upper stiffener 3900a and the lower stiffener 3900b are made from the same material; although in other embodiments, they may be different materials.

In the illustrated embodiment, the upper and lower stiffeners 3900a, 3900b are positioned proximate outer edges 3154 of the seal-forming structure 3100. Together, the upper and lower stiffeners 3900a, 3900b substantially traverse the perimeter of the seal-forming structure 3100. Each stiffener 3900a, 3900b is also a continuous member (e.g., the upper stiffener 3900a is made from a continuous thread).

By including the stiffeners 3900a, 3900b around substantially the entire perimeter of the seal-forming structure 3100, the entire outer perimeter of the seal-forming structure 3100 can maintain its shape under the application of a force (e.g., a compressive and/or tensile force). By maintaining its shape, particularly under tensile forces from the positioning and stabilizing structure 3300, the seal-forming structure 3100 can maintain a better seal against the patient's face.

In some forms, having stiffeners 3900a, 3900b extend around substantially the entire perimeter of the seal-forming structure 3100 may not be ideal. Certain portions of the patient's face may be better adapted to support tensile forces than others (e.g., the nasal bridge or sellion is less adapted to handle a tensile force than the corner of mouth region or nasolabial sulcus). In this case, it is beneficial to include stiffeners 3900a, 3900b only along those regions, so that the seal-forming structure 3100 has more flexibility at other locations (e.g., to adapt to contours unique to a patient's face).

In some forms, the stiffeners 3900a, 3900b may extend at least partially around a cushion, or a portion of the seal-forming structure 3100 that is intended to contact the patient's face without forming a seal. The same advantages as described above can still be achieved in directing forces away from sensitive regions of the patient's face.

When a force is applied to the seal-forming structure 3100, the stiffeners 3900a, 3900b direct the forces toward locations that do not include stiffeners 3900a, 3900b. In other words, the patient may feel the forces proximate the nasolabial sulcus (e.g., where there is more skin, muscle, etc.), where receiving forces are more comfortable. The patient may feel limited forces at the sellion (e.g., where there is less skin, muscle, etc.), where applied forces create additional discomfort. Creating greater discontinuities in the stiffeners 3900a, 3900b (e.g., positioning the stiffeners 3900a, 3900b around only a portion of the perimeter of the seal-forming structure 3100) may reduce manufacturing costs because fewer stiffeners and/or treatments are needed. Additionally, this may promote patient compliance because the seal-forming structure 3100 may be more comfortable to wear, since it is able to form to the contours of the patient's face, while also limiting forces on sensitive areas (e.g., the sellion).

In the illustrated embodiment, the stiffeners 3900a, 3900b each extend onto the side straps 3302 of the positioning and stabilizing structure 3300. As described above, the seal-forming structure 3100 and the positioning and stabilizing structure 3300 are formed from a single piece of textile material. At least one of the side straps 3302 is permanently connected to the seal-forming structure 3100, so the stiffeners 3900a, 3900b may extend continuously from one side strap 3302, along the seal-forming structure 3100, and to the other side strap 3302.

In one form, each stiffener 3900a, 3900b is disposed proximate an outer edge of each side strap 3302. This maintains a spacing between the stiffeners 3900a, 3900b. The stiffeners 3900a, 3900b, are capable of transferring forces from the seal-forming structure 3100 to the positioning and stabilizing structure 3300. This substantially limits forces applied directly to the front of a patient's face, and instead directs the forces to the lateral regions of the patient's head (e.g., the cheeks). This may be more comfortable for a patient, as force is directed away from sensitive areas in the oro-nasal region. Additionally, the stiffeners 3900a, 3900b may assist in maintaining the shape of the seal-forming structure 3100, while also providing a seal sufficiently strong enough to maintain the therapeutic pressure within the plenum chamber 3200. The transition 3328 between the seal-forming structure 3100 and the positioning and stabilizing structure 3300 may be in contact or to proximate the patient's face. It may be beneficial to have this region remain proximate to the patient's face in order to maintain the seal between the seal-forming structure 3100 and the patient's face. Since the side straps 3302 and the seal-forming structure 3100 may be formed as one piece, an exact line delineating the two regions may not be readily apparent. Thus, the side straps 3302 may provide some assistance in maintaining pressurized air within the plenum chamber 3200. The side straps 3302 are more resilient to deformation, and therefore creating areas for pressurized air to escape, by incorporating the stiffeners 3900a, 3900b.

In certain forms, multiple stiffeners 3900 may be used along the length of the positioning and stabilizing structure 3300. For example, stiffeners 3900 may be purposefully left out of certain areas of the positioning and stabilizing structure 3300. These areas may sit along regions of the patient's face most suited for receiving a load (e.g., cheeks). Stiffeners 3900 may be disposed on either side of these areas in order to direct the force specifically to those areas. As shown in FIG. 93, third or right side stiffeners 3900c are spaced apart from the upper and lower stiffeners 3900a, 3900b on the right side strap 3302. Similarly, fourth or left side stiffeners 3900d are spaced apart from the upper and lower stiffeners 3900a, 3900b on the left side strap 3302. An unstiffened region 3902 is disposed in the gap between the upper and lower stiffeners 3900a, 3900b, and the respective right and left side stiffeners 3900c, 3900d. The unstiffened regions 3902 may have a greater degree of flexibility as compared to the regions with the stiffeners 3900a-3900d.

In other forms, the stiffeners 3900a, 3900b may extend substantially along the length of the side straps 3302 (e.g., a single stiffener 3900a may extend the entire length of the positioning and stabilizing structure 3300). In other words, there may be no unstiffened regions along the side straps 3302, or along the positioning and stabilizing structure 3300 as a whole.

In one form, the positioning and stabilizing structure includes ear pieces 3326 that define a generally ring shape and fit around a patient's ear. As shown in FIG. 47, the ear pieces 3326 are formed from a textile material, and stretch and deform as they pass over the patient's ear. In certain forms, the ear pieces 3326 may also include a portion of the hollow tubes 3334 that convey pressurized air to the seal-forming structure 3100.

In either case, it is desirable for the ear pieces 3326 to maintain their ring shape. This will assist the patient in more easily removing the ear pieces 3326, and preventing unnecessary forces on the ear (e.g., pinching), which may be uncomfortable or painful. Additionally, if the ear pieces 3326 include a hollow tube 3334, maintaining the hollow tubes 3334 at a particular diameter in necessary to insure sufficient airflow to the seal-forming structure 3100.

The ear pieces 3326 may be formed with stiffeners 3900 so that they maintain their ring shape under forces. In the illustrated embodiment, each ear piece 3326 includes a pair of ear stiffeners 3900e. The ear stiffeners 3900e are separate from the stiffeners 3900 on the side straps 3302 (e.g., separate pieces of thread). Together, each pair of ear stiffeners 3900e may extend only partially around the ear pieces 3326. This allows the ear piece 3326 to flex in order to fit around different shaped ears, but also maintains rigidity in the ear piece 3326 in order to maintain the general shape of the ear piece 3326.

In one form, the positioning and stabilizing structure 3300 includes a top strap 3306 that extends between the side straps 3302. In the illustrated embodiment, the top strap 3306 may also connect to the ear pieces 3326 (i.e., the ear pieces 3326 are between the side straps 3302 and the top strap 3306). As described above, a connector 3335 may be coupled to the top strap 3306 when the top strap 3306 includes hollow tubes 3334. Top stiffeners 3900f can be coupled at various positions along the top strap 3306 between the ear pieces 3326 and the connector 3335.

In the illustrated embodiment, multiple stiffeners 3900f (e.g., formed from multiple threads) are formed along the length of the top strap 3306. The stiffeners 3900f may assist in maintaining the shape of the hollow tube 3334 in order to permit airflow from the connector 3335 and to the seal-forming structure 3100. The top strap 3306 may also be allowed to flex (e.g., expand) along locations without the stiffeners 3900f. This allows the top strap 3306 to adjust to a specific contour and/or size of a patient's head. In other words, the top strap 3306 may expand in predetermined locations in order to provide a better fit on the patient's head (e.g., so that it is not too tight), will also maintaining a shape conducive to conveying pressurized fluid.

In one form, the positioning and stabilizing structure 3300 includes a back strap 3304 that also extends between the side straps 3302. In the illustrated embodiment, the back strap 3304 may also connect to the ear pieces 3326 (i.e., the ear pieces 3326 are between the side straps 3302 and the top strap 3306). Interconnecting all of these straps 3302, 3304, 3306 allows the positioning and stabilizing structure 3300 as a whole to be formed from a one-piece textile construction.

The back strap 3304 engages the occiput of the patient's head. In order to provide a secure fit for the patient, the back strap 3304 is able to adjust (e.g., stretch) in a length adjustable fashion in order to conform to the patient's head. Back stiffeners 3900g can limit the adjustment, so that the back strap 3304 may remain snug against the patient's head. This may assist the seal-forming structure 3100 in creating a seal with the patient's face (e.g., pulling the seal-forming structure 3100 tight against the patient's face).

5.3.12.2 Combinations of Materials

As shown in FIGS. 95 and 96, the textile 3812 is movable between a relaxed position (see e.g., FIG. 95) and a stressed position (see e.g., FIG. 96). In the relaxed position, the unstiffened region 3902 is substantially the same thickness as the regions with the stiffeners 3900.

As shown in FIG. 96, when a tensile force is applied to the textile 3812 (e.g., the textile 3812 stretches as a result of a larger patient's head), a thickness of the unstiffened region 3902 decreases, and the total length of the textile 3812 increases. The stiffeners 3900 direct the force to act in the unstiffened region 3902, so that the region with the stiffeners 3900 does not stretch, or stretches by a limited amount as compared to the unstiffened region 3902. By directing the forces, the patient may only experience the force in an unstiffened region 3902.

As shown in FIGS. 97 and 98, an adaptive material 3800 is disposed in the unstiffened region 3902. Specifically, the adaptive material 3800 may be an auxetic material, although other types of adaptive materials may be used. In the relaxed position, the auxetic material 3800 is unstressed and is substantially the same thickness as the region with stiffeners 3900.

As shown in FIG. 98, when a tensile force is applied to the textile 3812 a thickness of the unstiffened region 3902 increases, and the total length of the textile 3812 increases. As described above, the auxetic material 3800 is disposed in specific places on the patient interface in order to provide specific benefits (e.g., improved sealing, improved cushioning, etc.) to the patient. The stiffeners 3900 transfer forces to the auxetic material, so that the auxetic material 3800 expands. The stiffeners 3900 also limit expansion in areas lacking the auxetic material so that only the auxetic materials 3800 are able to expand. Additionally, the stiffeners 3900 limit expansion of other materials into the stiffeners (i.e., compression of the region containing the stiffeners 3900). This is particularly useful in controlling the expansion of the auxetic materials 3800 so that the expansion only occurs in desired locations.

With reference to FIG. 46b, the rigidizers 3150 may alternatively be stiffeners 3900. As with the rigidizers 3150, the stiffeners 3900 direct forces applied to the seal-forming structure 3100 (e.g., by the positioning and stabilizing structure 3300) toward the adaptive material 3800. Therefore, areas at the upper and lower portions of the seal-forming structure 3100 that need to keep their shape and limit pressure applied to the patient's skin do not substantially deform. Instead, the deformation is directed and substantially contained in areas with the adaptive material 3800, where a patient can most benefit from the adaptive material 3800. Replacing the rigidizers 3150 with the stiffeners 3900 may decrease the weight of the patient interface 3000, thereby making the patient interface 3000 more comfortable.

With reference to FIGS. 47b and 47c, the skeletal support 3202 may alternatively be formed from stiffeners 3900. The skeletal support 3202 may be constructed (e.g., sewn) using the stiffeners 3900 (e.g., a thread) to form the latticework 3205. Treatment may be applied to the latticework 3205 prior to the textile cover 3204 encasing the latticework 3205. The treatment causes the latticework 3205 to stiffen, and provide rigidity to the plenum chamber 3200.

With reference to FIG. 48, stiffeners 3900 may be included proximate the first magnetic section 3316 and the second magnetic section 3318. For example, the entire perimeter of the magnetic sections 3316, 3318 may include stiffeners 3900. Treatment can be applied to these stiffeners 3900 to increase the stiffness of the first and second magnetic sections 3316, 3318. In use, this may provide for a stronger magnetic connection between the first and second magnetic sections 3316, 3318 because the sections are stiffeners and better able to sit flush with one another. In other words, the textile on the side straps 3302 is less likely to bunch up proximate to the magnetic sections 3316, 3318, so that the magnetic sections 3316, 3318 can make unobstructed contact with one another.

As shown in FIGS. 99-100b, the stiffeners 3900 may be made from a thread of adaptive material. In other words, the adaptive material may be a textile, and a thread of that textile may be used to construct the stiffener 3900. In the relaxed position (see e.g., FIG. 99), the stiffeners 3900 are also in a relaxed position, as is the rest of the textile material 3812.

The textile 3812 of FIGS. 100a and 100b work in reverse from the textile in FIG. 98. In other words, instead of using the stiffeners 3900 to direct the forces to the unstiffened region 3902, the forces are directed to the stiffeners 3900 themselves. The textile 3812 functions as a staged spring. In other words, as a force is applied, the auxetic material 3800 in the stiffeners 3900 expands. However, the region containing the stiffeners 3900 may not substantially expand. This may provide benefits to the patient in those specific regions. Additionally, the unstiffened region 3902 is configured to not deform while this occurs (see e.g., FIG. 100a). As the force increases, the auxetic material 3800 reaches its maximum expansion, and the unstiffened region begins to deform (see e.g., FIG. 100b).

In other embodiments, the staged process may be reversed. In other words, the unstiffened region 3902 expands first to a maximum length (see e.g., FIG. 100b). While this occurs, expansion into the region with the stiffeners 3900 does not occur. If a force is applied past the maximum expansion of the unstiffened region 3902, the auxetic material in the stiffeners 3900 then expands (see e.g., FIG. 100a).

In either embodiment, the patient may receive benefits from the staged expansion in the textile 3812. The patient is able to stretch the textile 3812 in order to comfortably wear the patient interface 3000. The auxetic material 3800 may also provide benefits to the user in sensitive locations, while still directing the forces to the unstiffened region 3902.

5.3.12.3 Custom Fitted Patient Interfaces

In one form, the patient interface 3000 is constructed with the textile material 3812 and include one or more sections with thread 3900 that has not been treated (i.e., is not stiffened). The thread 3900 may have a similar stiffness (or other material property) to the textile material 3812, or the thread 3900 may have a different stiffness (i.e. be stiffer or less stiff) compared to the textile material 3812. In some embodiments, the sections with the thread 3900 is not at its maximum stiffness.

In certain forms, the patient interface 3000 is customizable for an individual patient. The entire patient interface 3000 may include the thread 3900, and selective areas will be stiffened in order to conform to an individual patient's facial structure or contour. Alternatively, certain sections of the patient interface 3000 include the thread 3900 and selective areas of the sections may be stiffened to conform an individual patient's facial structure. This will provide each patient with a custom fit that may improve comfort and/or sealing, in order to promote compliance with therapy and/or improve effectiveness of therapy.

As shown in FIG. 101a, the patient interface 3000 is constructed at step 3950 (e.g., as one piece from the textile material 3812). The thread 3900 may be added to the patient interface 3000 at step 3950. Alternatively, the thread 3900 may be added at step 3955. The thread 3900 may be added at step 3955 as one continuous thread 3900, or multiple threads 3900 may be added in order to provide discontinuities between the threads 3900 (e.g., and create unstiffened regions 3902).

In some embodiments, an individual patient's face is scanned, analyzed and/or measured at step 3960 in order to identify and map facial topography. For example, a computing device (e.g a laptop, mobile phone or tablet) receives data associated with a patient's face (e.g. uploaded by a patient or retrieved from data storage). Advantageously, the computing device includes a camera which is configured to capture an image of the patient's face or an infrared camera, for example, configured to obtain a 3D scan of a patient's face. A computer system may use this data to map out the ideal locations for stiffening i.e. locations where treatment should be applied to the thread 3900. For example, the computer system may determine locations on the patient's face less adapted to support a tensile load. The computer system may also determine the amount of stiffening needed at each of the identified locations. For example, there may be degrees of adjustment for each stiffener 3900 so locations least adapted to support a tensile load may be determined to require the most stiffening. There may be a relationship (e.g., linear, exponential, logarithmic, etc.) between the points identified as less adapted to support a tensile load, and the amount of stiffening applied. The computer system may be part of the computing device used to receive data associated with the patient's face. Alternatively, the computer system part of a cloud computing network and is in communication with the computing device.

This may be useful for customizing the stiffening in the seal-forming structure 3100 in order to better form a seal with each patient's unique facial contours. For example, a patient with a larger nose (e.g., a larger sellion) may require additional stiffening in that region than a patient with a smaller nose.

In other examples, the computer system may map out locations which would benefit from reshaping i.e. locations where treatment should be applied to the thread 3900 to reshape or reform certain sections of the patient interface 3000 to better fit the patient's unique facial contours. The computer system may display recommendations for customizing the patient interface 3000, for example, on a display. For example, an image, or a plurality of images, of the patient interface 3000 and may indicate which sections of the thread 3900 that should be stiffened or reshaped to achieve better comfort or seal.

In other examples, the patient (or clinician) may use a form-to-shape template in order to manually map or trace the patient's face. The template may be provided or sent to the patient. Subsequently, the template may be pressed against the patient's face so that the template conforms to the shape of the patient's facial structure. In other words, a trace of the patient's face is obtained. This technique may similarly identify locations on the patient's face where stiffening may be beneficial (e.g., at locations not adapted to support tensile loads) without requiring a computer to scan the patient's face. In some forms, the template may be loaded into a computer after the trace is complete.

A treatment can be applied, at step 3965, to an individual's patient interface 3000 after the scanning step 3960 is complete. The treatment further stiffens the thread 3900 at locations identified by the computer system as needing additional stiffness. These treatments may include applying lasers, heat (e.g. adjusting the temperature surrounding the patient interface), pressure, or any other similar method. After the treatment is applied 3965, the patient interface 3000 is customized for a specific patient. In some embodiments, a successive treatment may be applied in order to remove some stiffness from the threads 3900. For example, the patient's face may need to be rescanned 3960 and the treatment reapplied 3965 if the initial fit was not appropriate (e.g., not comfortable, provided insufficient sealing, etc.).

In some forms, the treatment can be applied, at step 3965, by an individual user. For example, the stiffener 3900 may be a thermal fusible yarn, which may stiffen upon the application of heat. The user may general sufficient heat from common household appliances (e.g., a hairdryer, an iron, etc.). This may allow a single or relatively few varieties of manufactured patient interfaces 3000, and each individual user may be able to customize their own unique fit, which may reduce manufacturing costs.

In certain embodiments, the computer system or computing device receives or calculates position data from step 3960. For example, position data corresponds to ideal locations on the patient interface 3000 for treatment-induced stiffness increases, based on the patient's facial geometry and/or contours. In some embodiments, the computer system or computing device may actuate a device to provide treatment based on the position data i.e. to the threads 3900 to the identified locations. The actuation of the laser emitting device may include a mapped route of locations (i.e. coordinates) and/or the total time of treatment to be applied at each location. A greater amount of treatment may be applied to locations less adapted to handle tensile forces (e.g., the bridge of the patient's nose). The position data may also instruct a laser emitting device to stop emitting at certain locations on the patient interface 3000 where treatment-induced stiffness increases are not needed for the particular patient. In this way, each patient interface 3000 may be customized for a particular patient using the individual position data.

In other forms, the laser may be replaced with any other treatment applicator. For example, the position data may be used to control a heat source, a pressure source, a chemical applicator, or any other similar device. Each applicator may be controlled in a similar manner as the laser emitting device.

In still other forms, the laser emitting device, or other applicator, may be controlled by hand. For example, at the step of scanning and measuring 3960, position data is obtained from one or more images or scanned media of the patient's face. A person, e.g. the patient, can then use the position data to identify corresponding locations on the patient interface 3000 which would benefit from treatment and apply the treatment 3965.

As shown in FIG. 101*b*, the patient interface 3000 is constructed at step 3950 (e.g., as one piece from the textile material 3812). In this embodiment, the threads 3900 are not included on the patient interface 3000 at this step (e.g., the patient interface 3000 includes no stiffeners 3900).

Next, an individual patient's face is scanned and measured at step 3960 in order to identify and map facial topography. The computer system can use this data and map out the ideal locations threads 3900 to be applied. Specifically, this may be useful for customizing the stiffening in the seal-forming structure 3100 in order to identify where stiffeners 3900 would be most useful to be applied on a patient interface 3000 for a specific patient.

Treatment is then applied at step 3965 to threads 3900 using any method previously described to stiffen the threads 3900. In this embodiment, the treatment is applied indiscriminately to the thread 3900. At the instant that the treatment is applied 3965, the threads 3900 are separate (e.g., uncoupled) from the patient interface 3000, and stiffening the thread 3900 does not affect the patient interface 3000.

Once the threads 3900 have been treated, they are coupled at step 3955 (e.g., sewn into) to the patient interface 3000 at locations identified by the computer system. For example, the computer system or computing device may have identified specific locations along the seal-forming structure 3100 where the threads 3900 may provide increased benefits to the patient. In some embodiments, some stiffeners 3900 may be coupled to the patient interface 3000 prior to scanning the patient (e.g., on the positioning and stabilizing structure 3300), and the results from scanning the patient 3960 may be used to couple stiffeners 3900 to the seal-forming structure 3100.

As shown in FIG. 101c, the patient interface 3000 or a portion of the patient interface 3000 (e.g., the seal-forming structure 3100) may be constructed at step 3950 from the thread 3900. In other words, the material used to make the thread 3900 is used to construct the patient interface 3000. In this embodiment, the locations that can be stiffened are not delineated by when a thread may be coupled. In other words, any portion of the patient interface 3000 that includes the material 3900 may be stiffened. This may allow for greater customization, and ultimately greater benefits to the patient.

Next, an individual patient's face is scanned and measured at step 3960 in order to identify and map facial topography. The computer system or computing device can use this data and map out the ideal locations for treatment to be applied. While threads are thin and may only be able to be coupled in particular locations, constructing the patient interface 3000 from the material allows more locations to be stiffened, while also easily changing the thickness of the stiffened area.

Treatment is then applied at step 3965 to material 3900 using any method previously described to stiffen the threads 3900. In this embodiment, the treatment is applied across the surface of the patient interface 3000 at any location identified by the computer system. Once the treatment is applied, the patient interface 3000 (e.g., the seal-forming structure 3100) is stiffened and customized for a particular patient.

In certain forms, any combination of these steps can be used on a single patient interface 3000. For example, portions of the patient interface 3000 may be constructed out of the material 3900, while other portions may be constructed out of the textile material 3812 with threads 3900 added and/or stiffened at locations specified by the computer program.

5.3.13 Cleaning Assisted Textiles

As shown in FIGS. 50-1 and 102a-d, one form of the present technology includes a patient interface 3000 made from a material such as textile materials 3101, for example, that promotes a sanitary environment for using the patient interface 3000. The textile materials 3101 assist the patient in maintaining a clean or substantially clean patient interface 3000 (e.g., reduce pathogens, adhesion of biofilm and/or other debris), in order to promote compliance with therapy and/or minimize illness associated with wearing the patient interface 3000.

As shown in FIG. 50-1, the inner surface 3130 of the seal-forming structure 3100 rests against the patient's face while the patient wears the patient interface 3000. Over the course of use, sweat and other debris (e.g., dirt, bacterial, etc.) may transfer from the user to the patient interface 3000, for example on inner surface 3130 Similarly, sweat and debris may also transfer to other locations on the patient interface 3000 in contact with the patient (e.g., the inner surface 3342 of the side straps 3302 or other parts of the positioning and stabilizing structure 3300). During normal use, a layer of debris (e.g., biofilm) may build up along locations in contact with, or adjacent to, the patient. In addition, some growth of microorganisms/microbrial organisms such as bacteria, fungi, yeast or algae may occur on some textile materials which may have been exacerbated by adhesion of biofilm on the textile material. The adhesion of biofilm is undesirable as it may cause odour (due to the growth of bacteria, for example) and/or may also cause degradation of the textile material.

Exhaled air from the patient's lungs is warm and relatively humid (i.e., exhaled air includes water vapor). The vapor settles and may condensate on the seal-forming structure 3100 and/or the plenum chamber 3200. The condensate may include additional debris and/or it may promote the growth of debris (e.g., bacterial biofilm growth) on the seal-forming structure 3100 and/or the plenum chamber 3200.

Additionally, biofilm may build up along the airflow path of the patient interface 3000. The RPT device 4000 may use the pressure generator 4140 and the humidifier 5000 to deliver humidified air to the patient through the patient interface 3000. Humidified air travels through the hollow tubes 3334 of the side and top straps 3302, 3306, and continues into the hollow sealing tube 3104 before reaching the patient. Debris present in the water may travel along the hollow tubes 3334 and the hollow sealing tube 3104 and become trapped in the patient interface 3000. Water in the pressurized airflow may also condense when the patient interface 3000 is not in use (e.g., when the patient interface 3000 is removed in the morning). The condensation may include additional debris and/or it may promote the growth of debris within the hollow tube 3334 or the hollow sealing tube 3104 (e.g., the condensed water may provide a better environment for bacterial growth). The humidified air may also condensate outside of the hollow sealing tube 3104 on the seal-forming structure 3100 or the plenum chamber 3200 with along with the exhaled air.

The condensation, sweat, and/or debris built up during use of the patient interface 3000 may settle while the device is not being worn (e.g., during daylight hours). The biofilm present when the patient interface 3000 is removed after use may remain and or increase (e.g., aided by the condensate). When the user dons the patient interface 3000 for a successive use (e.g., the next night), the built up biofilm may be transferred back to the patient's skin or to their airways. This could introduce new bacteria to the patient's immune system, which could lead to various illnesses.

5.3.13.1 Materials

In one form, the textile 3101 used to construct the patient interface 3000 has one or more surface properties that assist in limiting and/or preventing the build-up or adhesion of biofilm or other debris on the patient interface 3000 i.e. the material properties of the textile 3101 makes it a self-cleaning or easily cleanable material. For example, the surface property of the textile 3101 may be imparted by or attributable to a surface structure (e.g. microstructure) or a chemical or biological substance (e.g. coating).

For example, a chemical treatment including one or more chemicals or biological substances that provide anti-bacterial or anti-microbial properties may be coated on a surface of the textile 3101. For example, anti-microbial technology or antibacterial agents may work at a cellular level to continually disrupt the growth and reproduction of microorganisms. Some examples of anti-microbial agents includes quaternary ammonium compounds (QACs), triclosan (i.e., 2,4,4'-trichloro-2'-hydroxydiphenyl ether ($C_{12}H_7Cl_3O_2$)), metals or metal compounds (e.g. oxide or salt compounds based on silver, copper, zinc or cobalt).

The surface structure may be a formation and/or contour on a surface of the textile 3101. In some embodiments, the surface structure may be a microstructure that is not visible to the naked eye. Advantageously, the size of the microstructure prevents or limits adhesion of biofilm or other debris. In some embodiments, the size of the microstructure is at a sub-micron level. Preferably, the size of the microstructure results in the water contact angle being low thereby resulting in a reduction in surface tension which limits adhesion of water and/or debris on the textile. The microstructure may be included throughout various parts of the patient interface 3000. For example, the microstructure may only be present on portions of the patient interface 3000 that regularly contact the patient's skin (e.g., the inner surface 3130) or is adjacent or nearby these contact areas. In another embodiment, the microstructure may also be included throughout the entire patient interface 3000 (e.g., interior and exterior surfaces). Alternatively, the microstructure may be present on selected parts of the patient interface 3000 which are susceptible to debris or biofilm adhesion. Advantageously, the surface structure of the textile 3101 is hydrophobic (i.e. with a water contact angle of larger than 150°) thereby acting as a shield to avoid water molecules from penetrating inside the fabric layer. This surface structure may be provided by means of a coating (e.g. nanocoating) and/or a water or oil repellent barrier agent.

In some forms, the surface structure may be a natural structure of a given material. In some forms, the surface structure may be formed (e.g., laser edged) into a mold in order to form a molded part with the desired surface structure. In some forms, the surface structure may be formed (e.g., laser edged) onto a component after an initial assembly process (e.g., after molding is completed).

In some forms, different surface structures may provide different visual indications to a user. In some forms, a color may be added to the component with the surface structure. The combination of the color and surface structure may make surface imperfections more apparent to the user.

5.3.13.1.1 Rough

As shown schematically and on an enlarged scale in FIG. 102a, the textile 3101 of the patient interface 3000 may be formed as a relatively rough surface 7800. A microstructure of the rough surface 7800 includes a plurality of peaks 7802 and valleys 7804. Preferably, the distance between the peaks 7802 and valleys 7804 is a distance which limits and/or prevents the adhesion of biofilm. As shown in FIG. 102a, the peaks are separated from each other by a valley i.e. the peak-to-peak distance is the length of a valley. The peak-to-peak distance should be smaller than the size of a water molecule which advantageously limits the penetration of water molecules into the textile 3101. For example, as particularly shown in FIG. 102a, the tops of the peaks 7802 are flat. In other embodiments, the tops of the peaks 7802 are rounded and in some other embodiments, the tops of the peaks 7802 are sharp.

While the surface is relatively rough, it is smooth enough so as not to cause discomfort to a patient's skin. Advantageously, the coefficient of friction of the textile 3101 is a pre-determined value and low enough that it touch-feel against a patient's skin is comfortable yet high enough for limiting adhesion of biofilm on the peaks.

The rough surface 7800 assists in reducing the adhesive force between biofilm and the textile 3101. The microstructure (i.e., 7802, 7804) is formed so that the biofilm forms on the peaks 7802, but is substantially prevented from reaching the valleys 7804. Thus, the surface contact area of the biofilm is reduced, compared to a surface without the rough microstructure. Any biofilm formed on the textile 3101 may be washed away with a cleaning solution (e.g., water, soapy water, etc.). The low adhesive force between the biofilm and the textile 3101 makes removing the biofilm easier, than if the microstructure was not present.

In one form, the peaks 7802 may include a hydrophilic layer (e.g., coating) and the valleys 7804 may include a hydrophobic layer (e.g., coating). The hydrophobic layer may limit material (e.g., water, biofilm, etc.) from settling in the valleys 7804, and promote material to settle on the peaks 7802. This may keep material at or near the peaks 7802 so that the material may be more easily cleaned (e.g., because the material is not lodged in the valleys 7804).

5.3.13.1.2 Rough with Coated Tips

As shown schematically and on an enlarged scale in FIG. 102b, the textile 3101 of the patient interface 3000 may be infused with a material 7806 to limit the formation of a biofilm. The textile 3101 may include a grooved microstructure 7808, with the layer of material 7806 substantially covering the peaks 7810 and valleys 7812 of the microstructure 7808. The material 7806 may be applied at only the peaks 7810 (e.g., the location where the biofilm can adhere). In other forms, the material 7806 may be applied to the valleys 7812 or to both the peaks 7810 and valleys 7812. In some embodiments, only certain peaks 7810 and/or valleys 7812 are coated with the layer of material 7806. In other embodiments, the peaks 7810 are coated with the layer of material 7806 but some valleys 7812 are also coated with the layer of material 7806.

In one form, the material 7808 is a material which provides self-cleaning or anti-bacterial properties such as a metal oxide such as silver or zinc (e.g., pure silver, a silver compound, etc.). The silver 7808 may be applied to the textile 3101 as a coat of material. The silver 7808 may also be nano-particles or nano-membrane that are infused with the textile 3101, and form an outer layer. The silver may also be a silver thread that is woven into the textile 3101. Of course, other material which provide similar surface properties may be used as a coating on the textile 3101.

In one form, the silver particles 7808 interfere with the growth of microorganisms that make up the biofilm. In other words, the silver interferes with the microorganism's cells, and limits their growth on the textile 3101. In this way, the textile 3101 may be self-cleaning in that it can inactivate or kill microorganisms without a separate inactivation agent (e.g., UV light, soap and/or water, etc.). The silver 7808 present in the textile 3101 is itself an inactivation agent. In some embodiments, a self-cleaning textile may also mean a textile which have material properties which make it more easily cleanable.

In certain forms, the valleys 7812 may include a hydrophobic layer (e.g., coating). The hydrophobic layer may limit material (e.g., water, biofilm, etc.) from settling in the valleys 7812, and promote material to settle on the peaks 7810. This may keep material at or near the peaks 7810 so that the material may be forced to interact with the silver 7808 (e.g., and limit the biofilm's growth). Including a hydrophobic layer may also make the textile 3101 easier to clean (e.g., because the material is not lodged in the valleys 7812).

5.3.13.1.3 Rough with Coated Layer

As shown in FIG. 102c, the textile 3101 of the patient interface 3000 may be coated with a layer of material 7814 intended to assist in the removal of biofilm. The textile 3101 may include a grooved microstructure 7816, with the layer of material 7814 substantially covering the peaks 7818 and valleys 7820 of the microstructure 7816. The layer of material 7814 may be applied so that the peaks 7818 and valleys 7820 are still present. In other words, the layer of material 7814 does not completely fill in the valleys 7820.

In one form, the material 7814 is titanium dioxide or zinc oxide. The titanium dioxide 7814 may be applied to the textile 3101 as a coat of material. The titanium dioxide 7814 may also be nano-particles or nano-membrane that are infused with the textile 3101, and form an outer layer.

In one form, titanium dioxide 7814 defines a photocatalytic material (e.g., a material that speeds up a chemical reaction in the presence of light). For example, titanium dioxide 7814 may specifically react with ultraviolet (UV) light. As the reaction occurs, the titanium dioxide 7814 releases free radicals that interact with the air (e.g., to form ozone). The free radicals then break down and interact with biofilm. This interaction can kill pathogens in the biofilm.

In certain forms, the chemical reaction between the titanium dioxide 7814 and the UV light transforms the surface on which the photocatalytic material is present into a hydrophilic surface. The hydrophilic surface allows water to spread out around the surface (e.g., because the surface attracts water). The water can fill the valleys 7820 and move the biofilm away from the surface of the textile 3101. The water can then be washed away, and carry the biofilm along so that the patient interface 3000 is substantially clean.

In some embodiments, the patient interface 3000 may be used together with the container 7850 which may include UV light sources 7860*a*.

5.3.13.1.4 Smooth

As shown in FIG. 102*d*, the microstructure 7822 may be smooth and have a relatively low coefficient of friction (e.g., as compared to the embodiments of FIGS. 102*a-c*). While the microstructure 7822 is relatively smooth, it still has a coefficient of friction necessary to enable proper positioning on a patients face. The smooth microstructure 7822 may provide resistance to biofilm formation. In other words, the texture of the surface substantially prevents biofilm from adhering to the surface. As opposed to the rough microstructure 7800 where the grooves reduced the adhesive force of the biofilm, the smooth microstructure 7822 substantially negates any adhesive force so that the biofilm is substantially unable to adhere to the textile 3101.

In certain forms, the microstructure 7822 may include a hydrophobic layer (e.g., coating). The hydrophobic layer may limit material (e.g., water, biofilm, etc.) from settling on the textile 3101, and/or promote material to flow off of the textile 3101 so that the material may be more easily cleaned. For example, a coating which imparts hydrophobic properties may be applied on the textile 3101 for creating a barrier against water or debris thereby limiting or preventing adhesion on the textile 3101.

5.3.13.1.5 Rough with Varying Length

As shown schematically and on an enlarged scale in FIG. 102*e*, the textile 3101 of the patient interface 3000 may be formed as a relatively rough surface 7824. A microstructure of the rough surface 7824 includes a plurality of peaks 7826 and valleys 7828. Preferably, the distance between the peaks 7826 and valleys 7828 is a distance which limits and/or prevents the adhesion of biofilm. As shown in FIG. 102*e*, the peaks are separated from each other by a valley. The peak-to-peak distance should be smaller than the size of a water molecule which advantageously limits the penetration of water molecules into the textile 3101. For example, as particularly shown in FIG. 102*e*, the tops of the peaks 7826 are flat. In other examples, the tops of the peaks 7826 are rounded and in some other embodiments, the tops of the peaks 7826 are sharp.

While the surface is relatively rough, it is smooth enough so as not to cause discomfort to a patient's skin. Advantageously, the coefficient of friction of the textile 3101 is a pre-determined value and low enough that it touch-feel against a patient's skin is comfortable yet high enough for limiting adhesion of biofilm on the peaks.

The rough surface 7824 assists in reducing the adhesive force between biofilm and the textile 3101. The microstructure (i.e., 7826, 7828) is formed so that the biofilm forms on the peaks 7826, but is substantially prevented from reaching the valleys 7828. Thus, the surface contact area of the biofilm is reduced, compared to a surface without the rough microstructure. Any biofilm formed on the textile 3101 may be washed away with a cleaning solution (e.g., water, soapy water, etc.). The low adhesive force between the biofilm and the textile 3101 makes removing the biofilm easier, than if the microstructure was not present.

In one form, the peaks 7826 may include a hydrophilic layer (e.g., coating) and the valleys 7828 may include a hydrophobic layer (e.g., coating). The hydrophobic layer may limit material (e.g., water, biofilm, etc.) from settling in the valleys 7828, and promote material to settle on the peaks 7826. This may keep material at or near the peaks 7826 so that the material may be more easily cleaned (e.g., because the material is not lodged in the valleys 7828).

In some forms, the peaks 7826 may be non-uniform. For example, a length of each peak 7826 may be different so that adjacent peaks 7826 are different sizes. As shown in FIG. 102*e*, the peaks 7826 may form a repeating diamond pattern, where the length of the peak 7826 oscillates from a minimum, to a maximum, and back to a minimum.

5.3.13.1.6 Rough with Overlap

As shown schematically and on an enlarged scale in FIG. 102*f*, the textile 3101 of the patient interface 3000 may be formed as a relatively rough surface 7830. A microstructure of the rough surface 7830 includes a plurality of peaks 7832 and valleys 7834. Preferably, the distance between the peaks 7832 and valleys 7834 is a distance which limits and/or prevents the adhesion of biofilm. As shown in FIG. 102*f*, the peaks are separated from each other by a valley. The peak-to-peak distance should be smaller than the size of a water molecule which advantageously limits the penetration of water molecules into the textile 3101. For example, as particularly shown in FIG. 102*f*, the tops of the peaks 7832 are rounded or pointed. In other examples, the tops of the peaks 7832 are flat.

While the surface is relatively rough, it is smooth enough so as not to cause discomfort to a patient's skin. Advantageously, the coefficient of friction of the textile 3101 is a pre-determined value and low enough that it touch-feel against a patient's skin is comfortable yet high enough for limiting adhesion of biofilm on the peaks.

The rough surface 7832 assists in reducing the adhesive force between biofilm and the textile 3101. The microstructure (i.e., 7832, 7834) is formed so that the biofilm forms on the peaks 7832, but is substantially prevented from reaching the valleys 7834. Thus, the surface contact area of the biofilm is reduced, compared to a surface without the rough microstructure. Any biofilm formed on the textile 3101 may be washed away with a cleaning solution (e.g., water, soapy water, etc.). The low adhesive force between the biofilm and the textile 3101 makes removing the biofilm easier, than if the microstructure was not present.

In one form, the peaks 7832 may include a hydrophilic layer (e.g., coating) and the valleys 7834 may include a hydrophobic layer (e.g., coating). The hydrophobic layer may limit material (e.g., water, biofilm, etc.) from settling in the valleys 7834, and promote material to settle on the peaks 7832. This may keep material at or near the peaks 7832 so that the material may be more easily cleaned (e.g., because the material is not lodged in the valleys 7834).

In some forms, the peaks 7832 may be non-uniform. For example, a length of each peak 7832 may be different so that adjacent peaks 7832 are different sizes. As shown in FIG. 102f, the peaks 7832 may form a repeating diamond pattern, where the length of the peak 7832 oscillates from a minimum, to a maximum, and back to a minimum (e.g., similar to the example shown in FIG. 102e). Each unit (i.e., a minimum to minimum) may be formed separately from the other units. The units may be arranged in an overlapping pattern, where each unit is at least partially covered by adjacent units.

5.3.13.2 Cleaning

The textile material 3101 comprising the patient interface 3000 may not be entirely self-cleaning (e.g., biofilm or other debris may remain on a surface of the patient interface 3000) and/or the patient may desire to clean the patient interface (e.g., to ensure that substantially all biofilm is removed). For example, the structure of the textile 3101 may limit adhesion of debris, but it may not inactivate the debris (e.g., it is more difficult for pathogens to stick to the textile 3101, but they are still living). In another example, the structure of the textile 3101 may reduce the number of pathogens on the textile 3101, but a layer of biofilm (e.g., dead pathogens) may remain. Patient preference and/or industry standards may determine in what situation the textile 3101 is clean (i.e., certain users may accept one situation as being clean, while other users may not).

Cleaning the patient interface 3000 may provide the patient with an additional assurance that a substantial amount of debris from a previous use will not be transferred to the patient or another patient on a successive use. Cleaning the patient interface 3000 also provides the patient the opportunity to take ownership of the cleaning. Either of these may help promote compliance with the therapy, as the patient may be more assured that the patient interface 3000 is clean and ready to use.

5.3.13.2.1 Cleaning Container

As shown in FIGS. 103-108, a cleaning receptacle or container 7850 may be used to clean the patient interface 3000 after being worn. The container 7850 works in conjunction with and/or in addition to the textile 3101 in order to substantially remove debris from the patient interface 3000 and/or to deactivate the debris. Of course, other patient interfaces (not shown) may be used with the container 7850. Advantageously, the cleaning container 7850 is particularly effective to clean patient interface 3000 including textile 3101.

In one form, the container 7850 includes walls 7852 that define an internal cavity 7854. The cavity 7854 is sized to selectively house at least a portion of the patient interface 3000. For example, the seal-forming structure 3100, plenum chamber 3200, positioning and stabilizing structure 3300, and decoupling structure 3500 may all fit within the internal cavity 7854 at the same time (e.g., in a coupled position and/or in an uncoupled position). In other examples, the internal cavity 7854 may only be able to hold some of the seal-forming structure 3100, plenum chamber 3200, positioning and stabilizing structure 3300, and decoupling structure 3500 at one time. The container 7850 may include a stand 7886 that supports the patient interface 3000.

In one form, the container 7850 includes a lid 7856 movably (e.g., pivotably, slidably, etc.) coupled to one wall 7852. The lid 7856 is movable between an open position, where the internal cavity 7854 is at least partially exposed, and a closed position, where the internal cavity 7854 is covered. The lid 7856 may be retained in the closed position by fasteners 7858a, 7858b (e.g., a mechanical fastener, a magnetic fastener, etc.) in order to substantially prevent the ingress or egress of fluids from the internal cavity 7854 (see e.g., FIG. 104).

In certain forms, at least one hook 7888 is coupled to the lid 7856. In the closed position, the hooks 7888 are positioned within the internal cavity 7854. The hooks can support the weight of the patient interface 3000, and suspend the patient interface 3000 so that all sides are exposed to be cleaned. Of course, other forms of temporary coupling of the patient interface 3000 to the container 7850 may be possible.

As shown in FIGS. 107-114, one or more cleaning modules 7860 are disposed throughout the internal cavity 7854. The cleaning modules 7860 are coupled to the walls 7852 and face toward a center of the internal cavity 7854, where the patient interface 3000 may be temporarily coupled to the container 7850.

In other embodiments, cleaning may take place in more than one stages. For example, the patient interface 3000 may be configured to move with respect to the cleaning modules 7860. Advantageously, this enables more surfaces of the patient interface 3000 to be exposed to the cleaning modules 7860. This may also require less cleaning modules 7860 to clean a patient interface 3000. For example, the stand 7886 may further include a rotating member which is configured to actuate the stand 7886 to rotate along a central axis so as to rotate the patient interface 3000 with respect to the cleaning modules 7860. In certain embodiments, the stand 7886 is exposed to the cleaning modules 7860 for a predetermined amount of time sufficient to clean the exposed surfaces of the patient interface 3000, after which the stand 7886 is rotated along a central axis for a predetermined angle of rotation (e.g. 10°) and these steps are repeated until all (or a substantial amount of) the surfaces of the patient interface 3000 have been cleaned (i.e. exposed to the cleaning modules 7860).

In one form, the container 7850 is independent of the RPT device 4000. In other words, the container does not derive electrical power or fluid flow from the RPT device 4000. The container 7850 may be disposed any distance from the RPT device 4000, because there are no physical connections between the container 7850 and the RPT device 4000.

In one form, the container 7850 may be physically connected to the RPT device 4000 (see e.g., FIGS. 112 and 116). The connection could be in the form of fluid connection via the air circuit 4170 (see e.g., FIG. 112). The connection could also be electrical via a communication cable 7892 (see e.g., FIG. 116). In other forms, the container 7850 may be independent from the RPT device 4000 (see e.g., FIG. 111).

In another embodiment, the container 7850 conforms to the outline of the patient interface 3000 to achieve a more compact form factor which may be more easily transported.

5.3.13.2.1.1 UV Light

As shown in FIGS. 107 and 108, one form of the cleaning modules 7860*a* are UV light sources that emit inactivation agents in the form of UV light. The UV light sources 7860*a* emit UV light into the internal cavity 7854. The UV light may contact articles within the internal cavity 7854 and provide antiseptic properties.

In certain forms, surfaces of the internal cavity 7854 may be made of a reflective material in order to further distribute the UV light to the cavity 7854. This may assist in directing photons of the UV light to contact all surfaces of the patient interface 3000. The UV light sources 7860*a* may also include an optic (e.g., a diffuser, a diffractor, a reflector, etc.). The optic may be a removable piece or it may be permanently fixed to the UV light source 7860*a*. The optic may further assist in distributing the UV light around the internal cavity 7854.

In certain forms (see e.g., FIG. 105), the container 7850 includes an electrical cord 7862 to power the UV light sources. The electrical cord plugs into a wall socket, and provides the UV light sources with electrical current. Alternatively, the electrical cord plugs into a port such as a USB, micro USB or USB type-c powered port.

In certain forms (see e.g., FIG. 105), the container 7850 includes an external compartment 7864 that houses batteries 7866 (e.g., rechargeable batteries), which can be selectively positionable within the external compartment 7864 in order provide electrical current to the UV light sources 7860*a*. The batteries 7866 may be a back up to the electrical cord 7862 (e.g., only provide current when the cord 7862 is not plugged in or the power is out), or the container 7850 may have only batteries 7866 or an electrical cord 7862.

In one form (see e.g., FIG. 106), a wall 7852 of the container 7850 includes a control 7868 that selectively operates the UV light source. The control 7868 may be an electronic screen (e.g., an LCD screen) that allows a patient to control a variety of functions of the UV light source 7860*a*. For example, the control 7868 may turn the UV lights on and off, change the intensity of the UV light, control how longer the UV lights remain on for (e.g., a timer), and/or set a timed delay for the UV lights. Buttons 7870 may be disposed next to the screen 7868 in order to enable patient input. In other embodiments, the screen 7868 may be a touch screen or touch switch and the container may not include physical buttons 7870.

In certain forms, the control 7868 may only be operable by the patient when the lid 7856 is in the closed position. For example, the fasteners 7858*a*, 7858*b* may be electrically connected to the control. In the open position, the fasteners 7858*a*, 7858*b* form an open circuit, and the control 7868, or a portion of the control 7868 (e.g., certain features), is inoperable. The patient may be unable to turn the UV light sources 7860*a* on while the internal cavity 7854 is exposed to the ambient. In the closed position, the fasteners 7858*a*, 7858*b* form a closed circuit, and the control 7868 is operable.

In use, the patient may insert the entire patient interface 3000 or a portion of the patient interface 3000 into the internal cavity 7854 while the lid 7856 is in the open position. The patient may then move the lid 7856 into the closed position. Once the first fastener 7858*a* is secured to the second fastener 7858*b*, the patient may operate the control 7868. The patient selects a desired control pattern (e.g., elapsed time, intensity, etc.). The control 7868 then operates the UV light sources 7860*a* at the selected control pattern. While the UV light sources 7860*a* are on, the lid 7856 may remain in the closed position (e.g., locked) so that the patient is unable to open the lid 7856. Once the selected control pattern is complete, the lid 7856 unlocks and the patient is able to pivot the lid 7856 to the open position and remove the patient interface 3000.

Light emitted from the UV light source 7860*a* interacts with any pathogens present in the internal compartment (e.g., on the patient interface 3000). The UV light may kill substantially all of the pathogens present on the patient interface 3000. This may reduce adhesion of or eliminate any built up biofilm on exterior surfaces of the patient interface 3000 (e.g., the inner surface 3130). The UV light may also penetrate through the hollow tubes 3334 and/or the hollow sealing tube 3104 to reduce or eliminate biofilm present on the internal surfaces.

In one form, the light emitted from the UV light source interacts with the photocatalytic layer (see e.g., FIG. 102*c*). Free radicals are generated as the photocatalytic layer absorbs the UV light. These free radicals interact with the air in the internal cavity 7854 (e.g., and create ozone). The free radicals break down and interact with pathogens in present in the internal cavity 7854. The free radicals further assist in reducing or eliminating any built up biofilm on exterior surfaces of the patient interface 3000.

In some forms, other types of light may be used to remove biofilm form the patient interface 3000. For example, infrared light and/or visible light may be used instead of and/or in addition to UV light. In other forms, sunlight may be used to remove the biofilm, and the patient may be able to at least partially clean the patient interface without the container 7850.

5.3.13.2.1.2 Negative Air Ions

In one form, the cleaning modules 7860*a* emit negative air ions that act as inactivation agents in the form. The negative air ion sources 7860*a* emit ions into the internal cavity 7854. The ion may contact articles within the internal cavity 7854 and provide antiseptic properties. The negative air ions may be used alone or with the UV light source (or any other type of cleaning module 7860) in order to more effective remove biofilm from the patient interface 3000. In some forms, the UV light source 7860*a* may provide negative air ions.

5.3.13.2.1.3 Liquid Washing

As shown in FIGS. 109-114, one form of the cleaning modules 7860*b* are fluid spray nozzles 7860*b* that emit inactivation agents in the form of cleaning fluid. The fluid spray nozzles 7860*b* emit a fluid mixture into the internal cavity 7854. The fluid mixture may contact articles within the internal cavity 7854 and provide antiseptic properties, for example.

As described above (see e.g., FIG. 105), the fluid spray nozzles 7860*b* may be powered using the electrical cord 7862 and/or batteries 7866. Either of these provide electrical current to the fluid spray nozzles 7860*b*.

In one form, the container 7850 includes a reservoir 7872 for storing a cleaning fluid (e.g., water, soap and/or antibacterial disinfectant). The reservoir 7872 may be selectively accessible by the user in order to fill the reservoir 3872 with cleaning fluid. For example the reservoir 7872 may be slidable with respect to a wall 7852 of the container 7850 in order to allow access to the reservoir 7872. Fluid conduits 7874 (e.g., hoses) may fluidly connect the reservoir 7872 to the fluid spray nozzles 7860b.

Alternatively, the container 7850 includes two or more reservoirs. For example, one reservoir may house water and the other may house a cleaning liquid such as soap. In this embodiment, the patient interface 3000 may first be exposed to soap and thereafter water is emitted so as to rinse the patient interface 3000 so that the soap is substantially removed from the patient interface 3000.

In one form (see e.g., FIG. 106), a wall 7852 of the container 7850 includes a control 7868 that selectively operates the fluid spray nozzles 7860b. The control 7868 may be an electronic screen (e.g., an LCD screen) that allows a patient to control a variety of functions of the fluid spray nozzles 7860b. For example, the control may turn the fluid spray nozzles 7860b on and off, change the intensity of the fluid spray, control how longer the fluid spray remains on for (e.g., a timer), and/or set a timed delay for the fluid spray. Buttons 7870 may be disposed next to the screen in order to enable patient input. In other embodiments, the screen 7868 may be a touch screen or touch switch and the container 7850 may not include buttons 7870.

In certain forms, the control 7868 may only be operable by the patient when the lid 7856 and the reservoir 7872 are in the closed position. For example, the fasteners 7858a, 7858b may be electrically connected to the control 7868. Similarly, the reservoir 7872 and the wall 7852 may be electronically connected to the control 7868. In the open position, the fasteners 7858a, 7858b form an open circuit, and the control 7868, or a portion of the control 7868 (e.g., certain features), is inoperable. In the open position, the reservoir 7872 and the wall 7852 also form an open circuit, and the control 7868, or a portion of the control 7868 (e.g., certain features), is inoperable. The patient may be unable to turn the fluid spray nozzles 7860b on while either of these open circuit conditions persist. When the circuits are closed, the control 7868 is operable.

As shown in FIGS. 110-112, certain forms of the container 7850 include a collection chamber 7876 connected to the internal cavity 7854 through a drain 7878. The drain provides fluid communication from the internal cavity 7854 to the collection chamber 7876. In the illustrated embodiment, the collection chamber 7876 is positioned below the internal cavity 7854, so that gravity provides assistance in draining fluid from the internal cavity 7854 to the collection chamber 7876. The patient may remove the collection chamber 7876 from the container 7850 in order to dispose of any waste (e.g., dirty water) in the collection chamber 7876. Removing the collection chamber 7876 may create an additional open circuit, and may further prevent the control 7868 from operating.

In use, the patient may insert the entire patient interface 3000 or a portion of the patient interface 3000 into the internal cavity 7854 while the lid 7856 is in the open position. The patient may then move the lid 7856 into the closed position. The patient may also fill the reservoir 7872 with cleaning fluid. Once the lid 7856 and the reservoir 7872 are secured to the wall 7852, the patient may operate the control 7868. The patient selects a desired control pattern (e.g., elapsed time, intensity, etc.). In some embodiments, there may be a variety of cleaning programs—an express clean (to be used every day) or deep clean (to be used once a week) which may each take different pre-determined lengths of time to complete a cycle, for example. The control 7868 then operates the fluid spray nozzles 7860b at the selected control pattern. While the fluid spray nozzles 7860b are on, the lid 7856 and the reservoir 7872 may remain in the closed position (e.g., locked) so that the patient is unable to open or remove them. Once the selected control pattern is complete, the lid 7856 and the reservoir 7872 unlocks and the patient is able to pivot the lid 7856 to the open position and remove the patient interface 3000. The patient is also able to remove the reservoir 7872 and optionally refill the reservoir 7872 with cleaning fluid (see e.g., FIG. 113). After the control pattern is complete, the patient is also able to remove the collection chamber 7876 and dispose of the contents (e.g., waste water) in a sink 7880 (see e.g., FIG. 114).

Cleaning fluid emitted from the fluid spray nozzles 7860b may interact with any pathogens present in the internal cavity 7854 (e.g., on the patient interface 3000). The cleaning fluid may rinse off biofilm present on the patient interface 3000. For example, the fluid spray nozzles 7860b may provide a pressurized fluid flow to dislodge biofilm present on the patient interface 3000. The textile material 3101 of the patient interface 3000 may further aid in the removal of the biofilm, because the material limits growth of biofilm on its surface. In other words, the surface contours of the textile material 3101 limit the biofilm from being firmly affixed to the patient interface 3000, so that the biofilm is removable with a stream of fluid. Soap, or other cleaning substance, mixed in the cleaning fluid may further kill remaining pathogens so that the patient interface 3000 is substantially clean.

The cleaning fluid may also work in conjunction with light emitted by the UV light sources 7860a (e.g., the container includes both UV light sources 7860a and fluid spray nozzles 7860b). The UV light may kill substantially all of the pathogens present on the patient interface 3000. This may reduce or eliminate any built up biofilm on exterior surfaces of the patient interface 3000 (e.g., the inner surface 3130). The UV light may also penetrate through the hollow tubes 3334 and/or the hollow sealing tube 3104 to reduce or eliminate biofilm present on the internal surfaces INS.

Although the UV light may kill the pathogens of the biofilm, the biofilm itself may remain on the patient interface 3000. The pressurized stream of cleaning fluid may be used to remove the biofilm from the patient interface 3000, so that substantially no biofilm (i.e., alive or dead) remains on the patient interface 3000 when the control pattern is complete.

The patient interface 3000 may be removed from the container 7850 and allowed to dry before it is worn again. Alternatively, the lid may be activated to open after cleaning takes place so that the patient interface 3000 is exposed to ambient air and may dry more quickly before it is worn again. The textile 3101 may be quick drying, in order to assist in speeding up the evaporation of cleaning fluid from the patient interface 3000. The container 7850 may also include a dryer 7882 (e.g., a fan, a heater, etc.) in order to assist in drying the patient interface 3000 inside of the internal cavity 7854. In some embodiments, air may be emitted by the fluid nozzles, for example, to assist with drying.

As shown in FIG. 112 of the present technology, the RPT device 4000 may be connected to the container 7850 to assist in drying the patient interface 3000. The container may include a conduit aperture 7890 to removably receive the air circuit 4170. After the fluid spray nozzles 7860b are finished spraying water, the air circuit 4170 may deliver an airflow (e.g., an air knife) to the interior cavity 7854. The airflow may contact the patient interface 3000 and speed up the drying process. The air circuit 4170 may be connected the entire time the container 7850 is in use, or the air circuit 4170 may only be connected when the fluid spray nozzles 7860b is switched off. While connected, a seal is created between the conduit aperture 7890 and the air circuit 4170. In the event that the air circuit 4170 is removed, a plug may be positioned in the conduit aperture 7890 in order to seal the internal cavity 7854.

In certain forms, the container 7850 is electrically connected to the RPT device 4000 by a communication cable 7892. The communication cable 3892 is connected to a connection port 7894, and provides electrical communication between the container 7850 and the RPT device 4000. The control 7868 (via the communication cable 7892) can communicate with the RPT device 4000 to control (e.g. initiate, adjust the flow rate and/or deactivate) the airflow (i.e. pressurized stream of cleaning fluid) into the interior cavity 7854 to remove biofilm which may remain on the patient interface 3000. Other means of removing biofilm may include acoustic waves such as ultrasonic cleaning.

As shown in FIG. 111, certain forms of the container 7850 may not be connected to an RPT device 4000, and the cleaned patient interface 3000 may air dry within the interior cavity 7854, or the patient may remove the patient interface 3000 to dry outside of the interior cavity 7854.

5.3.13.2.1.4 Sensing

In one form, the container 7850 may include a sensor 7884 that detects tears or micro-tears, biofilm, or other imperfections in the patient interface 3000. The sensor 7884 may be operated via the control 7868. For example, the patient can select the sensor 7884 using the buttons 7870 of the control 7868 and instruct the sensor 7884 to detect one or more imperfections during the selected control pattern.

In one form, the sensor 7884 may move (e.g., along a surface of the lid 7856, pivot in place, etc.) in order to fully scan the internal cavity 7854 or certain sections of the patient interface 3000. Alternatively, the patient interface 3000 may be placed on a rotating platform so as to allow the sensor 7884 to scan more section of the patient interface 3000. The sensor 7884 may track from one side to another in order to detect anything within the internal cavity 7854 (e.g., the patient interface 3000), and any associated imperfections.

In certain forms (see e.g., FIG. 115), the sensor 7884 may be a scanner that moves along a length of the container 7850. The sensor 7884 scans the patient interface 3000 positioned in the container and detects any imperfections. The container 7850 may include a structure to promote a certain orientation of the patient interface 3000 to provide the optimal surface to sense (e.g., the inner surface 3130 of the seal-forming structure 3100).

In one form, the container 7850 may include a plurality of sensors 7884 that cover the lid 7856. Each sensor 7884 is responsible for scanning only a portion of the interior cavity 7854. Together, all of the sensors 7884 scan the entire interior cavity 7854 without the need for the individual sensors 7884 to move. In other words, the control 7868 is able to piece together a reading from each sensor 7884 and map the interior cavity 7854 without the individual sensors having to move.

In one form, the sensor 7884 may determine a quantity of inactivation agent to provide to the internal cavity 7854. For example, the sensor 7884 may determine how much UV light and/or cleaning solution to apply to the internal cavity 7854.

5.3.13.2.1.4.1 Communication

As shown in FIGS. 116 and 117, the container 7850 can communicate with an external device. These devices may include the RPT device 4000 or a communication device 7900 (e.g., a cell phone, a laptop, a tablet, a server, etc.). The communication device 7900 may also not be a physical device, and may instead be a cloud that can store information.

As the container 7850 operates, the control 7868 may communicate with the RPT device 4000 and/or the communication device 7900 to provide the results from the sensor 7884. For example, the sensor 7884 may inform the external device 7900, 4000 that a control pattern elapsed (i.e., the patient interface 3000 was cleaned by the container 7850). The sensor 7884 may also inform the device 7900, 4000 as to the presence of imperfections.

In certain forms, this communication may take places with a wired connection (e.g., via the communication cable 7892). Alternatively or in addition, the communication may take place wirelessly (e.g., via Bluetooth, WiFi, radio frequency, etc.).

As shown in FIG. 117, the container 7850 and the RPT device 4000 can communicate via a first communication path 7902. The container 7850 may send sensed results to a hard drive of the RPT device 4000. The RPT device 4000 may also control the container 7850 based on the sensed results (e.g., supply an airflow through the air circuit 4170 to the interior cavity 7854).

The container 7850 and the communication device 7900 can communicate via a second communication path 7904. The container 7850 may send sensed results to the communication device 7900. For example, this may be a smartphone app, an external server, and/or a cloud. In some embodiments, the communication device 7900 may be controlled by the patient. For example, the patient may use the device 7900 to determine when the patient interface 3000 was last cleaned and/or whether any imperfections were detected on the patient interface 3000. The patient may use this data to determine if/when the patient interface 3000 needs to be replaced (e.g., because a predetermined number of cleaning cycles have been run and/or because an imperfection is detected). In other embodiments, the communication device 7900 may be controlled by a third party (e.g., a healthcare company). For example, the third party may monitor the patient's compliance with using the container 7850, as this may be a prerequisite for receiving a new patient interface 3000.

The communication device 7900 and the RPT device 4000 can communicate via a third communication path 7906. The communication device 7900 can send signals to the RPT device 4000. For example, the communication device 7900 can direct the RPT device to supply an airflow to the internal cavity through the air circuit 4170. The RPT device 4000 can also communicate with the communication device 7900 in order to transmit data from the RPT device 4000. For example, the container 7850 may be connected to the RPT device 4000 via the communication cable 7892 and unable to communicate with the communication device 7900 directly. Data may be transferred from the container 7850 to the RPT device 4000, and then to the communication device 7900.

5.3.13.2.1.5 Air Cleaning

As shown in FIG. 112, one form of the container 7850 may clean the patient interface using an airstream (e.g., via the air circuit 4170). The container may force air across the surface of the patient interface 3000 in order to dislodge the biofilm. The container 7850 may also incorporate ultrasonic waves to assist in cleaning the patient interface 3000. The airstream may be used on its own as an additional cleaning module that does not require the other cleaning modules 3860*a*, 3860*b*. As described above, the airstream may be remotely started using the communication device 7900. It may also be started because of a signal from the control 7868. The airstream also may be started locally using buttons 7870, or similar buttons on the RPT device 4000.

5.3.13.2.1.6 Temperature Control

In one form, the dryer 7882 and/or the air circuit 4170 may be used to preheat the patient interface 3000 prior to use. For example, the patient may use the buttons 7870 and/or at least one of the control paths 7902, 7904, 7906 to turn the dryer 7882 on. The dryer 7882 may warm the internal cavity 7854 (and the patient interface 3000 within the internal cavity 7854) so that the patient interface 3000 is warm before use (e.g., on a cold night). The patient may similarly use airflow from the air circuit 4170 to warm the internal cavity 7854.

In one form, the air circuit 4170 may be used to cool the patient interface 3000 prior to use. For example, the patient may use the buttons 7870 and/or at least one of the control paths 7902, 7904, 7906 to turn the RPT device 4000 on. The RPT device 4000 may cool the internal cavity 7854 (and the patient interface 3000 within the internal cavity 7854) so that the patient interface 3000 is cool before use (e.g., on a warm night).

5.3.13.2.2 Hand Washing

As shown in FIG. 118, the patient may hand wash the patient interface 3000 after use. The patient may run the patient interface under a stream of water (e.g., from a sink) and/or may use a cleaning substance (e.g., soap) to scrub the surface of the patient interface 3000.

In one form, the surface contours of different microstructures (see e.g., FIGS. 102*a-d*) may limit the adhesion of the biofilm to the patient interface 3000. When the patient interface 3000 is exposed to water (or a similar fluid stream), the biofilm is rinsed away (e.g., down a drain of the sink 7880). The patient 1000 may scrub the patient interface 3000 with the cleaning substance in order to further assist in removing the biofilm.

In certain forms, the patient 1000 may clean the patient interface 3000 while it is in its assembled position (e.g., the seal-forming structure 3100, the plenum chamber 3200, and the positioning and stabilizing structure 3300 are coupled together). The patient 1000 may be able to manipulate the patient interface 3000 in order to clean all surfaces of the patient interface 3000.

In certain forms, the patient 1000 may clean the patient interface 3000 while it is in the decoupled position (e.g., the plenum chamber 3200 is separate from the seal-forming structure 3100). This allows the patient 1000 to clean the crevices along an interface between the plenum chamber 3200 and the seal-forming structure 3100. The patient interface 3000 may then be set out to dry.

In certain forms, the patient may place the cleaned patient interface 3000 in the container 7850 after handwashing the patient interface 3000. The patient may use the dryer 7882 and/or the air circuit 4170 of the RPT device to more rapidly dry the hand-washed patient interface 3000. The patient may also use the dryer 7882 and/or the air circuit 4170 to preheat and/or precool the patient interface 3000.

5.4 RPT Device

An RPT device 4000 in accordance with one aspect of the present technology comprises mechanical, pneumatic, and/ or electrical components and is configured to execute one or more algorithms, such as any of the methods, in whole or in part, described herein. The RPT device 4000 may be configured to pressurize a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cm $H_2O$, or at least 10 cm $H_2O$, or at least 20 cm $H_2O$.

The RPT device may have an external housing 4010. The external housing 4010 may be formed in two parts, an upper portion 4012 and a lower portion 4014. Furthermore, the external housing 4010 may include one or more panel(s) 4015. The RPT device 4000 may comprise a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124, and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016. The pneumatic block 4020 may include one or more pneumatic components 4100.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000 or.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000 or.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cm $H_2O$ to about 20 cm $H_2O$, or in other forms up to about 30 cm $H_2O$ when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000 or.

In one form, a signal from a transducer 4270 may be filtered, such as by low-pass, high-pass or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.5 Air Circuit

An air circuit 4170 in accordance with an aspect of the present technology is a conduit or a tube constructed and arranged to allow, in use, a flow of air to travel between two components such as RPT device 4000 and the patient interface 3000 or.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas 4180, e.g. oxygen, is delivered to one or more points in the pneumatic path, such as upstream of the pneumatic block 4020, to the air circuit 4170, and/or to the patient interface 3000 or.

5.6 Humidifier

5.6.1 Humidifier Overview

In one form of the present technology there is provided a humidifier 5000 to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir, a humidifier inlet to receive a flow of air, and a humidifier outlet to deliver a humidified flow of air. In some forms, an inlet and an outlet of the humidifier reservoir may be the humidifier inlet and the humidifier outlet respectively. The humidifier 5000 may further comprise a humidifier base, which may be adapted to receive the humidifier reservoir and comprise a heating element.

5.7 Breathing Waveforms

FIG. 42 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g., atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g., the humidity in the room where a patient is sleeping. Such ambient humidity may be different to the humidity outside the room where a patient is sleeping.

In another example, ambient pressure may be the pressure immediately surrounding or external to the body.

In certain forms, ambient noise (e.g., acoustic) may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g., from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including cm $H_2O$, g-f/cm$^2$ and hectopascal. 1 cm $H_2O$ is equal to 1 g-f/cm$^2$ and is approximately 0.98 hectopascal (1 hectopascal=100 Pa=100 N/m$^2$=1 millibar ~0.001 atm). In this specification, unless otherwise stated, pressure is given in units of cm $H_2O$.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Auxetics: A material with a negative Poisson's ratio so that it becomes thicker in a direction orthogonal to a direction force (e.g., tensile force) is applied.

Polycarbonate: a thermoplastic polymer of Bisphenol-A Carbonate.

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC® (included in the range of products sold under this trademark), manufactured by DuPont. Another manufacturer of LSR is Wacker. Unless otherwise specified to the contrary, an exemplary form of LSR has a Shore A (or Type A) indentation hardness in the range of about 35 to about 45 as measured using ASTM D2240.

Textile: A flexible material made from interlaced fibers using techniques that include, but are not limited to weaving, knitting, crocheting, or braiding. Specific types of textiles may include fabrics, which are produced specific techniques (e.g., weaving and knitting).

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardized sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cm $H_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Anatomy

5.8.3.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

5.8.3.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air traveling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g., about 360 degrees. In certain forms an elbow may be removable from a mating component, e.g., via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. The headgear can also be used to retain other types of interfaces on the user's head.

Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurized above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface INS and an exterior surface. In another example, a seal-forming structure may comprise a face-contacting (e.g., outer) surface, and a separate non-face-contacting (e.g., underside or inner) surface. In another example, a structure may comprise a first surface and a second surface.

To facilitate describing the shape of the three-dimensional structures and the surfaces, we first consider a cross-section through a surface of the structure at a point, p. See FIG. 17 to FIG. 21, which illustrate examples of cross-sections at point p on a surface, and the resulting plane curves. FIGS. 17 to 21 also illustrate an outward normal vector at p. The outward normal vector at p points away from the surface. In some examples we describe the surface from the point of view of an imaginary small person standing upright on the surface.

5.8.5.1 Curvature in One Dimension

The curvature of a plane curve at p may be described as having a sign (e.g., positive, negative) and a magnitude (e.g., 1/radius of a circle that just touches the curve at p).

Positive curvature: If the curve at p turns towards the outward normal, the curvature at that point will be taken to be positive (if the imaginary small person leaves the point p they must walk uphill). See FIG. 17 (relatively large positive curvature compared to FIG. 18) and FIG. 18 (relatively small positive curvature compared to FIG. 17). Such curves are often referred to as concave.

Zero curvature: If the curve at p is a straight line, the curvature will be taken to be zero (if the imaginary small person leaves the point p, they can walk on a level, neither up nor down). See FIG. 19.

Negative curvature: If the curve at p turns away from the outward normal, the curvature in that direction at that point will be taken to be negative (if the imaginary small person leaves the point p they must walk downhill). See FIG. 20 (relatively small negative curvature compared to FIG. 21) and FIG. 21 (relatively large negative curvature compared to FIG. 20). Such curves are often referred to as convex.

5.8.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g., relatively small. The plane curves in FIGS. 17 to 21 could be examples of such multiple cross-sections at a particular point.

Principal curvatures and directions: The directions of the normal planes where the curvature of the curve takes its maximum and minimum values are called the principal directions. In the examples of FIG. 17 to FIG. 21, the maximum curvature occurs in FIG. 17, and the minimum occurs in FIG. 21, hence FIG. 17 and FIG. 21 are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g., both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 32. A typical human right ear comprises a helix, which is a right-hand helix, see FIG. 33. FIG. 34 shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterized with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be traveling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g., FIG. 31), or alternatively by a left-hand rule (FIG. 30).

Osculating plane: The plane containing the unit tangent vector and the unit principal normal vector. See FIGS. 30 and 31.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g., a gently sloping helical path). A space curve which deviates a relatively large amount from the osculating plane will have a relatively large magnitude of torsion (e.g., a steeply sloping helical path). With reference to FIG. 34, since T2>T1, the magnitude of the torsion near the top coils of the helix of FIG. 34 is greater than the magnitude of the torsion of the bottom coils of the helix of FIG. 34

With reference to the right-hand rule of FIG. 31, a space curve turning towards the direction of the right-hand binormal may be considered as having a right-hand positive torsion (e.g., a right-hand helix as shown in FIG. 34). A space curve turning away from the direction of the right-hand binormal may be considered as having a right-hand negative torsion (e.g., a left-hand helix).

Equivalently, and with reference to a left-hand rule (see FIG. 30), a space curve turning towards the direction of the left-hand binormal may be considered as having a left-hand positive torsion (e.g., a left-hand helix). Hence left-hand positive is equivalent to right-hand negative. See FIG. 35.

5.8.5.4 Holes

A surface may have a one-dimensional hole, e.g. a hole bounded by a plane curve or by a space curve. Thin structures (e.g., a membrane) with a hole, may be described as having a one-dimensional hole. See for example the one dimensional hole in the surface of structure shown in FIG. 24, bounded by a plane curve.

A structure may have a two-dimensional hole, e.g. a hole bounded by a surface. For example, an inflatable tyre has a two dimensional hole bounded by the interior surface INS of the tyre. In another example, a bladder with a cavity for air or gel could have a two-dimensional hole. See for example the cushion of FIG. 27 and the example cross-sections therethrough in FIG. 28 and FIG. 29, with the interior surface INS bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 26, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means +/−5 to +/−10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilized to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| REFERENCE SIGNS LIST | |
|---|---|
| patient | 1000 |
| sleeping patient | 1000 |
| bed partner | 1100 |
| patient interface | 3000 |
| seal - forming structure | 3100 |
| textile material | 3101 |
| hollow sealing tube | 3104 |
| holes | 3108 |
| retention mechanism | 3112 |
| first magnetic portion | 3114 |
| first clip structure | 3116 |
| first clip | 3116a |
| second clip | 3116b |
| gasket | 3116c |
| detachment mechanism | 3118 |
| inner surface | 3130 |
| insert | 3134 |
| magnetic thread | 3142 |
| recess | 3144 |
| tab | 3146 |
| rigidizer | 3150 |
| opening | 3152 |
| nose opening | 3152a |
| mouth opening | 3152b |
| outer edge | 3154 |
| plenum chamber | 3200 |
| skeletal support | 3202 |
| textile cover | 3204 |
| outer surface | 3204a |
| inner surface | 3204b |
| latticework | 3205 |
| valve | 3206 |
| flap | 3207 |
| first inlet port | 3208 |
| second magnetic portion | 3210 |
| third magnetic portion | 3212 |
| chord | 3215 |
| second clip structure | 3216 |
| edge | 3220 |
| superior point | 3225 |
| inferior point | 3235 |
| first end | 3240 |
| second end | 3241 |
| conduit | 3242 |
| positioning and stabilising structure | 3300 |
| side strap | 3302 |
| side strap | 3302a |
| side strap | 3302b |
| rear strap | 3304 |
| top strap | 3306 |
| hook | 3312 |
| loop | 3314 |
| first magnetic section | 3316 |
| second magnetic section | 3318 |
| sleeve | 3320 |
| projection | 3322 |
| headgear | 3324 |
| ear piece | 3326 |
| transition | 3328 |
| rigidized thread | 3329 |
| rigidized piece of material | 3330 |
| hollow tubes | 3334 |
| connector | 3335 |
| inlet port | 3336 |
| flap | 3338 |
| valve | 3339 |
| inner surface | 3342 |
| opening | 3346 |
| vent | 3400 |

REFERENCE SIGNS LIST (continued)

| | |
|---|---|
| hole | 3404 |
| decoupling structure | 3500 |
| plug | 3550 |
| connection port | 3600 |
| forehead support | 3700 |
| adaptive material | 3800 |
| first adaptive material | 3800a |
| second adaptive material | 3800b |
| bellows | 3804 |
| rigidized material | 3808 |
| textile material | 3812 |
| inner surface | 3816 |
| outer surface | 3820 |
| stiffened portion | 3900 |
| upper stiffened portion | 3900a |
| lower stiffened portion | 3900b |
| right stiffened portion | 3900c |
| left stiffened portion | 3900d |
| ear stiffener | 3900e |
| unstiffened region | 3902 |
| constructing patient interface | 3950 |
| coupling threads | 3955 |
| scanning patient's face | 3960 |
| applying treatment to threads | 3965 |
| RPT Device | 4000 |
| external housing | 4010 |
| upper portion | 4012 |
| lower portion | 4014 |
| panel | 4015 |
| chassis | 4016 |
| handle | 4018 |
| pneumatic block | 4020 |
| pneumatic component | 4100 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| end cap | 4144 |
| anti-spill back valve | 4160 |
| air circuit | 4170 |
| first stator | 4180 |
| electrical component | 4200 |
| printed circuit board assembly | 4202 |
| power supply | 4210 |
| input device | 4220 |
| central controller | 4230 |
| transducer | 4270 |
| humidifier | 5000 |
| rough surface | 7800 |
| peaks | 7802 |
| valleys | 7804 |
| material | 7806 |
| microstructure | 7808 |
| peaks | 7810 |
| valleys | 7812 |
| titanium dioxide | 7814 |
| microstructure | 7816 |
| peaks | 7818 |
| valleys | 7820 |
| smooth microstructure | 7822 |
| microstructure | 7824 |
| peaks | 7826 |
| valleys | 7828 |
| microstructure | 7830 |
| peaks | 7832 |
| valleys | 7834 |
| container | 7850 |
| wall | 7852 |
| internal cavity | 7854 |
| lid | 7856 |
| first fastener | 7858a |
| second fastener | 7858b |
| cleaning modules | 7860 |
| UV light source | 7860a |
| fluid spray nozzles | 7860b |
| electrical cord | 7862 |
| external compartment | 7864 |
| batteries | 7866 |
| control | 7868 |
| buttons | 7870 |
| reservoir | 7872 |
| fluid conduits | 7874 |
| collection chamber | 7876 |
| drain | 7878 |
| sink | 7880 |
| dryer | 7882 |
| sensor | 7884 |
| stand | 7886 |
| hook | 7888 |
| conduit aperture | 7890 |
| communication cable | 7892 |
| connection port | 7894 |
| device | 7900 |
| first communication path | 7902 |
| second communication path | 7904 |
| third communication path | 7906 |

The invention claimed is:

1. A patient interface structured to receive a flow of pressurised air for breathing by a patient, the patient interface comprising:
a plenum chamber pressurisable to a therapeutic pressure of at least 4 cmH2O above ambient air pressure;
a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use;
a positioning and stabilising structure configured to hold the seal-forming structure in a therapeutically effective position on a patient's head; and
a stiffener coupled to the plenum chamber, the seal-forming structure, and/or the positioning and stabilizing structure,
wherein the patient interface is configured to leave a patient's mouth uncovered, or if the seal-forming structure is configured to seal around a patient's nose and mouth, the patient interface is configured to allow the patient to breathe from ambient in an absence of the flow of pressurised air,
wherein the seal-forming structure and/or the positioning and stabilizing structure is constructed from a first textile material, and
wherein the stiffener is constructed from a second textile material configured, upon application of a treatment, to have a treatment-induced stiffness that is greater than a stiffness of the first textile material.

2. The patient interface of claim 1, wherein the second textile material is a rigidized thread.

3. The patient interface of claim 1, wherein the stiffness of the first textile material is not affected by the application of the treatment.

4. The patient interface of claim 1, wherein the second textile material is configured to increase in stiffness with the application of a laser treatment, a heat treatment, and/or a pressure treatment.

5. The patient interface of claim 4, wherein the second textile material has a stiffness greater than the stiffness of the first textile material before the application of the treatment.

6. The patient interface of claim 1, wherein the second textile material is a thermoplastic material.

7. The patient interface of claim 1, wherein the positioning and stabilizing structure includes a left side strap coupled to the seal-forming structure, the second textile material positioned along a length of the left side strap.

8. The patient interface of claim 7, further comprising a right side strap coupled to an opposite side of the seal-forming structure than the left side strap, the second textile material positioned along a length of the right side strap substantially equivalent to the length of the left side strap.

9. The patient interface of claim 7, wherein the second textile material extends from the seal-forming structure and is configured, once treated, to limit deformation along the length of the left side strap.

10. The patient interface of claim 7, wherein the second textile material includes a first portion and a second portion, the first portion extends from the seal-forming structure, and the second portion is spaced apart from the first portion, the left side strap configured to deform in locations without the second textile material.

11. The patient interface of claim 1, wherein the positioning and stabilizing structure includes ear pieces that define a hole, wherein each ear piece is configured to receive a patient's ear in use, the second textile material positioned around at least a portion of each ear piece.

12. The patient interface of claim 11, wherein each ear piece of the ear pieces includes a first section of the second textile material and a second section of the second textile material spaced apart from the first section, so that, in use, each ear piece is configured to deform in a first direction with an application of a force, and is configured to remain static in a second direction with the application of the force.

13. The patient interface of claim 11, wherein the positioning and stabilizing structure includes a left side strap coupled to the seal-forming structure, the second textile material positioned along a length of the left side strap, wherein a right side strap is coupled to an opposite side of the seal-forming structure than the left side strap, the second textile material positioned along a length of the right side strap substantially equivalent to the length of the left side strap, and wherein the right side strap and the left side strap each extend between the plenum chamber and one of the ear pieces.

14. The patient interface of claim 1, wherein the positioning and stabilizing structure includes a rear strap configured to be positioned on a posterior of the patient's head in use, the second textile material positioned along a length of the rear strap.

15. The patient interface of claim 14, wherein the positioning and stabilizing structure includes ear pieces that define a hole, wherein each ear piece is configured to receive a patient's ear in use, the second textile material positioned around at least a portion of each ear piece, and wherein the rear strap is connected between the ear pieces, and wherein the second textile material on the rear strap is spaced apart from each of the ear pieces.

16. The patient interface of claim 1, wherein the seal-forming structure includes the second textile material that is positioned around at least a portion of a seal-forming structure perimeter.

17. The patient interface of claim 16, wherein the positioning and stabilizing structure includes a left side strap coupled to the seal-forming structure, the second textile material positioned along a length of the left side strap, wherein a right side strap is coupled to an opposite side of the seal-forming structure than the left side strap, the second textile material positioned along a length of the right side strap substantially equivalent to the length of the left side strap, and further comprising a first thread of the second textile material extending between the seal-forming structure and the left side strap, and a second thread of the second textile material extending between the seal-forming structure and the right side strap.

18. The patient interface of claim 1, wherein the second textile material is configured to be a tie that is coupled to the first textile material and is configured to assist the first textile material in retaining its shape under application of a force.

19. The patient interface of claim 1, wherein the second textile material is configured to increase in stiffness with the application of an electrical treatment, heat treatment, a chemical treatment, and/or a laser treatment directly to the second textile material.

20. The patient interface of claim 1, wherein the second textile material is configured to increase in stiffness with the application of a laser and/or heat.

21. The patient interface of claim 1, wherein the second textile material having the treatment-induced stiffness is configured to customize the shape of the patient interface to fit facial contours or topography specific to the patient's face.

22. A patient interface structured to receive a flow of pressurised air for breathing by a patient, the patient interface comprising:
- a plenum chamber pressurisable to a therapeutic pressure of at least 4 cmH2O above ambient air pressure;
- a seal-forming structure constructed and arranged to seal with a region of a patient's face surrounding an entrance to a patient's airways, the seal-forming structure constructed and arranged to maintain said therapeutic pressure in the plenum chamber throughout a patient's respiratory cycle in use;
- a positioning and stabilising structure configured to hold the seal-forming structure in a therapeutically effective position on a patient's head; and
- a stiffener coupled to the plenum chamber, the seal-forming structure, and/or the positioning and stabilizing structure,
- wherein the patient interface is configured to leave a patient's mouth uncovered, or if the seal-forming structure is configured to seal around a patient's nose and mouth, the patient interface is configured to allow the patient to breathe from ambient in an absence of the flow of pressurised air,
- wherein the seal-forming structure and/or the positioning and stabilizing structure is constructed from a first textile material, and
- wherein the stiffener is constructed from a second textile material configured to change its stiffness from a first stiffness to a second stiffness and the second textile material having the second stiffness is configured to customize a shape of the patient interface specific to contours or topography of the patient's face.

23. The patient interface of claim 22, wherein the second stiffness is greater than the first stiffness and a stiffness of the first textile material.

24. The patient interface of claim 22, wherein the second textile material has a first textile material portion with the first stiffness and a second textile material portion, adjacent the first material textile portion, with the second stiffness, due to application of a treatment to the second textile material portion; and wherein the second stiffness is greater than the first stiffness.

* * * * *